US012338291B2

(12) United States Patent
Chaganty et al.

(10) Patent No.: US 12,338,291 B2
(45) Date of Patent: Jun. 24, 2025

(54) HUMANIZED ANTIBODY MOLECULES TO CD138 AND USES THEREOF

(71) Applicant: VISTERRA, INC., Waltham, MA (US)

(72) Inventors: Bharat Chaganty, Concord, MA (US); Boopathy Ramakrishnan, Braintree, MA (US); Hedy Adari-Hall, Sudbury, MA (US); Karthik Viswanathan, Acton, MA (US); James R. Myette, Waltham, MA (US); Zachary Shriver, Winchester, MA (US); Andrew M. Wollacott, Milton, MA (US)

(73) Assignee: VISTERRA, INC., Waltham, MA (US)

( * ) Notice: Subject to any disclaimer, the term of this patent is extended or adjusted under 35 U.S.C. 154(b) by 637 days.

(21) Appl. No.: 16/904,090

(22) Filed: Jun. 17, 2020

(65) Prior Publication Data

US 2020/0392241 A1 Dec. 17, 2020

Related U.S. Application Data

(60) Provisional application No. 63/035,323, filed on Jun. 5, 2020, provisional application No. 62/862,457, filed on Jun. 17, 2019.

(51) Int. Cl.
| | |
|---|---|
| *C07K 16/30* | (2006.01) |
| *A61P 35/00* | (2006.01) |
| *C07K 16/28* | (2006.01) |
| *C07K 16/46* | (2006.01) |
| *A61K 31/69* | (2006.01) |
| *A61K 39/00* | (2006.01) |

(52) U.S. Cl.
CPC .......... *C07K 16/2896* (2013.01); *A61P 35/00* (2018.01); *A61K 31/69* (2013.01); *A61K 2039/545* (2013.01); *C07K 2317/24* (2013.01); *C07K 2317/31* (2013.01); *C07K 2317/35* (2013.01); *C07K 2317/52* (2013.01); *C07K 2317/565* (2013.01); *C07K 2317/732* (2013.01); *C07K 2317/734* (2013.01)

(58) Field of Classification Search
CPC .......... C07K 16/30; A61K 39/39558
See application file for complete search history.

(56) References Cited

U.S. PATENT DOCUMENTS

| | | | |
|---|---|---|---|
| 4,816,567 A | | 3/1989 | Cabilly et al. |
| 5,223,409 A | | 6/1993 | Ladner et al. |
| 5,225,539 A | | 7/1993 | Winter |
| 5,585,089 A | | 12/1996 | Queen et al. |
| 5,693,762 A | | 12/1997 | Queen et al. |
| 8,840,898 B2 | | 9/2014 | Goldmakher |
| 9,221,914 B2 | | 12/2015 | Kraus et al. |
| 9,249,467 B2 | | 2/2016 | Goodison et al. |
| 9,289,509 B2 | | 3/2016 | Osterroth et al. |
| 9,387,261 B2 | | 7/2016 | Kraus et al. |
| 9,803,021 B2 | | 10/2017 | Morrison |
| 9,862,772 B2 | | 1/2018 | Radbruch et al. |
| 9,964,542 B2 | | 5/2018 | Goodison et al. |
| 10,117,932 B2 | | 11/2018 | Schulz et al. |
| 10,662,250 B2 | | 5/2020 | Dukhovlinov et al. |
| 10,975,158 B2 | | 4/2021 | Morrison |
| 11,945,868 B2 | | 4/2024 | Chaganty et al. |
| 2003/0215828 A1 | * | 11/2003 | Mitsuhashi .......... C12Q 1/6809 435/6.12 |
| 2006/0045877 A1 | | 3/2006 | Goldmakher et al. |
| 2007/0054332 A1 | | 3/2007 | Rapraeger et al. |
| 2009/0169570 A1 | | 7/2009 | Daelken et al. |
| 2012/0100588 A1 | | 4/2012 | Wallage |
| 2014/0170159 A9 | | 6/2014 | Wei et al. |
| 2019/0100588 A1 | * | 4/2019 | Chaganty ............ C07K 16/2818 |
| 2020/0392241 A1 | | 12/2020 | Chaganty et al. |
| 2022/0281997 A1 | * | 9/2022 | Qin ....................... C12N 15/85 |
| 2023/0348614 A1 | | 11/2023 | Myette et al. |

FOREIGN PATENT DOCUMENTS

| | | |
|---|---|---|
| CN | 104059151 A | 9/2014 |
| EP | 125023 A1 | 11/1984 |
| EP | 171496 A2 | 2/1986 |
| EP | 173494 A2 | 3/1986 |
| EP | 184187 A2 | 6/1986 |
| EP | 0519596 A1 | 12/1992 |
| EP | 2238168 B1 | 10/2010 |
| EP | 2240516 B1 | 10/2010 |
| EP | 2427216 B1 | 3/2012 |
| EP | 2242772 B1 | 11/2014 |
| EP | 2801584 B1 | 11/2014 |
| EP | 2892926 B1 | 7/2015 |
| EP | 2788030 B1 | 6/2018 |
| GB | 2188638 A | 10/1987 |
| TW | I501778 B | 10/2015 |
| WO | 86/01533 A1 | 3/1986 |
| WO | 1987/002671 A1 | 5/1987 |

(Continued)

OTHER PUBLICATIONS

Dubel (Handbook of Therapeutic Antibodies, 2007, p. 100-101) (Year: 2007).*
Johnson and Wu (Methods in Molecular Biology, Antibody Engineering: Methods and Protocols, vol. 248, p. 11-25, 2004) (Year: 2004).*
Harris (Biotechnology, vol. 11, p. 1293-1297, 1993) (Year: 1993).*
Colman P. M. (Research in Immunology, 145:33-36, 1994) (Year: 1994).*
Paul (Fundamental Immunology, 3rd Edition, 1993, pp. 292-295) (Year: 1993).*
Bendig M. M. (Methods: A Companion to Methods in Enzymology, 1995; 8:83-93) (Year: 1995).*
Rudikoff et al. (Proc Natl Acad Sci USA 79: 1979-1983, 1982) (Year: 1982).*

(Continued)

*Primary Examiner* — Michael Allen
(74) *Attorney, Agent, or Firm* — K&L Gates LLP

(57) ABSTRACT

Humanized antibody molecules that specifically bind to CD138 are disclosed. The humanized antibody molecules can be used to treat, prevent, and/or diagnose disorders, such as multiple myeloma.

21 Claims, 26 Drawing Sheets

Specification includes a Sequence Listing.

(56) References Cited

FOREIGN PATENT DOCUMENTS

| | | |
|---|---|---|
| WO | 90/02809 A1 | 3/1990 |
| WO | 91/00906 A1 | 1/1991 |
| WO | 91/10741 A1 | 7/1991 |
| WO | 91/17271 A1 | 11/1991 |
| WO | 92/01047 A1 | 1/1992 |
| WO | 92/03917 A1 | 3/1992 |
| WO | 92/03918 A1 | 3/1992 |
| WO | 92/09690 A2 | 6/1992 |
| WO | 92/15679 A1 | 9/1992 |
| WO | 92/18619 A1 | 10/1992 |
| WO | 92/20791 A1 | 11/1992 |
| WO | 93/01288 A1 | 1/1993 |
| WO | 94/04678 A1 | 3/1994 |
| WO | 2006099875 A1 | 9/2006 |
| WO | 2008047242 A2 | 4/2008 |
| WO | 2009/080830 A1 | 1/2009 |
| WO | 2009/080829 A1 | 7/2009 |
| WO | 2009/080831 A1 | 7/2009 |
| WO | 2009080832 A1 | 7/2009 |
| WO | 2010/128087 A9 | 11/2010 |
| WO | 2013/083817 A1 | 6/2013 |
| WO | 2014/037519 A3 | 3/2014 |
| WO | 2014/042763 A1 | 3/2014 |
| WO | 2014/089354 A1 | 6/2014 |
| WO | 2017/014679 A3 | 1/2017 |
| WO | 2018199176 A1 | 11/2018 |
| WO | 2019/070726 A1 | 4/2019 |
| WO | 2023097254 A1 | 6/2020 |
| WO | 2019232449 A1 | 12/2020 |
| WO | 2020247932 A1 | 12/2020 |
| WO | 2020257289 A2 | 12/2020 |
| WO | 2020/257289 A3 | 2/2021 |

OTHER PUBLICATIONS

Rudikoff et al. (Proceedings of the National Academy of Sciences USA, vol. 79, p. 1979-1983, 1982) (Year: 1982).*
Gharbaran, R. "Advances in the molecular functions of syndecan-1 (SDC1/CD138) in the pathogenesis of malignancies," Critical Reviews in Oncology/Hematology (2015) vol. 94, pp. 1-17.
McCarthy, B. J. & Hill, A. S. "Altering the fine specificity of an anti-Legionella single chain antibody by a single amino acid insertion," Journal of Immunological Methods (2001) vol. 251, pp. 137-149.
Lin, Y. et al. "Improved affinity of a chicken single-chain antibody to avian infectious bronchitis virus by site-directed mutagenesis of complementarity-determining region H3," African Journal of Biotechnology (2011) vol. 10, No. 79, pp. 18294-18302.
Lee, J. H. et al. "A Broadly Neutralizing Antibody Targets the Dynamic HIV Envelope Trimer Apex via a Long, Rigidified, and Anionic β-Hairpin Structure," Immunity (2017) vol. 46, No. 4, pp. 690-702.
Diab, M. et al. "Production and characterization of monoclonal antibodies specific for canine CD138 (syndecan-1) for nuclear medicine preclinical trials on spontaneous tumours," Veterinary and Comparative Oncology vol. 15, No. 3 (2017): 932-951.
Gattei, V. et al. "Characterization of anti-CD138 monoclonal antibodies as tools for investigating the molecular polymorphism of syndecan-1 in human lymphoma cells," British Journal of Haematology vol. 104, No. 1 (1999): 152-162.
Search Report and Written Opinion issued in Singapore Application No. 11202002248T, dated Nov. 5, 2021.
Alexander et al., "Syndecan-1 is required for Wnt-1-induced mammary tumorigenesis in mice," Nat Genet. 2000; 25 (3): 329-32.
Anttonen et al., "High syndecan-1 expression is associated with favourable outcome in squamous cell lung carcinoma treated with radical surgery," Lung Cancer. 2001; 32:297-305.
Birchmeier et al., "Met, metastasis, motility and more," Nat Rev Mol Cell Biol. 2003; 4(12): 915-925.
Juuti et al., "Syndecan-1 expression—a novel prognostic marker in pancreatic cancer," Oncology. 2005; 68(2-3): 97-106.
Kim et al., "Immunohistochemical study identifying prognostic biomolecular markers in nasopharyngeal carcinoma treated by radiotherapy," Head Neck. 2011; 33:1458-1466.
Kiviniemi et al., "Altered expression of syndecan-1 in prostate cancer," APMIS. 2004; 112: 89-97.
Kumar-Singh et al., "Syndecan-1 expression in malignant mesothelioma: correlation with cell differentiation, WT1 expression, and clinical outcome," J Pathol. 1998; 186:300-305.
Raab et al., "Multiple myeloma," Lancet. 2009; 374(9686): 324-39.
Roh et al., "Syndecan-1 expression in gallbladder cancer and its prognostic significance," Eur Surg Res. 2008; 41(2): 245-250.
Tsanou et al., "Clinicopathological study of the expression of syndecan-1 in invasive breast carcinomas. correlation with extracellular matrix components," J Exp Clin Cancer Res. 2004; 23(4):641-650.
Xu et al., "Syndecan-1 expression in human glioma is correlated with advanced tumor progression and poor prognosis," Mol Biol Rep. 2012; 39(9): 8979-8985.
Zellweger et al., "Tissue microarray analysis reveals prognostic significance of syndecan-1 expression in prostate cancer," Prostate. 2003; 55: 20-29.
Rudikoff, S. et al. "Single amino acid substitution altering antigen-binding specificity," Proceedings of The National Academy of Sciences USA (1982) vol. 79, No. 6, pp. 1979-1983.
Gershoni, J. M. et al. "Epitope mapping—The first step in developing epitope-based vaccines," Biodrugs (2007) vol. 21, No. 3, pp. 145-156.
Sun et al., "A Novel Anti-Human Syndecan-1(CD138) Monoclonal Antibody 4B3: Characterization and Application," Cellular & Molecular Immunology (2007) vol. 4, No. 3, pp. 209-214.
Yu, T. et al. "An Immune Based, Anti-CD138 Targeting Antibody for the Treatment of Multiple Myeloma," Blood—American Society of Hematology, (2018) vol. 132 (Supplement 1), pp. 1-3.
Dubel, S.—Editor, "Molecular Engineering I: Humanization," Handbook of Therapeutic Antibodies, Chapter 6, Saldanha, J. W.—Wiley-Vch, Weinheim (2007) Ch. 6, pp. 119-144.
International Search Report and Written Opinion in corresponding International Patent Application No. PCT/US2020/038143 dated Jan. 28, 2021.
Yu et al., "VIS832, a novel CD138-targeting monoclonal antibody, potently induces killing of human multiple myeloma and further synergizes with IMiDs or bortezomib in vitro and in vivo," Blood Cancer Journal (2020) vol. 10, No. 110, pp. 1-13.
Akl et al. "Molecular and clinical profiles of syndecan-1 in solid and hematological cancer for prognosis and precision medicine," Oncotarget. 2015; 6(30):28693-28715.
Al-Otaibi et al., "Syndecan-1 (CD 138) surface expression marks cell type and differentiation in ameloblastoma, keratocystic odontogenic tumor, and dentigerous cyst," J Oral Pathol Med. 2013; 42: 186-193.
Anttonen et al., "Syndecan-1 expression has prognostic significance in head and neck carcinoma," Br J Cancer. 1999; 79: 558-564.
Barbareschi et al., "High syndecan-1 expression in breast carcinoma is related to an aggressive phenotype and to poorer prognosis," Cancer. 2003; 98(3): 474-483.
Bodoor et al., "Evaluation of BCL-6, CD10, CD138 and MUM-1 expression in diffuse large B-cell lymphoma patients: CD138 is a marker of poor prognosis," Asian Pac J Cancer Prev. 2012; 13: 3037-3046.
Cleary et al., "Antibody Distance from the Cell Membrane Regulates Antibody Effector Mechanisms," J Immunol. 2017; 198(10): 3999-4011.
Davies et al. "Distribution and clinical significance of heparan sulfate proteoglycans in ovarian cancer," Clin Cancer Res. 2004; 10: 5178-5186.
Derksen et al., "Cell surface proteoglycan syndecan-1 mediates hepatocyte growth factor binding and promotes Met signaling in multiple myeloma," Blood. 2002; 99(4): 1405-1410.
Fuki et al., "The syndecan family of proteoglycans. Novel receptors mediating internalization of atherogenic lipoproteins in vitro," J Clin Invest. 1997; 100(6):1611-1622.

(56) References Cited

OTHER PUBLICATIONS

Gharbaran et al., "Fibroblast growth factor-2 (FGF2) and syndecan-1 (SDC1) are potential biomarkers for putative circulating CD15+/CD30+ cells in poor outcome Hodgkin lymphoma patients," J Hematol Oncol. 2013; 6:62.

Götte et al., "An expression signature of syndecan-1 (CD138), E-cadherin and c-met is associated with factors of angiogenesis and lymphangiogenesis in ductal breast carcinoma in situ," Breast Cancer Res. 2007; 9(1):R8.

Hasengaowa et al., "Prognostic significance of syndecan-1 expression in human endometrial cancer," Ann Oncol. 2005; 16:1109-1115.

Hashimoto et al. "Association of loss of epithelial syndecan-1 with stage and local metastasis of colorectal adenocarcinomas: an immunohistochemical study of clinically annotated tumors," BMC Cancer. 2008; 8: 185.

Herbener, P. et al. "Functional relevance of in vivo half antibody exchange of an IgG4 therapeutic antibody-drug conjugate," PLOS ONE (2018) vol. 13, No. 4, pp. 1-22.

Hose et al., "Induction of angiogenesis by normal and malignant plasma cells," Blood. 2009; 114(1): 128-143.

Hu et al., "Syndecan-1-dependent suppression of PDK1/Akt/bad signaling by docosahexaenoic acid induces apoptosis in prostate cancer," Neoplasia. 2010; 12(10): 826-836.

Inki et al., "Association between syndecan-1 expression and clinical outcome in squamous cell carcinoma of the head and neck," Br J Cancer. 1994; 70: 319-323.

International Search Report and Written Opinion in International Patent Application No. PCT/US2018/053989 dated Feb. 11, 2019.

Jiang, H. et al. "Transfection of chimeric anti-CD138 gene enhances natural killer cell activation and killing of multiple myeloma cells," Molecular Oncology (2014) vol. 8, No. 2, pp. 297-310.

Jilani et al., "Soluble syndecan-1 (sCD138) as a prognostic factor independent of mutation status in patients with chronic lymphocytic leukemia," Int J Lab Hematol. 2009; 31:97-105.

Joensuu et al., "Soluble syndecan-1 and serum basic fibroblast growth factor are new prognostic factors in lung cancer," Cancer Res. 2002; 62(18):5210-5217.

Khotskaya et al., "Syndecan-1 is required for robust growth, vascularization, and metastasis of myeloma tumors in vivo," J Biol Chem. 2009; 284(38): 26085-26095.

Kusumoto et al., "Clinical significance of syndecan-1 and versican expression in human epithelial ovarian cancer," Oncol Rep. 2010; 23(4): 917-25.

Kyle & Rajkumar, "Criteria for diagnosis, staging, risk stratification and response assessment of multiple myeloma," Leukemia. 2009; 23(1): 3-9.

Ledezma et al., "Altered expression patterns of syndecan-1 and -2 predict biochemical recurrence in prostate cancer," Asian J Androl. 2011; 13: 476-480.

Lendorf et al., "Syndecan-1 and syndecan-4 are independent indicators in breast carcinoma," J Histochem Cytochem. 2011; 59(6): 615-629.

Lim et al., "Syndecan-1 is a potential biomarker for triple-positive breast carcinomas in Asian women with correlation to survival," Singapore Med J. 2014; 55: 468-472.

Maeda et al., "Syndecan-1 expression by stromal fibroblasts promotes breast carcinoma growth in vivo and stimulates tumor angiogenesis," Oncogene. 2006; 25(9): 1408-1412.

Maeda et al., "Induction of syndecan-1 expression in stromal fibroblasts promotes proliferation of human breast cancer cells," Cancer Res. 2004; 64(2):612-621.

Mali et al., "Sequence of human syndecan indicates a novel gene family of integral membrane proteoglycans," J Biol Chem. 1990; 265(12): 6884-6889.

Nguyen et al., "Syndecan-1 overexpression is associated with nonluminal subtypes and poor prognosis in advanced breast cancer," Am J Clin Pathol. 2013; 140: 468-474.

Oh & Park, "Prognostic evaluation of nodal diffuse large B cell lymphoma by immunohistochemical profiles with emphasis on CD138 expression as a poor prognostic factor," J Korean Med Sci. 2006; 21: 397-405.

Orecchia, P. et al. "A novel human anti-syndecan-1 antibody inhibits vascular maturation and tumour growth in melanoma," European Journal of Cancer (2013) vol. 49, No. 8, pp. 2022-2033.

Saunders et al., "Molecular cloning of syndecan, an integral membrane proteoglycan," J Cell Biol. 1989; 108(4): 1547-1556.

Seidel et al., "Serum syndecan-1: a new independent prognostic marker in multiple myeloma," Blood. 2000; 95(2): 388-392.

Shariat et al., "Prognostic value of syndecan-1 expression in patients treated with radical prostatectomy," BJU Int. 2008; 101:232-237.

Stanley et al., "Syndecan-1 expression is induced in the stroma of infiltrating breast carcinoma," Am J Clin Pathol. 1999; 112(3): 377-383.

Stepp et al., "Syndecan-1 and Its Expanding List of Contacts," Adv Wound Care (New Rochelle). 2015; 4(4):235-249.

Sun et al., "Peroxisome proliferator-activated receptor gamma-mediated up-regulation of syndecan-1 by n-3 fatty acids promotes apoptosis of human breast cancer cells," Cancer Res. 2008; 68(8):2912-2919.

Tassone et al., "Cytotoxic activity of the maytansinoid immunoconjugate B-B4-DM1 against CD138+ multiple myeloma cells," Blood (2004) vol. 104(12): 3688-3696.

Teng et al. "Molecular functions of syndecan-1 in disease," Matrix Biol. 2012; 31(1): 3-16.

Vassilakopoulos et al., "Serum levels of soluble syndecan-1 in Hodgkin's lymphoma," Anticancer Res. 2005; 25: 4743-4746.

Vidarsson, G. et al. "IgG Subclasses and Allotypes: From Structure to Effector Functions," Frontiers in Immunology (2014) vol. 5, No. 20, pp. 1-17.

Vihinen et al., "Structural organization and genomic sequence of mouse syndecan-1 gene," J Biol Chem. 1993; 268 (23): 17261-17269.

Wiksten et al., "Epithelial and stromal syndecan-1 expression as predictor of outcome in patients with gastric cancer," Int J Cancer. 2001; 95(1): 1-6.

Mariuzza, R. A. et al. "The structural basis of antigen-antibody recognition," Annual Review of Biophysics and Biophysical Chemistry (1987) vol. 16, pp. 139-159.

International Search Report and Written Opinion in International Patent Application No. PCT/US2022/080397 dated Mar. 3, 2023.

Chen, Chun-Rong et al. "Crystal structure of a TSH receptor monoclonal antibody: insight into Graves' disease pathogenesis." Molecular Endocrinology vol. 29,1 (2015): 99-107.

Kucharska, Iga et al. "Structural ordering of the Plasmodium berghei circumsporozoite protein repeats by inhibitory antibody 3D11."eLife vol. 9 (2020) e59018.

Chen, D. et al. "Development and application of anti-human CD138 monoclonal antibody and recombinant bispecific antibody." Journal of Immunology, vol. 31, No. 1 (2015): 7-11.

\* cited by examiner

SEQUENCE LISTING

```
<160> NUMBER OF SEQ ID NOS: 534

<210> SEQ ID NO 1
<211> LENGTH: 310
<212> TYPE: PRT
<213> ORGANISM: Homo sapiens

<400> SEQUENCE: 1

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
            85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
            165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205
```

```
Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 2
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
    50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255
```

```
Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
            290                 295                 300

Gln Glu Glu Phe Tyr Ala
305                 310

<210> SEQ ID NO 3
<211> LENGTH: 310
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
            35                  40                  45

Ala Gly Ala Leu Gln Asp Ile Thr Leu Ser Gln Gln Thr Pro Ser Thr
        50                  55                  60

Trp Lys Asp Thr Gln Leu Leu Thr Ala Ile Pro Met Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Thr Ala Thr Thr
        130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
            195                 200                 205

Gln Asp Phe Thr Phe Glu Thr Ser Gly Glu Asn Thr Ala Val Val Ala
        210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
            275                 280                 285

Glu Glu Pro Lys Gln Ala Asn Gly Gly Ala Tyr Gln Lys Pro Thr Lys
```

```
                  290                 295                 300
Gln Glu Glu Phe Tyr Ala
305                 310
```

<210> SEQ ID NO 4
<211> LENGTH: 933
<212> TYPE: DNA
<213> ORGANISM: Homo sapiens

<400> SEQUENCE: 4

```
atgaggcgcg cggcgctctg gctctggctg tgcgcgctgg cgctgagcct gcagccggcc     60
ctgccgcaaa ttgtggctac taatttgccc cctgaagatc aagatggctc tggggatgac    120
tctgacaact tctccggctc aggtgcaggt gctttgcaag atatcacctt gtcacagcag    180
accccctcca cttggaagga cacgcagctc ctgacggcta ttcccacgtc tccagaaccc    240
accggcctgg aggctacagc tgcctccacc tccaccctgc cggctggaga ggggcccaag    300
gagggagagg ctgtagtcct gccagaagtg gagcctggcc tcaccgcccg ggagcaggag    360
gccaccccc  gacccaggga gaccacacag ctcccgacca ctcatcaggc ctcaacgacc    420
acagccacca cggcccagga gcccgccacc tcccacccc  acaggacat  gcagcctggc    480
caccatgaga cctcaacccc tgcaggaccc agccaagctg accttcacac tccccacaca    540
gaggatggag gtccttctgc caccgagagg gctgctgagg atggagcctc cagtcagctc    600
ccagcagcag agggctctgg ggagcaggac ttcacctttg aaacctcggg ggagaatacg    660
gctgtagtgg ccgtggagcc tgaccgccgg aaccagtccc cagtggatca gggggccacg    720
ggggcctcac agggcctcct ggacaggaaa gaggtgctgg gaggggtcat tgccggaggc    780
ctcgtggggc tcatctttgc tgtgtgcctg gtgggtttca tgctgtaccg catgaagaag    840
aaggacgaag gcagctactc cttggaggag ccgaaacaag ccaacggcgg ggcctaccag    900
aagcccacca acaggagga  attctatgcc tga                                 933
```

<210> SEQ ID NO 5
<211> LENGTH: 933
<212> TYPE: DNA
<213> ORGANISM: Homo sapiens

<400> SEQUENCE: 5

```
atgaggcgcg cggcgctctg gctctggctg tgcgcgctgg cgctgagcct gcagccggcc     60
ctgccgcaaa ttgtggctac taatttgccc cctgaagatc aagatggctc tggggatgac    120
tctgacaact tctccggctc aggtgcaggt gctttgcaag atatcacctt gtcacagcag    180
accccctcca cttggaagga cacgcagctc ctgacggcta ttcccacgtc tccagaaccc    240
accggcctgg aggctacagc tgcctccacc tccaccctgc cggctggaga ggggcccaag    300
gagggagagg ctgtagtcct gccagaagtg gagcctggcc tcaccgcccg ggagcaggag    360
gccaccccc  gacccaggga gaccacacag ctcccgacca ctcatcaggc ctcaacgacc    420
acagccacca cggcccagga gcccgccacc tcccacccc  acaggacat  gcagcctggc    480
caccatgaga cctcaacccc tgcaggaccc agccaagctg accttcacac tccccacaca    540
gaggatggag gtccttctgc caccgagagg gctgctgagg atggagcctc cagtcagctc    600
ccagcagcag agggctctgg ggagcaggac ttcacctttg aaacctcggg ggagaatacg    660
gctgtagtgg ccgtggagcc tgaccgccgg aaccagtccc cagtggatca gggggccacg    720
ggggcctcac agggcctcct ggacaggaaa gaggtgctgg gaggggtcat tgccggaggc    780
```

```
ctcgtggggc tcatctttgc tgtgtgcctg gtgggtttca tgctgtaccg catgaagaag      840
aaggacgaag gcagctactc cttggaggag ccgaaacaag ccaacggcgg ggcctaccag      900
aagcccacca acaggagga attctatgcc tga                                    933
```

<210> SEQ ID NO 6
<211> LENGTH: 311
<212> TYPE: PRT
<213> ORGANISM: Mus musculus

<400> SEQUENCE: 6

```
Met Arg Arg Ala Ala Leu Trp Leu Trp Leu Cys Ala Leu Ala Leu Arg
1               5                   10                  15

Leu Gln Pro Ala Leu Pro Gln Ile Val Ala Val Asn Val Pro Pro Glu
            20                  25                  30

Asp Gln Asp Gly Ser Gly Asp Asp Ser Asp Asn Phe Ser Gly Ser Gly
        35                  40                  45

Thr Gly Ala Leu Pro Asp Thr Leu Ser Arg Gln Thr Pro Ser Thr Trp
    50                  55                  60

Lys Asp Val Trp Leu Leu Thr Ala Thr Pro Thr Ala Pro Glu Pro Thr
65                  70                  75                  80

Ser Ser Asn Thr Glu Thr Ala Phe Thr Ser Val Leu Pro Ala Gly Glu
                85                  90                  95

Lys Pro Glu Glu Gly Glu Pro Val Leu His Val Glu Ala Glu Pro Gly
            100                 105                 110

Phe Thr Ala Arg Asp Lys Glu Lys Glu Val Thr Thr Arg Pro Arg Glu
        115                 120                 125

Thr Val Gln Leu Pro Ile Thr Gln Arg Ala Ser Thr Val Arg Val Thr
    130                 135                 140

Thr Ala Gln Ala Ala Val Thr Ser His Pro His Gly Gly Met Gln Pro
145                 150                 155                 160

Gly Leu His Glu Thr Ser Ala Pro Thr Ala Pro Gly Gln Pro Asp His
                165                 170                 175

Gln Pro Pro Arg Val Glu Gly Gly Thr Ser Val Ile Lys Glu Val
            180                 185                 190

Val Glu Asp Gly Thr Ala Asn Gln Leu Pro Ala Gly Glu Gly Ser Gly
        195                 200                 205

Glu Gln Asp Phe Thr Phe Glu Thr Ser Gly Glu Asn Thr Ala Val Ala
    210                 215                 220

Ala Val Glu Pro Gly Leu Arg Asn Gln Pro Val Asp Glu Gly Ala
225                 230                 235                 240

Thr Gly Ala Ser Gln Ser Leu Leu Asp Arg Lys Glu Val Leu Gly Gly
                245                 250                 255

Val Ile Ala Gly Gly Leu Val Gly Leu Ile Phe Ala Val Cys Leu Val
            260                 265                 270

Ala Phe Met Leu Tyr Arg Met Lys Lys Lys Asp Glu Gly Ser Tyr Ser
        275                 280                 285

Leu Glu Glu Pro Lys Gln Ala Asn Gly Gly Ala Tyr Gln Lys Pro Thr
    290                 295                 300

Lys Gln Glu Glu Phe Tyr Ala
305                 310
```

<210> SEQ ID NO 7
<211> LENGTH: 936
<212> TYPE: DNA
<213> ORGANISM: Mus musculus

<400> SEQUENCE: 7

```
atgagacgcg cggcgctctg gctctggctc tgcgcgctgg cgctgcgcct gcagcctgcc      60
ctcccgcaaa ttgtggctgt aaatgttcct cctgaagatc aggatggctc tggggatgac     120
tctgacaact tctctggctc tggcacaggt gctttgccag atactttgtc acggcagaca     180
ccttccactt ggaaggacgt gtggctgttg acagccacgc ccacagctcc agagcccacc     240
agcagcaaca ccgagactgc ttttacctct gtcctgccag ccggagagaa gcccgaggag     300
ggagagcctg tgctccatgt agaagcagag cctggcttca ctgctcggga caaggaaaag     360
gaggtcacca ccaggcccag ggagaccgtg cagctcccca tcacccaacg ggcctcaaca     420
gtcagagtca ccacagccca ggcagctgtc acatctcatc cgcacgggg catgcaacct      480
ggcctccatg agacctcggc tcccacagca cctggtcaac ctgaccatca gcctccacgt     540
gtggagggtg gcggcacttc tgtcatcaaa gaggttgtcg aggatggaac tgccaatcag     600
cttcccgcag gagagggctc tggagaacaa gacttcacct ttgaaacatc tggggagaac     660
acagctgtgg ctgccgtaga gcccggcctg cggaatcagc cccggtgga cgaaggagcc      720
acaggtgctt ctcagagcct tttggacagg aaggaagtgc tggaggtgt cattgccgga      780
ggcctagtgg gcctcatctt tgctgtgtgc ctggtggctt tcatgctgta ccggatgaag     840
aagaaggacg aaggcagcta ctccttggag gagcccaaac aagccaatgg cggtgcctac     900
cagaaaccca ccaagcagga ggagttctac gcctga                               936
```

<210> SEQ ID NO 8
<211> LENGTH: 39
<212> TYPE: PRT
<213> ORGANISM: Homo sapiens

<400> SEQUENCE: 8

```
Gln Ile Val Ala Thr Asn Leu Pro Pro Glu Asp Gln Asp Gly Ser Gly
1               5                   10                  15
Asp Asp Ser Asp Asn Phe Ser Gly Ser Gly Ala Gly Ala Leu Gln Asp
            20                  25                  30
Ile Thr Leu Ser Gln Gln Thr
        35
```

<210> SEQ ID NO 9
<211> LENGTH: 45
<212> TYPE: PRT
<213> ORGANISM: Homo sapiens

<400> SEQUENCE: 9

```
Ala Leu Gln Asp Ile Thr Leu Ser Gln Gln Thr Pro Ser Thr Trp Lys
1               5                   10                  15
Asp Thr Gln Leu Leu Thr Ala Ile Pro Thr Ser Pro Glu Pro Thr Gly
            20                  25                  30
Leu Glu Ala Thr Ala Ala Ser Thr Ser Thr Leu Pro Ala
        35                  40                  45
```

<210> SEQ ID NO 10
<211> LENGTH: 34
<212> TYPE: PRT
<213> ORGANISM: Homo sapiens

<400> SEQUENCE: 10

```
Ala Ser Thr Ser Thr Leu Pro Ala Gly Glu Gly Pro Lys Glu Gly Glu
1               5                   10                  15
```

Ala Val Val Leu Pro Glu Val Glu Pro Gly Leu Thr Ala Arg Glu Gln
            20                  25                  30

Glu Ala

<210> SEQ ID NO 11
<211> LENGTH: 15
<212> TYPE: PRT
<213> ORGANISM: Homo sapiens

<400> SEQUENCE: 11

Ala Ser Thr Ser Thr Leu Pro Ala Gly Glu Gly Pro Lys Glu Gly
1               5                   10                  15

<210> SEQ ID NO 12
<211> LENGTH: 40
<212> TYPE: PRT
<213> ORGANISM: Homo sapiens

<400> SEQUENCE: 12

Glu Pro Gly Leu Thr Ala Arg Glu Gln Glu Ala Thr Pro Arg Pro Arg
1               5                   10                  15

Glu Thr Thr Gln Leu Pro Thr Thr His Gln Ala Ser Thr Thr Thr Ala
            20                  25                  30

Thr Thr Ala Gln Glu Pro Ala Thr
        35                  40

<210> SEQ ID NO 13
<211> LENGTH: 35
<212> TYPE: PRT
<213> ORGANISM: Homo sapiens

<400> SEQUENCE: 13

Gln Glu Pro Ala Thr Ser His Pro His Arg Asp Met Gln Pro Gly His
1               5                   10                  15

His Glu Thr Ser Thr Pro Ala Gly Pro Ser Gln Ala Asp Leu His Thr
            20                  25                  30

Pro His Thr
        35

<210> SEQ ID NO 14
<211> LENGTH: 75
<212> TYPE: PRT
<213> ORGANISM: Homo sapiens

<400> SEQUENCE: 14

His Thr Pro His Thr Glu Asp Gly Gly Pro Ser Ala Thr Glu Arg Ala
1               5                   10                  15

Ala Glu Asp Gly Ala Ser Ser Gln Leu Pro Ala Ala Glu Gly Ser Gly
            20                  25                  30

Glu Gln Asp Phe Thr Phe Glu Thr Ser Gly Glu Asn Thr Ala Val Val
        35                  40                  45

Ala Val Glu Pro Asp Arg Arg Asn Gln Ser Pro Val Asp Gln Gly Ala
    50                  55                  60

Thr Gly Ala Ser Gln Gly Leu Leu Asp Arg Lys
65                  70                  75

<210> SEQ ID NO 15
<211> LENGTH: 39
<212> TYPE: PRT
<213> ORGANISM: Homo sapiens

<400> SEQUENCE: 15

His Thr Pro His Thr Glu Asp Gly Gly Pro Ser Ala Thr Glu Arg Ala
1               5                   10                  15

Ala Glu Asp Gly Ala Ser Ser Gln Leu Pro Ala Ala Glu Gly Ser Gly
            20                  25                  30

Glu Gln Asp Phe Thr Phe Glu
        35

<210> SEQ ID NO 16
<211> LENGTH: 41
<212> TYPE: PRT
<213> ORGANISM: Homo sapiens

<400> SEQUENCE: 16

Asp Phe Thr Phe Glu Thr Ser Gly Glu Asn Thr Ala Val Val Ala Val
1               5                   10                  15

Glu Pro Asp Arg Arg Asn Gln Ser Pro Val Asp Gln Gly Ala Thr Gly
            20                  25                  30

Ala Ser Gln Gly Leu Leu Asp Arg Lys
        35                  40

<210> SEQ ID NO 17
<211> LENGTH: 26
<212> TYPE: PRT
<213> ORGANISM: Homo sapiens

<400> SEQUENCE: 17

Thr Ala Val Val Ala Val Glu Pro Asp Arg Arg Asn Gln Ser Pro Val
1               5                   10                  15

Asp Gln Gly Ala Thr Gly Ala Ser Gln Gly
            20                  25

<210> SEQ ID NO 18
<211> LENGTH: 4
<212> TYPE: PRT
<213> ORGANISM: Homo sapiens

<400> SEQUENCE: 18

Asp Phe Thr Phe
1

<210> SEQ ID NO 19
<211> LENGTH: 4
<212> TYPE: PRT
<213> ORGANISM: Homo sapiens

<400> SEQUENCE: 19

Phe Thr Phe Glu
1

<210> SEQ ID NO 20
<211> LENGTH: 4
<212> TYPE: PRT
<213> ORGANISM: Homo sapiens

<400> SEQUENCE: 20

Thr Phe Glu Thr
1

<210> SEQ ID NO 21
<211> LENGTH: 4

```
<212> TYPE: PRT
<213> ORGANISM: Homo sapiens

<400> SEQUENCE: 21

Phe Glu Thr Ser
1

<210> SEQ ID NO 22
<211> LENGTH: 4
<212> TYPE: PRT
<213> ORGANISM: Homo sapiens

<400> SEQUENCE: 22

Glu Thr Ser Gly
1

<210> SEQ ID NO 23
<211> LENGTH: 4
<212> TYPE: PRT
<213> ORGANISM: Homo sapiens

<400> SEQUENCE: 23

Thr Ser Gly Glu
1

<210> SEQ ID NO 24
<211> LENGTH: 4
<212> TYPE: PRT
<213> ORGANISM: Homo sapiens

<400> SEQUENCE: 24

Ser Gly Glu Asn
1

<210> SEQ ID NO 25
<211> LENGTH: 4
<212> TYPE: PRT
<213> ORGANISM: Homo sapiens

<400> SEQUENCE: 25

Gly Glu Asn Thr
1

<210> SEQ ID NO 26
<211> LENGTH: 4
<212> TYPE: PRT
<213> ORGANISM: Homo sapiens

<400> SEQUENCE: 26

Glu Asn Thr Ala
1

<210> SEQ ID NO 27
<211> LENGTH: 4
<212> TYPE: PRT
<213> ORGANISM: Homo sapiens

<400> SEQUENCE: 27

Asn Thr Ala Val
1

<210> SEQ ID NO 28
<211> LENGTH: 4
<212> TYPE: PRT
<213> ORGANISM: Homo sapiens
```

```
<400> SEQUENCE: 28

Thr Ala Val Val
1

<210> SEQ ID NO 29
<211> LENGTH: 4
<212> TYPE: PRT
<213> ORGANISM: Homo sapiens

<400> SEQUENCE: 29

Ala Val Val Ala
1

<210> SEQ ID NO 30
<211> LENGTH: 4
<212> TYPE: PRT
<213> ORGANISM: Homo sapiens

<400> SEQUENCE: 30

Val Val Ala Val
1

<210> SEQ ID NO 31
<211> LENGTH: 4
<212> TYPE: PRT
<213> ORGANISM: Homo sapiens

<400> SEQUENCE: 31

Val Ala Val Glu
1

<210> SEQ ID NO 32
<211> LENGTH: 4
<212> TYPE: PRT
<213> ORGANISM: Homo sapiens

<400> SEQUENCE: 32

Ala Val Glu Pro
1

<210> SEQ ID NO 33
<211> LENGTH: 4
<212> TYPE: PRT
<213> ORGANISM: Homo sapiens

<400> SEQUENCE: 33

Val Glu Pro Asp
1

<210> SEQ ID NO 34
<211> LENGTH: 4
<212> TYPE: PRT
<213> ORGANISM: Homo sapiens

<400> SEQUENCE: 34

Glu Pro Asp Arg
1

<210> SEQ ID NO 35
<211> LENGTH: 4
<212> TYPE: PRT
<213> ORGANISM: Homo sapiens

<400> SEQUENCE: 35
```

```
Pro Asp Arg Arg
1

<210> SEQ ID NO 36
<211> LENGTH: 4
<212> TYPE: PRT
<213> ORGANISM: Homo sapiens

<400> SEQUENCE: 36

Asp Arg Arg Asn
1

<210> SEQ ID NO 37
<211> LENGTH: 4
<212> TYPE: PRT
<213> ORGANISM: Homo sapiens

<400> SEQUENCE: 37

Arg Arg Asn Gln
1

<210> SEQ ID NO 38
<211> LENGTH: 4
<212> TYPE: PRT
<213> ORGANISM: Homo sapiens

<400> SEQUENCE: 38

Arg Asn Gln Ser
1

<210> SEQ ID NO 39
<211> LENGTH: 4
<212> TYPE: PRT
<213> ORGANISM: Homo sapiens

<400> SEQUENCE: 39

Asn Gln Ser Pro
1

<210> SEQ ID NO 40
<211> LENGTH: 4
<212> TYPE: PRT
<213> ORGANISM: Homo sapiens

<400> SEQUENCE: 40

Gln Ser Pro Val
1

<210> SEQ ID NO 41
<211> LENGTH: 4
<212> TYPE: PRT
<213> ORGANISM: Homo sapiens

<400> SEQUENCE: 41

Ser Pro Val Asp
1

<210> SEQ ID NO 42
<211> LENGTH: 4
<212> TYPE: PRT
<213> ORGANISM: Homo sapiens

<400> SEQUENCE: 42

Pro Val Asp Gln
```

```
<210> SEQ ID NO 43
<211> LENGTH: 4
<212> TYPE: PRT
<213> ORGANISM: Homo sapiens

<400> SEQUENCE: 43

Val Asp Gln Gly
1

<210> SEQ ID NO 44
<211> LENGTH: 4
<212> TYPE: PRT
<213> ORGANISM: Homo sapiens

<400> SEQUENCE: 44

Asp Gln Gly Ala
1

<210> SEQ ID NO 45
<211> LENGTH: 4
<212> TYPE: PRT
<213> ORGANISM: Homo sapiens

<400> SEQUENCE: 45

Gln Gly Ala Thr
1

<210> SEQ ID NO 46
<211> LENGTH: 4
<212> TYPE: PRT
<213> ORGANISM: Homo sapiens

<400> SEQUENCE: 46

Gly Ala Thr Gly
1

<210> SEQ ID NO 47
<211> LENGTH: 4
<212> TYPE: PRT
<213> ORGANISM: Homo sapiens

<400> SEQUENCE: 47

Ala Thr Gly Ala
1

<210> SEQ ID NO 48
<211> LENGTH: 4
<212> TYPE: PRT
<213> ORGANISM: Homo sapiens

<400> SEQUENCE: 48

Thr Gly Ala Ser
1

<210> SEQ ID NO 49
<211> LENGTH: 4
<212> TYPE: PRT
<213> ORGANISM: Homo sapiens

<400> SEQUENCE: 49

Gly Ala Ser Gln
1
```

```
<210> SEQ ID NO 50
<211> LENGTH: 4
<212> TYPE: PRT
<213> ORGANISM: Homo sapiens

<400> SEQUENCE: 50

Ala Ser Gln Gly
1

<210> SEQ ID NO 51
<211> LENGTH: 4
<212> TYPE: PRT
<213> ORGANISM: Homo sapiens

<400> SEQUENCE: 51

Ser Gln Gly Leu
1

<210> SEQ ID NO 52
<211> LENGTH: 4
<212> TYPE: PRT
<213> ORGANISM: Homo sapiens

<400> SEQUENCE: 52

Gln Gly Leu Leu
1

<210> SEQ ID NO 53
<211> LENGTH: 4
<212> TYPE: PRT
<213> ORGANISM: Homo sapiens

<400> SEQUENCE: 53

Gly Leu Leu Asp
1

<210> SEQ ID NO 54
<211> LENGTH: 4
<212> TYPE: PRT
<213> ORGANISM: Homo sapiens

<400> SEQUENCE: 54

Leu Leu Asp Arg
1

<210> SEQ ID NO 55
<211> LENGTH: 4
<212> TYPE: PRT
<213> ORGANISM: Homo sapiens

<400> SEQUENCE: 55

Leu Asp Arg Lys
1

<210> SEQ ID NO 56
<211> LENGTH: 5
<212> TYPE: PRT
<213> ORGANISM: Homo sapiens

<400> SEQUENCE: 56

Asp Phe Thr Phe Glu
1               5

<210> SEQ ID NO 57
```

```
<211> LENGTH: 5
<212> TYPE: PRT
<213> ORGANISM: Homo sapiens

<400> SEQUENCE: 57

Phe Thr Phe Glu Thr
1               5

<210> SEQ ID NO 58
<211> LENGTH: 5
<212> TYPE: PRT
<213> ORGANISM: Homo sapiens

<400> SEQUENCE: 58

Thr Phe Glu Thr Ser
1               5

<210> SEQ ID NO 59
<211> LENGTH: 5
<212> TYPE: PRT
<213> ORGANISM: Homo sapiens

<400> SEQUENCE: 59

Phe Glu Thr Ser Gly
1               5

<210> SEQ ID NO 60
<211> LENGTH: 5
<212> TYPE: PRT
<213> ORGANISM: Homo sapiens

<400> SEQUENCE: 60

Glu Thr Ser Gly Glu
1               5

<210> SEQ ID NO 61
<211> LENGTH: 5
<212> TYPE: PRT
<213> ORGANISM: Homo sapiens

<400> SEQUENCE: 61

Thr Ser Gly Glu Asn
1               5

<210> SEQ ID NO 62
<211> LENGTH: 5
<212> TYPE: PRT
<213> ORGANISM: Homo sapiens

<400> SEQUENCE: 62

Ser Gly Glu Asn Thr
1               5

<210> SEQ ID NO 63
<211> LENGTH: 5
<212> TYPE: PRT
<213> ORGANISM: Homo sapiens

<400> SEQUENCE: 63

Gly Glu Asn Thr Ala
1               5

<210> SEQ ID NO 64
<211> LENGTH: 5
<212> TYPE: PRT
```

<213> ORGANISM: Homo sapiens

<400> SEQUENCE: 64

Glu Asn Thr Ala Val
1               5

<210> SEQ ID NO 65
<211> LENGTH: 5
<212> TYPE: PRT
<213> ORGANISM: Homo sapiens

<400> SEQUENCE: 65

Asn Thr Ala Val Val
1               5

<210> SEQ ID NO 66
<211> LENGTH: 5
<212> TYPE: PRT
<213> ORGANISM: Homo sapiens

<400> SEQUENCE: 66

Thr Ala Val Val Ala
1               5

<210> SEQ ID NO 67
<211> LENGTH: 5
<212> TYPE: PRT
<213> ORGANISM: Homo sapiens

<400> SEQUENCE: 67

Ala Val Val Ala Val
1               5

<210> SEQ ID NO 68
<211> LENGTH: 5
<212> TYPE: PRT
<213> ORGANISM: Homo sapiens

<400> SEQUENCE: 68

Val Val Ala Val Glu
1               5

<210> SEQ ID NO 69
<211> LENGTH: 5
<212> TYPE: PRT
<213> ORGANISM: Homo sapiens

<400> SEQUENCE: 69

Val Ala Val Glu Pro
1               5

<210> SEQ ID NO 70
<211> LENGTH: 5
<212> TYPE: PRT
<213> ORGANISM: Homo sapiens

<400> SEQUENCE: 70

Ala Val Glu Pro Asp
1               5

<210> SEQ ID NO 71
<211> LENGTH: 5
<212> TYPE: PRT
<213> ORGANISM: Homo sapiens

<400> SEQUENCE: 71

Val Glu Pro Asp Arg
1               5

<210> SEQ ID NO 72
<211> LENGTH: 5
<212> TYPE: PRT
<213> ORGANISM: Homo sapiens

<400> SEQUENCE: 72

Glu Pro Asp Arg Arg
1               5

<210> SEQ ID NO 73
<211> LENGTH: 5
<212> TYPE: PRT
<213> ORGANISM: Homo sapiens

<400> SEQUENCE: 73

Pro Asp Arg Arg Asn
1               5

<210> SEQ ID NO 74
<211> LENGTH: 5
<212> TYPE: PRT
<213> ORGANISM: Homo sapiens

<400> SEQUENCE: 74

Asp Arg Arg Asn Gln
1               5

<210> SEQ ID NO 75
<211> LENGTH: 5
<212> TYPE: PRT
<213> ORGANISM: Homo sapiens

<400> SEQUENCE: 75

Arg Arg Asn Gln Ser
1               5

<210> SEQ ID NO 76
<211> LENGTH: 5
<212> TYPE: PRT
<213> ORGANISM: Homo sapiens

<400> SEQUENCE: 76

Arg Asn Gln Ser Pro
1               5

<210> SEQ ID NO 77
<211> LENGTH: 5
<212> TYPE: PRT
<213> ORGANISM: Homo sapiens

<400> SEQUENCE: 77

Asn Gln Ser Pro Val
1               5

<210> SEQ ID NO 78
<211> LENGTH: 5
<212> TYPE: PRT
<213> ORGANISM: Homo sapiens

<400> SEQUENCE: 78

Gln Ser Pro Val Asp
1               5

<210> SEQ ID NO 79
<211> LENGTH: 5
<212> TYPE: PRT
<213> ORGANISM: Homo sapiens

<400> SEQUENCE: 79

Ser Pro Val Asp Gln
1               5

<210> SEQ ID NO 80
<211> LENGTH: 5
<212> TYPE: PRT
<213> ORGANISM: Homo sapiens

<400> SEQUENCE: 80

Pro Val Asp Gln Gly
1               5

<210> SEQ ID NO 81
<211> LENGTH: 5
<212> TYPE: PRT
<213> ORGANISM: Homo sapiens

<400> SEQUENCE: 81

Val Asp Gln Gly Ala
1               5

<210> SEQ ID NO 82
<211> LENGTH: 5
<212> TYPE: PRT
<213> ORGANISM: Homo sapiens

<400> SEQUENCE: 82

Asp Gln Gly Ala Thr
1               5

<210> SEQ ID NO 83
<211> LENGTH: 5
<212> TYPE: PRT
<213> ORGANISM: Homo sapiens

<400> SEQUENCE: 83

Gln Gly Ala Thr Gly
1               5

<210> SEQ ID NO 84
<211> LENGTH: 5
<212> TYPE: PRT
<213> ORGANISM: Homo sapiens

<400> SEQUENCE: 84

Gly Ala Thr Gly Ala
1               5

<210> SEQ ID NO 85
<211> LENGTH: 5
<212> TYPE: PRT
<213> ORGANISM: Homo sapiens

<400> SEQUENCE: 85

Ala Thr Gly Ala Ser
1               5

```
<210> SEQ ID NO 86
<211> LENGTH: 5
<212> TYPE: PRT
<213> ORGANISM: Homo sapiens

<400> SEQUENCE: 86

Thr Gly Ala Ser Gln
1               5

<210> SEQ ID NO 87
<211> LENGTH: 5
<212> TYPE: PRT
<213> ORGANISM: Homo sapiens

<400> SEQUENCE: 87

Gly Ala Ser Gln Gly
1               5

<210> SEQ ID NO 88
<211> LENGTH: 5
<212> TYPE: PRT
<213> ORGANISM: Homo sapiens

<400> SEQUENCE: 88

Ala Ser Gln Gly Leu
1               5

<210> SEQ ID NO 89
<211> LENGTH: 5
<212> TYPE: PRT
<213> ORGANISM: Homo sapiens

<400> SEQUENCE: 89

Ser Gln Gly Leu Leu
1               5

<210> SEQ ID NO 90
<211> LENGTH: 5
<212> TYPE: PRT
<213> ORGANISM: Homo sapiens

<400> SEQUENCE: 90

Gln Gly Leu Leu Asp
1               5

<210> SEQ ID NO 91
<211> LENGTH: 5
<212> TYPE: PRT
<213> ORGANISM: Homo sapiens

<400> SEQUENCE: 91

Gly Leu Leu Asp Arg
1               5

<210> SEQ ID NO 92
<211> LENGTH: 5
<212> TYPE: PRT
<213> ORGANISM: Homo sapiens

<400> SEQUENCE: 92

Leu Leu Asp Arg Lys
1               5
```

-continued

```
<210> SEQ ID NO 93
<211> LENGTH: 6
<212> TYPE: PRT
<213> ORGANISM: Homo sapiens

<400> SEQUENCE: 93

Asp Phe Thr Phe Glu Thr
1               5

<210> SEQ ID NO 94
<211> LENGTH: 6
<212> TYPE: PRT
<213> ORGANISM: Homo sapiens

<400> SEQUENCE: 94

Phe Thr Phe Glu Thr Ser
1               5

<210> SEQ ID NO 95
<211> LENGTH: 6
<212> TYPE: PRT
<213> ORGANISM: Homo sapiens

<400> SEQUENCE: 95

Thr Phe Glu Thr Ser Gly
1               5

<210> SEQ ID NO 96
<211> LENGTH: 6
<212> TYPE: PRT
<213> ORGANISM: Homo sapiens

<400> SEQUENCE: 96

Phe Glu Thr Ser Gly Glu
1               5

<210> SEQ ID NO 97
<211> LENGTH: 6
<212> TYPE: PRT
<213> ORGANISM: Homo sapiens

<400> SEQUENCE: 97

Glu Thr Ser Gly Glu Asn
1               5

<210> SEQ ID NO 98
<211> LENGTH: 6
<212> TYPE: PRT
<213> ORGANISM: Homo sapiens

<400> SEQUENCE: 98

Thr Ser Gly Glu Asn Thr
1               5

<210> SEQ ID NO 99
<211> LENGTH: 6
<212> TYPE: PRT
<213> ORGANISM: Homo sapiens

<400> SEQUENCE: 99

Ser Gly Glu Asn Thr Ala
1               5

<210> SEQ ID NO 100
<211> LENGTH: 6
```

```
<212> TYPE: PRT
<213> ORGANISM: Homo sapiens

<400> SEQUENCE: 100

Gly Glu Asn Thr Ala Val
1               5

<210> SEQ ID NO 101
<211> LENGTH: 6
<212> TYPE: PRT
<213> ORGANISM: Homo sapiens

<400> SEQUENCE: 101

Glu Asn Thr Ala Val Val
1               5

<210> SEQ ID NO 102
<211> LENGTH: 6
<212> TYPE: PRT
<213> ORGANISM: Homo sapiens

<400> SEQUENCE: 102

Asn Thr Ala Val Val Ala
1               5

<210> SEQ ID NO 103
<211> LENGTH: 6
<212> TYPE: PRT
<213> ORGANISM: Homo sapiens

<400> SEQUENCE: 103

Thr Ala Val Val Ala Val
1               5

<210> SEQ ID NO 104
<211> LENGTH: 6
<212> TYPE: PRT
<213> ORGANISM: Homo sapiens

<400> SEQUENCE: 104

Ala Val Val Ala Val Glu
1               5

<210> SEQ ID NO 105
<211> LENGTH: 6
<212> TYPE: PRT
<213> ORGANISM: Homo sapiens

<400> SEQUENCE: 105

Val Val Ala Val Glu Pro
1               5

<210> SEQ ID NO 106
<211> LENGTH: 6
<212> TYPE: PRT
<213> ORGANISM: Homo sapiens

<400> SEQUENCE: 106

Val Ala Val Glu Pro Asp
1               5

<210> SEQ ID NO 107
<211> LENGTH: 6
<212> TYPE: PRT
<213> ORGANISM: Homo sapiens
```

<400> SEQUENCE: 107

Ala Val Glu Pro Asp Arg
1               5

<210> SEQ ID NO 108
<211> LENGTH: 6
<212> TYPE: PRT
<213> ORGANISM: Homo sapiens

<400> SEQUENCE: 108

Val Glu Pro Asp Arg Arg
1               5

<210> SEQ ID NO 109
<211> LENGTH: 6
<212> TYPE: PRT
<213> ORGANISM: Homo sapiens

<400> SEQUENCE: 109

Glu Pro Asp Arg Arg Asn
1               5

<210> SEQ ID NO 110
<211> LENGTH: 6
<212> TYPE: PRT
<213> ORGANISM: Homo sapiens

<400> SEQUENCE: 110

Pro Asp Arg Arg Asn Gln
1               5

<210> SEQ ID NO 111
<211> LENGTH: 6
<212> TYPE: PRT
<213> ORGANISM: Homo sapiens

<400> SEQUENCE: 111

Asp Arg Arg Asn Gln Ser
1               5

<210> SEQ ID NO 112
<211> LENGTH: 6
<212> TYPE: PRT
<213> ORGANISM: Homo sapiens

<400> SEQUENCE: 112

Arg Arg Asn Gln Ser Pro
1               5

<210> SEQ ID NO 113
<211> LENGTH: 6
<212> TYPE: PRT
<213> ORGANISM: Homo sapiens

<400> SEQUENCE: 113

Arg Asn Gln Ser Pro Val
1               5

<210> SEQ ID NO 114
<211> LENGTH: 6
<212> TYPE: PRT
<213> ORGANISM: Homo sapiens

<400> SEQUENCE: 114

```
Asn Gln Ser Pro Val Asp
1               5

<210> SEQ ID NO 115
<211> LENGTH: 6
<212> TYPE: PRT
<213> ORGANISM: Homo sapiens

<400> SEQUENCE: 115

Gln Ser Pro Val Asp Gln
1               5

<210> SEQ ID NO 116
<211> LENGTH: 6
<212> TYPE: PRT
<213> ORGANISM: Homo sapiens

<400> SEQUENCE: 116

Ser Pro Val Asp Gln Gly
1               5

<210> SEQ ID NO 117
<211> LENGTH: 6
<212> TYPE: PRT
<213> ORGANISM: Homo sapiens

<400> SEQUENCE: 117

Pro Val Asp Gln Gly Ala
1               5

<210> SEQ ID NO 118
<211> LENGTH: 6
<212> TYPE: PRT
<213> ORGANISM: Homo sapiens

<400> SEQUENCE: 118

Val Asp Gln Gly Ala Thr
1               5

<210> SEQ ID NO 119
<211> LENGTH: 6
<212> TYPE: PRT
<213> ORGANISM: Homo sapiens

<400> SEQUENCE: 119

Asp Gln Gly Ala Thr Gly
1               5

<210> SEQ ID NO 120
<211> LENGTH: 6
<212> TYPE: PRT
<213> ORGANISM: Homo sapiens

<400> SEQUENCE: 120

Gln Gly Ala Thr Gly Ala
1               5

<210> SEQ ID NO 121
<211> LENGTH: 6
<212> TYPE: PRT
<213> ORGANISM: Homo sapiens

<400> SEQUENCE: 121

Gly Ala Thr Gly Ala Ser
```

```
<210> SEQ ID NO 122
<211> LENGTH: 6
<212> TYPE: PRT
<213> ORGANISM: Homo sapiens

<400> SEQUENCE: 122

Ala Thr Gly Ala Ser Gln
1               5

<210> SEQ ID NO 123
<211> LENGTH: 6
<212> TYPE: PRT
<213> ORGANISM: Homo sapiens

<400> SEQUENCE: 123

Thr Gly Ala Ser Gln Gly
1               5

<210> SEQ ID NO 124
<211> LENGTH: 6
<212> TYPE: PRT
<213> ORGANISM: Homo sapiens

<400> SEQUENCE: 124

Gly Ala Ser Gln Gly Leu
1               5

<210> SEQ ID NO 125
<211> LENGTH: 6
<212> TYPE: PRT
<213> ORGANISM: Homo sapiens

<400> SEQUENCE: 125

Ala Ser Gln Gly Leu Leu
1               5

<210> SEQ ID NO 126
<211> LENGTH: 6
<212> TYPE: PRT
<213> ORGANISM: Homo sapiens

<400> SEQUENCE: 126

Ser Gln Gly Leu Leu Asp
1               5

<210> SEQ ID NO 127
<211> LENGTH: 6
<212> TYPE: PRT
<213> ORGANISM: Homo sapiens

<400> SEQUENCE: 127

Gln Gly Leu Leu Asp Arg
1               5

<210> SEQ ID NO 128
<211> LENGTH: 6
<212> TYPE: PRT
<213> ORGANISM: Homo sapiens

<400> SEQUENCE: 128

Gly Leu Leu Asp Arg Lys
1               5
```

```
<210> SEQ ID NO 129
<211> LENGTH: 4
<212> TYPE: PRT
<213> ORGANISM: Homo sapiens

<400> SEQUENCE: 129

His Thr Pro His
1

<210> SEQ ID NO 130
<211> LENGTH: 4
<212> TYPE: PRT
<213> ORGANISM: Homo sapiens

<400> SEQUENCE: 130

Thr Pro His Thr
1

<210> SEQ ID NO 131
<211> LENGTH: 4
<212> TYPE: PRT
<213> ORGANISM: Homo sapiens

<400> SEQUENCE: 131

Pro His Thr Glu
1

<210> SEQ ID NO 132
<211> LENGTH: 4
<212> TYPE: PRT
<213> ORGANISM: Homo sapiens

<400> SEQUENCE: 132

His Thr Glu Asp
1

<210> SEQ ID NO 133
<211> LENGTH: 4
<212> TYPE: PRT
<213> ORGANISM: Homo sapiens

<400> SEQUENCE: 133

Thr Glu Asp Gly
1

<210> SEQ ID NO 134
<211> LENGTH: 4
<212> TYPE: PRT
<213> ORGANISM: Homo sapiens

<400> SEQUENCE: 134

Glu Asp Gly Gly
1

<210> SEQ ID NO 135
<211> LENGTH: 4
<212> TYPE: PRT
<213> ORGANISM: Homo sapiens

<400> SEQUENCE: 135

Asp Gly Gly Pro
1

<210> SEQ ID NO 136
```

```
<211> LENGTH: 4
<212> TYPE: PRT
<213> ORGANISM: Homo sapiens

<400> SEQUENCE: 136

Gly Gly Pro Ser
1

<210> SEQ ID NO 137
<211> LENGTH: 4
<212> TYPE: PRT
<213> ORGANISM: Homo sapiens

<400> SEQUENCE: 137

Gly Pro Ser Ala
1

<210> SEQ ID NO 138
<211> LENGTH: 4
<212> TYPE: PRT
<213> ORGANISM: Homo sapiens

<400> SEQUENCE: 138

Pro Ser Ala Thr
1

<210> SEQ ID NO 139
<211> LENGTH: 4
<212> TYPE: PRT
<213> ORGANISM: Homo sapiens

<400> SEQUENCE: 139

Ser Ala Thr Glu
1

<210> SEQ ID NO 140
<211> LENGTH: 4
<212> TYPE: PRT
<213> ORGANISM: Homo sapiens

<400> SEQUENCE: 140

Ala Thr Glu Arg
1

<210> SEQ ID NO 141
<211> LENGTH: 4
<212> TYPE: PRT
<213> ORGANISM: Homo sapiens

<400> SEQUENCE: 141

Thr Glu Arg Ala
1

<210> SEQ ID NO 142
<211> LENGTH: 4
<212> TYPE: PRT
<213> ORGANISM: Homo sapiens

<400> SEQUENCE: 142

Glu Arg Ala Ala
1

<210> SEQ ID NO 143
<211> LENGTH: 4
<212> TYPE: PRT
```

```
<213> ORGANISM: Homo sapiens

<400> SEQUENCE: 143

Arg Ala Ala Glu
1

<210> SEQ ID NO 144
<211> LENGTH: 4
<212> TYPE: PRT
<213> ORGANISM: Homo sapiens

<400> SEQUENCE: 144

Ala Ala Glu Asp
1

<210> SEQ ID NO 145
<211> LENGTH: 4
<212> TYPE: PRT
<213> ORGANISM: Homo sapiens

<400> SEQUENCE: 145

Ala Glu Asp Gly
1

<210> SEQ ID NO 146
<211> LENGTH: 4
<212> TYPE: PRT
<213> ORGANISM: Homo sapiens

<400> SEQUENCE: 146

Glu Asp Gly Ala
1

<210> SEQ ID NO 147
<211> LENGTH: 4
<212> TYPE: PRT
<213> ORGANISM: Homo sapiens

<400> SEQUENCE: 147

Asp Gly Ala Ser
1

<210> SEQ ID NO 148
<211> LENGTH: 4
<212> TYPE: PRT
<213> ORGANISM: Homo sapiens

<400> SEQUENCE: 148

Gly Ala Ser Ser
1

<210> SEQ ID NO 149
<211> LENGTH: 4
<212> TYPE: PRT
<213> ORGANISM: Homo sapiens

<400> SEQUENCE: 149

Ala Ser Ser Gln
1

<210> SEQ ID NO 150
<211> LENGTH: 4
<212> TYPE: PRT
<213> ORGANISM: Homo sapiens
```

```
<400> SEQUENCE: 150

Ser Ser Gln Leu
1

<210> SEQ ID NO 151
<211> LENGTH: 4
<212> TYPE: PRT
<213> ORGANISM: Homo sapiens

<400> SEQUENCE: 151

Ser Gln Leu Pro
1

<210> SEQ ID NO 152
<211> LENGTH: 4
<212> TYPE: PRT
<213> ORGANISM: Homo sapiens

<400> SEQUENCE: 152

Gln Leu Pro Ala
1

<210> SEQ ID NO 153
<211> LENGTH: 4
<212> TYPE: PRT
<213> ORGANISM: Homo sapiens

<400> SEQUENCE: 153

Leu Pro Ala Ala
1

<210> SEQ ID NO 154
<211> LENGTH: 4
<212> TYPE: PRT
<213> ORGANISM: Homo sapiens

<400> SEQUENCE: 154

Pro Ala Ala Glu
1

<210> SEQ ID NO 155
<211> LENGTH: 4
<212> TYPE: PRT
<213> ORGANISM: Homo sapiens

<400> SEQUENCE: 155

Ala Ala Glu Gly
1

<210> SEQ ID NO 156
<211> LENGTH: 4
<212> TYPE: PRT
<213> ORGANISM: Homo sapiens

<400> SEQUENCE: 156

Ala Glu Gly Ser
1

<210> SEQ ID NO 157
<211> LENGTH: 4
<212> TYPE: PRT
<213> ORGANISM: Homo sapiens

<400> SEQUENCE: 157
```

```
Glu Gly Ser Gly
1

<210> SEQ ID NO 158
<211> LENGTH: 4
<212> TYPE: PRT
<213> ORGANISM: Homo sapiens

<400> SEQUENCE: 158

Gly Ser Gly Glu
1

<210> SEQ ID NO 159
<211> LENGTH: 4
<212> TYPE: PRT
<213> ORGANISM: Homo sapiens

<400> SEQUENCE: 159

Ser Gly Glu Gln
1

<210> SEQ ID NO 160
<211> LENGTH: 4
<212> TYPE: PRT
<213> ORGANISM: Homo sapiens

<400> SEQUENCE: 160

Gly Glu Gln Asp
1

<210> SEQ ID NO 161
<211> LENGTH: 4
<212> TYPE: PRT
<213> ORGANISM: Homo sapiens

<400> SEQUENCE: 161

Glu Gln Asp Phe
1

<210> SEQ ID NO 162
<211> LENGTH: 4
<212> TYPE: PRT
<213> ORGANISM: Homo sapiens

<400> SEQUENCE: 162

Gln Asp Phe Thr
1

<210> SEQ ID NO 163
<211> LENGTH: 5
<212> TYPE: PRT
<213> ORGANISM: Homo sapiens

<400> SEQUENCE: 163

His Thr Pro His Thr
1               5

<210> SEQ ID NO 164
<211> LENGTH: 5
<212> TYPE: PRT
<213> ORGANISM: Homo sapiens

<400> SEQUENCE: 164

Thr Pro His Thr Glu
1               5
```

<210> SEQ ID NO 165
<211> LENGTH: 5
<212> TYPE: PRT
<213> ORGANISM: Homo sapiens

<400> SEQUENCE: 165

Pro His Thr Glu Asp
1               5

<210> SEQ ID NO 166
<211> LENGTH: 5
<212> TYPE: PRT
<213> ORGANISM: Homo sapiens

<400> SEQUENCE: 166

His Thr Glu Asp Gly
1               5

<210> SEQ ID NO 167
<211> LENGTH: 5
<212> TYPE: PRT
<213> ORGANISM: Homo sapiens

<400> SEQUENCE: 167

Thr Glu Asp Gly Gly
1               5

<210> SEQ ID NO 168
<211> LENGTH: 5
<212> TYPE: PRT
<213> ORGANISM: Homo sapiens

<400> SEQUENCE: 168

Glu Asp Gly Gly Pro
1               5

<210> SEQ ID NO 169
<211> LENGTH: 5
<212> TYPE: PRT
<213> ORGANISM: Homo sapiens

<400> SEQUENCE: 169

Asp Gly Gly Pro Ser
1               5

<210> SEQ ID NO 170
<211> LENGTH: 5
<212> TYPE: PRT
<213> ORGANISM: Homo sapiens

<400> SEQUENCE: 170

Gly Gly Pro Ser Ala
1               5

<210> SEQ ID NO 171
<211> LENGTH: 5
<212> TYPE: PRT
<213> ORGANISM: Homo sapiens

<400> SEQUENCE: 171

Gly Pro Ser Ala Thr
1               5

```
<210> SEQ ID NO 172
<211> LENGTH: 5
<212> TYPE: PRT
<213> ORGANISM: Homo sapiens

<400> SEQUENCE: 172

Pro Ser Ala Thr Glu
1               5

<210> SEQ ID NO 173
<211> LENGTH: 5
<212> TYPE: PRT
<213> ORGANISM: Homo sapiens

<400> SEQUENCE: 173

Ser Ala Thr Glu Arg
1               5

<210> SEQ ID NO 174
<211> LENGTH: 5
<212> TYPE: PRT
<213> ORGANISM: Homo sapiens

<400> SEQUENCE: 174

Ala Thr Glu Arg Ala
1               5

<210> SEQ ID NO 175
<211> LENGTH: 5
<212> TYPE: PRT
<213> ORGANISM: Homo sapiens

<400> SEQUENCE: 175

Thr Glu Arg Ala Ala
1               5

<210> SEQ ID NO 176
<211> LENGTH: 5
<212> TYPE: PRT
<213> ORGANISM: Homo sapiens

<400> SEQUENCE: 176

Glu Arg Ala Ala Glu
1               5

<210> SEQ ID NO 177
<211> LENGTH: 5
<212> TYPE: PRT
<213> ORGANISM: Homo sapiens

<400> SEQUENCE: 177

Arg Ala Ala Glu Asp
1               5

<210> SEQ ID NO 178
<211> LENGTH: 5
<212> TYPE: PRT
<213> ORGANISM: Homo sapiens

<400> SEQUENCE: 178

Ala Ala Glu Asp Gly
1               5

<210> SEQ ID NO 179
<211> LENGTH: 5
```

```
<212> TYPE: PRT
<213> ORGANISM: Homo sapiens

<400> SEQUENCE: 179

Ala Glu Asp Gly Ala
1               5

<210> SEQ ID NO 180
<211> LENGTH: 5
<212> TYPE: PRT
<213> ORGANISM: Homo sapiens

<400> SEQUENCE: 180

Glu Asp Gly Ala Ser
1               5

<210> SEQ ID NO 181
<211> LENGTH: 5
<212> TYPE: PRT
<213> ORGANISM: Homo sapiens

<400> SEQUENCE: 181

Asp Gly Ala Ser Ser
1               5

<210> SEQ ID NO 182
<211> LENGTH: 5
<212> TYPE: PRT
<213> ORGANISM: Homo sapiens

<400> SEQUENCE: 182

Gly Ala Ser Ser Gln
1               5

<210> SEQ ID NO 183
<211> LENGTH: 5
<212> TYPE: PRT
<213> ORGANISM: Homo sapiens

<400> SEQUENCE: 183

Ala Ser Ser Gln Leu
1               5

<210> SEQ ID NO 184
<211> LENGTH: 5
<212> TYPE: PRT
<213> ORGANISM: Homo sapiens

<400> SEQUENCE: 184

Ser Ser Gln Leu Pro
1               5

<210> SEQ ID NO 185
<211> LENGTH: 5
<212> TYPE: PRT
<213> ORGANISM: Homo sapiens

<400> SEQUENCE: 185

Ser Gln Leu Pro Ala
1               5

<210> SEQ ID NO 186
<211> LENGTH: 5
<212> TYPE: PRT
<213> ORGANISM: Homo sapiens
```

<400> SEQUENCE: 186

Gln Leu Pro Ala Ala
1               5

<210> SEQ ID NO 187
<211> LENGTH: 5
<212> TYPE: PRT
<213> ORGANISM: Homo sapiens

<400> SEQUENCE: 187

Leu Pro Ala Ala Glu
1               5

<210> SEQ ID NO 188
<211> LENGTH: 5
<212> TYPE: PRT
<213> ORGANISM: Homo sapiens

<400> SEQUENCE: 188

Pro Ala Ala Glu Gly
1               5

<210> SEQ ID NO 189
<211> LENGTH: 5
<212> TYPE: PRT
<213> ORGANISM: Homo sapiens

<400> SEQUENCE: 189

Ala Ala Glu Gly Ser
1               5

<210> SEQ ID NO 190
<211> LENGTH: 5
<212> TYPE: PRT
<213> ORGANISM: Homo sapiens

<400> SEQUENCE: 190

Ala Glu Gly Ser Gly
1               5

<210> SEQ ID NO 191
<211> LENGTH: 5
<212> TYPE: PRT
<213> ORGANISM: Homo sapiens

<400> SEQUENCE: 191

Glu Gly Ser Gly Glu
1               5

<210> SEQ ID NO 192
<211> LENGTH: 5
<212> TYPE: PRT
<213> ORGANISM: Homo sapiens

<400> SEQUENCE: 192

Gly Ser Gly Glu Gln
1               5

<210> SEQ ID NO 193
<211> LENGTH: 5
<212> TYPE: PRT
<213> ORGANISM: Homo sapiens

<400> SEQUENCE: 193

```
Ser Gly Glu Gln Asp
1               5

<210> SEQ ID NO 194
<211> LENGTH: 5
<212> TYPE: PRT
<213> ORGANISM: Homo sapiens

<400> SEQUENCE: 194

Gly Glu Gln Asp Phe
1               5

<210> SEQ ID NO 195
<211> LENGTH: 5
<212> TYPE: PRT
<213> ORGANISM: Homo sapiens

<400> SEQUENCE: 195

Glu Gln Asp Phe Thr
1               5

<210> SEQ ID NO 196
<211> LENGTH: 5
<212> TYPE: PRT
<213> ORGANISM: Homo sapiens

<400> SEQUENCE: 196

Gln Asp Phe Thr Phe
1               5

<210> SEQ ID NO 197
<211> LENGTH: 6
<212> TYPE: PRT
<213> ORGANISM: Homo sapiens

<400> SEQUENCE: 197

His Thr Pro His Thr Glu
1               5

<210> SEQ ID NO 198
<211> LENGTH: 6
<212> TYPE: PRT
<213> ORGANISM: Homo sapiens

<400> SEQUENCE: 198

Thr Pro His Thr Glu Asp
1               5

<210> SEQ ID NO 199
<211> LENGTH: 6
<212> TYPE: PRT
<213> ORGANISM: Homo sapiens

<400> SEQUENCE: 199

Pro His Thr Glu Asp Gly
1               5

<210> SEQ ID NO 200
<211> LENGTH: 6
<212> TYPE: PRT
<213> ORGANISM: Homo sapiens

<400> SEQUENCE: 200

His Thr Glu Asp Gly Gly
```

```
1               5

<210> SEQ ID NO 201
<211> LENGTH: 6
<212> TYPE: PRT
<213> ORGANISM: Homo sapiens

<400> SEQUENCE: 201

Thr Glu Asp Gly Gly Pro
1               5

<210> SEQ ID NO 202
<211> LENGTH: 6
<212> TYPE: PRT
<213> ORGANISM: Homo sapiens

<400> SEQUENCE: 202

Glu Asp Gly Gly Pro Ser
1               5

<210> SEQ ID NO 203
<211> LENGTH: 6
<212> TYPE: PRT
<213> ORGANISM: Homo sapiens

<400> SEQUENCE: 203

Asp Gly Gly Pro Ser Ala
1               5

<210> SEQ ID NO 204
<211> LENGTH: 6
<212> TYPE: PRT
<213> ORGANISM: Homo sapiens

<400> SEQUENCE: 204

Gly Gly Pro Ser Ala Thr
1               5

<210> SEQ ID NO 205
<211> LENGTH: 6
<212> TYPE: PRT
<213> ORGANISM: Homo sapiens

<400> SEQUENCE: 205

Gly Pro Ser Ala Thr Glu
1               5

<210> SEQ ID NO 206
<211> LENGTH: 6
<212> TYPE: PRT
<213> ORGANISM: Homo sapiens

<400> SEQUENCE: 206

Pro Ser Ala Thr Glu Arg
1               5

<210> SEQ ID NO 207
<211> LENGTH: 6
<212> TYPE: PRT
<213> ORGANISM: Homo sapiens

<400> SEQUENCE: 207

Ser Ala Thr Glu Arg Ala
1               5
```

```
<210> SEQ ID NO 208
<211> LENGTH: 6
<212> TYPE: PRT
<213> ORGANISM: Homo sapiens

<400> SEQUENCE: 208

Ala Thr Glu Arg Ala Ala
1               5

<210> SEQ ID NO 209
<211> LENGTH: 6
<212> TYPE: PRT
<213> ORGANISM: Homo sapiens

<400> SEQUENCE: 209

Thr Glu Arg Ala Ala Glu
1               5

<210> SEQ ID NO 210
<211> LENGTH: 6
<212> TYPE: PRT
<213> ORGANISM: Homo sapiens

<400> SEQUENCE: 210

Glu Arg Ala Ala Glu Asp
1               5

<210> SEQ ID NO 211
<211> LENGTH: 6
<212> TYPE: PRT
<213> ORGANISM: Homo sapiens

<400> SEQUENCE: 211

Arg Ala Ala Glu Asp Gly
1               5

<210> SEQ ID NO 212
<211> LENGTH: 6
<212> TYPE: PRT
<213> ORGANISM: Homo sapiens

<400> SEQUENCE: 212

Ala Ala Glu Asp Gly Ala
1               5

<210> SEQ ID NO 213
<211> LENGTH: 6
<212> TYPE: PRT
<213> ORGANISM: Homo sapiens

<400> SEQUENCE: 213

Ala Glu Asp Gly Ala Ser
1               5

<210> SEQ ID NO 214
<211> LENGTH: 6
<212> TYPE: PRT
<213> ORGANISM: Homo sapiens

<400> SEQUENCE: 214

Glu Asp Gly Ala Ser Ser
1               5

<210> SEQ ID NO 215
```

```
<211> LENGTH: 6
<212> TYPE: PRT
<213> ORGANISM: Homo sapiens

<400> SEQUENCE: 215

Asp Gly Ala Ser Ser Gln
1               5

<210> SEQ ID NO 216
<211> LENGTH: 6
<212> TYPE: PRT
<213> ORGANISM: Homo sapiens

<400> SEQUENCE: 216

Gly Ala Ser Ser Gln Leu
1               5

<210> SEQ ID NO 217
<211> LENGTH: 6
<212> TYPE: PRT
<213> ORGANISM: Homo sapiens

<400> SEQUENCE: 217

Ala Ser Ser Gln Leu Pro
1               5

<210> SEQ ID NO 218
<211> LENGTH: 6
<212> TYPE: PRT
<213> ORGANISM: Homo sapiens

<400> SEQUENCE: 218

Ser Ser Gln Leu Pro Ala
1               5

<210> SEQ ID NO 219
<211> LENGTH: 6
<212> TYPE: PRT
<213> ORGANISM: Homo sapiens

<400> SEQUENCE: 219

Ser Gln Leu Pro Ala Ala
1               5

<210> SEQ ID NO 220
<211> LENGTH: 6
<212> TYPE: PRT
<213> ORGANISM: Homo sapiens

<400> SEQUENCE: 220

Gln Leu Pro Ala Ala Glu
1               5

<210> SEQ ID NO 221
<211> LENGTH: 6
<212> TYPE: PRT
<213> ORGANISM: Homo sapiens

<400> SEQUENCE: 221

Leu Pro Ala Ala Glu Gly
1               5

<210> SEQ ID NO 222
<211> LENGTH: 6
<212> TYPE: PRT
```

```
<213> ORGANISM: Homo sapiens

<400> SEQUENCE: 222

Pro Ala Ala Glu Gly Ser
1               5

<210> SEQ ID NO 223
<211> LENGTH: 6
<212> TYPE: PRT
<213> ORGANISM: Homo sapiens

<400> SEQUENCE: 223

Ala Ala Glu Gly Ser Gly
1               5

<210> SEQ ID NO 224
<211> LENGTH: 6
<212> TYPE: PRT
<213> ORGANISM: Homo sapiens

<400> SEQUENCE: 224

Ala Glu Gly Ser Gly Glu
1               5

<210> SEQ ID NO 225
<211> LENGTH: 6
<212> TYPE: PRT
<213> ORGANISM: Homo sapiens

<400> SEQUENCE: 225

Glu Gly Ser Gly Glu Gln
1               5

<210> SEQ ID NO 226
<211> LENGTH: 6
<212> TYPE: PRT
<213> ORGANISM: Homo sapiens

<400> SEQUENCE: 226

Gly Ser Gly Glu Gln Asp
1               5

<210> SEQ ID NO 227
<211> LENGTH: 6
<212> TYPE: PRT
<213> ORGANISM: Homo sapiens

<400> SEQUENCE: 227

Ser Gly Glu Gln Asp Phe
1               5

<210> SEQ ID NO 228
<211> LENGTH: 6
<212> TYPE: PRT
<213> ORGANISM: Homo sapiens

<400> SEQUENCE: 228

Gly Glu Gln Asp Phe Thr
1               5

<210> SEQ ID NO 229
<211> LENGTH: 6
<212> TYPE: PRT
<213> ORGANISM: Homo sapiens
```

```
<400> SEQUENCE: 229

Glu Gln Asp Phe Thr Phe
1               5

<210> SEQ ID NO 230
<211> LENGTH: 6
<212> TYPE: PRT
<213> ORGANISM: Homo sapiens

<400> SEQUENCE: 230

Gln Asp Phe Thr Phe Glu
1               5

<210> SEQ ID NO 231
<211> LENGTH: 4
<212> TYPE: PRT
<213> ORGANISM: Homo sapiens

<400> SEQUENCE: 231

Ala Ser Thr Ser
1

<210> SEQ ID NO 232
<211> LENGTH: 4
<212> TYPE: PRT
<213> ORGANISM: Homo sapiens

<400> SEQUENCE: 232

Ser Thr Ser Thr
1

<210> SEQ ID NO 233
<211> LENGTH: 4
<212> TYPE: PRT
<213> ORGANISM: Homo sapiens

<400> SEQUENCE: 233

Thr Ser Thr Leu
1

<210> SEQ ID NO 234
<211> LENGTH: 4
<212> TYPE: PRT
<213> ORGANISM: Homo sapiens

<400> SEQUENCE: 234

Ser Thr Leu Pro
1

<210> SEQ ID NO 235
<211> LENGTH: 4
<212> TYPE: PRT
<213> ORGANISM: Homo sapiens

<400> SEQUENCE: 235

Thr Leu Pro Ala
1

<210> SEQ ID NO 236
<211> LENGTH: 4
<212> TYPE: PRT
<213> ORGANISM: Homo sapiens

<400> SEQUENCE: 236
```

Leu Pro Ala Gly
1

<210> SEQ ID NO 237
<211> LENGTH: 4
<212> TYPE: PRT
<213> ORGANISM: Homo sapiens

<400> SEQUENCE: 237

Pro Ala Gly Glu
1

<210> SEQ ID NO 238
<211> LENGTH: 4
<212> TYPE: PRT
<213> ORGANISM: Homo sapiens

<400> SEQUENCE: 238

Ala Gly Glu Gly
1

<210> SEQ ID NO 239
<211> LENGTH: 4
<212> TYPE: PRT
<213> ORGANISM: Homo sapiens

<400> SEQUENCE: 239

Gly Glu Gly Pro
1

<210> SEQ ID NO 240
<211> LENGTH: 4
<212> TYPE: PRT
<213> ORGANISM: Homo sapiens

<400> SEQUENCE: 240

Glu Gly Pro Lys
1

<210> SEQ ID NO 241
<211> LENGTH: 4
<212> TYPE: PRT
<213> ORGANISM: Homo sapiens

<400> SEQUENCE: 241

Gly Pro Lys Glu
1

<210> SEQ ID NO 242
<211> LENGTH: 4
<212> TYPE: PRT
<213> ORGANISM: Homo sapiens

<400> SEQUENCE: 242

Pro Lys Glu Gly
1

<210> SEQ ID NO 243
<211> LENGTH: 4
<212> TYPE: PRT
<213> ORGANISM: Homo sapiens

<400> SEQUENCE: 243

Lys Glu Gly Glu
1

```
<210> SEQ ID NO 244
<211> LENGTH: 4
<212> TYPE: PRT
<213> ORGANISM: Homo sapiens

<400> SEQUENCE: 244

Glu Gly Glu Ala
1

<210> SEQ ID NO 245
<211> LENGTH: 4
<212> TYPE: PRT
<213> ORGANISM: Homo sapiens

<400> SEQUENCE: 245

Gly Glu Ala Val
1

<210> SEQ ID NO 246
<211> LENGTH: 4
<212> TYPE: PRT
<213> ORGANISM: Homo sapiens

<400> SEQUENCE: 246

Glu Ala Val Val
1

<210> SEQ ID NO 247
<211> LENGTH: 4
<212> TYPE: PRT
<213> ORGANISM: Homo sapiens

<400> SEQUENCE: 247

Ala Val Val Leu
1

<210> SEQ ID NO 248
<211> LENGTH: 4
<212> TYPE: PRT
<213> ORGANISM: Homo sapiens

<400> SEQUENCE: 248

Val Val Leu Pro
1

<210> SEQ ID NO 249
<211> LENGTH: 4
<212> TYPE: PRT
<213> ORGANISM: Homo sapiens

<400> SEQUENCE: 249

Val Leu Pro Glu
1

<210> SEQ ID NO 250
<211> LENGTH: 4
<212> TYPE: PRT
<213> ORGANISM: Homo sapiens

<400> SEQUENCE: 250

Leu Pro Glu Val
1
```

```
<210> SEQ ID NO 251
<211> LENGTH: 4
<212> TYPE: PRT
<213> ORGANISM: Homo sapiens

<400> SEQUENCE: 251

Pro Glu Val Glu
1

<210> SEQ ID NO 252
<211> LENGTH: 4
<212> TYPE: PRT
<213> ORGANISM: Homo sapiens

<400> SEQUENCE: 252

Glu Val Glu Pro
1

<210> SEQ ID NO 253
<211> LENGTH: 4
<212> TYPE: PRT
<213> ORGANISM: Homo sapiens

<400> SEQUENCE: 253

Val Glu Pro Gly
1

<210> SEQ ID NO 254
<211> LENGTH: 4
<212> TYPE: PRT
<213> ORGANISM: Homo sapiens

<400> SEQUENCE: 254

Glu Pro Gly Leu
1

<210> SEQ ID NO 255
<211> LENGTH: 4
<212> TYPE: PRT
<213> ORGANISM: Homo sapiens

<400> SEQUENCE: 255

Pro Gly Leu Thr
1

<210> SEQ ID NO 256
<211> LENGTH: 4
<212> TYPE: PRT
<213> ORGANISM: Homo sapiens

<400> SEQUENCE: 256

Gly Leu Thr Ala
1

<210> SEQ ID NO 257
<211> LENGTH: 4
<212> TYPE: PRT
<213> ORGANISM: Homo sapiens

<400> SEQUENCE: 257

Leu Thr Ala Arg
1

<210> SEQ ID NO 258
<211> LENGTH: 4
```

```
<212> TYPE: PRT
<213> ORGANISM: Homo sapiens

<400> SEQUENCE: 258

Thr Ala Arg Glu
1

<210> SEQ ID NO 259
<211> LENGTH: 4
<212> TYPE: PRT
<213> ORGANISM: Homo sapiens

<400> SEQUENCE: 259

Ala Arg Glu Gln
1

<210> SEQ ID NO 260
<211> LENGTH: 4
<212> TYPE: PRT
<213> ORGANISM: Homo sapiens

<400> SEQUENCE: 260

Arg Glu Gln Glu
1

<210> SEQ ID NO 261
<211> LENGTH: 4
<212> TYPE: PRT
<213> ORGANISM: Homo sapiens

<400> SEQUENCE: 261

Glu Gln Glu Ala
1

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267
```

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288
<400> SEQUENCE: 288
000

<210> SEQ ID NO 289
<400> SEQUENCE: 289
000

<210> SEQ ID NO 290

<400> SEQUENCE: 290

000

<210> SEQ ID NO 291

<400> SEQUENCE: 291

000

<210> SEQ ID NO 292
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

```
Asp Ile Val Ile Thr Gln Asp Glu Leu Ser Asn Pro Val Thr Ser Gly
1               5                   10                  15
Asp Ser Val Ser Ile Ser Cys Arg Ser Ser Lys Ser Leu Leu Tyr Lys
            20                  25                  30
Asp Gly Lys Thr Tyr Leu Asn Trp Phe Leu Gln Arg Pro Gly Gln Ser
        35                  40                  45
Pro Gln Leu Leu Ile Tyr Val Val Ser Thr Arg Ala Ser Gly Val Ser
    50                  55                  60
Asp Arg Phe Ser Gly Ser Gly Ser Gly Thr Asp Phe Thr Leu Glu Ile
65                  70                  75                  80
Ser Arg Val Lys Ala Glu Asp Val Gly Val Tyr Tyr Cys Gln Gln Leu
                85                  90                  95
Val Glu Tyr Pro Tyr Thr Phe Gly Gly Gly Thr Lys Leu Glu Ile Lys
            100                 105                 110
```

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Val Gln Leu His Gln Pro Gly Thr Ser Leu Val Lys Pro Gly Ala

```
              1               5              10              15
            Ser Val Lys Leu Ser Cys Lys Ala Ser Gly Tyr Ser Phe Ser Tyr
                           20              25              30
            Tyr Met His Trp Val Lys Gln Arg Pro Gly Gln Gly Leu Glu Trp Ile
                           35              40              45
            Gly Thr Ile His Pro Ser Asp Ser Thr Thr Asn Tyr Asn Gln Lys Phe
                   50              55              60
            Lys Gly Lys Ala Thr Leu Thr Val Asp Lys Ser Ser Arg Thr Ala Tyr
            65              70              75              80
            Met Gln Leu Asn Ser Leu Thr Phe Glu Asp Ser Ala Val Tyr Tyr Cys
                           85              90              95
            Ala Asn Phe Val Tyr Trp Gly Gln Gly Thr Ser Val Thr Val Ser Ser
                          100             105             110
```

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

```
<210> SEQ ID NO 317
<400> SEQUENCE: 317
000

<210> SEQ ID NO 318
<400> SEQUENCE: 318
000

<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Tyr Thr Phe Thr Ser Tyr
1               5

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000
```

-continued

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000

<210> SEQ ID NO 330
<400> SEQUENCE: 330
000

<210> SEQ ID NO 331
<400> SEQUENCE: 331
000

<210> SEQ ID NO 332
<400> SEQUENCE: 332
000

<210> SEQ ID NO 333
<400> SEQUENCE: 333
000

<210> SEQ ID NO 334
<400> SEQUENCE: 334
000

<210> SEQ ID NO 335
<400> SEQUENCE: 335
000

<210> SEQ ID NO 336
<400> SEQUENCE: 336
000

<210> SEQ ID NO 337
<400> SEQUENCE: 337
000

<210> SEQ ID NO 338

```
<400> SEQUENCE: 338
000

<210> SEQ ID NO 339
<400> SEQUENCE: 339
000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
```

000

<210> SEQ ID NO 350

<400> SEQUENCE: 350

000

<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

His Pro Ser Asp Ser Thr
1               5

<210> SEQ ID NO 352
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Arg Ser Ser Lys Ser Leu Leu Tyr Lys Asp Gly Lys Thr Tyr Leu Asn
1               5                   10                  15

<210> SEQ ID NO 353
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Val Val Ser Thr Arg Ala Ser
1               5

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Gln Leu Val Glu Tyr Pro Tyr Thr
1               5

<210> SEQ ID NO 355
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Gly Tyr Ser Phe Ser Ser Tyr
1               5

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Gly Tyr Thr Phe Ser Ser Tyr
1               5

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

```
<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
000

<210> SEQ ID NO 376
<400> SEQUENCE: 376
000

<210> SEQ ID NO 377
```

```
<400> SEQUENCE: 377

000

<210> SEQ ID NO 378

<400> SEQUENCE: 378

000

<210> SEQ ID NO 379

<400> SEQUENCE: 379

000

<210> SEQ ID NO 380
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Ser Tyr Tyr Met His
1               5

<210> SEQ ID NO 381

<400> SEQUENCE: 381

000

<210> SEQ ID NO 382
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Thr Ile His Pro Ser Asp Ser Thr Thr Asn Tyr Asn Gln Lys Phe Lys
1               5                   10                  15

Gly

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386
```

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398
<400> SEQUENCE: 398
000

<210> SEQ ID NO 399
<400> SEQUENCE: 399
000

<210> SEQ ID NO 400
<400> SEQUENCE: 400
000

<210> SEQ ID NO 401
<400> SEQUENCE: 401
000

<210> SEQ ID NO 402
<400> SEQUENCE: 402
000

<210> SEQ ID NO 403
<400> SEQUENCE: 403
000

<210> SEQ ID NO 404
<400> SEQUENCE: 404
000

<210> SEQ ID NO 405
<400> SEQUENCE: 405
000

<210> SEQ ID NO 406
<400> SEQUENCE: 406
000

<210> SEQ ID NO 407
<400> SEQUENCE: 407
000

<210> SEQ ID NO 408
<400> SEQUENCE: 408
000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

```
<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431
```

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asn, Ser or Thr
<220> FEATURE:
<221> NAME/KEY: MOD_RES
<222> LOCATION: (5)..(5)
<223> OTHER INFORMATION: Ala, Ser or Thr

<400> SEQUENCE: 438

Gly Tyr Xaa Phe Xaa Ser Tyr
1               5

<210> SEQ ID NO 439

<400> SEQUENCE: 439

000

<210> SEQ ID NO 440
<211> LENGTH: 37
<212> TYPE: PRT
<213> ORGANISM: Homo sapiens

```
<400> SEQUENCE: 440

Glu Asn Thr Ala Val Val Ala Val Glu Pro Asp Arg Arg Asn Gln Ser
1               5                   10                  15

Pro Val Asp Gln Gly Ala Thr Gly Ala Ser Gln Gly Leu Leu Asp Arg
            20                  25                  30

Lys Glu Val Leu Gly
        35

<210> SEQ ID NO 441
<211> LENGTH: 25
<212> TYPE: PRT
<213> ORGANISM: Homo sapiens

<400> SEQUENCE: 441

Thr Ala Val Val Ala Val Glu Pro Asp Arg Arg Asn Gln Ser Pro Val
1               5                   10                  15

Asp Gln Gly Ala Thr Gly Ala Ser Gln
            20                  25

<210> SEQ ID NO 442
<211> LENGTH: 24
<212> TYPE: PRT
<213> ORGANISM: Homo sapiens

<400> SEQUENCE: 442

Glu Asn Thr Ala Val Val Ala Val Glu Pro Asp Arg Arg Asn Gln Ser
1               5                   10                  15

Pro Val Asp Gln Gly Ala Thr Gly
            20

<210> SEQ ID NO 443
<211> LENGTH: 15
<212> TYPE: PRT
<213> ORGANISM: Homo sapiens

<400> SEQUENCE: 443

Glu Asn Thr Ala Val Val Ala Val Glu Pro Asp Arg Arg Asn Gln
1               5                   10                  15

<210> SEQ ID NO 444
<211> LENGTH: 25
<212> TYPE: PRT
<213> ORGANISM: Homo sapiens

<400> SEQUENCE: 444

Arg Asn Gln Ser Pro Val Asp Gln Gly Ala Thr Gly Ala Ser Gln Gly
1               5                   10                  15

Leu Leu Asp Arg Lys Glu Val Leu Gly
            20                  25

<210> SEQ ID NO 445
<211> LENGTH: 15
<212> TYPE: PRT
<213> ORGANISM: Homo sapiens

<400> SEQUENCE: 445

Gly Glu Ala Val Val Leu Pro Glu Val Glu Pro Gly Leu Thr Ala
1               5                   10                  15

<210> SEQ ID NO 446
<211> LENGTH: 330
```

```
<212> TYPE: PRT
<213> ORGANISM: Homo sapiens

<400> SEQUENCE: 446

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 447
<211> LENGTH: 326
<212> TYPE: PRT
<213> ORGANISM: Homo sapiens

<400> SEQUENCE: 447

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
         115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 448
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Leu Val Gly Leu Ile Phe Ala Val
1               5

<210> SEQ ID NO 449

<400> SEQUENCE: 449
```

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Asn Phe Ala Ser Tyr
            20                  25                  30

Tyr Met His Trp Val Arg Gln Ala Pro Gly Lys Gly Leu Glu Trp Val
        35                  40                  45

Ala Thr Ile His Pro Ser Asp Ser Thr Lys Asn Tyr Ala Asp Ser Val

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 459
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

```
Gln Val Gln Leu Val Glu Ser Gly Gly Val Val Gln Pro Gly Arg
  1               5                  10                  15

Ser Leu Arg Leu Ser Cys Ala Ala Ser Gly Tyr Ser Phe Ser Ser Tyr
                 20                  25                  30

Tyr Met His Trp Val Arg Gln Ala Pro Gly Lys Gly Leu Glu Trp Val
             35                  40                  45

Gly Thr Ile His Pro Ser Asp Ser Thr Lys Asn Tyr Asn Gln Lys Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 460
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Tyr Ser Phe Ser Ser Tyr
                 20                  25                  30

Tyr Met His Trp Val Arg Gln Ala Pro Gly Lys Gly Leu Glu Trp Val
             35                  40                  45

Ala Val Ile His Pro Ser Asp Ser Thr Lys Tyr Ala Asp Ser Val
         50                  55                  60

Lys Gly Arg Phe Thr Ile Ser Val Asp Lys Ser Ser Arg Thr Ala Tyr
 65                  70                  75                  80

Leu Gln Met Asn Ser Leu Arg Ala Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 461
<211> LENGTH: 112
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 461

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Ser Tyr
            20                  25                  30

Tyr Met His Trp Val Arg Gln Ala Pro Gly Lys Gly Leu Glu Trp Val
        35                  40                  45

Gly Thr Ile His Pro Ser Asp Ser Thr Lys Asn Tyr Ala Asp Ser Val
    50                  55                  60

Lys Gly Arg Phe Thr Ile Ser Val Asp Lys Ser Ser Arg Thr Ala Tyr
65                  70                  75                  80

Leu Gln Met Asn Ser Leu Arg Ala Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 462
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Tyr Met His Trp Val Arg Gln Ala Pro Gly Lys Gly Leu Glu Trp Val
        35                  40                  45

Ala Thr Ile His Pro Ser Asp Ser Thr Thr Asn Tyr Asn Gln Lys Phe
    50                  55                  60

Lys Gly Arg Phe Thr Ile Ser Arg Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 463
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Tyr Ile His Trp Val Arg Gln Ala Pro Gly Gln Gly Leu Glu Trp Met
        35                  40                  45

Gly Thr Ile His Pro Ser Asp Ser Thr Thr Asn Tyr Asn Gln Lys Phe
            50                  55                  60

Gln Gly Arg Val Thr Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 464
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Ser Tyr
                20                  25                  30

Tyr Ile His Trp Val Arg Gln Ala Pro Gly Gln Gly Leu Glu Trp Met
            35                  40                  45

Gly Thr Ile His Pro Ser Asp Ser Thr Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 465
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Asn Phe Ala Ser Tyr
                20                  25                  30

Tyr Ile His Trp Val Arg Gln Ala Pro Gly Gln Gly Leu Glu Trp Met
            35                  40                  45

Gly Thr Ile His Pro Ser Asp Ser Thr Ala Asn Tyr Ala Gln Lys Phe
            50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 466

<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Gln Val Gln Leu Val Gln Ser Gly Ala Glu Val Lys Pro Gly Ser
1               5                   10                  15

Ser Val Lys Val Ser Cys Lys Ala Ser Gly Tyr Ser Phe Ser Tyr
                20                  25                  30

Tyr Met His Trp Val Arg Gln Ala Pro Gly Gln Gly Leu Glu Trp Met
            35                  40                  45

Gly Thr Ile His Pro Ser Asp Ser Thr Ala Asn Tyr Asn Gln Lys Phe
    50                  55                  60

Lys Gly Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
                100                 105                 110

<210> SEQ ID NO 467
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Asn Phe Ala Ser Tyr
                20                  25                  30

Tyr Met His Trp Val Arg Gln Ala Pro Gly Lys Gly Leu Glu Trp Val
            35                  40                  45

Ser Thr Ile His Pro Ser Asp Ser Thr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Phe Val Tyr Trp Gly Gln Gly Thr Thr Val Thr Val Ser Ser
                100                 105                 110

<210> SEQ ID NO 468
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

```
Tyr Met His Trp Val Arg Gln Ala Pro Gly Lys Gly Leu Glu Trp Val
            35                  40                  45

Ser Thr Ile His Pro Ser Asp Ser Thr Thr Asn Tyr Asn Gln Lys Phe
 50                  55                  60

Lys Gly Arg Phe Thr Ile Ser Arg Asp Asn Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 469
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                 20                  25                  30

Tyr Met His Trp Ile Arg Gln Ala Pro Gly Lys Gly Leu Glu Trp Val
            35                  40                  45

Ser Thr Ile His Pro Ser Asp Ser Thr Thr Asn Tyr Asn Gln Lys Phe
 50                  55                  60

Lys Gly Arg Phe Thr Ile Ser Val Asp Asn Ala Lys Asn Ser Ala Tyr
 65                  70                  75                  80

Leu Gln Met Asn Ser Leu Arg Ala Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 470
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Ser Ser Tyr
                 20                  25                  30

Tyr Met His Trp Val Arg Gln Ala Pro Gly Gln Gly Leu Glu Trp Met
            35                  40                  45

Gly Thr Ile His Pro Ser Asp Ser Thr Thr Asn Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Asn Phe Val Tyr Trp Gly Gln Gly Thr Thr Val Thr Val Ser Ser
                100                 105                 110
```

<210> SEQ ID NO 471
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Ser Tyr
            20                  25                  30

Tyr Met His Trp Val Arg Gln Ala Pro Gly Gln Gly Leu Glu Trp Met
        35                  40                  45

Gly Thr Ile His Pro Ser Asp Ser Thr Thr Asn Tyr Asn Gln Lys Phe
    50                  55                  60

Gln Gly Arg Val Thr Met Thr Val Asp Thr Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 472
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Thr Ile His Pro Ser Asp Ser Thr Thr Asn Tyr Asn Gln Lys Phe
    50                  55                  60

Lys Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
            100                 105                 110

<210> SEQ ID NO 473
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ala Ser Tyr

```
                20                  25                  30

Tyr Met His Trp Val Arg Gln Ala Pro Gly Gln Gly Leu Glu Trp Met
            35                  40                  45

Gly Thr Ile His Pro Ser Asp Ser Thr Thr Asn Tyr Asn Gln Lys Phe
 50                  55                  60

Lys Gly Arg Val Thr Met Thr Val Asp Thr Ser Thr Thr Ala Tyr
 65                  70                  75                  80

Met Glu Leu Ser Ser Leu Arg Ser Glu Asp Thr Ala Val Tyr Tyr Cys
                85                  90                  95

Ala Asn Phe Val Tyr Trp Gly Gln Gly Thr Thr Val Thr Val Ser Ser
                100                 105                 110
```

<210> SEQ ID NO 474
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

```
Glu Val Gln Leu Val Glu Ser Gly Gly Gly Leu Val Lys Pro Gly Gly
 1                   5                  10                  15

Ser Leu Arg Leu Ser Cys Ala Ala Ser Gly Tyr Ser Phe Ser Ser Tyr
                20                  25                  30

Tyr Met His Trp Val Arg Gln Ala Pro Gly Lys Gly Leu Glu Trp Val
            35                  40                  45

Gly Thr Ile His Pro Ser Asp Ser Thr Thr Asn Tyr Ala Ala Pro Val
 50                  55                  60

Lys Gly Arg Phe Thr Ile Ser Arg Asp Ser Lys Asn Thr Ala Tyr
 65                  70                  75                  80

Leu Gln Met Asn Ser Leu Lys Thr Glu Asp Thr Ala Val Tyr Tyr Cys
                85                  90                  95

Ala Asn Phe Val Tyr Trp Gly Gln Gly Thr Thr Val Thr Val Ser Ser
                100                 105                 110
```

<210> SEQ ID NO 475
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

```
Asp Ile Val Met Thr Gln Thr Pro Leu Ser Leu Ser Val Thr Pro Gly
 1                   5                  10                  15

Gln Pro Ala Ser Ile Ser Cys Lys Ser Ser Lys Ser Leu Leu Tyr Lys
                20                  25                  30

Asp Gly Lys Thr Tyr Leu Asn Trp Phe Leu Gln Lys Pro Gly Gln Ser
            35                  40                  45

Pro Gln Leu Leu Ile Tyr Val Val Ser Thr Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Leu
                85                  90                  95

Val Glu Tyr Pro Tyr Thr Phe Gly Gln Gly Thr Lys Leu Glu Ile Lys
```

<210> SEQ ID NO 476
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Asp Ile Val Met Thr Gln Thr Pro Leu Ser Leu Ser Val Thr Pro Gly
1               5                   10                  15

Gln Pro Ala Ser Ile Ser Cys Lys Ser Ser Lys Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Val Val Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Gln Tyr Pro Tyr Thr Phe Gly Gln Gly Thr Lys Leu Glu Ile Lys
            100                 105                 110

<210> SEQ ID NO 477
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Leu Leu Tyr Lys
            20                  25                  30

Asp Gly Lys Thr Tyr Leu Asn Trp Tyr Gln Gln Lys Pro Gly Lys Ala
        35                  40                  45

Pro Lys Leu Leu Ile Tyr Val Val Ser Ser Leu Gln Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Leu
                85                  90                  95

Val Glu Tyr Pro Tyr Thr Phe Gly Gln Gly Thr Lys Leu Glu Ile Lys
            100                 105                 110

<210> SEQ ID NO 478
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ser Ser Tyr
            20                  25                  30

Leu Asn Trp Phe Gln Gln Lys Pro Gly Lys Ala Pro Lys Leu Leu Ile
        35                  40                  45

Tyr Val Val Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Leu Val Glu Tyr Pro Tyr
                85                  90                  95

Thr Phe Gly Gln Gly Thr Lys Leu Glu Ile Lys
                100                 105
```

```
<210> SEQ ID NO 479
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Asp Ser
            20                  25                  30

Asp Asp Gly Asn Thr Tyr Leu Asn Trp Phe Leu Gln Lys Pro Gly Gln
        35                  40                  45

Ser Pro Gln Leu Leu Ile Tyr Val Leu Ser Asn Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                85                  90                  95

Leu Val Glu Tyr Pro Tyr Thr Phe Gly Gln Gly Thr Lys Leu Glu Ile
                100                 105                 110

Lys
```

```
<210> SEQ ID NO 480
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Asp Ile Val Met Thr Gln Thr Pro Leu Ser Leu Pro Val Thr Pro Gly
 1               5                  10                  15

Glu Pro Ala Ser Ile Ser Cys Arg Ser Ser Gln Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Val Leu Ser Thr Arg Ala Ser Gly Val Pro
 50                  55                  60

Asp Arg Phe Ser Gly Ser Gly Ser Gly Thr Asp Phe Thr Leu Lys Ile
 65                  70                  75                  80
```

Ser Arg Val Glu Ala Glu Asp Val Gly Val Tyr Tyr Cys Gln Gln Leu
              85                  90                  95

Val Glu Tyr Pro Tyr Thr Phe Gly Gln Gly Thr Lys Leu Glu Ile Lys
            100                 105                 110

<210> SEQ ID NO 481
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Lys
            20                  25                  30

Asp Gly Lys Thr Tyr Leu Asn Trp Phe Gln Gln Lys Pro Gly Gln Pro
        35                  40                  45

Pro Lys Leu Leu Ile Tyr Val Val Ser Thr Arg Ala Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Leu
                85                  90                  95

Val Glu Tyr Pro Tyr Thr Phe Gly Gln Gly Thr Lys Leu Glu Ile Lys
            100                 105                 110

<210> SEQ ID NO 482
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Asn Trp Phe Gln Gln Lys Pro Gly Gln
        35                  40                  45

Pro Pro Lys Leu Leu Ile Tyr Val Val Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Leu Val Glu Tyr Pro Tyr Thr Phe Gly Gln Gly Thr Lys Leu Glu Ile
            100                 105                 110

Lys

<210> SEQ ID NO 483
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 483

```
tctgctctgc ctggccgggc gcgccttggc ccaggtccag cttgtggaat ctggggagg      60
agttgtgcaa ccgggcagaa gcctccgact gtcttgcgct gcgtccggtt acaattttgc    120
ttcatactat atgcattggg tccgccaagc gcccggtaaa gggttggaat gggttgcaac    180
tattcacccg tctgatagta ccaaaaatta cgcagattct gtgaaaggca gatttaccat    240
ttcaagggat aattccaaga atactctcta cctccaaatg aactcattgc gggctgagga    300
tacagcggtg tattactgcg ctaatttttgt ctattgggga cagggtacaa ctgtgacagt    360
cagctctgcg agcaccaagg gcccctccgt gttcccgttg gcgcc                    405
```

<210> SEQ ID NO 484
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 484

```
tctgctctgc ctggccgggc gcgccttggc ccaagttcag ctcgttgaat ccggtggtgg     60
ggtggttcaa ccgggcagaa gtttgcgact gagttgcgca gcttctggat attcattctc   120
ctcatactat atgcactggg tacgacaggc ccccggaaag ggcttggaat gggttggtac   180
aattcaccca agcgattcta cgaagaatta caaccaaaaa gttaagggga gatttactat   240
aagccgagac aatagcaaga atactctta tcttcagatg aatagtctcc gcgctgagga    300
tacagcggtg tattattgtg cgaatttcgt atattggggt caaggcacta ccgtaaccgt   360
ttcatccgcg agcaccaagg gcccctccgt gttcccgttg gcgcc                   405
```

<210> SEQ ID NO 485
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 485

```
tctgctctgc ctggccgggc gcgccttggc ccaggtacag ttggttgagt ctggcggagg     60
ggttgtccag cctggcagga gcttgcgact cagttgtgcc gcttcagggt atagttttag   120
cagctactac atgcactggg tacggcaggc accagggaag ggacttgagt gggtcgcagt   180
tatccatcca tctgactcaa ctaaaaacta cgcagattct gtcaagggca gatttaccat   240
atcagttgac aagtcatccc ggacggctta cctgcagatg aactcactcc gcgcggagga   300
tacagcggtt tactactgcg ccaatttttgt ttactgggc caaggtacga ccgtgacggt   360
gagcagtgcg agcaccaagg gcccctccgt gttcccgttg gcgcc                   405
```

<210> SEQ ID NO 486
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 486

```
tctgctctgc ctggccgggc gcgccttggc ccaagtccag ctcgtcgaat caggtggagg    60
agttgttcag ccaggaagga gcttgcggct tagctgtgcg gccagcggct atacgttttc   120
atcttattat atgcactggg tgcgccaagc cccaggaaag ggcctcgaat gggttggcac   180
aattcatcca tcagatagca caaagaacta cgcggattcc gttaaaggtc gatttactat   240
atccgtcgat aagagctcac ggacggcata cctccagatg aacagcttga gggcggaaga   300
caccgccgtc tactactgtg ccaatttcgt ctattggggc cagggcacca ccgtcacagt   360
gtcttctgcg agcaccaagg gcccctccgt gttcccgttg gcgcc              405
```

<210> SEQ ID NO 487
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 487

```
tctgctctgc ctggccgggc gcgccttggc ccaggtccaa ctggtagaat caggaggtgg    60
ggtggtgcaa ccgggcaggt ctctccggtt gtcatgtgca gcttccgggt tcacctttag   120
ctcttattac atgcattggg tacgccaggc gccaggtaaa ggtcttgaat gggttgctac   180
gatccacccc tctgattcca ctaccaatta caaccaaaaa tttaagggac gcttcaccat   240
ttcccgcgac aacagcaaaa acacggcata tttgcaaatg aatagcctcc gcgccgaaga   300
cactgcggta tattattgcg ccaattttgt ttactgggga caaggacaa cggttacagt   360 atccagtgcg agcaccaagg gcccctccgt gttcccgttg gcgcc              405
```

<210> SEQ ID NO 488
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 488

```
tctgctctgc ctggccgggc gcgccttggc ccaagttcag ttggtacaga gtggggctga    60
agtcaagaag cccggttcaa gcgttaaagt ttcttgcaag gcgagtgggt acactttcag   120
cagttattat atccactggg tcaggcaggc accggggcag ggtcttgagt ggatggggac   180
gatacatcca tcagactcaa ctacaaatta caatcagaag ttccagggac gggtgacgat   240
cacagtagac gagtctacga gtacagccta tatggaactt tcatccctca ggagcgaaga   300
tacagccgtt tactattgtg ctaactttgt ctattggggg caaggaacca cagtcaccgt   360
ctcatccgcg agcaccaagg gcccctccgt gttcccgttg gcgcc              405
```

<210> SEQ ID NO 489
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 489

```
tctgctctgc ctggccgggc gcgccttggc ccaagtccag ttggtccaat ccggcgcgga    60
agtgaagaag ccgggatcat ctgtaaaagt ttcatgtaag gcgtctggat attccttcag   120
```

```
ttcatattat atccactggg tacgccaggc ccctggacaa ggtttggaat ggatgggaac    180
catacatcca agcgacagta ccgcaaacta tgcgcaaaaa ttccaggggc gggtgactat    240
tactgcggat aaaagcacaa gcactgctta catggagctg tcctccctgc gatcagagga    300
caccgctgtc tactactgcg ctaatttttgt gtattggggc caaggaacta ccgtgacggt    360
tagttctgcg agcaccaagg gcccctccgt gttcccgttg gcgcc                    405
```

<210> SEQ ID NO 490
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 490

```
tctgctctgc ctggccgggc gcgccttggc ccaagtacaa ctggtgcaat ctggagccga    60
ggttaaaaag cccggcagtt ccgttaaagt gtcttgcaag gcatctggct ataacttcgc    120
cagttattac atccattggg tcagacaagc gcctggacaa ggtctggaat ggatggggac    180
gatccatcct tccgactcaa cggcgaatta tgcccagaag tttcagggta gggtgactat    240
cacagccgat aagtctacca gcaccgctta tatggagttg tccagtctga aagcgaaga    300 taccgctgtc tattattgcg ccaacttcgt gtattggggg caaggaacca ccgtcactgt    360
gtcatcagcg agcaccaagg gcccctccgt gttcccgttg gcgcc                    405
```

<210> SEQ ID NO 491
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 491

```
tctgctctgc ctggccgggc gcgccttggc ccaagtccag ttggtccagt ctggggcgga    60
ggtgaaaaag ccaggtagta gcgttaaagt ttcctgtaaa gcgtccggtt attcctttag    120
ctcctactat atgcactggg tccggcaggc cccaggacag gggcttgagt ggatgggaac    180
cattcatcct tcagactcca ctgctaacta taatcagaaa tttaaaggcc gcgttaccat    240
cacagttgac aaaagcacct ctacggccta tatggagctt tcttctttgc gatccgagga    300
caccgcggtg tattattgcg ctaactttgt atattgggc caggggacga cagttactgt    360
cagttcagcg agcaccaagg gcccctccgt gttcccgttg gcgcc                    405
```

<210> SEQ ID NO 492
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 492

```
tctgctctgc ctggccgggc gcgccttggc cgaggttcaa ctcttggaat caggggcgg    60 tttggttcag cccggcggat cactcaggct ttcctgtgcg catctgggt acaatttcgc    120 atcttactac atgcattggg tcagacaagc tccaggtaaa ggtttggaat gggtttccac    180
gatccatcct tccgacagta cgacgaatta cgctgacagc gttaagggca ggtttactat    240
```

```
cagtcgcgat aatagcaaga atacccttta tcttcaaatg aactccctta gagccgagga      300
taccgctgtc tattattgtg cgaacttcgt ctactgggc  cagggtacta cggtcaccgt      360
gagttcagcg agcaccaagg cccctccgt  gttcccgttg gcgcc                      405
```

```
<210> SEQ ID NO 493
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 493
tctgctctgc ctggccgggc gcgccttggc cgaagtccag cttttggaga gcggtggtgg      60
actggtgcag ccaggggat  ctcttcgctt gtcctgtgct gcctctggct ttacattttc      120
atcttattac atgcattggg ttcggcaagc tcctgggaag ggcttggagt gggtttccac      180
aattcatcca agcgatagca cgacgaacta taaccaaaag ttcaagggac gcttcactat      240
ctcaagagac aactctaaaa acaccgcata cttgcaaatg aacagcttga gagctgaaga      300
tacagcagtg tactattgtg caaatttcgt gtactgggc  caggggacta ctgtcactgt      360
atcatcagcg agcaccaagg cccctccgt  gttcccgttg gcgcc                      405
```

```
<210> SEQ ID NO 494
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 494
tctgctctgc ctggccgggc gcgccttggc ccaagttcaa ctggtggagt ccggaggcgg      60
tctggttaag cctggtggct ctctccgcct tagttgtgca gcttctggtt ttaccttcag      120
ctcctattat atgcactgga tcagacaagc tccgggcaag ggtcttgaat gggtcagtac      180
catacacccc tctgactcaa ccactaatta caaccagaag tttaaaggac gcttcaccat      240
cagcgtcgat aacgcgaaaa attcagctta tctccagatg aactccctgc gggctgaaga      300
tacagcagtc tactattgtg ccaacttcgt ttattgggga caaggcacaa ctgttactgt      360
cagttctgcg agcaccaagg cccctccgt  gttcccgttg gcgcc                      405
```

```
<210> SEQ ID NO 495
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 495
tctgctctgc ctggccgggc gcgccttggc ccaagtccaa cttgtgcaga gtggagcgga      60
ggtcaagaaa cccggcgctt ccgttaaagt ctcatgcaaa gcctcaggtt attctttctc      120
ctcatactat atgcactggg tgcgccaagc tcctggccaa ggtttggaat ggatgggaac      180
tattcacccc agcgactcca ctacgaacta cgcacagaag tttcaaggca gagttacgat      240
gacacgcgat acaagcactt caactgttta tatggaactg tcttctttga gaagtgaaga      300
cacagccgtc tattattgcg cgaacttcgt ctattgggga cagggcacca cagttaccgt      360
```
ttcaagcgcg agcaccaagg gcccctccgt gttcccgttg gcgcc            405

<210> SEQ ID NO 496
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 496
tctgctctgc ctggccgggc gcgccttggc ccaagtacag cttgtccagt caggtgcaga     60
ggtaaaaaag cccggcgcat cagtgaaggt atcttgtaaa gcgtccggtt attcattttc    120
atcttactac atgcattggg ttcggcaggc accgggacag ggcctggaat ggatggggac    180
gatccatcca tctgacagca caacaaatta caatcagaaa tttcaaggtc gggtcacaat    240
gaccgtggat acaagcacaa gaacagcata tatggaactg agctcacttc ggagtgaaga    300
tactgccgtg tattattgtg ctaatttcgt ctattggggg cagggacgca cggtgacagt    360
aagtagtgcg agcaccaagg gcccctccgt gttcccgttg gcgcc                   405

<210> SEQ ID NO 497
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 497
tctgctctgc ctggccgggc gcgccttggc ccaggtccaa ctcgtgcaaa gtggtgccga     60
ggtaaaaaag cccggcgcat cagtaaaggt gagttgcaag gcgtccggtt acacattcac    120
ttcatattac atgcactggg tgagacaagc gcctgggcag gcctggagt ggatggggac     180
aatccacccg tccgactcaa ccacgaacta caaccagaaa ttcaagggtc gcgtgaccat    240
gacagttgac acatcaacaa gcacggcgta tatggaactt cttccctca gaagtgagga     300
caccgctgta tactattgtg caaactttgt gtattggggg caaggcacta ccgtcacagt    360
atcatccgcg agcaccaagg gcccctccgt gttcccgttg gcgcc                   405

<210> SEQ ID NO 498
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 498
tctgctctgc ctggccgggc gcgccttggc ccaagtgcag ttggtacaat ctggagccga     60
ggtaaagaag ccaggagcct ccgtcaaagt gagttgtaag gcatctggct acaatttgc    120
ttcttactat atgcattggg ttcggcaggc accgggtcag gggcttgagt ggatggggac    180
tattcatccg tcagatagca cgactaacta taaccagaag tttaagggac gggtaaccat    240
gactgttgac acctccacgt ctacagcgta catggaactc tccagtcttc ggagcgaaga    300
cacagcggtc tactactgcg ctaactttgt ctactggggg caaggcacga ccgttacagt    360
atcttctgcg agcaccaagg gcccctccgt gttcccgttg gcgcc                   405

<210> SEQ ID NO 499

```
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 499
tctgctctgc ctggccgggc gcgccttggc cgaggtacag cttgtcgagt ccggcggtgg    60
acttgtaaaa cctggaggtt cacttaggtt gagttgtgct gcttccgggt atagtttcag   120
ttcttattac atgcattggg tacgacaggc tccaggaaaa gggttggagt gggtgggcac   180
aatacatcct agcgattcta ctaccaatta tgccgctccg gtgaaaggac gctttacgat   240
aagccgagac gatagcaaga acactgcata cttgcaaatg aatagtttga agaccgagga   300
cacggcggtg tactactgcg caaattttgt gtactgggga cagggaacga cagtcaccgt   360
ctctagtgcg agcaccaagg gcccctccgt gttcccgttg gcgcc              405

<210> SEQ ID NO 500
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 500
tctgctctgc ctggccgggc gcgccttggc cgatattgtc atgacacaaa ccccctgag    60 tcttagcgtc acccctgggc agcccgcttc aataagttgt aagtcctcta aatcattgct   120
gtataaagat gggaagacct atcttaactg gtttctccaa aagccagggc agtcaccaca   180
actgttgatc tacgttgtaa gcaccagggc gagtggagtc cccgacagat tcagtggtag   240
cggctctggt acagatttta ccttgaaaat atctagggtg gaagcggagg atgtcggtgt   300
ctactactgt cagcagctcg tagaatatcc atacacattt ggacaaggta cgaaactgga   360
gataaaacgt acggtggcag cgccttccgt gttc                              394

<210> SEQ ID NO 501
<211> LENGTH: 394
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 501
tctgctctgc ctggccgggc gcgccttggc cgacattgtc atgactcaaa caccgctctc    60
tctgtcagtg actccgggac aacctgcatc tataagctgt aaatctagta aatctctgct   120
ctacaaagat ggtaaaactt acctgaattg gttccttcaa aaaccaggcc aaagtccaca   180
acttctcatc tatgttgtgt ctactcgcgc aagtggcgta cccgacaggt tttccggtag   240
cggctcaggt accgacttca ctctcaaaat ttctcgagta gaagctgagg atgtcggcgt   300
ctactattgc caacaactcg tacaatatcc ataccccttc gggcagggaa ctaaactcga   360 aataagcgt acggtggcag cgccttccgt gttc                               394

<210> SEQ ID NO 502
<211> LENGTH: 394
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 502

```
tctgctctgc ctggccgggc gcgccttggc cgacatccaa atgactcaaa gtccaagcag      60
cctgtcagca tctgtggggg acagagtcac gataacctgc cgcgcgagta agagtctgct     120
ctacaaggac gggaaaacgt acctgaattg gtatcagcag aagccaggga agcaccgaa      180
gttgctgatt tacgttgtga gttccctcca atccggcgtc ccgagcagat tcagtgggag     240
cggcagcgga actgacttta cgcttaccat ctcctcactt caaccggaag acttcgccac     300
ttactactgt caacagcttg ttgagtaccc atacactttc ggtcagggga cgaaactgga     360
aatcaaacgt acggtggcag cgccttccgt gttc                                 394
```

<210> SEQ ID NO 503
<211> LENGTH: 379
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 503

```
tctgctctgc ctggccgggc gcgccttggc cgacatacag atgactcaga gcccgtccag      60
cctctctgcg tcagtcggtg atagggtcac gatcacatgt cgcgccagtc aaagcatatc     120
cagctacttg aactggttcc agcaaaagcc agggaaggca ccgaagctcc ttatatacgt     180
ggtcagtagt ctccaaagtg gtgttccttc acgctttagc ggtagcggca gtggtactga     240
ctttacactt acgattagca gtcttcagcc agaggatttt gcaacctact actgccagca     300
gctcgtcgag tatccgtata cgtttggtca gggaacgaag ctggagatca agcgtacggt     360
ggcagcgcct tccgtgttc                                                  379
```

<210> SEQ ID NO 504
<211> LENGTH: 397
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 504

```
tctgctctgc ctggccgggc gcgccttggc cgacatcgtt atgactcaaa gcccgctcag      60
ccttcccgtg acccctggcg agccggcgtc tatatcctgt cggtcttctc aatctttgtt     120
ggattccgat gacggtaaca catacctgaa ttggttcctt cagaaaccgg ccagtcccc      180
acaacttctc atatacgtgt tgagcaacag ggcttcaggc gtacccgata ggttttccgg     240
tagtggatca ggaaccgatt tcacattgaa aatcagcaga gtagaagccg aggacgtagg     300
tgtttactat tgtcagcaac ttgtagagta cccatacacc ttcggtcagg gcaccaaatt     360
ggaaattaag cgtacggtgg cagcgccttc cgtgttc                              397
```

<210> SEQ ID NO 505
<211> LENGTH: 394
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 505

```
tctgctctgc ctggccgggc gcgccttggc cgacattgtg atgacgcaga ccccattgtc    60
actgcccgtt accccagggg aaccggcaag catatcatgt cgatcaagtc aatctctttt   120
gtacaaggac gggaaaacat atctgaattg gttcttgcag aagcctggtc aatctccgca   180
gttgttgatt tatgtgctct caacaagggc gtccggggta cccgacagat ttagtgggag   240
cggttctggc acggatttca ctttgaaaat atccagggtt gaagccgaag atgtcggagt   300
ctattattgt cagcaactcg tagagtatcc ctacactttc gggcagggca caaaacttga   360
gattaagcgt acggtggcag cgccttccgt gttc                               394
```

<210> SEQ ID NO 506  
<211> LENGTH: 394  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 506

```
tctgctctgc ctggccgggc gcgccttggc cgacattgtc atgacacagt caccggatag    60
tttggccgtc tccctgggtg aacgggccac gataaactgc aaatccagtc agtccctgct   120
ctataaggac gggaagacct acttgaactg gttccaacag aagccaggcc agcctcccaa   180
attgctcatt tacgtcgtaa gcacaagggc aagtggagta ccagacaggt tctcaggaag   240
tgggagcggc acagacttca cgcttaccat ctccagtctg caggcagagg atgtagctgt   300
gtactattgc caacaacttg tagaataccc ttacacgttc ggacagggga ccaaacttga   360
gataaagcgt acggtggcag cgccttccgt gttc                               394
```

<210> SEQ ID NO 507  
<211> LENGTH: 397  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 507

```
tctgctctgc ctggccgggc gcgccttggc cgatattgtg atgactcaat caccggacag    60
cttggcagta agcctcgggg agcgagccac aataaactgc aaatcctccc aaagtgttct   120
ctatagcagt aacaataaga attaccttaa ttggttccaa caaaaacccg gtcagccacc   180
aaaactgctc atatatgtgg tgtccacaag ggcttcagga gttcccgacc gattcagcgg   240
aagcgggagt ggcacggatt ttacacttac catctcttcc cttcaagcgg aagacgtcgc   300
ggtgtactac tgtcaacaac ttgtagaata cccttacacg ttcgggcagg gcaccaaaact   360 ggagattaag cgtacggtgg cagcgccttc cgtgttc                             397
```

<210> SEQ ID NO 508  
<211> LENGTH: 3  
<212> TYPE: PRT  
<213> ORGANISM: Artificial Sequence  
<220> FEATURE:  
<223> OTHER INFORMATION: Description of Artificial Sequence: Synthetic peptide

<400> SEQUENCE: 508

Phe Val Tyr  
1

```
<210> SEQ ID NO 509
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Thr Ile His Pro Ser Asp Ser Thr Ala Asn Tyr Asn Gln Lys Phe Lys
1               5                   10                  15

Gly

<210> SEQ ID NO 510
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Lys Ser Ser Lys Ser Leu Leu Tyr Lys Asp Gly Lys Thr Tyr Leu Asn
1               5                   10                  15

<210> SEQ ID NO 511
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Gln Gln Leu Val Gln Tyr Pro Tyr Thr
1               5

<210> SEQ ID NO 512
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Lys Ser Ser Gln Ser Leu Leu Tyr Lys Asp Gly Lys Thr Tyr Leu Asn
1               5                   10                  15

<210> SEQ ID NO 513
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Thr Ile His Pro Ser Asp Ser Thr Thr Asn Tyr Ala Gln Lys Phe Gln
1               5                   10                  15

Gly

<210> SEQ ID NO 514
<211> LENGTH: 17
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 514

Thr Ile His Pro Ser Asp Ser Thr Thr Asn Tyr Asn Gln Lys Phe Gln
1               5                   10                  15

Gly

<210> SEQ ID NO 515
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Arg Ala Ser Lys Ser Leu Leu Tyr Lys Asp Gly Lys Thr Tyr Leu Asn
1               5                   10                  15

<210> SEQ ID NO 516
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Val Val Ser Ser Leu Gln Ser
1               5

<210> SEQ ID NO 517
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Gly Tyr Asn Phe Ala Ser Tyr
1               5

<210> SEQ ID NO 518
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Ser Tyr Tyr Ile His
1               5

<210> SEQ ID NO 519
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Thr Ile His Pro Ser Asp Ser Thr Ala Asn Tyr Ala Gln Lys Phe Gln

```
                1               5                    10                  15

Gly

<210> SEQ ID NO 520
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Arg Ser Ser Gln Ser Leu Leu Tyr Lys Asp Gly Lys Thr Tyr Leu Asn
 1               5                   10                  15

<210> SEQ ID NO 521
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Val Leu Ser Thr Arg Ala Ser
 1               5

<210> SEQ ID NO 522
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (4)..(4)
<223> OTHER INFORMATION: Lys or Gln

<400> SEQUENCE: 522

Xaa Xaa Ser Xaa Ser Leu Leu Tyr Lys Asp Gly Lys Thr Tyr Leu Asn
 1               5                   10                  15

<210> SEQ ID NO 523
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Val
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Leu or Arg
<220> FEATURE:
```

```
<221> NAME/KEY: MOD_RES
<222> LOCATION: (6)..(6)
<223> OTHER INFORMATION: Ala or Gln

<400> SEQUENCE: 523

Val Xaa Ser Xaa Xaa Xaa Ser
1               5

<210> SEQ ID NO 524
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glu or Gln

<400> SEQUENCE: 524

Gln Gln Leu Val Xaa Tyr Pro Tyr Thr
1               5

<210> SEQ ID NO 525
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ile or Met

<400> SEQUENCE: 525

Ser Tyr Tyr Xaa His
1               5

<210> SEQ ID NO 526
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (12)..(12)
<223> OTHER INFORMATION: Ala or Asn
<220> FEATURE:
<221> NAME/KEY: MOD_RES
<222> LOCATION: (16)..(16)
<223> OTHER INFORMATION: Lys or Gln

<400> SEQUENCE: 526

Thr Ile His Pro Ser Asp Ser Thr Xaa Asn Tyr Xaa Gln Lys Phe Xaa
1               5                   10                  15
Gly

<210> SEQ ID NO 527
<211> LENGTH: 442
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 527

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Pro | Gly | Ala |
| 1 | | | | 5 | | | | | 10 | | | | | 15 |
| Ser | Val | Lys | Val | Ser | Cys | Lys | Ala | Ser | Gly | Tyr | Ser | Phe | Ser | Tyr |
| | | | 20 | | | | | 25 | | | | | 30 | |
| Tyr | Met | His | Trp | Val | Arg | Gln | Ala | Pro | Gly | Gln | Gly | Leu | Glu | Trp | Met |
| | | 35 | | | | | 40 | | | | | 45 | | |
| Gly | Thr | Ile | His | Pro | Ser | Asp | Ser | Thr | Thr | Asn | Tyr | Asn | Gln | Lys | Phe |
| | 50 | | | | | 55 | | | | | 60 | | | | |
| Gln | Gly | Arg | Val | Thr | Met | Thr | Val | Asp | Thr | Ser | Thr | Arg | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Asn | Phe | Val | Tyr | Trp | Gly | Gln | Gly | Thr | Thr | Val | Thr | Val | Ser | Ser |
| | | | 100 | | | | | 105 | | | | | 110 | | |
| Ala | Ser | Thr | Lys | Gly | Pro | Ser | Val | Phe | Pro | Leu | Ala | Pro | Ser | Ser | Lys |
| | | 115 | | | | | 120 | | | | | 125 | | | |
| Ser | Thr | Ser | Gly | Gly | Thr | Ala | Ala | Leu | Gly | Cys | Leu | Val | Lys | Asp | Tyr |
| | 130 | | | | | 135 | | | | | 140 | | | | |
| Phe | Pro | Glu | Pro | Val | Thr | Val | Ser | Trp | Asn | Ser | Gly | Ala | Leu | Thr | Ser |
| 145 | | | | | 150 | | | | | 155 | | | | | 160 |
| Gly | Val | His | Thr | Phe | Pro | Ala | Val | Leu | Gln | Ser | Ser | Gly | Leu | Tyr | Ser |
| | | | | 165 | | | | | 170 | | | | | 175 | |
| Leu | Ser | Ser | Val | Val | Thr | Val | Pro | Ser | Ser | Ser | Leu | Gly | Thr | Gln | Thr |
| | | | 180 | | | | | 185 | | | | | 190 | | |
| Tyr | Ile | Cys | Asn | Val | Asn | His | Lys | Pro | Ser | Asn | Thr | Lys | Val | Asp | Lys |
| | | 195 | | | | | 200 | | | | | 205 | | | |
| Arg | Val | Glu | Pro | Lys | Ser | Cys | Asp | Lys | Thr | His | Thr | Cys | Pro | Pro | Cys |
| | 210 | | | | | 215 | | | | | 220 | | | | |
| Pro | Ala | Pro | Glu | Leu | Leu | Gly | Gly | Pro | Ser | Val | Phe | Leu | Phe | Pro | Pro |
| 225 | | | | | 230 | | | | | 235 | | | | | 240 |
| Lys | Pro | Lys | Asp | Thr | Leu | Met | Ile | Ser | Arg | Thr | Pro | Glu | Val | Thr | Cys |
| | | | | 245 | | | | | 250 | | | | | 255 | |
| Val | Val | Val | Asp | Val | Ser | His | Glu | Asp | Pro | Glu | Val | Lys | Phe | Asn | Trp |
| | | | 260 | | | | | 265 | | | | | 270 | | |
| Tyr | Val | Asp | Gly | Val | Glu | Val | His | Asn | Ala | Lys | Thr | Lys | Pro | Arg | Glu |
| | | 275 | | | | | 280 | | | | | 285 | | | |
| Glu | Gln | Tyr | Asn | Ser | Thr | Tyr | Arg | Val | Val | Ser | Val | Leu | Thr | Val | Leu |
| | 290 | | | | | 295 | | | | | 300 | | | | |
| His | Gln | Asp | Trp | Leu | Asn | Gly | Lys | Glu | Tyr | Lys | Cys | Lys | Val | Ser | Asn |
| 305 | | | | | 310 | | | | | 315 | | | | | 320 |
| Lys | Ala | Leu | Pro | Ala | Pro | Ile | Glu | Lys | Thr | Ile | Ser | Lys | Ala | Lys | Gly |
| | | | | 325 | | | | | 330 | | | | | 335 | |
| Gln | Pro | Arg | Glu | Pro | Gln | Val | Tyr | Thr | Leu | Pro | Pro | Ser | Arg | Glu | Glu |
| | | | 340 | | | | | 345 | | | | | 350 | | |
| Met | Thr | Lys | Asn | Gln | Val | Ser | Leu | Thr | Cys | Leu | Val | Lys | Gly | Phe | Tyr |
| | | 355 | | | | | 360 | | | | | 365 | | | |
| Pro | Ser | Asp | Ile | Ala | Val | Glu | Trp | Glu | Ser | Asn | Gly | Gln | Pro | Glu | Asn |
| | 370 | | | | | 375 | | | | | 380 | | | | |
| Asn | Tyr | Lys | Thr | Thr | Pro | Pro | Val | Leu | Asp | Ser | Asp | Gly | Ser | Phe | Phe |
| 385 | | | | | 390 | | | | | 395 | | | | | 400 |

```
Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
        420                 425                 430

Gln Lys Ser Leu Ser Leu Ser Pro Gly Lys
        435                 440
```

<210> SEQ ID NO 528
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Lys Ser Leu Leu Tyr Lys
            20                  25                  30

Asp Gly Lys Thr Tyr Leu Asn Trp Phe Leu Gln Lys Pro Gly Gln Ser
        35                  40                  45

Pro Gln Leu Leu Ile Tyr Val Val Ser Thr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Leu
                85                  90                  95

Val Glu Tyr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 529
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 530
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Glu Pro Lys Ser Cys Asp Lys Thr His Thr Cys Pro Pro Cys Pro
1               5                   10                  15

<210> SEQ ID NO 531
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 532
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
```

```
                35                  40                  45
Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
                100                 105

<210> SEQ ID NO 533
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Arg Thr Val Ala Ala Pro
1               5

<210> SEQ ID NO 534
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Ser Val Phe Ile Phe Pro Pro Ser Asp Glu Gln Leu Lys Ser Gly Thr
1               5                  10                  15

Ala Ser Val Val Cys Leu Leu Asn Asn Phe Tyr Pro Arg Glu Ala Lys
                20                  25                  30

Val Gln Trp Lys Val Asp Asn Ala Leu Gln Ser Gly Asn Ser Gln Glu
        35                  40                  45

Ser Val Thr Glu Gln Asp Ser Lys Asp Ser Thr Tyr Ser Leu Ser Ser
    50                  55                  60

Thr Leu Thr Leu Ser Lys Ala Asp Tyr Glu Lys His Lys Val Tyr Ala
 65                  70                  75                  80

Cys Glu Val Thr His Gln Gly Leu Ser Ser Pro Val Thr Lys Ser Phe
                 85                  90                  95

Asn Arg Gly Glu Cys
                100
```

HUMANIZED ANTIBODY MOLECULES TO CD138 AND USES THEREOF

CROSS REFERENCE TO RELATED APPLICATIONS

This application claims the benefit of U.S. Provisional Application No. 62/862,457, filed Jun. 17, 2019, and U.S. Provisional Application No. 63/035,323, filed Jun. 5, 2020. The contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 12, 2020, is named P2029-702910_SL.txt and is 125,400 bytes in size.

BACKGROUND

Multiple myeloma (MM) is a cancer formed by malignant plasma cells. These tumors generally develop in bone, but occasionally are found in other tissues. Disease with a single plasma cell tumor is known as an isolated (or solitary) plasmacytoma. When more than one plasmacytoma is present, it is known as multiple myeloma. In the United States, the estimated new cases are about 30,000 in 2017 and more than 10,000 deaths are expected to occur. Despite treatment advances in multiple myeloma therapy, multiple myeloma remains an incurable disease in most patients.

There is a need for developing new approaches for treating, preventing and diagnosing multiple myeloma and other disorders that share similar disease mechanisms.

SUMMARY

This disclosure provides, at least in part, humanized antibody molecules that bind to CD138, e.g., human CD138, and that comprise one or more properties, e.g., one or more functional, biophysical, and structural properties disclosed herein. For example, the humanized antibody molecules described herein can have reduced immunogenicity, greater therapeutic efficacy (e.g., lower tumor burden and/or increased overall survival), improved target binding (e.g., affinity), improved in vitro or in vivo stability, and higher mammalian recombinant expression levels. In an embodiment, the antibody molecule is capable of causing an effector function (e.g., an antibody-dependent cellular cytotoxicity (ADCC) activity) on a cell expressing CD138. In an embodiment, the antibody molecule preferentially binds to a membrane-bound CD138 versus a soluble CD138. In an embodiment, the antibody molecule binds to an epitope in an extracellular region of CD138 that is proximal to the transmembrane domain In an embodiment, the antibody molecule does not bind to the integrin binding domain (IBD) of CD138. In an embodiment, the antibody molecule does not bind exclusively to the IBD of CD138. While not wishing to be bound by theory, it is believed that in an embodiment, improved or optimal cytotoxicity can be achieved, by targeting certain extracellular region(s) on membrane-bound CD138 that is proximal to the cell membrane.

In an embodiment, the antibody molecule is selected from Table 1, or competes for binding to CD138 with an anti-CD138 monoclonal antibody selected from Table 1. In an embodiment, the antibody molecule binds to the same or overlapping epitope as the epitope recognized by an anti-CD138 monoclonal antibody selected from Table 1. In an embodiment, the antibody molecule comprises one or more heavy chain variable regions (VHs) and/or one or more light chain variable regions (VLs) described in Table 1. In an embodiment, the antibody molecule comprises the heavy chain (HC) and the light chain (LC) described in Tables 6-8. In an embodiment, the antibody molecule comprises one or more heavy chain CDRs and/or one or more light chain CDRs described in Tables 1. 7 or 8.

In an embodiment, the antibody molecule comprises a heavy chain variable region (VH) comprising an amino acid sequence selected from Table 2, or competes for binding to CD138 with an anti-CD138 monoclonal antibody comprising a VH comprising an amino acid sequence selected from Table 2. In an embodiment, the antibody molecule comprises a light chain variable region (VL) comprising an amino acid sequence selected from Table 2, or competes for binding to CD138 with an anti-CD138 monoclonal antibody comprising a VL comprising an amino acid sequence selected from Table 2. In an embodiment, the antibody molecule comprises a VH and a VL, each comprising an amino acid sequence selected from Table 2, or competes for binding to CD138 with an anti-CD138 monoclonal antibody comprising a VH and a VL, each comprising an amino acid sequence selected from Table 2. In an embodiment, the antibody molecule binds to the same or overlapping epitope as the epitope recognized by an anti-CD138 monoclonal antibody comprising a VH and/or a VL, each comprising an amino acid sequence selected from Table 2. In an embodiment, the antibody molecule comprises one or more (e.g., 1, 2, or 3) heavy chain CDRs and/or one or more (e.g., 1, 2, or 3) light chain CDRs described in Table 2.

In an embodiment, the antibody molecule comprises a heavy chain (HC) comprising an amino acid sequence selected from Table 6 or 7, or competes for binding to CD138 with an anti-CD138 monoclonal antibody comprising an HC comprising an amino acid sequence selected from Table 6 or 7. In an embodiment, the antibody molecule comprises a light chain (LC) comprising an amino acid sequence selected from Table 6 or 8, or competes for binding to CD138 with an anti-CD138 monoclonal antibody comprising a LC comprising an amino acid sequence selected from Table 6 or 8. In an embodiment, the antibody molecule comprises an HC and an LC, each comprising an amino acid sequence selected from Table 6 or 7 or Table 6 or 8, or competes for binding to CD138 with an anti-CD138 monoclonal antibody comprising an HC and an LC, each comprising an amino acid sequence selected from Table 6 or 7 or Table 6 or 8. In an embodiment, the antibody molecule binds to the same or overlapping epitope as the epitope recognized by an anti-CD138 monoclonal antibody comprising an HC and/or an LC, each comprising an amino acid sequence selected from Table 6 or 7 or Table 6 or 8. In an embodiment, the antibody molecule comprises one or more (e.g., 1, 2, or 3) heavy chain CDRs and/or one or more (e.g., 1, 2, or 3) light chain CDRs described in Table 7 or 8.

In an embodiment, antibody molecule-drug conjugates (ADCs), nucleic acid molecules encoding the antibody molecules, expression vectors, host cells, compositions (e.g., pharmaceutical compositions), kits, containers, and methods for making the antibody molecules, are also provided. The antibody molecules disclosed herein can be used (alone or in combination with other agents or therapeutic modalities) to treat, prevent and/or diagnose disorders associated with CD138, e.g., cancer or precancerous conditions (e.g., multiple myeloma or smoldering myeloma).

Accordingly, in certain aspects, this disclosure provides a humanized antibody molecule, e.g., a humanized antibody molecule described herein, having one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or all) of the following properties a)-dd):

a) Binds to CD138 (e.g., human CD138) with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, b) Binds to a membrane-bound CD138 with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM, c) Binds to a soluble CD138 i) with high affinity, e.g., with a dissociation constant ($K_D$) of less than about 100 nM, typically about 10 nM, and more typically, about 10-0.001 nM, about 10-0.01 nM, about 5-0.01 nM, about 3-0.05 nM, about 1-0.1 nM, or stronger, e.g., less than about 80, 70, 60, 50, 40, 30, 20, 10, 8, 6, 4, 3, 2, 1, 0.5, 0.2, 0.1, 0.05, 0.01, 0.005, or 0.001 nM; or ii) with low affinity, e.g., with a dissociation constant ($K_D$) of greater than about 100 nM, e.g., greater than about 200, 300, 400, or 500 nM, d) Binds to a membrane-bound CD138, or an intact ectodomain of CD138, i) preferably over a soluble CD138, e.g., the binding affinity to a membrane-bound CD138, or an intact ectodomain of CD138, is at least 2, 3, 4, 5, 6, 7, 8, 9, or 10-fold higher than the binding affinity to a soluble CD138; or ii) with a binding affinity similar to the binding affinity to a soluble CD138, e.g., the binding affinity to a membrane-bound CD138, or an intact ectodomain of CD138, is less than about 10%, 20%, 30%, 40%, 50%, 60%, 70%, 80%, 90%, or 100% higher than the binding affinity to a soluble CD138, e) Binds to one or more (e.g., 2, 3, 4, 5, 6, 7, 8, 9, 10, 11, 12, 13, 14, 15, 20, 25, 30, 35, 40, 45, 50, 55, 60, 65, 70, 75, or more) amino acid residues of CD138 in an extracellular region proximal to the transmembrane domain of CD138, e.g., within 75, 70, 65, 60, 55, 50, 45, 40, 35, 30, 25, 20, 15, 10, or 5 amino acids from the N-terminus of the transmembrane domain, f) i) Binds to an extracellular region of CD138 distant from the transmembrane domain, e.g., the C-terminus of the region is at least 100, 110, 120, 130, 140, 150, 160, 170, 180, 190, or 200 amino acids from the N-terminus of the transmembrane domain; or ii) does not bind, or binds with low affinity, to an extracellular region of CD138 distant from the transmembrane domain, e.g., the C-terminus of the region is at least 100, 110, 120, 130, 140, 150, 160, 170, 180, 190, or 200 amino acids from the N-terminus of the transmembrane domain, g) Binds to the integrin binding domain (IBD) of CD138 or a region N-terminal to the IBD; or ii) does not bind, or binds with low affinity, to the IBD of CD138 or a region N-terminal to the IBD, h) Binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in an extracellular region proximal to the transmembrane domain, e.g., a region comprising amino acids 176-250 (e.g., 176-214 or 210-250) of any of SEQ ID NOS: 1-3 or 450, optionally, wherein the epitope further comprises four or more (e.g., 5, 6, 7, 8, 9, 10, 11, 12, 13, 14, 15, 20, 25, 30, 35, or more) consecutive amino acid residues in an extracellular region distant from the transmembrane domain, e.g., a region comprising amino acids 23-50, 51-95, 88-121, 88-102, or 111-150 of any of SEQ ID NOS: 1-3 or 450, i) Binds to two or more different regions in CD138, e.g., a multivalent (e.g., bivalent, trivalent, or tetravalent) antibody molecule comprising two sets of identical, or substantially identical, VH-VL pairs that each bind to the same two or more regions, or comprising different sets of VH-VL pairs that each independently bind to different regions, j) Does not bind to an epitope on CD138 comprising four or more (e.g., 5, 6, 7, 8, 9, 10, 11, 12, 13, 14, 15, 20, 25, 30, 35, or more) consecutive amino acid residues in an extracellular region distant from the transmembrane domain, e.g., a region comprising amino acids 23-50, 51-95, 88-121, 88-101, or 111-150 of any of SEQ ID NOS: 1-3 or 450, k) Binds to a cancer or precancerous cell (e.g., a myeloma cell) expressing CD138 with high affinity, l) Binds to an Fc receptor (FcR) (e.g., one or more of FcγRI, FcγRIIa, FcγRIIb, FcγRIIc, FcγRIIIa, or FcγRIIIb) on the surface of an immune cell (e.g., a natural killer (NK) cell, a macrophage, a monocyte, or an eosinophil), m) Causes an effector function (e.g., an ADCC activity) on a target cell expressing CD138, n) Binds to C1q and causes complement-dependent cytotoxicity (CDC) on a target cell expressing CD138, o) Mediates homotypic adhesion of one or more CD138-expressing cells, p) Inhibits the action of a protease on a membrane-bound CD138, e.g., to reduce shedding of CD138;

q) Reduces (e.g., inhibits) one or more biological activities of a cell expressing CD138, in vitro, ex vivo, or in vivo, r) Reduces (e.g., inhibits) one or more functions of CD138 (e.g., binding of CD138 to a ligand), in vitro, ex vivo, or in vivo, s) Reduces (e.g., inhibits) proliferation of a cancer or precancerous cell expressing CD138, t) Binds to the same, similar, or overlapping epitope on CD138 as the epitope recognized by an anti-CD138 monoclonal antibody described herein, u) Shows the same or similar binding affinity or specificity, or both, as an anti-CD138 monoclonal antibody described herein, v) Shows the same or similar binding affinity or specificity, or both, as a humanized antibody molecule comprising a heavy chain variable region and/or light chain variable region described herein, e.g., a heavy chain variable region and/or light chain variable region of any of the anti-CD138 monoclonal antibodies described herein, w) Shows the same or similar binding affinity or specificity, or both, as a humanized antibody molecule comprising one or more (e.g., two or three) heavy chain CDRs and/or one or more (e.g., two or three) light chain CDRs described herein, e.g., one or more (e.g., two or three) heavy chain CDRs and/or one or more (two or three) light chain CDRs of any of the anti-CD138 monoclonal antibodies described herein, x) Shows the same or similar binding affinity or specificity, or both, as a humanized antibody molecule comprising an amino acid sequence described herein, y) Shows the same or similar binding affinity or specificity, or both, as a humanized antibody molecule comprising an amino acid sequence encoded by a nucleotide sequence described herein, z) Inhibits, e.g., competitively inhibits, the binding of a second antibody molecule to CD138, wherein the second antibody molecule is a humanized antibody molecule described herein, aa) Competes for binding with a second antibody molecule to CD138, wherein the second antibody molecule is a humanized anti-CD138 monoclonal antibody described herein, bb) Has one or more biological properties of a humanized anti-CD138 monoclonal antibody described herein, cc) Has one or more structural properties of a humanized anti-CD138 monoclonal antibody described herein, or dd) Has one or more pharmacokinetic properties of a humanized anti-CD138 monoclonal antibody described herein.

In an aspect, the disclosure features a humanized anti-CD138 antibody molecule comprising one or both of:

(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of an anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422, e.g., as listed in Table 1 or 2; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; or (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody.

In an embodiment, the VH comprises: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the VL comprises: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the antibody molecule comprises:

(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody, and (b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

In an embodiment, the antibody molecule comprises: (a) a VH comprising: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody. In an embodiment, the antibody molecule the VH comprises the amino acid sequence of the VH of the anti-CD138 antibody.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL of the anti-CD138 antibody. In an embodiment, the VL comprises the amino acid sequence of the VL of the anti-CD138 antibody.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL of the anti-CD138 antibody.

In an embodiment, the VH comprises the amino acid sequence of the VH of the anti-CD138 antibody and the VL comprises the amino acid sequence of the VL of the anti-CD138 antibody.

In an embodiment, the antibody molecule comprises an Fc region (e.g., an Fc region described herein). In an embodiment, the antibody molecule comprises a heavy chain constant region of IgG, e.g., IgG1. In an embodiment, the antibody molecule comprises a light chain constant region of kappa.

In an embodiment, the antibody molecule comprises a heavy chain (HC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the HC of the anti-CD138 antibody. In an embodiment, the HC comprises the amino acid sequence of the HC of the anti-CD138 antibody.

In an embodiment, the antibody molecule comprises a light chain (LC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the LC of the anti-CD138 antibody. In an embodiment, the LC comprises the amino acid sequence of the LC of the anti-CD138 antibody.

In an embodiment, the antibody molecule comprises (a) a heavy chain (HC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the HC of the anti-CD138 antibody; and (b) a light chain (LC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the LC of the anti-CD138 antibody. In an embodiment, the HC comprises the amino acid sequence of the HC of the anti-CD138 antibody and the LC comprises the amino acid sequence of the LC of the anti-CD138 antibody.

In an embodiment, the antibody molecule comprises (a) a heavy chain (HC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of SEQ ID NO: 527; and/or (b) a light chain (LC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of SEQ ID NO:528. In an embodiment, the HC comprises the amino acid sequence of SEQ ID NO: 527 or the LC comprises the amino acid sequence of SEQ ID NO: 528. In an embodiment, the HC comprises the amino acid sequence of SEQ ID NO: 527 and the LC comprises the amino acid sequence of SEQ ID NO: 528.

In an aspect, the disclosure features an antibody molecule, which competes for binding to CD138 with a humanized anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422).

In an aspect, the disclosure features an antibody molecule, which binds, or substantially binds, to an epitope that completely or partially overlaps with the epitope of a humanized anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422).

In an aspect, the disclosure features an antibody-molecule drug conjugate (ADC) comprising a humanized antibody molecule described herein, optionally comprising a cytotoxic agent, further optionally comprising a linker.

In an aspect, the disclosure features a composition comprising a humanized antibody molecule described herein, or an ADC described herein, optionally, wherein the composition is a pharmaceutical composition.

In an embodiment, the composition further comprises a pharmaceutically acceptable carrier.

In an aspect, the disclosure features a nucleic acid molecule encoding a heavy chain variable region (VH), a light chain variable region (VL), or both, of a humanized antibody molecule described herein.

In an aspect, the disclosure features a vector comprising a nucleic acid molecule described herein.

In an aspect, the disclosure features a cell comprising a nucleic acid molecule described herein or a vector described herein, optionally, wherein the cell is an isolated cell.

In an aspect, the disclosure features a kit comprising a humanized antibody molecule described herein, an ADC described herein, or a composition described herein, and instructions to use of the antibody molecule or composition.

In an aspect, the disclosure features a container comprising a humanized antibody molecule described herein, an ADC described herein, or a composition described herein.

In an aspect, the disclosure features a method of producing a humanized anti-CD138 antibody molecule, the method comprising culturing a cell described herein under conditions that allow production of a humanized antibody molecule, thereby producing the antibody molecule.

In an embodiment, the method further comprises isolating or purifying the antibody molecule.

In an aspect, the disclosure features a humanized antibody molecule of described herein, an ADC described herein, or a composition described herein, for use in a method of treating a cancer in a subject.

In an embodiment, the cancer is a hematological cancer. In an embodiment, the cancer is a multiple myeloma. In an embodiment, the cancer is a solid tumor, e.g., a solid tumor described herein. In an embodiment, the antibody molecule reduces tumor burden in a subject, e.g., a subject having multiple myeloma.

In an embodiment, the antibody molecule, ADC, or composition is administered to the subject intravenously. In an embodiment, the antibody molecule is administered to the subject intraperitoneally.

In an embodiment, the antibody molecule, ADC, or composition is administered to the subject at a dose between 0.1 mg/kg and 50 mg/kg, between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg. In an embodiment, the antibody molecule, ADC, or composition is administered at a dose of between 1 and 50 mg/kg, e.g., between 1 and 40 mg/kg, between 1 mg/kg and 30 mg/kg, between 1 mg/kg and 20 mg/kg, between 1 mg/kg and 10 mg/kg, or between 1 mg/kg and 5 mg/kg. In an embodiment, the antibody molecule is administered at a dose of about 4 mg/kg, e.g., about 1, 2, 3, 4, 5, 6, 7, 8, 9, 10, 11, 12, 13, 14, 15, 16, 17, 18, 19, or 20 mg/kg.

In an embodiment, the antibody molecule, ADC, or composition is administered to the subject at a fixed dose between 10 mg and 1000 mg, between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg.

In an embodiment, the antibody molecule, ADC, or composition is administered once a week, twice a week, once every two weeks, once every three weeks, or once every four weeks.

In an embodiment, the use further comprises determining the level of CD138 in a sample from the subject. In an embodiment, the use further comprises administering to the subject a second therapy for cancer.

In an aspect, the disclosure features a humanized antibody molecule described herein, an ADC described herein, or a composition described herein, for use in a method of treating a precancerous condition or preventing a cancer.

In an embodiment, the precancerous condition is smoldering myeloma or monoclonal gammopathy of undetermined significance (MGUS). In an embodiment, the cancer is multiple myeloma.

In an aspect, the disclosure features a method of causing an ADCC activity, the method comprising contacting a cell or subject a humanized antibody molecule described herein, an ADC described herein, or a composition described herein, thereby causing the ADCC activity.

In an aspect, the disclosure features a method of treating a cancer, the method comprising administering to a subject in need thereof an effective amount of a humanized antibody molecule described herein, an ADC described herein, or a composition described herein, thereby treating the cancer.

In an aspect, the disclosure features a method of treating a precancerous condition or preventing a cancer, the method comprising administering to a subject in need thereof an effective amount of a humanized antibody molecule described herein, an ADC described herein, or a composition described herein, thereby treating the precancerous condition or preventing the cancer.

In an aspect, the disclosure features, a method of detecting an anti-CD138 molecule, the method comprising contacting a cell or a subject with a humanized antibody molecule described herein, thereby detecting the CD138 molecule.

In an embodiment, the antibody molecule is coupled with a detectable label. In an embodiment, the CD138 molecule is detected in vitro, ex vivo, or in vivo.

The disclosure contemplates all combinations of any one or more of the foregoing aspects and/or embodiments, as well as combinations with any one or more of the embodiments set forth in the detailed description and examples.

Other features, objects, and advantages of the compositions and methods herein will be apparent from the description and drawings, and from the claims.

and does not imply lack of tumor burden at day 14 (day of staging and prior to first dose). All animals in vehicle control group were deceased by day 53.

Figure 20:
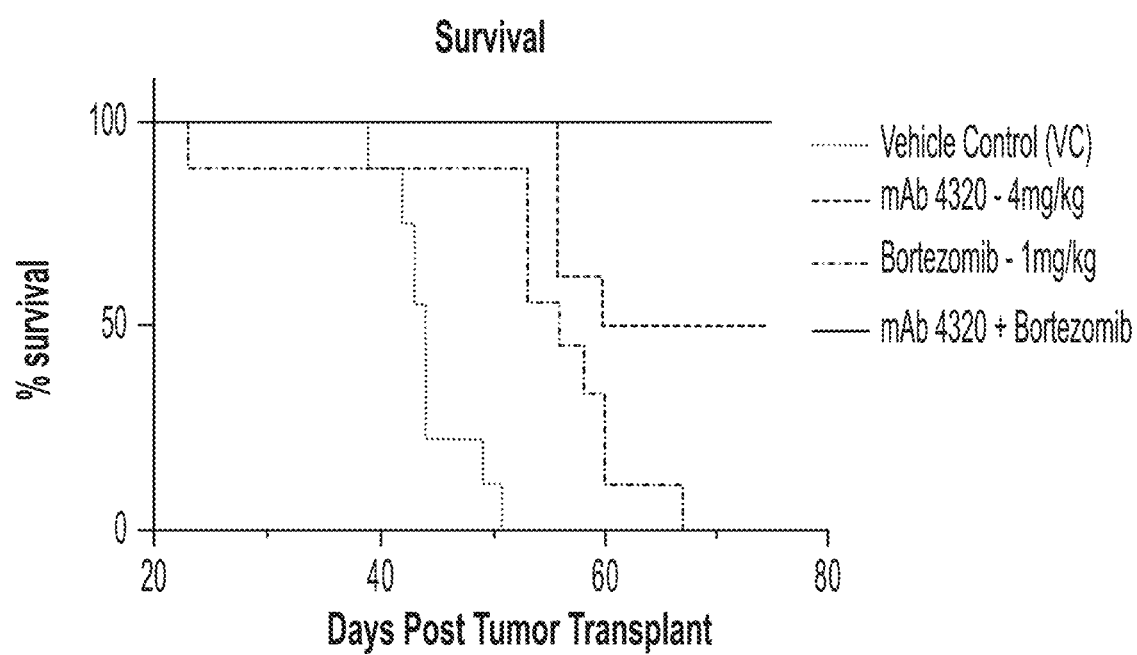

FIG. 20 is a graph showing survival over time in mice given the indicated treatments as Kaplan-Meier survival curves. Treatment was discontinued on day 53. Percent survival was defined as mice surviving to a pre-determined euthanasia criterion related to disease-related morbidity such as weight loss >20%, severely impaired CNS function or severely impaired movement or loss of righting reflexes.

Figure 21:
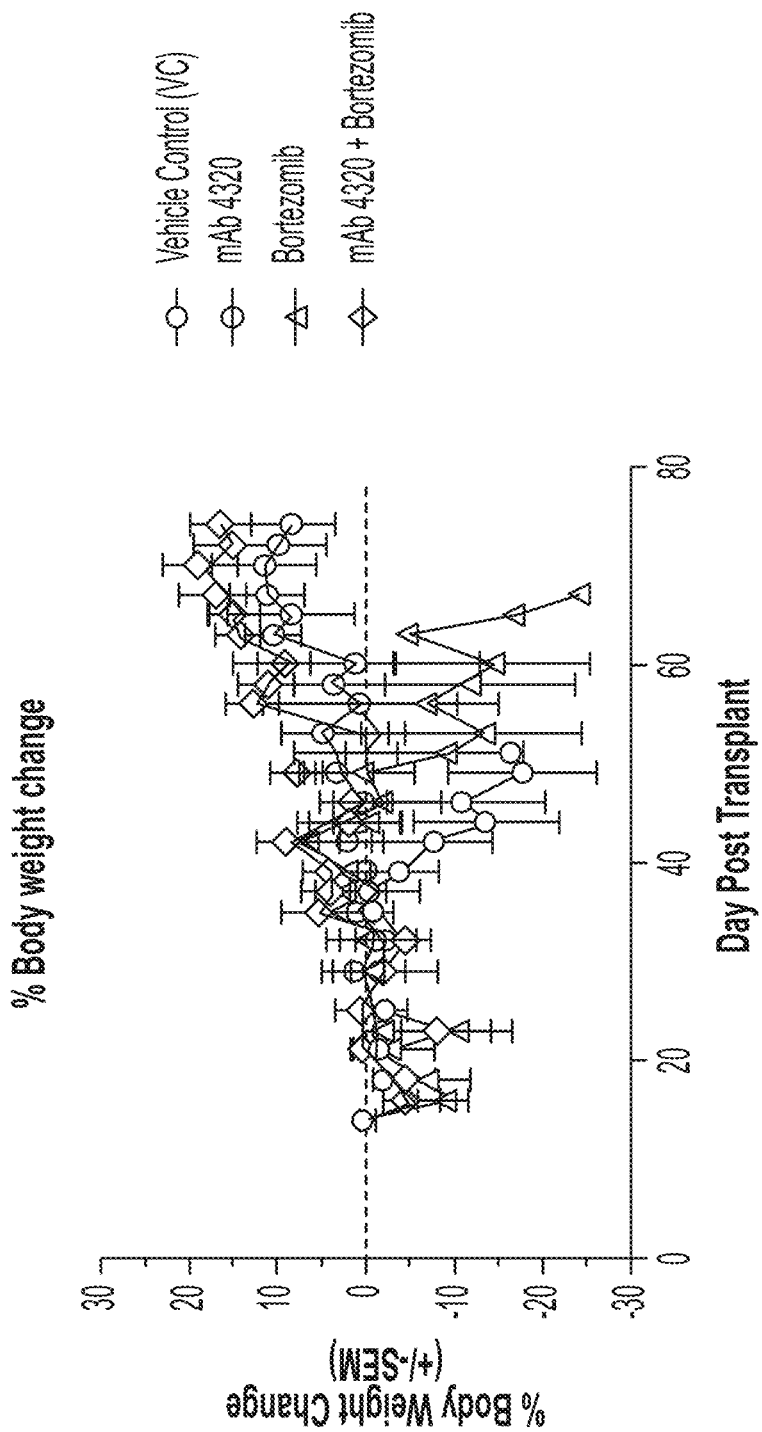

FIG. 21 is a graph showing change in animal body weight after being administered the indicated treatments. Percent change in body weight was plotted as standard error of the means. The largest change in body weight was observed for animals in the vehicle control group, indicating correspondence to disease progression. Loss of body weight in the bortezomib single agent treatment group was also observed and may be due to drug toxicity.

DETAILED DESCRIPTION

Disclosed herein are humanized antibody molecules that bind to CD138, e.g., human CD138. Advantageously, at least several of the humanized antibody molecules describe herein have improved ability to inhibit cells expressing CD138, e.g., by eliciting an effector function. Without wishing to be bound by theory, it is believed that in an embodiment, anti-CD138 antibodies that bind to a desired epitope described herein have increased effector functions and preferential binding to the membrane-associated form of CD138. Targeting CD138 effectively can result in broad activity and favorable therapeutic index across myelomas and other cancers.

The humanized antibody molecules described herein can have one or more improved properties, e.g., one or more properties described herein, e.g., compared to the parental non-humanized antibody molecule. For example, the improved properties can include, but are not limited to, therapeutic efficacy, mitigation of immunogenicity, improvement of biophysical, physicochemical, and pharmaceutical properties, improvement of target binding, biological activity, and higher recombinant expression in mammalian cell lines used for purposes of antibody production. Without wishing to be bound by theory, it is believed that in an embodiment, the humanized antibody molecules described herein are more suitable for therapeutic or pharmaceutical use in human than non-humanized antibody molecules. In an embodiment, the humanized antibody molecule greater therapeutic efficacy (e.g., lower tumor burden and/or increased survival). In an embodiment, the humanized antibody molecule has increased stability (in vitro and/or in vivo). In an embodiment, the humanized antibody molecule has higher expression level (e.g., in cell lines). In an embodiment, the humanized antibody molecule has comparable or improved CD138 binding affinity, effector function (e.g., ADCC activity), or both, compared to the parental non-humanized antibody.

The anti-CD138 antibody molecules (e.g., humanized anti-CD138 antibody molecules) described herein can be used for the treatment of a number of disorders, e.g., multiple myeloma and other oncology indications. Without wishing to be bound by theory, it is believed that in an embodiment, the disorders involve CD138 positive cancer cells and/or CD138 mediated biological activities relevant to disease pathophysiology. For example, CD138 plays an important role in KRAS driven pathways underlying tumorigenesis and resistance in various carcinomas exemplified by pancreatic ductal adenocarcinoma.

The anti-CD138 antibody molecules (e.g., humanized anti-CD138 antibody molecules) described herein, can have biological activities that are particularly suitable for treating human disorders. For example, an exemplary humanized anti-CD138 antibody molecule, mAb 4320, exhibits potent in vitro activity relevant to its immune mediated therapeutic mechanism of action. These attributes include, e.g., both sub-nanomolar binding to CD138+ myeloma cells and antibody-dependent cell-mediated cytotoxicity (ADCC) against several MM cell lines, e.g., as assessed in biologically relevant natural killer (NK) cell-based ADCC assays using human-derived NK cells. This potent cell killing activity is both dose-dependent and target-dependent and has been shown to be highly effective against a number of variably expressing CD138 multiple myeloma cell lines including drug resistant MM cell lines, e.g., stable cell lines that are propagated to be resistant to either bortezomib or lenalidomide, two front-line therapies commonly used in combination as standard of care in patients for purposes of induction, consolidation, or maintenance therapy. mAb 4320 effectively kills autologously-derived myeloma cells from relapsed/refractory patients who do not respond to such treatments. Other relevant mechanisms of action, such as antibody-dependent cellular phagocytosis (ADCP), direct inhibition of myeloma cell survival, and blocking of integrin binding, can also exist. mAb 4320 efficacy in vivo also has been demonstrated, as a single agent or in combination with a proteasome inhibitor (e.g., bortezomib) to achieve a synergistic effect, in a murine xenograft model of disease involving the use of disseminated MM1.S tumors in CB.17 mice.

Antibody-drug conjugates (ADCs), nucleic acid molecules encoding the antibody molecules, expression vectors, host cells, compositions (e.g., pharmaceutical compositions), kits, and methods for making the antibody molecules, are also provided. The antibody molecules and pharmaceutical compositions disclosed herein can be used (alone or in combination with other agents or therapeutic modalities) to treat, prevent and/or diagnose disorders and conditions, e.g., disorders and conditions associated with CD138, e.g., cancer or precancerous conditions.

DEFINITIONS

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values. When "about" or "approximately" is present before a series of numbers or a range, it is understood that "about" or "approximately" can modify each of the numbers in the series or range. Similarly, when "at least," "more than," "no more than," "less than," "no less than," or "within" is present before a series of numbers or a range, it is understood that "at least," "more than," "no more than," "less than," "no less than," or "within" can modify each of the numbers in the series or range. As used herein, ranges include both the upper and lower limit.

The compositions and methods disclosed herein encompass polypeptides and nucleic acids having the sequences specified, or sequences substantially identical or similar thereto, e.g., sequences at least 85%, 90%, 95% identical or higher to the sequence specified.

In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a typical embodiment, the length of a reference sequence aligned for comparison purposes is at least 30%, e.g., at least 40%, 50%, 60%, e.g., at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch ((1970) *J. Mol. Biol.* 48:444-453) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package (available at gcg.com), using a NWSgapdna.CMP matrix and a gap weight of 40, 50, 60, 70, or 80 and a length weight of 1, 2, 3, 4, 5, or 6. One suitable set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid as described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (1997) *Nucleic Acids Res.* 25:3389-3402. When utilizing BLAST and gapped BLAST programs, the default parameters of the respective programs (e.g., XBLAST and NBLAST) can be used. See ncbi.nlm.nih.gov.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions 4) are suitable conditions and the ones that should be used unless otherwise specified.

It is understood that the molecules described herein may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide," "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "treat," a disorder, e.g., a myeloma, means that a subject (e.g., a human) who has a disorder, e.g., a myeloma, and/or experiences a symptom of a disorder, e.g., a myeloma, will, in an embodiment, suffer less a severe symptom and/or recover faster when an antibody molecule is administered than if the antibody molecule were never administered. In an embodiment, when a myeloma is treated, a bone marrow biopsy will show fewer clonal plasma cells, after effective treatment for myeloma. For example, a diagnostic assay will detect fewer clonal plasma cells in a biological sample of a subject after administration of an antibody molecule described herein for the effective treatment of a myeloma. Other assays, urine tests, or blood tests, can also be used to monitor treatment in a patient, or to detect the presence, e.g., decreased presence (or absence), of a symptom of a myeloma, after treatment of a myeloma in the subject. In an embodiment, when a myeloma is treated, the level of β2 microglobulin (β2M) in serum or urine will be decreased, after effective treatment for myeloma. Treatment can, e.g., partially or completely, alleviate, ameliorate, relieve, inhibit, or reduce the severity of, and/or reduce incidence, and optionally, delay onset of, one or more manifestations of the effects or symptoms, features, and/or causes of a disorder, e.g., a myeloma. In an embodiment, treatment is of a subject who does not exhibit certain signs of a disorder, e.g., a myeloma, and/or of a subject who exhibits only early signs of a disorder, e.g., nephropathy. In an embodiment, treatment is of a subject who exhibits one or more established signs of a disorder, e.g., a myeloma. In an embodiment, treatment is of a subject diagnosed as suffering from a disorder, e.g., a myeloma.

As used herein, the term "prevent," a disorder, e.g., a myeloma, means that a subject (e.g., a human) is less likely to have the disorder, e.g., a myeloma, if the subject receives the antibody molecule.

Various aspects of the compositions and methods herein are described in further detail below. Additional definitions are set out throughout the specification.

CD138

CD138 is a protein which in human is encoded by the SDC1 gene. CD138 is also known as Syndecan 1, Syndecan Proteoglycan 1, CD138 Antigen, SYND1, SDC, Syndecan-1, or Syndecan.

CD138 is a transmembrane (type I) heparan sulfate proteoglycan (HSPG) and is a member of the syndecan proteoglycan family CD138 is highly expressed on differentiated plasma cells (PCs) and is both a primary diagnostic biomarker of multiple myeloma (MM) as well as an indicator of clinically poor prognosis. CD138 is also stably and significantly overexpressed on multiple myeloma cells derived from patients during multiple stages of disease progression with greater than 70% of these patients exhibiting increased CD138 cell surface expression on MM cells autologously derived from fresh BM aspirates. CD138 gene expression likewise is increased by several-fold in patient derived MM cells relative to "normal" plasma cells derived from healthy patient controls. Without wishing to be bound by theory, it is believed that in an embodiment, CD138 is targeted for immunotherapy for MM, including, but not limited to, smoldering myeloma, a relatively early and largely asymptomatic phase of disease amenable to early treatment intervention. Without wishing to be bound by theory, it is believed that in an embodiment, targeting CD138 can provide additional therapeutic benefit based on its key functions as a promoter of myeloma cell growth, adhesion and survival and other key aspects of myeloma cancer biology. The syndecans mediate cell binding, cell signaling, and cytoskeletal organization, and syndecan receptors are required for internalization of the HIV-1 t at protein. CD138 functions as an integral membrane protein and participates in cell proliferation, cell migration and cell-matrix interactions via its receptor for extracellular matrix proteins. Altered CD138 expression has been detected in several different tumor types.

The core of CD138 includes three major domains: 1) short cytoplasmic domain; 2) plasma membrane-spanning hydrophobic domain; and 3) long extracellular domain. The functions of CD138 domains are described, e.g., in Stepp et al. *Adv Wound Care (New Rochelle)*. 2015; 4(4):235-249). The cytoplasmic domains can transmit signals and also bind to anchoring molecules including PDZ family members. The heparan sulfate chains of CD138 also serve important biological functions. In mammals, CD138 is a major heparan sulfate proteoglycan (HSPG) on epithelial cells with high levels of expression (Fuki et al. *J Clin Invest*. 1997; 100(6): 1611-1622). Without wishing to be bound by theory, it is believed that the HSPGs of CD138 allow the proteoglycan to bind to the heparin-binding sites present on a number of ECM proteins, growth factors, cytokines, and other proteins (Stepp et al. *Adv Wound Care (New Rochelle)*. 2015; 4(4): 235-249).

For example, the signal peptide comprises residues 1-22; the extracellular domain comprises residues 23-254; the transmembrane domain comprises residues 255-275; the cytoplasmic domain comprises residues 276-310; or the integrin binding domain (IBD) comprises residues 88-122, of a human CD138 protein, e.g., any of SEQ ID NOS: 1-3 or 450.

In an embodiment, an anti-CD138 antibody molecule described herein can modulate (e.g., inhibit) the binding of CD138 to one or more proteins that interact (e.g., bind directly or indirectly) with the extracellular domain of CD138. In an embodiment, an anti-CD138 antibody molecule described herein can modulate (e.g., inhibit) a function associated with a protein that interacts (e.g., bind directly or indirectly) with the extracellular domain of CD138. In an embodiment, a CD138-interacting protein binds to the extracellular domain of CD138 directly. In an embodiment, a CD138-interacting protein binds to the extracellular domain of CD138 through a glycosaminoglycan (GAG) chain.

Exemplary of CD138-interacting proteins and their functions are described, e.g., in Stepp et al. *Adv Wound Care (New Rochelle)*. 2015; 4(4):235-249, the content of which is incorporated by reference in its entirety.

For example, proteins that are capable of interacting with the extracellular domain of CD138 directly or indirectly include, but are not limited to, a matrix protein (e.g., a laminin, a fibronectin, thrombospondin, collagen, fibrin, HB-GAM, tenascin, vitronectin, fibrillin, or tropoelastin), a protease (e.g., MMP7, MMP9, ADAMTS4, MT1-PPT, neutrophil elastase, cathepsin G, or carboxypeptidase), a receptor (e.g., an integrin, $\alpha_v\beta_3$, $\alpha_v\beta_5$, $\alpha_6\beta_4$, $\alpha_2\beta_1$, $\alpha_3\beta_1$, or $\alpha_M\beta_2$), a cytokine or growth factor (e.g., a morphogen (e.g., activin, BMP-2, BMP-4, chordin, Sonic Hedgehog, a Frizzled related protein, a Sprouty peptide, any of Wnt1 to Wnt13, an antiangiogenic factor (e.g., angistatin or endostatin), a growth factor (e.g., amphiregulin, batacellulin, HB-EGF, neuregulin, any of FGF1 to FGF23, PDGF, GDNF, an VEGF, HGF, TGFβ1, TGFβ2, TPA, or PAI-1), or a cytokine (e.g., GM-CSF, IL-2, IL-3, IL-4, IL-5, IL-7, IL-12, interferon, TNF-α, a CC chemokine, or a CXC chemokine), a protein associated with energy balance (e.g., ApoB, ApoE, or lipoprotein lipase), a complement or coagulation protein (e.g., antithrombin II, tissue factor (TF), pathway inhibitor, Factor IX, Factor X, Factor XI, or Factor XII), or a viral or parasite coat protein (e.g., HIV-1-tat, HIV-1 gp4l, HIV-1 gp120, HSV gB, HSV gC, HSV gD, a coat protein of HHV-6 or HHV-8, or G-protein of RSV).

CD138 expressed on the cell surface can be cleaved by specific proteases and the shed CD138 is responsible for mediating paracrine and autocrine functions. Shed CD138 is soluble and secreted ectodomain (ECD) in blood and matrix. Shed CD138 is an indicator of poor prognosis in multiple myeloma patients and enhanced tumor progression in myeloma mouse models. Typically, shed CD138 is not considered to be primarily responsible for the disease manifestation. Translocation of CD138 to the cell nucleus can correlate to the differentiation and proliferation of certain tumor cells. In an embodiment, the anti-CD138 antibody molecules described herein preferentially target membrane-associated CD138 over soluble CD138.

CD138 is generally not present on B lymphocytes and it is expressed after the onset of plasma cell differentiation. CD138 is highly expressed on malignant plasma cells (myeloma) and has a causal role in disease progression. CD138 is implicated in various biological functions. For example, it can bind to extracellular proteins, growth factors, and chemokines; engage and activate the αVβ3 and αVβ5 integrin when clustered; regulate the biogenesis of exosomes; and regulate bone marrow microenvironment that supports myeloma growth and metastasis. Multiple signals can be attenuated by targeting CD138.

CD138 is upregulated in multiple myeloma (Tassone et al. *Blood*. 104(12): 3688-3696). It is overexpressed on malignant plasma cells. Multiple myeloma cells typically express between 50-200 fold higher levels of CD138. Soluble CD138 (sCD138) levels are generally from less than 60 ng/mL in normal serum to 200-1500 ng/mL in sera of multiple myeloma patients. CD138 is overexpressed in about 80% multiple myeloma patients.

CD138 can be used as a primary diagnostic marker for multiple myeloma. Increased levels of shed CD138 in serum correlated to increased tumor burden and poorer outcomes. CD138+ myeloma cells show higher proliferation and CD138+ myeloma patients have lower overall survival rates. CD138+ myeloma cells aberrantly express angiogenic factors, e.g., HGF, IL-15, ANG, APRIL, CTGF, or TGFA (Hose et al. *Blood*. 2009; 114(1): 128-143). Expression levels of CD138 and its released extracellular domain correlate with tumor malignancy, phenotype, and metastatic potential for both solid and hematological tumors. CD138 expression varies among cancer types, but the differential expression signatures between normal and cancer cells in epithelial and stromal compartments are directly associated with aggressiveness of tumors and patient's clinical outcome and survival.

Exemplary amino acid and nucleotide sequences of human CD138 are described, e.g., in Mali et al. *J Biol Chem.* 1990; 265(12): 6884-6889; Lories et al. *J Biol Chem.* 1992; 267(2): 1116-1122; and in FIG. 1.

The amino acid sequence of an exemplary human CD138 precursor (SEQ ID NO: 1) is provided as follows.

MRRAALWLWLCALALSLQPALPQIVATNLPPEDQDGSGDDSDNFSGSGA

GALQDITLSQQTPSTWKDTQLLTAIPTSPEPTGLEATAASTSTLPAGEG

PKEGEAVVLPEVEPGLTAREQEATPRPRETTQLPTTHQASTTTATTAQE

PATSHPHRDMQPGHHETSTPAGPSQADLHTPHTEDGGPSATERAAEDGA

SSQLPAAEGSGEQDFTFETSGENTAVVAVEPDRRNQSPVDQGATGASQG

-continued

LLDRKEVLGGVIAGGLVGLIFAVCLVGFMLYRMKKKDEGSYSLEEPKQA

NGGAYQKPTKQEEFYA

The amino acid sequence of an exemplary human CD138 precursor variant (Q136L) (SEQ ID NO: 2) is provided as follows.

MRRAALWLWLCALALSLQPALPQIVATNLPPEDQDGSGDDSDNFSGSGA

GALQDITLSQQTPSTWKDTQLLTAIPTSPEPTGLEATAASTSTLPAGEG

PKEGEAVVLPEVEPGLTAREQEATPRPRETTQLPTTHLASTTTATTAQE

PATSHPHRDMQPGHHETSTPAGPSQADLHTPHTEDGGPSATERAAEDGA

SSQLPAAEGSGEQDFTFETSGENTAVVAVEPDRRNQSPVDQGATGASQG

LLDRKEVLGGVIAGGLVGLIFAVCLVGFMLYRMKKKDEGSYSLEEPKQA

NGGAYQKPTKQEEFYA

The amino acid sequence of an exemplary human CD138 precursor variant (T76M) (SEQ ID NO: 3) is provided as follows.

MRRAALWLWLCALALSLQPALPQIVATNLPPEDQDGSGDDSDNFSGSGA

GALQDITLSQQTPSTWKDTQLLTAIPMSPEPTGLEATAASTSTLPAGEG

PKEGEAVVLPEVEPGLTAREQEATPRPRETTQLPTTHQASTTTATTAQE

PATSHPHRDMQPGHHETSTPAGPSQADLHTPHTEDGGPSATERAAEDGA

SSQLPAAEGSGEQDFTFETSGENTAVVAVEPDRRNQSPVDQGATGASQG

LLDRKEVLGGVIAGGLVGLIFAVCLVGFMLYRMKKKDEGSYSLEEPKQA

NGGAYQKPTKQEEFYA

The signal peptide includes amino acids 1-22 of any of SEQ ID NOs: 1-3. The mature peptide includes amino acids 23-310 of any of SEQ ID NOs: 1-3. The extracellular domain includes amino acids 23-254 of any of SEQ ID NOs: 1-3. The transmembrane domain includes amino acids 255-275 of any of SEQ ID NOs: 1-3. The cytoplasmic domain includes amino acids 276-310 of any of SEQ ID NOs: 1-3.

An exemplary coding nucleotide sequence of human CD138 (SEQ ID NO: 4) is provided as follows. This nucleotide sequence encodes the amino acid sequence of SEQ ID NO: 1.

ATGAGGCGCGCGGCGCTCTGGCTCTGGCTGTGCGCGCTGGCGCTGAGCC

TGCAGCCGGCCCTGCCGCAAATTGTGGCTACTAATTTGCCCCCTGAAGA

TCAAGATGGCTCTGGGGATGACTCTGACAACTTCTCCGGCTCAGGTGCA

GGTGCTTTGCAAGATATCACCTTGTCACAGCAGACCCCCTCCACTTGGA

AGGACACGCAGCTCCTGACGGCTATTCCCACGTCTCCAGAACCCACCGG

CCTGGAGGCTACAGCTGCCTCCACCTCCACCCTGCCGGCTGGAGAGGGG

CCCAAGGAGGGAGAGGCTGTAGTCCTGCCAGAAGTGGAGCCTGGCCTCA

CCGCCCGGGAGCAGGAGGCCACCCCCCGACCCAGGGAGACCACACAGCT

CCCGACCACTCATCAGGCCTCAACGACCACAGCCACCACGGCCCAGGAG

CCCGCCACCTCCCACCCCCACAGGGACATGCAGCCTGGCCACCATGAGA

CCTCAACCCCTGCAGGACCCAGCCAAGCTGACCTTCACACTCCCCACAC

AGAGGATGGAGGTCCTTCTGCCACCGAGAGGGCTGCTGAGGATGGAGCC

TCCAGTCAGCTCCCAGCAGCAGAGGGCTCTGGGGAGCAGGACTTCACCT

TTGAAACCTCGGGGGAGAATACGGCTGTAGTGGCCGTGGAGCCTGACCG

CCGGAACCAGTCCCCAGTGGATCAGGGGGCCACGGGGGCCTCACAGGGC

CTCCTGGACAGGAAAGAGGTGCTGGGAGGGGTCATTGCCGGAGGCCTCG

TGGGGCTCATCTTTGCTGTGTGCCTGGTGGGTTTCATGCTGTACCGCAT

GAAGAAGAAGGACGAAGGCAGCTACTCCTTGGAGGAGCCGAAACAAGCC

AACGGCGGGGCCTACCAGAAGCCCACCAAACAGGAGGAATTCTATGCCT

GA

Another exemplary coding nucleotide sequence of human CD138 (SEQ ID NO: 5) is provided as follows. This nucleotide sequence also encodes the amino acid sequence of SEQ ID NO: 1.

ATGAGGCGCGCGGCGCTCTGGCTCTGGCTGTGCGCGCTGGCGCTGAGCC

TGCAGCCGGCCCTGCCGCAAATTGTGGCTACTAATTTGCCCCCTGAAGA

TCAAGATGGCTCTGGGGATGACTCTGACAACTTCTCCGGCTCAGGTGCA

GGTGCTTTGCAAGATATCACCTTGTCACAGCAGACCCCCTCCACTTGGA

AGGACACGCAGCTCCTGACGGCTATTCCCACGTCTCCAGAACCCACCGG

CCTGGAGGCTACAGCTGCCTCCACCTCCACCCTGCCGGCTGGAGAGGGG

CCCAAGGAGGGAGAGGCTGTAGTCCTGCCAGAAGTGGAGCCTGGCCTCA

CCGCCCGGGAGCAGGAGGCCACCCCCCGACCCAGGGAGACCACACAGCT

CCCGACCACTCATCAGGCCTCAACGACCACAGCCACCACGGCCCAGGAG

CCCGCCACCTCCCACCCCCACAGGGACATGCAGCCTGGCCACCATGAGA

CCTCAACCCCTGCAGGACCCAGCCAAGCTGACCTTCACACTCCCCACAC

AGAGGATGGAGGTCCTTCTGCCACCGAGAGGGCTGCTGAGGATGGAGCC

TCCAGTCAGCTCCCAGCAGCAGAGGGCTCTGGGGAGCAGGACTTCACCT

TTGAAACCTCGGGGGAGAATACGGCTGTAGTGGCCGTGGAGCCTGACCG

CCGGAACCAGTCCCCAGTGGATCAGGGGGCCACGGGGGCCTCACAGGGC

CTCCTGGACAGGAAAGAGGTGCTGGGAGGGGTCATTGCCGGAGGCCTCG

TGGGGCTCATCTTTGCTGTGTGCCTGGTGGGTTTCATGCTGTACCGCAT

GAAGAAGAAGGACGAAGGCAGCTACTCCTTGGAGGAGCCGAAACAAGCC

AACGGCGGGGCCTACCAGAAGCCCACCAAACAGGAGGAATTCTATGCCT

GA

As used herein, when an anti-CD138 antibody molecule binds, or substantially binds, to human CD138, it binds, or substantially binds, to one or more isoforms of human CD138. In an embodiment, the antibody molecule binds or substantially binds to human CD138 having an amino acid sequence described herein, or encoded by a nucleotide sequence described herein. In an embodiment, the antibody molecule binds or substantially binds to human CD138 comprising amino acids 23-254 of any of SEQ ID NOs: 1-3.

Exemplary amino acid and nucleotide sequences of mouse CD138 are described, e.g., in Saunders et al. *J Cell Biol.* 1989; 108(4): 1547-1556; and Vihinen et al. *J Biol Chem.* 1993; 268(23): 17261-17269.

The amino acid sequence of an exemplary mouse CD138 precursor (SEQ ID NO: 6) is provided as follows.

MRRAALWLWLCALALRLQPALPQIVAVNVPPEDQDGSGDDSDNFSGSGTG

ALPDTLSRQTPSTWKDVWLLTATPTAPEPTSSNTETAFTSVLPAGEKPEE

GEPVLHVEAEPGFTARDKEKEVTTRPRETVQLPITQRASTVRVTTAQAAV

TSHPHGGMQPGLHETSAPTAPGQPDHQPPRVEGGGTSVIKEVVEDGTANQ

LPAGEGSGEQDFTFETSGENTAVAAVEPGLRNQPPVDEGATGASQSLLDR

KEVLGGVIAGGLVGLIFAVCLVAFMLYRMKKKDEGSYSLEEPKQANGGAY

QKPTKQEEFYA

The signal peptide includes amino acids 1-22 of SEQ ID NO: 6. The mature peptide includes amino acids 23-311 of SEQ ID NO: 6. The extracellular domain includes amino acids 23-255 of SEQ ID NO: 6. The transmembrane domain includes amino acids 256-276 of SEQ ID NO: 4. The cytoplasmic domain includes amino acids 277-311 of SEQ ID NO: 6.

An exemplary coding nucleotide sequence of mouse CD138 (SEQ ID NO: 7) is provided as follows.

ATGAGACGCGCGGCGCTCTGGCTCTGGCTCTGCGCGCTGGCGCTGCGCCT

GCAGCCTGCCCTCCCGCAAATTGTGGCTGTAAATGTTCCTCCTGAAGATC

AGGATGGCTCTGGGGATGACTCTGACAACTTCTCTGGCTCTGGCACAGGT

GCTTTGCCAGATACTTTGTCACGGCAGACACCTTCCACTTGGAAGGACGT

GTGGCTGTTGACAGCCACGCCCACAGCTCCAGAGCCCACCAGCAGCAACA

CCGAGACTGCTTTTACCTCTGTCCTGCCAGCCGGAGAGAAGCCCGAGGAG

GGAGAGCCTGTGCTCCATGTAGAAGCAGAGCCTGGCTTCACTGCTCGGGA

CAAGGAAAAGGAGGTCACCACCAGGCCCAGGGAGACCGTGCAGCTCCCCA

TCACCCAACGGGCCTCAACAGTCAGAGTCACCACAGCCCAGGCAGCTGTC

ACATCTCATCCGCACGGGGCATGCAACCTGGCCTCCATGAGACCTCGGC

TCCCACAGCACCTGGTCAACCTGACCATCAGCCTCCACGTGTGGAGGGTG

GCGGCACTTCTGTCATCAAAGAGGTTGTCGAGGATGGAACTGCCAATCAG

CTTCCCGCAGGAGAGGGCTCTGGAGAACAAGACTTCACCTTTGAAACATC

TGGGGAGAACACAGCTGTGGCTGCCGTAGAGCCCGGCCTGCGGAATCAGC

CCCCGGTGGACGAAGGAGCCACAGGTGCTTCTCAGAGCCTTTTGGACAGG

AAGGAAGTGCTGGGAGGTGTCATTGCCGGAGGCCTAGTGGGCCTCATCTT

TGCTGTGTGCCTGGTGGCTTTCATGCTGTACCGGATGAAGAAGAAGGACG

AAGGCAGCTACTCCTTGGAGGAGCCCAAACAAGCCAATGGCGGTGCCTAC

CAGAAACCCACCAAGCAGGAGGAGTTCTACGCCTGA

As used herein, when an anti-CD138 antibody molecule binds, or substantially binds, to mouse CD138, it binds, or substantially binds, to one or more isoforms of mouse CD138. In an embodiment, the antibody molecule binds or substantially binds to human CD138 having an amino acid sequence described herein, or encoded by a nucleotide sequence described herein. In an embodiment, the antibody molecule binds or substantially binds to mouse CD138 comprising amino acids 23-255 of SEQ ID NO: 6.

Epitope

The humanized antibody molecules described herein can bind to an epitope on CD138 (e.g., human CD138). For example, an epitope bound by a humanized antibody molecule described herein can include one or more epitope contact points described herein.

Without wishing to be bound by theory, it is believed that in an embodiment, an antibody bound to the IBD (e.g., residues 88-122 of any of SEQ ID NOS: 1-3 or 450) or any region distant from the membrane of CD138 may not be effective in signaling transduction for NK cell activation and/or may not efficiently deliver molecules such as perforins and/or granzymes for cytotoxicity. In an embodiment, the antibody molecule binds to an epitope of CD138 comprising a membrane proximal region. In an embodiment, the antibody molecule binds to an epitope of CD138 comprising at least two distinct peptide regions (e.g., comprising peptide 2A and/or 6A, and/or portions thereof). In an embodiment, the antibody molecule binds to an epitope of CD138 distinct from the epitope bound by antibody BB4.

In an embodiment, the antibody molecule binds to CD138 (e.g., human CD138) with at least 10% (e.g., at least 10%, 15%, 20%, 25%, 30%, 35%, 40%, 50%, 55%, 60%, 70%, 80%, or 90%) greater affinity relative to a reference anti-CD138 antibody (e.g., antibody BB4), e.g., as determined by a cell-binding assay described herein. In an embodiment, the CD138 is membrane-associated. In an embodiment, the antibody molecule binds to a soluble CD138, e.g., the extracellular domain of soluble CD138 (e.g., having the sequence of amino acids 18-251 of SEQ ID NO: 1). In an embodiment, the antibody molecule binds to peptide 2A of human CD138. In certain embodiments, the antibody molecule binds to peptide 6A of human CD138.

In some embodiments, the anti-CD138 antibody molecules described herein have one, two, or all of the following properties: optimal distance of epitope from the cell membrane (e.g., not on the N-terminal of IDB); appropriate orientation of the Fc region for CD16 engagement; or proper CD138 engagement that allows for CD16 clustering on NK cells (e.g., to overcome the effect of high amount of glycosylation on CD138 molecules that may restrict the access of NK cells).

Without wishing to be bound by theory, it is believed that in an embodiment altering the position of the antibody epitope can change certain effector mechanisms engaged. For example, antibody-dependent cellular cytotoxicity (ADCC) and complement-dependent cytotoxicity (CDC) may favor a membrane-proximal epitope versus a membrane-distal epitope (Cleary et al. *J Immunol*. 2017; 198(10): 3999-4011). In an embodiment, antibodies designed to delete target cells through specific effector mechanisms can be selected by altering the position of the antibody epitope (e.g., the distance of epitope from membrane).

In an embodiment, the mode of engagement can affect the ability of the antibody to mediate effector functions. For example, the angle of antibody binding to the extracellular loop with regard to the membrane surface may be different (e.g., parallel or perpendicular to the membrane surface) between antibodies that bind to the same peptide epitopes.

In an embodiment, the anti-CD138 antibody molecules described herein bind to an epitope that has one, two, or all of the following properties: proximal to the cell membrane; not restricted or occluded by the glycosaminoglycan (GAG) chains; or preferentially present on membrane-associated CD138. In an embodiment, the anti-CD138 antibody molecules described herein can bind to a desired epitope region and engage with the optimal pose relative to the membrane. In an embodiment, the epitope is a linear epitope. In an embodiment, the antibody molecule binds to an extracellular region of CD138 distant from the transmembrane region. In an embodiment, the epitope is a non-contiguous or conformational epitope.

Figure 1:
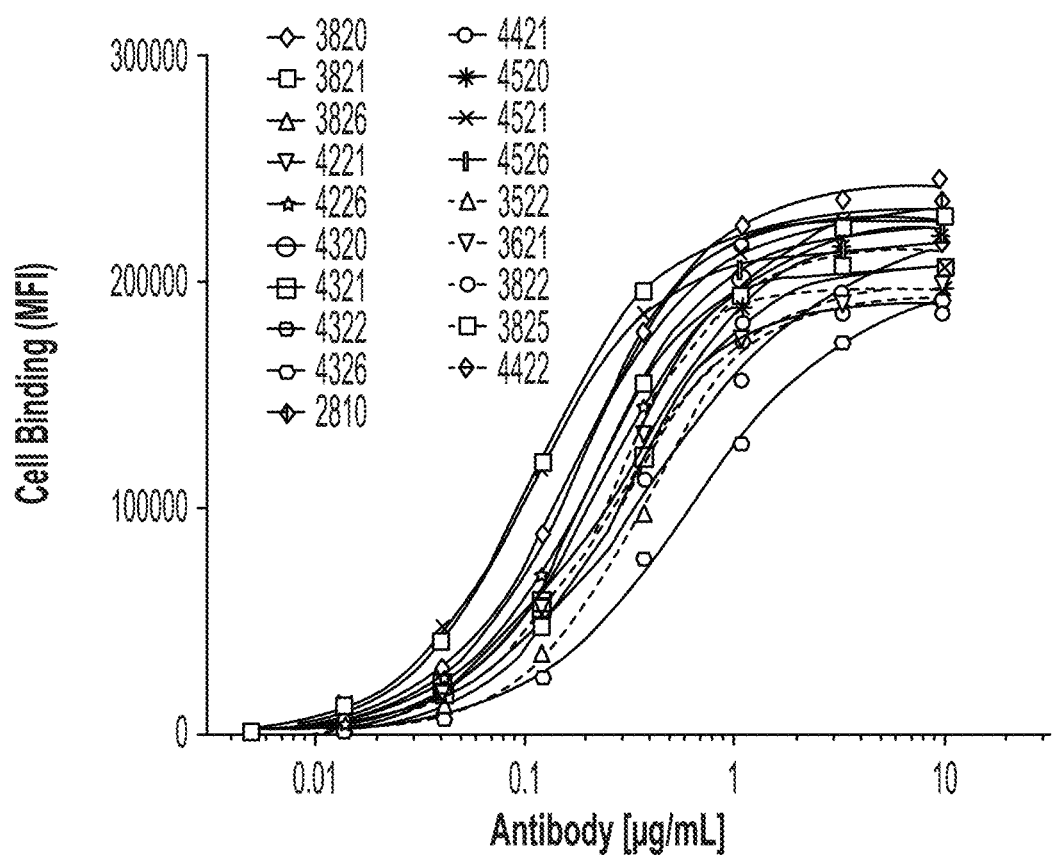
FIG. 1 is a graph showing binding of humanized anti-CD138 antibodies at varying dosages to a CD138+ multiple myeloma cell line U266.
Figure 2:
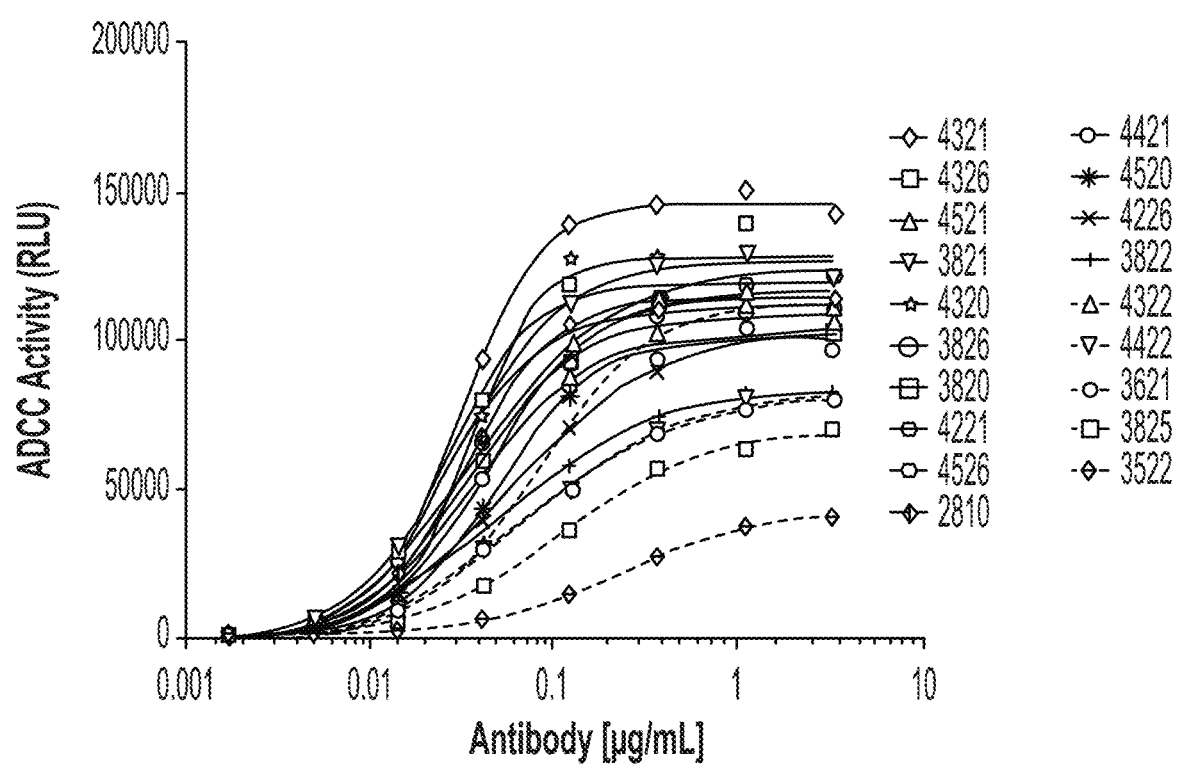
FIG. 2 is a graph showing ADCC activity of humanized anti-CD138 antibodies at varying dosages targeting CD138+ lymphoblastic myeloma cells. ADCC activity is assessed using a bioluminescent reporter assay for quantifying biological activity on pathway activation by antibodies in an ADCC mechanism of action (MOA) assay. This bioassay includes engineered Jurkat cells stably expressing the FcγRIIIa receptor, and an NFAT response element driving expression of firefly luciferase as effector cells.

Peptides for identification of desired epitopes for anti-CD138 antibodies are shown, e.g., in FIG. 2 of PCT Publication No. WO 2019/070726 or U.S. Patent Application Publication No. US 2019/0100588. Without wishing to be bound by theory, it is believed that in an embodiment, the anti-CD138 antibody molecules described herein target a peptide region between residues Gly217 to Glu251 of human CD138, e.g., as shown in FIG. 1 of PCT Publication No. WO 2019/070726 or U.S. Patent Application Publication No. US 2019/0100588. This region is expected to have a linear random coil conformation. In an embodiment, the anti-CD138 antibody molecule binds to at least one linear tetrapeptide in the aforesaid region. In an embodiment, the anti-CD138 antibody molecule binds to a combination of linear tetrapeptides (e.g., two, three, four, or more adjacent tetrapeptides) in the aforesaid region.

The amino acid sequences of the aforesaid peptides are shown in Table 3.

TABLE 3

Peptides for Identification of CD138 Epitopes

| Peptide | Region | Amino Acid Sequence | SEQ ID NO | Length |
|---|---|---|---|---|
| Pep1a | 23-50 | QIVATNLPPEDQDGSGDDS DNFSGSGAGAALQDITLSQQ T | 8 | 39 |
| Pep1b | 51-95 | ALQDITLSQQTPSTWKDTQ LLTAIPTSPEPTGLEATAA STSTLPA | 9 | 45 |
| Pep2a | 88-121 | ASTSTLPAGEGPKEGEAVV *LPEV*EPGLTAREQEA | 10 | 34 |
| Pep2b | 88-102 | ASTSTLPAGEGPKEG | 11 | 15 |
| Pep3 | 111-150 | EPGLTAREQEATPRPRETT QLPTTHQASTTTATTAQEP AT | 12 | 40 |
| Pep4 | 146-180 | QEPATSHPHRDMQPGHHET STPAGPSQADLHTPHT | 13 | 35 |
| Pep5-6 | 176-250 | HTPHTEDG*GPSAT*ERAAE *DGASSQ*LPAAEGSGEQ *DFTFE*TSGENTAVVAVEPD RRNQSPVDQGATGASQGLL DRK | 14 | 75 |
| Pep5 | 176-214 | HTPHTEDG*GPSAT*ERAAE *DGASSQ*LPAAEGSGEQDFT FE | 15 | 39 |
| Pep6 | 210-250 | DFTFETSGENTAVVAVEPD RRNQSPVDQGATGASQGLL DRK | 16 | 41 |
| Pep6a | 220-245 | TAVVAVEPDRRNQSPVDQG ATGASQG | 17 | 26 |

In Table 3, the overlapping amino acids among the peptides are shown in bold; the BB4 epitope residues are shown in italic; the glycosaminoglycan (heparan sulfate, chondroitin sulfate) chain carrying serine residues are underlined. The terms "Peptide" and "Pep" are used interchangeably herein. For peptide designations, the lower case and upper-case letters are intended to have the same meaning.

For example, the terms "Peptide 1A," "Peptide 1a," "Pep1A," and "Pep1a" can be used to refer to the same peptide.

Figure 13:
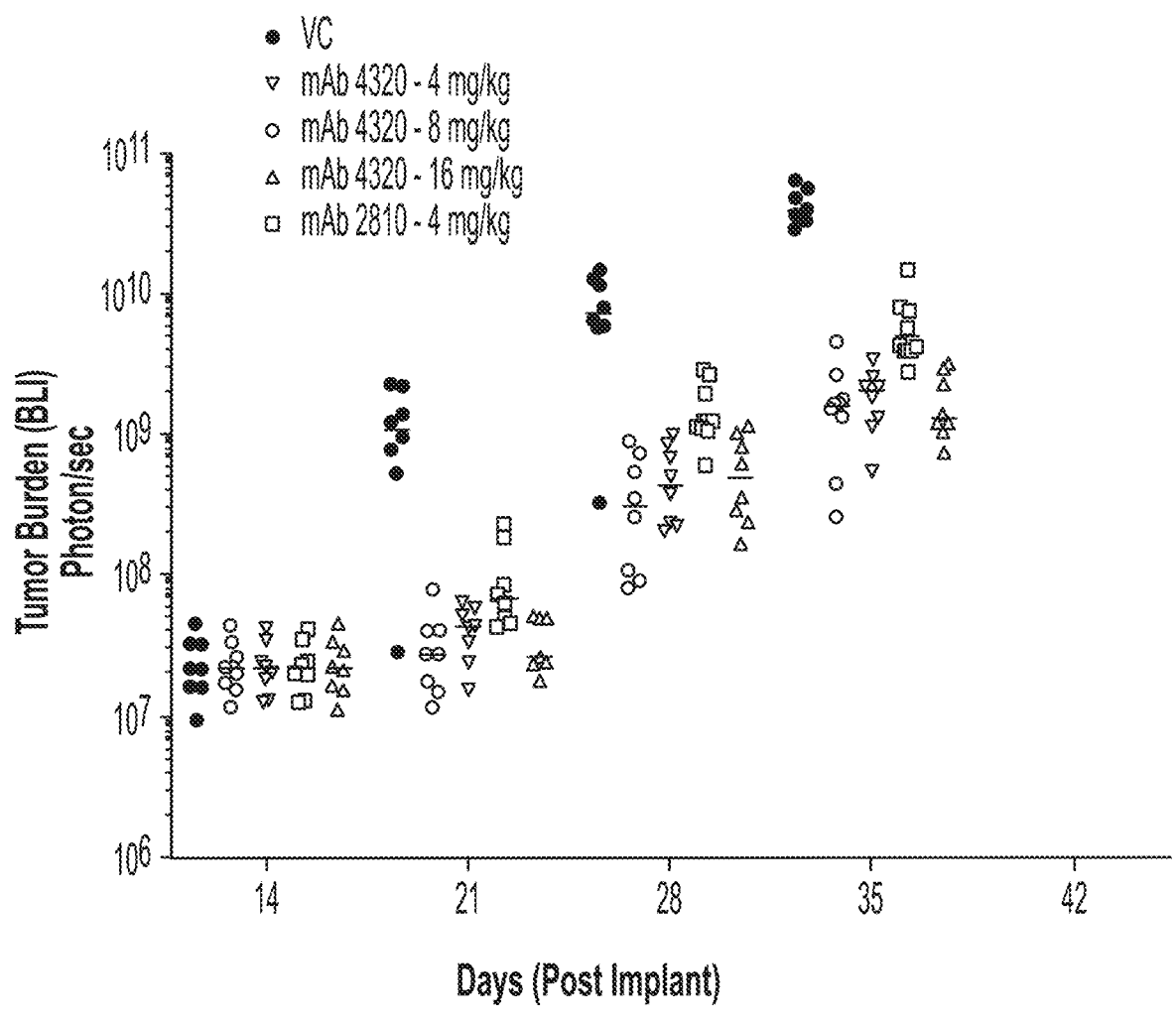
FIG. 13 is a graph showing efficacy data for individual mice in the multiple myeloma xenograft model after treatment with the indicated antibody molecules. Comparison of whole-body tumor burden in individual mice in vehicle control vs. antibody treatment groups. Mean BLI values are depicted as horizontal bars.

Other exemplary peptides used for identification of desired epitopes for anti-CD138 antibodies are described herein, e.g., in FIGS. 13 and 22C of PCT Publication No. WO 2019/070726 or U.S. Patent Application Publication No. US 2019/0100588.

In an embodiment, the antibody molecule contacts (e.g., binds, or substantially binds, to) a region in CD138 corresponding to one or more peptides as described in Table 3, or in FIG. 13 or 22C of PCT Publication No. WO 2019/070726 or U.S. Patent Application Publication No. US 2019/0100588. In an embodiment, the peptide is Pep6. In an embodiment, the peptide is Pep6a. In an embodiment, the peptide is Pep5. In an embodiment, the peptide is Pep4. In an embodiment, the antibody molecule contacts Pep6 or Pep6a and does not contact Pep4. In an embodiment, the antibody molecule does not contact any of Pep1a, Pep1b, Pep2a, Pep2b, Pep3, Pep4, or Pep5. In an embodiment, the antibody molecule does not contact Pep2a. In an embodiment, the antibody molecule contacts Pep2a but does not bind to the same epitope as BB4.

In an embodiment, the antibody molecule contacts Pep2a and Pep6. In an embodiment, the antibody molecule contacts Pep2a and Pep2c. In an embodiment, the antibody molecule contacts Pep6b. In an embodiment, the antibody molecule contacts Pep2a, Pep2c, and Pep6b. In an embodiment, the antibody molecule does not contact Pep6e. In an embodiment, the antibody molecule contacts Pep6b and does not contact Pep6e. In an embodiment, the antibody molecule contacts Pep2a and Pep2c and does not contact Pep6e. In an embodiment, the antibody molecule contacts Pep2a, Pep2c, and Pep6b and does not contact Pep6e.

In an embodiment, the antibody molecule contacts Pep2a and Pep2d. In an embodiment, the antibody molecule contacts Pep6b and Pep6f. In an embodiment, the antibody molecule contacts Pep2a, Pep2d, Pep6b, and Pep6f.

In an embodiment, the antibody molecule binds, or substantially binds, to CD138 in an extracellular region proximal to the transmembrane domain of CD138. In an embodiment, the C-terminus of the extracellular region proximal to the transmembrane domain is within 70, 65, 60, 55, 50, 45, 40, 35, 30, 25, 20, 15, 10, or 5 amino acids from the N-terminus of the transmembrane domain In an embodiment, the N-terminus of the extracellular region proximal to the transmembrane domain is within 75, 70, 65, 60, 55, 50, 45, 40, 35, 30, 25, 20, 15, 10, or 5 amino acids from the N-terminus of the transmembrane domain.

In an embodiment, the antibody molecule binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in the extracellular region proximal to the transmembrane domain.

In an embodiment, the antibody molecule binds to an epitope on CD138 comprising five or more consecutive amino acid residues in the extracellular region proximal to the transmembrane domain In an embodiment, the antibody molecule binds to an epitope on CD138 comprising six or more consecutive amino acid residues in the extracellular region proximal to the transmembrane domain In an embodiment, the antibody molecule binds to an epitope on CD138 comprising seven or more consecutive amino acid residues in the extracellular region proximal to the transmembrane domain In an embodiment, the antibody molecule binds to an epitope on CD138 comprising eight or more consecutive amino acid residues in the extracellular region proximal to the transmembrane domain In an embodiment, the antibody molecule binds to an epitope on CD138 comprising nine or more consecutive amino acid residues in the extracellular region proximal to the transmembrane domain In an embodiment, the antibody molecule binds to an epitope on CD138 comprising ten or more consecutive amino acid residues in the extracellular region proximal to the transmembrane domain In an embodiment, the antibody molecule binds to an epitope on CD138 comprising eleven or more consecutive amino acid residues in the extracellular region proximal to the transmembrane domain In an embodiment, the antibody molecule binds to an epitope on CD138 comprising twelve or more consecutive amino acid residues in the extracellular region proximal to the transmembrane domain.

In an embodiment, the extracellular region proximal to the transmembrane domain corresponds to (e.g., comprises or consists of) Pep6. In an embodiment, the extracellular region proximal to the transmembrane domain corresponds to (e.g., comprises or consists of) Pep6a, 6b, 6e, and/or 6f. In an embodiment, the extracellular region proximal to the transmembrane domain corresponds to (e.g., comprises or consists of) Pep5.

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6. In an embodiment, the antibody molecule contacts four or more (e.g., 5, 6, 7, 8, 9, 10, 11, 12, 13, 14, 15, 16, 17, 18, 19, 20, 21, 22, 23, 24, 25, or 26) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38) of the following peptides (e.g., from Pep6a): DFTF (SEQ ID NO: 18); FTFE (SEQ ID NO: 19); TFET (SEQ ID NO: 20); FETS (SEQ ID NO: 21); ETSG (SEQ ID NO: 22); TSGE (SEQ ID NO: 23); SGEN (SEQ ID NO: 24); GENT (SEQ ID NO: 25); ENTA (SEQ ID NO: 26); NTAV (SEQ ID NO: 27); TAVV (SEQ ID NO: 28); AVVA (SEQ ID NO: 29); VVAV (SEQ ID NO: 30); VAVE (SEQ ID NO: 31); AVEP (SEQ ID NO: 32); VEPD (SEQ ID NO: 33); EPDR (SEQ ID NO: 34); PDRR (SEQ ID NO: 35); DRRN (SEQ ID NO: 36); RRNQ (SEQ ID NO: 37); RNQS (SEQ ID NO: 38); NQSP (SEQ ID NO: 39); QSPV (SEQ ID NO: 40); SPVD (SEQ ID NO: 41); PVDQ (SEQ ID NO: 42); VDQG (SEQ ID NO: 43); DQGA (SEQ ID NO: 44); QGAT (SEQ ID NO: 45); GATG (SEQ ID NO: 46); ATGA (SEQ ID NO: 47); TGAS (SEQ ID NO: 48); GASQ (SEQ ID NO: 49); ASQG (SEQ ID NO: 50); SQGL (SEQ ID NO: 51); QGLL (SEQ ID NO: 52); GLLD (SEQ ID NO: 53); LLDR (SEQ ID NO: 54); or LDRK (SEQ ID NO: 55).

In an embodiment, the antibody molecule contacts five or more (e.g., 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37) of the following peptides (e.g., from Pep6a): DFTFE (SEQ ID NO: 56); FTFET (SEQ ID NO: 57); TFETS (SEQ ID NO: 58); FETSG (SEQ ID NO: 59); ETSGE (SEQ ID NO: 60); TSGEN (SEQ ID NO: 61); SGENT (SEQ ID NO: 62); GENTA (SEQ ID NO: 63); ENTAV (SEQ ID NO: 64); NTAVV (SEQ ID NO: 65); TAVVA (SEQ ID NO: 66); AVVAV (SEQ ID NO: 67); VVAVE (SEQ ID NO: 68); VAVEP (SEQ ID NO: 69); AVEPD (SEQ ID NO: 70); VEPDR (SEQ ID NO: 71); EPDRR (SEQ ID NO: 72); PDRRN (SEQ ID NO: 73); DRRNQ (SEQ ID NO: 74); RRNQS (SEQ ID NO: 75); RNQSP (SEQ ID NO: 76); NQSPV (SEQ ID NO: 77); QSPVD (SEQ ID NO: 78); SPVDQ (SEQ ID NO: 79); PVDQG (SEQ ID NO: 80); VDQGA (SEQ ID NO: 81); DQGAT (SEQ ID NO: 82); QGATG (SEQ ID NO: 83); GATGA (SEQ ID NO: 84); ATGAS (SEQ ID NO: 85); TGASQ (SEQ ID NO: 86); GASQG (SEQ ID NO: 87); ASQGL (SEQ ID NO: 88); SQGLL (SEQ ID NO: 89); QGLLD (SEQ ID NO: 90); GLLDR (SEQ ID NO: 91); or LLDRK (SEQ ID NO: 92).

In an embodiment, the antibody molecule contacts six or more (e.g., 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41) consecutive amino acid residues in Pep6a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following peptides (e.g., from Pep6a): DFTFET (SEQ ID NO: 93); FTFETS (SEQ ID NO: 94); TFETSG (SEQ ID NO: 95); FETSGE (SEQ ID NO: 96); ETSGEN (SEQ ID NO: 97); TSGENT (SEQ ID NO: 98); SGENTA (SEQ ID NO: 99); GENTAV (SEQ ID NO: 100); ENTAVV (SEQ ID NO: 101); NTAVVA (SEQ ID NO: 102); TAVVAV (SEQ ID NO: 103); AVVAVE (SEQ ID NO: 104); VVAVEP (SEQ ID NO: 105); VAVEPD (SEQ ID NO: 106); AVEPDR (SEQ ID NO: 107); VEPDRR (SEQ ID NO: 108); EPDRRN (SEQ ID NO: 109); PDRRNQ (SEQ ID NO: 110); DRRNQS (SEQ ID NO: 111); RRNQSP (SEQ ID NO: 112); RNQSPV (SEQ ID NO: 113); NQSPVD (SEQ ID NO: 114); QSPVDQ (SEQ ID NO: 115); SPVDQG (SEQ ID NO: 116); PVDQGA (SEQ ID NO: 117); VDQGAT (SEQ ID NO: 118); DQGATG (SEQ ID NO: 119); QGATGA (SEQ ID NO: 120); GATGAS (SEQ ID NO: 121); ATGASQ (SEQ ID NO: 122); TGASQG (SEQ ID NO: 123); GASQGL (SEQ ID NO: 124); ASQGLL (SEQ ID NO: 125); SQGLLD (SEQ ID NO: 126); QGLLDR (SEQ ID NO: 127); or GLLDRK (SEQ ID NO: 128).

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36) of the following peptides (e.g., from Pep5): HTPH (SEQ ID NO: 129), TPHT (SEQ ID NO: 130), PHTE (SEQ ID NO: 131), HTED (SEQ ID NO: 132), TEDG (SEQ ID NO: 133), EDGG (SEQ ID NO: 134), DGGP (SEQ ID NO: 135), GGPS (SEQ ID NO: 136), GPSA (SEQ ID NO: 137), PSAT (SEQ ID NO: 138), SATE (SEQ ID NO: 139), ATER (SEQ ID NO: 140), TERA (SEQ ID NO: 141), ERAA (SEQ ID NO: 142), RAAE (SEQ ID NO: 143), AAED (SEQ ID NO: 144), AEDG (SEQ ID NO: 145), EDGA (SEQ ID NO: 146), DGAS (SEQ ID NO: 147), GASS (SEQ ID NO: 148), ASSQ (SEQ ID NO: 149), SSQL (SEQ ID NO: 150), SQLP (SEQ ID NO: 151), QLPA (SEQ ID NO: 152), LPAA (SEQ ID NO: 153), PAAE (SEQ ID NO: 154), AAEG (SEQ ID NO: 155), AEGS (SEQ ID NO: 156), EGSG (SEQ ID NO: 157), GSGE (SEQ ID NO: 158), SGEQ (SEQ ID NO: 159), GEQD (SEQ ID NO: 160), EQDF (SEQ ID NO: 161), QDFT (SEQ ID NO: 162), DFTF (SEQ ID NO: 18), or FTFE (SEQ ID NO: 19).

In an embodiment, the antibody molecule contacts five or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35) of the following peptides (e.g., from Pep5): HTPHT (SEQ ID NO: 163), TPHTE (SEQ ID NO: 164), PHTED (SEQ ID NO: 165), HTEDG (SEQ ID NO: 166), TEDGG (SEQ ID NO: 167), EDGGP (SEQ ID NO: 168), DGGPS (SEQ ID NO: 169), GGPSA (SEQ ID NO: 170), GPSAT (SEQ ID NO: 171), PSATE (SEQ ID NO: 172), SATER (SEQ ID NO: 173), ATERA (SEQ ID NO: 174), TERAA (SEQ ID NO: 175), ERAAE (SEQ ID NO: 176), RAAED (SEQ ID NO: 177), AAEDG (SEQ ID NO: 178), AEDGA (SEQ ID NO: 179), EDGAS (SEQ ID NO: 180), DGASS (SEQ ID NO: 181), GASSQ (SEQ ID NO: 182), ASSQL (SEQ ID NO: 183), SSQLP (SEQ ID NO: 184), SQLPA (SEQ ID NO: 185), QLPAA (SEQ ID NO: 186), LPAAE (SEQ ID NO: 187), PAAEG (SEQ ID NO: 188), AAEGS (SEQ ID NO: 189), AEGSG (SEQ ID NO: 190), EGSGE (SEQ ID NO: 191), GSGEQ (SEQ ID NO: 192), SGEQD (SEQ ID NO: 193), GEQDF (SEQ ID NO: 194), EQDFT (SEQ ID NO: 195), QDFTF (SEQ ID NO: 196), or DFTFE (SEQ ID NO: 56).

In an embodiment, the antibody molecule contacts six or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) consecutive amino acid residues in Pep5.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) of the following peptides (e.g., from Pep5): HTPHTE (SEQ ID NO: 197), TPHTED (SEQ ID NO: 198), PHTEDG (SEQ ID NO: 199), HTEDGG (SEQ ID NO: 200), TEDGGP (SEQ ID NO: 201), EDGGPS (SEQ ID NO: 202), DGGPSA (SEQ ID NO: 203), GGPSAT (SEQ ID NO: 204), GPSATE (SEQ ID NO: 205), PSATER (SEQ ID NO: 206), SATERA (SEQ ID NO: 207), ATERAA (SEQ ID NO: 208), TERAAE (SEQ ID NO: 209), ERAAED (SEQ ID NO: 210), RAAEDG (SEQ ID NO: 211), AAEDGA (SEQ ID NO: 212), AEDGAS (SEQ ID NO: 213), EDGASS (SEQ ID NO: 214), DGASSQ (SEQ ID NO: 215), GASSQL (SEQ ID NO: 216), ASSQLP (SEQ ID NO: 217), SSQLPA (SEQ ID NO: 218), SQLPAA (SEQ ID NO: 219), QLPAAE (SEQ ID NO: 220), LPAAEG (SEQ ID NO: 221), PAAEGS (SEQ ID NO: 222), AAEGSG (SEQ ID NO: 223), AEGSGE (SEQ ID NO: 224), EGSGEQ (SEQ ID NO: 225), GSGEQD (SEQ ID NO: 226), SGEQDF (SEQ ID NO: 227), GEQDFT (SEQ ID NO: 228), EQDFTF (SEQ ID NO: 229), or QDFTFE (SEQ ID NO: 230).

In an embodiment, the antibody molecule does not bind, or binds with low affinity, to an extracellular region of CD138 distant from the transmembrane domain. In an embodiment, the antibody molecule does not bind to an epitope on CD138 comprising four or more (e.g., 5, 6, 7, 8, 9, 10, 11, 12, 13, 14, 15, 20, 25, 30, 35, or more) consecutive amino acid residues in an extracellular region distant from the transmembrane domain. In an embodiment, the C-terminus of the extracellular region distant from the transmembrane domain is at least 100, 110, 120, 130, 140, 150, 160, 170, 180, 190, or 200 amino acids away from the N-terminus of the transmembrane domain In an embodiment, the extracellular region distant from the transmembrane domain corresponds to Pep1a, Pep1b, Pep2a, Pep2b, Pep2c, Pep2d, Pep3, Pep4, or a combination thereof. In an embodiment, the antibody molecule does not bind, or binds with low affinity, to the integrin binding domain (IBD) of CD138. In an embodiment, the antibody molecule does not bind, or binds with low affinity, to a region N-terminal to the IBD of CD138.

In an embodiment, the antibody molecule binds, or substantially binds, to an extracellular region of CD138 distant from the transmembrane domain In an embodiment, the C-terminus of the extracellular region distant from the transmembrane domain is at least 100, 110, 120, 130, 140, 150, 160, 170, 180, 190, or 200 amino acids away from the N-terminus of the transmembrane domain In an embodiment, the extracellular region distant from the transmembrane domain corresponds to Pep1a, Pep1b, Pep2a, Pep2b, Pep2c, Pep2d, Pep3, Pep4, or a combination thereof. In an embodiment, the antibody molecule binds, or substantially binds, to the integrin binding domain (IBD) of CD138. In an embodiment, the antibody molecule binds, or substantially binds, to a region N-terminal to the IBD of CD138. In an embodiment, the antibody molecule does not bind, or binds with low affinity, to the epitope of BB4.

In an embodiment, the antibody molecule binds to an epitope on CD138 comprising four or more (e.g., 5, 6, 7, 8, 9, 10, 11, 12, 13, 14, 15, 20, 25, 30, 35, 40, 45, 50, 55, 60, 65, 70, 75, or more) consecutive amino acid residues in the extracellular region distant from the transmembrane domain.

In an embodiment, the antibody molecule binds to an epitope on CD138 comprising five or more consecutive amino acid residues in the extracellular region distant to the transmembrane domain In an embodiment, the antibody molecule binds to an epitope on CD138 comprising six or more consecutive amino acid residues in the extracellular region distant to the transmembrane domain In an embodiment, the antibody molecule binds to an epitope on CD138 comprising seven or more consecutive amino acid residues in the extracellular region distant to the transmembrane domain In an embodiment, the antibody molecule binds to an epitope on CD138 comprising eight or more consecutive amino acid residues in the extracellular region distant to the transmembrane domain In an embodiment, the antibody molecule binds to an epitope on CD138 comprising nine or more consecutive amino acid residues in the extracellular region distant to the transmembrane domain In an embodiment, the antibody molecule binds to an epitope on CD138 comprising ten or more consecutive amino acid residues in the extracellular region distant to the transmembrane domain In an embodiment, the antibody molecule binds to an epitope on CD138 comprising eleven or more consecutive amino acid residues in the extracellular region distant to the transmembrane domain In an embodiment, the antibody molecule binds to an epitope on CD138 comprising twelve or more consecutive amino acid residues in the extracellular region distant to the transmembrane domain.

In an embodiment, the extracellular region distant to the transmembrane domain corresponds to (e.g., comprises or consists of) Pep2a.

In an embodiment, the antibody molecule contacts four or more (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), or EQEA (SEQ ID NO: 261). In an embodiment, the antibody molecule does not contact LPEV (SEQ ID NO: 250).

In an embodiment, the antibody molecule contacts five or more (e.g., 6, 7, 8, 9, 10, 11, 12, 13, 14, 15, 16, 17, 18, 19, 20, 21, 22, 23, 24, 25, 26, 27, 28, 29, or 30) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), or EQEA (SEQ ID NO: 261). In an embodiment, the antibody molecule does not contact a peptide comprising LPEV (SEQ ID NO: 250).

In an embodiment, the antibody molecule contacts six or more (e.g., 7, 8, 9, 10, 11, 12, 13, 14, 15, 16, 17, 18, 19, 20, 21, 22, 23, 24, 25, 26, 27, 28, or 29) consecutive amino acid residues in Pep2a.

In an embodiment, the antibody molecule contacts one or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32) of the following peptides (e.g., from Pep2a): ASTS (SEQ ID NO: 231), STST (SEQ ID NO: 232), TSTL (SEQ ID NO: 233), STLP (SEQ ID NO: 234), TLPA (SEQ ID NO: 235), LPAG (SEQ ID NO: 236), PAGE (SEQ ID NO: 237), AGEG (SEQ ID NO: 238), GEGP (SEQ ID NO: 239), EGPK (SEQ ID NO: 240), GPKE (SEQ ID NO: 241), PKEG (SEQ ID NO: 242), KEGE (SEQ ID NO: 243), EGEA (SEQ ID NO: 244), GEAV (SEQ ID NO: 245), EAVV (SEQ ID NO: 246), AVVL (SEQ ID NO: 247), VVLP (SEQ ID NO: 248), VLPE (SEQ ID NO: 249), LPEV (SEQ ID NO: 250), PEVE (SEQ ID NO: 251), EVEP (SEQ ID NO: 252), VEPG (SEQ ID NO: 253), EPGL (SEQ ID NO: 254), PGLT (SEQ ID NO: 255), GLTA (SEQ ID NO: 256), LTAR (SEQ ID NO: 257), TARE (SEQ ID NO: 258), AREQ (SEQ ID NO: 259), REQE (SEQ ID NO: 260), EQEA (SEQ ID NO: 261). In an embodiment, the antibody molecule does not contact a peptide comprising LPEV (SEQ ID NO: 250).

In an embodiment, the antibody molecule binds, or substantially binds, to an extracellular region of CD138 proximal to the transmembrane domain (e.g., an extracellular region described herein) and an extracellular region of CD138 distant from the transmembrane domain (e.g., an extracellular region described herein). In an embodiment, the antibody molecule binds to the extracellular region of CD138 proximal to the transmembrane domain with a binding affinity that is higher (e.g., at least 2, 3, 4, 5, 6, 7, 8, 9, 10, 20, 30, 40, 50, 100, 200, 300, 400, or 500-fold higher) than the binding affinity to the extracellular region of CD138 distant from the transmembrane domain In an embodiment, the antibody molecule binds to the extracellular region of CD138 distant from the transmembrane domain with a binding affinity that is higher (e.g., at least 2, 3, 4, 5, 6, 7, 8, 9, 10, 20, 30, 40, 50, 100, 200, 300, 400, or 500-fold higher) than the binding affinity to the extracellular region of CD138 proximal to the transmembrane domain.

Antibody Molecules

Disclosed herein are humanized antibody molecules that bind to CD138, e.g., a CD138 molecule described herein.

As used herein, the term "antibody molecule" refers to a protein, e.g., an immunoglobulin chain or a fragment thereof, comprising at least one immunoglobulin variable domain sequence. The term "antibody molecule" includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibody molecules can be monoclonal or polyclonal. The antibody molecule can also be a human, humanized, CDR-grafted, or in vitro generated antibody. The antibody molecule can have a heavy chain constant region chosen from, e.g., IgG1, IgG2, IgG3, or IgG4. The antibody molecule can also have a light chain chosen from, e.g., kappa or lambda. The term "immunoglobulin" (Ig) is used interchangeably with the term "antibody" herein.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments may be obtained using any suitable method, including several conventional techniques known to those with skill in the art, and the fragments can be screened for utility in the same manner as are intact antibodies.

The term "antibody" includes intact molecules as well as functional fragments thereof. Constant regions of the antibodies can be altered, e.g., mutated, to modify the properties of the antibody (e.g., to increase or decrease one or more of:

Fc receptor binding, antibody glycosylation, the number of cysteine residues, effector cell function, or complement function).

The antibody molecule can be a single chain antibody. A single-chain antibody (scFv) may be engineered (see, e.g., Colcher et al. (1999) *Ann NY Acad Sci* 880: 263-280; and Reiter & Pastan (1996) *Clin Cancer Res* 2: 245-252). The single chain antibody can be dimerized or multimerized to generate multivalent antibodies having specificities for different epitopes of the same target protein.

The antibody molecules disclosed herein can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to some aspects, a single domain antibody is a naturally occurring single domain antibody known as heavy chain antibody devoid of light chains. Such single domain antibodies are disclosed in WO 94/04678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are also contemplated.

The VH and VL regions can be subdivided into regions of hypervariability, termed "complementarity determining regions" (CDR), interspersed with regions that are more conserved, termed "framework regions" (FR or FW). The terms "complementarity determining region," and "CDR," as used herein refer to the sequences of amino acids within antibody variable regions which confer antigen specificity and binding affinity. As used herein, the terms "framework," "FW" and "FR" are used interchangeably.

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). In an embodiment, the following definitions are used: AbM definition of CDR1 of the heavy chain variable domain and Kabat definitions for the other CDRs. In an embodiment, Kabat definitions are used for all CDRs. In addition, embodiments described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, and FR4.

As used herein, an "immunoglobulin variable domain sequence" refers to an amino acid sequence which can form the structure of an immunoglobulin variable domain. For example, the sequence may include all or part of the amino acid sequence of a naturally-occurring variable domain For example, the sequence may or may not include one, two, or more N- or C-terminal amino acids, or may include other alterations that are compatible with formation of the protein structure.

The term "antigen-binding region" refers to the part of an antibody molecule that comprises determinants that form an interface that binds to an antigen, e.g., CD138, or an epitope thereof. With respect to proteins (or protein mimetics), the antigen-binding region typically includes one or more loops (of at least, e.g., four amino acids or amino acid mimics) that form an interface that binds to the antigen, e.g., CD138. Typically, the antigen-binding region of an antibody molecule includes at least one or two CDRs and/or hypervariable loops, or more typically at least three, four, five or six CDRs and/or hypervariable loops.

The terms "compete" or "cross-compete" are used interchangeably herein to refer to the ability of an antibody molecule to interfere with binding of an anti-CD138 antibody molecule, e.g., an anti-CD138 antibody molecule provided herein, to a target, e.g., CD138. The interference with binding can be direct or indirect (e.g., through an allosteric modulation of the antibody molecule or the target). The extent to which an antibody molecule is able to interfere with the binding of another antibody molecule to the target, and therefore whether it can be said to compete, can be determined using a competition binding assay, for example, a FACS assay, an ELISA or BIACORE assay. In an embodiment, a competition binding assay is a quantitative competition assay. In an embodiment, a first anti-CD138 antibody molecule is said to compete for binding to the target with a second anti-CD138 antibody molecule when the binding of the first antibody molecule to the target is reduced by 10% or more, e.g., 20% or more, 30% or more, 40% or more, 50% or more, 55% or more, 60% or more, 65% or more, 70% or more, 75% or more, 80% or more, 85% or more, 90% or more, 95% or more, 98% or more, 99% or more in a competition binding assay (e.g., a competition assay described herein).

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

An "effectively human" protein is a protein that does not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see e.g., Saleh et al., *Cancer Immunol. Immunother.*, 32:180-190 (1990)) and also because of potential allergic reactions (see e.g., LoBuglio et al., *Hybridoma*, 5:5117-5123 (1986)).

The antibody molecule can be a polyclonal or a monoclonal antibody. In some embodiments, the antibody can be recombinantly produced, e.g., produced by any suitable phage display or combinatorial methods.

Various phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In an embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. In an embodiment, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by any suitable recombinant DNA technique. Several are known in the art (see Robinson et al., International Patent Application Publication No. WO1987/002671; Akira, et al., European Patent Application Publication No. 184,187; Taniguchi, M., European Patent Application Publication No. 171,496; Morrison et al., European Patent Application Publication No. 173,494; Neuberger et al., International Patent Application Publication No. WO 86/01533; Cabilly et al. U.S. Pat. No. 4,816,567; Cabilly et al., European Patent Application Publication No. 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) PNAS 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immunoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to lipopolysaccharide. In an embodiment, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In some embodiments, the donor immunoglobulin is a non-human (e.g., rodent). The acceptor framework is typically a naturally-occurring (e.g., a human) framework or a consensus framework, or a sequence about 85% or higher, e.g., 90%, 95%, 99% or higher identical thereto.

As used herein, the term "consensus sequence" refers to the sequence formed from the most frequently occurring amino acids (or nucleotides) in a family of related sequences (see, e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by any suitable method, and several such methods known in the art (see, e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See, e.g., U.S. Pat. No. 5,225,539; Jones et al. 1986 Nature 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare humanized antibodies (UK Patent Application GB 2188638A, filed on Mar. 26, 1987; Winter U.S. Pat. No. 5,225,539), the contents of which is expressly incorporated by reference.

Also provided are humanized antibodies in which specific amino acids have been substituted, deleted or added. Criteria for selecting amino acids from the donor are described in, e.g., U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In an embodiment, the antibody molecule has a heavy chain constant region chosen from, e.g., the heavy chain constant regions of IgG1, IgG2 (e.g., IgG2a), IgG3, IgG4, IgM, IgA1, IgA2, IgD, and IgE; particularly, chosen from, e.g., the (e.g., human) heavy chain constant regions of IgG1, IgG2, IgG3, and IgG4. In an embodiment, the antibody molecule comprises a heavy chain constant region of IgG1 (e.g., m3 allotype). In another embodiment, the antibody molecule has a light chain constant region chosen from, e.g., the (e.g., human) light chain constant regions of kappa or lambda. In an embodiment, the antibody molecule comprises a light chain constant region of kappa (e.g., kappa constant *01). In an embodiment, the antibody molecule comprises a heavy chain constant region of IgG1 and a light chain constant region of kappa. The constant region can be altered, e.g., mutated, to modify the properties of the antibody molecule (e.g., to increase or decrease one or more of: Fc receptor binding, antibody glycosylation, the number of cysteine residues, effector cell function, and/or complement function). In an embodiment, the antibody molecule has effector function and can fix complement. In another embodiment, the antibody molecule does not recruit effector cells or fix complement. In certain embodiments, the antibody molecule has reduced or no ability to bind an Fc receptor. For example, it may be an isotype or subtype, fragment or other mutant, which does not support binding to an Fc receptor, e.g., it has a mutagenized or deleted Fc receptor binding region.

In an embodiment, a constant region of the antibody molecule is altered. Methods for altering an antibody constant region are known in the art. Antibody molecules s with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference) Amino acid mutations which stabilize antibody structure, such as S228P (EU nomenclature, S241P in Kabat nomenclature) in human IgG4 are also contemplated. Similar type of alterations could be described which if applied to the murine, or other species immunoglobulin would reduce or eliminate these functions.

In an embodiment, the antibody molecule comprises an Fc region that comprise one or more (e.g., 2, 3, 4, 5, 6, 7, 8, 9, 10, 11, 12, 13, 14, 15, 16, 17, 18, 19, 20, 21, 22, 23, 24, 25, or more) of mutations or combinations of mutations described in Table 9.

TABLE 9

Exemplary Fc mutations

| Name | Mutation (according to EU numbering) |
|---|---|
| FcMut001 | I253M |
| FcMut002 | L309H_D312A_N315D |
| FcMut003 | L309N |
| FcMut004 | M252E_S254R |
| FcMut005 | M252E_S254R_R255Y |
| FcMut006 | S254H |
| FcMut007 | S254M |
| FcMut008 | T256D_T307R |
| FcMut009 | T256L_N286I_T307I |
| FcMut010 | T256I_N286I_T307I |
| FcMut011 | K248S_D376Q |
| FcMut012 | K248S_D376N |
| FcMut013 | D376Q_E380A |
| FcMut014 | D376N_E380A |
| FcMut015 | D376Q_M428L |
| FcMut016 | K248S_A378I |
| FcMut017 | L314K |
| FcMut018 | T250Q_M428L |
| FcMut019 | M428L_N434A |
| FcMut020 | N434A |
| FcMut021 | T307A_E380A_N434A |
| FcMut022 | M252W |
| FcMut023 | V308F |
| FcMut024 | V308F_N434Y |
| FcMut026 | T256D_T307R_D376N |
| FcMut027 | L309R_D312E |
| FcMut028 | L309R_Q311P_D312E |
| FcMut029 | K246N_P247A |

TABLE 9-continued

Exemplary Fc mutations

| Name | Mutation (according to EU numbering) |
|---|---|
| FcMut030 | K246N_P247A_D376N |
| FcMut031 | T256E_T307R |
| FcMut032 | T256R_T307D |
| FcMut033 | T256R_T307E |
| FcMut034 | Q311P |
| FcMut035 | D376Q |
| FcMut036 | L234A_L235A |
| FcMut037 | L235V_G236A |
| FcMut038 | L234P_L235P |
| FcMut039 | L235P |
| FcMut040 | P329G |
| FcMut041 | P329E |
| FcMut042 | E233K |
| FcMut043 | T256D_N286D_A287S_T307R |
| FcMut044 | T256D_P257L_T307R |
| FcMut045 | T256D_T307R_Q311V |
| FcMut046 | P247D_T256D_T307R |
| FcMut047 | P247D_N286D_A287S_Q311V |
| FcMut048 | P257M_V308N |
| FcMut049 | V279I_Q311L_N315T |
| FcMut050 | M428L_N434S |
| FcMut051 | N434S |
| FcMut052 | H433G_N434P |
| FcMut053 | V259I_V308F_M428L |
| FcMut067 | T256D_N286D_T307R |
| FcMut068 | T256D_N286E_T307R |
| FcMut069 | T256D_N286Q_T307R |
| FcMut070 | T256D_P257T_T307R |
| FcMut071 | T256D_P257V_T307R |
| FcMut072 | T256D_T307R_Q311I |
| FcMut073 | T256D_T307R_Q311L |
| FcMut074 | T256D_T307R_Q311M |
| FcMut075 | T256D_P257L_N286D_T307R_Q311V |
| FcMut076 | T256D_T307R_M428L |
| FcMut077 | M428L |
| FcMut078 | M252Y_S254T_T256Q |
| FcMut079 | M252Y_S254T_T256E_K288E |
| FcMut080 | T256K_K288E |
| FcMut081 | T256D_E258T |
| FcMut082 | E283Q_H285E |
| FcMut083 | R344D_D401R |
| FcMut084 | K248E_E380K |
| FcMut085 | K248E_E380R |
| FcMut086 | K246H |
| FcMut087 | K248H |
| FcMut088 | T250I |
| FcMut089 | T250V |
| FcMut090 | L251F |
| FcMut091 | L251M |
| FcMut093 | P257V |
| FcMut094 | N276D |
| FcMut095 | H285N |
| FcMut096 | H285D |
| FcMut097 | K288H |
| FcMut098 | K288Q |
| FcMut099 | K288E |
| FcMut100 | T307E |
| FcMut101 | T307Q |
| FcMut102 | V308P |
| FcMut103 | V308I |
| FcMut104 | V308L |
| FcMut105 | L309H |
| FcMut106 | L309M |
| FcMut107 | Q311H |
| FcMut108 | L314F |
| FcMut109 | Y319H |
| FcMut110 | I336T |
| FcMut111 | P343D |
| FcMut112 | P343V |
| FcMut113 | E345Q |
| FcMut114 | P346V |
| FcMut115 | P374T |
| FcMut116 | D376N |
| FcMut117 | A378S |
| FcMut118 | A431T |
| FcMut119 | A431P |

TABLE 9-continued

Exemplary Fc mutations

| Name | Mutation (according to EU numbering) |
|---|---|
| FcMut120 | A431G |
| FcMut121 | L432V |
| FcMut122 | L432I |
| FcMut123 | L432Q |
| FcMut124 | N434T |
| FcMut125 | H435N |
| FcMut126 | Y436H |
| FcMut127 | K439Q |
| FcMut128 | T256D |
| FcMut129 | T307R |
| FcMut130 | A378T |
| FcMut131 | A378D |
| FcMut132 | A378H |
| FcMut133 | A378Y |
| FcMut134 | A378V |
| FcMut135 | D376R |
| FcMut136 | D376F |
| FcMut137 | D376W |
| FcMut138 | L314H |
| FcMut139 | L432E_T437Q |
| FcMut140 | D376Q_A378T |
| FcMut141 | D376Q_I377M_A378T |
| FcMut142 | P244Q_D376Q |
| FcMut143 | P247T_A378T |
| FcMut144 | P247N_A378T |
| FcMut145 | T256D_T307R_L309T |
| FcMut146 | A339T_S375E_F404Y |
| FcMut147 | L235V_G236A_T256D_T307R |
| FcMut148 | L235V_G236A_D376Q_M428L |
| FcMut149 | L314N |
| FcMut150 | N315D |
| FcMut151 | A378T |
| FcMut152 | T437Q |
| FcMut153 | L432E |
| FcMut154 | Y436R |
| FcMut155 | L314M |
| FcMut156 | L234A_L235A_T256D_T307R_Q311V |
| FcMut157 | L234A_L235A_T256D_P257V_T307R |
| FcMut158 | L234A_L235A_T256D_P257L_N286D_T307R_Q311V |
| FcMut159 | L235V_G236A_T256D_T307R_Q311V |
| FcMut160 | L235V_G236A_T256D_P257V_T307R |
| FcMut161 | L235V_G236A_T256D_P257L_N286D_T307R_Q311V |
| FcMut162 | S267T_A327N_A330M |
| FcMut163 | S267T_A327N |
| FcMut164 | L235V_G236A_S267T_A327N_A330M |
| FcMut165 | L235V_G236A_S267T_A327N |
| FcMut166 | M252Y_S254T |
| FcMut167 | T256E |
| FcMut168 | G236A_I332E |
| FcMut169 | S239D_I332E |
| FcMut170 | G236A_S239D_I332E |
| FcMut171 | T256D_N286D_T307R_Q311V |
| FcMut172 | T256D_E258T_T307R |
| FcMut173 | T256D_E258T_T307R_Q311V |
| FcMut174 | T256D_P257V_E258T_T307R |
| FcMut175 | T256D_P257L_E258T_N286D_T307R_Q311V |
| FcMut176 | T256D_E258T_N286D_T307R_Q311V |
| FcMut177 | A378V_M428L |
| FcMut178 | A378V_M428I |
| FcMut179 | A378V_M428V |
| FcMut180 | T256D_N286D |
| FcMut181 | T256D_A378V |
| FcMut182 | T256D_Q311V |
| FcMut183 | T256D_Q311V_A378V |
| FcMut184 | T256D_T307R_A378V |
| FcMut185 | T256D_N286D_T307R_A378V |
| FcMut186 | T256D_T307R_Q311V_A378V |
| FcMut187 | H285D_A378V |
| FcMut188 | H285D_Q311V |
| FcMut189 | T256D_H285D |
| FcMut190 | T256D_H285D_Q311V |
| FcMut191 | T256D_H285D_T307R |
| FcMut192 | T256D_H285D_T307R_A378V |
| FcMut193 | H285D_L314M_A378V |
| FcMut194 | T256D_E258T_H285D_Q311H |
| FcMut195 | T256D_E258T_H285D |
| FcMut196 | H285D_N315D |
| FcMut197 | H285N_T307Q_N315D |
| FcMut198 | H285D_L432E_T437Q |
| FcMut199 | T256D_E258T_N315D |
| FcMut200 | P257V_H285N |
| FcMut201 | H285N_L432F |
| FcMut202 | H285N_T437I |
| FcMut203 | T256D_E258T_L314M |
| FcMut204 | T256D_E258T_T307Q |
| FcMut205 | T256D_E258T_A378V |
| FcMut206 | V308P_A378V |
| FcMut207 | P257V_A378T |
| FcMut208 | P257V_V308P_A378V |
| FcMut209 | N315D_A378T |
| FcMut210 | H285N_L314M |
| FcMut211 | L314M_L432E_T437Q |
| FcMut212 | T307Q_N315D |
| FcMut213 | H285D_T307Q_A378V |
| FcMut214 | L314M_N315D |
| FcMut215 | T307Q_Q311V_A378V |
| FcMut216 | H285D_Q311V_A378V |
| FcMut217 | Q311V_N315D_A378V |
| FcMut218 | T256D_E258T_Q311V |
| FcMut219 | T256D_N315D_A378V |
| FcMut220 | T256D_Q311V_N315D |
| FcMut221 | T256D_T307Q_A378V |
| FcMut222 | T256D_T307Q_Q311V |
| FcMut223 | T256D_H285D_A378V |
| FcMut224 | T256D_H285D_T307R_Q311V |
| FcMut225 | T256D_H285D_N286D_T307R |
| FcMut226 | T256D_H285D_N286D_T307R_Q311V |
| FcMut227 | T256D_H285D_N286D_T307R_A378V |
| FcMut228 | T256D_N286D_T307R_Q311V_A378V |
| FcMut229 | T256D_H285D_T307R_Q311V_A378V |
| FcMut230 | V308P_Q311V_A378V |
| FcMut231 | T256D_V308P_A378V |
| FcMut232 | T256D_V308P_Q311V |
| FcMut233 | T256D_E258T_V308P |
| FcMut234 | H285D_V308P_Q311V |
| FcMut242 | E258T |
| FcMut243 | N286D |
| FcMut244 | Q311V |
| YTE | M252Y_S254T_T256E |

In an embodiment, the Fc region comprises FcMut001. In an embodiment, the Fc region comprises FcMut002. In an embodiment, the Fc region comprises FcMut003. In an embodiment, the Fc region comprises FcMut004. In an embodiment, the Fc region comprises FcMut005. In an embodiment, the Fc region comprises FcMut006. In an embodiment, the Fc region comprises FcMut007. In an embodiment, the Fc region comprises FcMut008. In an embodiment, the Fc region comprises FcMut009. In an embodiment, the Fc region comprises FcMut010. In an embodiment, the Fc region comprises FcMut011. In an embodiment, the Fc region comprises FcMut012. In an embodiment, the Fc region comprises FcMut013. In an embodiment, the Fc region comprises FcMut014. In an embodiment, the Fc region comprises FcMut015. In an embodiment, the Fc region comprises FcMut016. In an embodiment, the Fc region comprises FcMut017. In an embodiment, the Fc region comprises FcMut018. In an embodiment, the Fc region comprises FcMut019. In an embodiment, the Fc region comprises FcMut020. In an embodiment, the Fc region comprises FcMut021. In an embodiment, the Fc region comprises FcMut022. In an embodiment, the Fc region comprises FcMut023. In an embodiment, the Fc region comprises FcMut024. In an embodiment, the Fc region comprises FcMut026. In an embodiment, the Fc region comprises FcMut027. In an embodiment, the Fc region comprises FcMut028. In an embodiment, the Fc region comprises FcMut029. In an embodiment, the Fc region comprises FcMut030. In an embodiment, the Fc region comprises FcMut031. In an embodiment, the Fc region comprises FcMut032. In an embodiment, the Fc region comprises FcMut033. In an embodiment, the Fc region comprises FcMut034. In an embodiment, the Fc region comprises FcMut035. In an embodiment, the Fc region comprises FcMut036. In an embodiment, the Fc region comprises FcMut037. In an embodiment, the Fc region comprises FcMut038. In an embodiment, the Fc region comprises FcMut039. In an embodiment, the Fc region comprises FcMut040. In an embodiment, the Fc region comprises FcMut041. In an embodiment, the Fc region comprises FcMut042. In an embodiment, the Fc region comprises FcMut043. In an embodiment, the Fc region comprises FcMut044. In an embodiment, the Fc region comprises FcMut045. In an embodiment, the Fc region comprises FcMut046. In an embodiment, the Fc region comprises FcMut047. In an embodiment, the Fc region comprises FcMut048. In an embodiment, the Fc region comprises FcMut049. In an embodiment, the Fc region comprises FcMut050. In an embodiment, the Fc region comprises FcMut051. In an embodiment, the Fc region comprises FcMut052. In an embodiment, the Fc region comprises FcMut053. In an embodiment, the Fc region comprises FcMut067. In an embodiment, the Fc region comprises FcMut068. In an embodiment, the Fc region comprises FcMut069. In an embodiment, the Fc region comprises FcMut070. In an embodiment, the Fc region comprises FcMut071. In an embodiment, the Fc region comprises FcMut072. In an embodiment, the Fc region comprises FcMut073. In an embodiment, the Fc region comprises FcMut074. In an embodiment, the Fc region comprises FcMut075. In an embodiment, the Fc region comprises FcMut076. In an embodiment, the Fc region comprises FcMut077. In an embodiment, the Fc region comprises FcMut078. In an embodiment, the Fc region comprises FcMut079. In an embodiment, the Fc region comprises FcMut080. In an embodiment, the Fc region comprises FcMut081. In an embodiment, the Fc region comprises FcMut082. In an embodiment, the Fc region comprises FcMut083. In an embodiment, the Fc region comprises FcMut084. In an embodiment, the Fc region comprises FcMut085. In an embodiment, the Fc region comprises FcMut086. In an embodiment, the Fc region comprises FcMut087. In an embodiment, the Fc region comprises FcMut088. In an embodiment, the Fc region comprises FcMut089. In an embodiment, the Fc region comprises FcMut090. In an embodiment, the Fc region comprises FcMut091. In an embodiment, the Fc region comprises FcMut093. In an embodiment, the Fc region comprises FcMut094. In an embodiment, the Fc region comprises FcMut095. In an embodiment, the Fc region comprises FcMut096. In an embodiment, the Fc region comprises FcMut097. In an embodiment, the Fc region comprises FcMut098. In an embodiment, the Fc region comprises FcMut099. In an embodiment, the Fc region comprises FcMut100. In an embodiment, the Fc region comprises FcMut101. In an embodiment, the Fc region comprises FcMut102. In an embodiment, the Fc region comprises FcMut103. In an embodiment, the Fc region comprises FcMut104. In an embodiment, the Fc region comprises FcMut105. In an embodiment, the Fc region comprises FcMut106. In an embodiment, the Fc region comprises FcMut107. In an embodiment, the Fc region comprises FcMut108. In an embodiment, the Fc region comprises FcMut109. In an embodiment, the Fc region comprises FcMut110. In an embodiment, the Fc region comprises FcMut111. In an embodiment, the Fc region comprises FcMut112. In an embodiment, the Fc region comprises FcMut113. In an embodiment, the Fc region comprises FcMut114. In an embodiment, the Fc region comprises FcMut115. In an embodiment, the Fc region comprises FcMut116. In an embodiment, the Fc region comprises FcMut117. In an embodiment, the Fc region comprises FcMut118. In an embodiment, the Fc region comprises FcMut119. In an embodiment, the Fc region comprises FcMut120. In an embodiment, the Fc region comprises FcMut121. In an embodiment, the Fc region comprises FcMut122. In an embodiment, the Fc region comprises FcMut123. In an embodiment, the Fc region comprises FcMut124. In an embodiment, the Fc region comprises FcMut125. In an embodiment, the Fc region comprises FcMut126. In an embodiment, the Fc region comprises FcMut127. In an embodiment, the Fc region comprises FcMut128. In an embodiment, the Fc region comprises FcMut129. In an embodiment, the Fc region comprises FcMut130. In an embodiment, the Fc region comprises FcMut131. In an embodiment, the Fc region comprises FcMut132. In an embodiment, the Fc region comprises FcMut133. In an embodiment, the Fc region comprises FcMut134. In an embodiment, the Fc region comprises FcMut135. In an embodiment, the Fc region comprises FcMut136. In an embodiment, the Fc region comprises FcMut137. In an embodiment, the Fc region comprises FcMut138. In an embodiment, the Fc region comprises FcMut139. In an embodiment, the Fc region comprises FcMut140. In an embodiment, the Fc region comprises FcMut141. In an embodiment, the Fc region comprises FcMut142. In an embodiment, the Fc region comprises FcMut143. In an embodiment, the Fc region comprises FcMut144. In an embodiment, the Fc region comprises FcMut145. In an embodiment, the Fc region comprises FcMut146. In an embodiment, the Fc region comprises FcMut147. In an embodiment, the Fc region comprises FcMut148. In an embodiment, the Fc region comprises FcMut149. In an embodiment, the Fc region comprises FcMut150. In an embodiment, the Fc region comprises FcMut151. In an embodiment, the Fc region comprises FcMut152. In an embodiment, the Fc region comprises FcMut153. In an embodiment, the Fc region comprises FcMut154. In an embodiment, the Fc region comprises FcMut155. In an embodiment, the Fc region comprises FcMut156. In an embodiment, the Fc region comprises FcMut157. In an embodiment, the Fc region comprises FcMut158. In an embodiment, the Fc region comprises FcMut159. In an embodiment, the Fc region comprises FcMut160. In an embodiment, the Fc region comprises FcMut161. In an embodiment, the Fc region comprises FcMut162. In an embodiment, the Fc region comprises FcMut163. In an embodiment, the Fc region comprises FcMut164. In an embodiment, the Fc region comprises FcMut165. In an embodiment, the Fc region comprises FcMut166. In an embodiment, the Fc region comprises FcMut167. In an embodiment, the Fc region comprises FcMut168. In an embodiment, the Fc region comprises FcMut169. In an embodiment, the Fc region comprises FcMut170. In an embodiment, the Fc region comprises FcMut171. In an embodiment, the Fc region comprises FcMut172. In an embodiment, the Fc region comprises FcMut173. In an embodiment, the Fc region comprises FcMut174. In an embodiment, the Fc region comprises FcMut175. In an embodiment, the Fc region comprises FcMut176. In an embodiment, the Fc region comprises FcMut177. In an embodiment, the Fc region comprises FcMut178. In an embodiment, the Fc region comprises FcMut179. In an embodiment, the Fc region comprises FcMut180. In an embodiment, the Fc region comprises FcMut181. In an embodiment, the Fc region comprises FcMut182. In an embodiment, the Fc region comprises FcMut183. In an embodiment, the Fc region comprises FcMut184. In an embodiment, the Fc region comprises FcMut185. In an embodiment, the Fc region comprises FcMut186. In an embodiment, the Fc region comprises FcMut187. In an embodiment, the Fc region comprises FcMut188. In an embodiment, the Fc region comprises FcMut189. In an embodiment, the Fc region comprises FcMut190. In an embodiment, the Fc region comprises FcMut191. In an embodiment, the Fc region comprises FcMut192. In an embodiment, the Fc region comprises FcMut193. In an embodiment, the Fc region comprises FcMut194. In an embodiment, the Fc region comprises FcMut195. In an embodiment, the Fc region comprises FcMut196. In an embodiment, the Fc region comprises FcMut197. In an embodiment, the Fc region comprises FcMut198. In an embodiment, the Fc region comprises FcMut199. In an embodiment, the Fc region comprises FcMut200. In an embodiment, the Fc region comprises FcMut201. In an embodiment, the Fc region comprises FcMut202. In an embodiment, the Fc region comprises FcMut203. In an embodiment, the Fc region comprises FcMut204. In an embodiment, the Fc region comprises FcMut205. In an embodiment, the Fc region comprises FcMut206. In an embodiment, the Fc region comprises FcMut207. In an embodiment, the Fc region comprises FcMut208. In an embodiment, the Fc region comprises FcMut209. In an embodiment, the Fc region comprises FcMut210. In an embodiment, the Fc region comprises FcMut211. In an embodiment, the Fc region comprises FcMut212. In an embodiment, the Fc region comprises FcMut213. In an embodiment, the Fc region comprises FcMut214. In an embodiment, the Fc region comprises FcMut215. In an embodiment, the Fc region comprises FcMut216. In an embodiment, the Fc region comprises FcMut217. In an embodiment, the Fc region comprises FcMut218. In an embodiment, the Fc region comprises FcMut219. In an embodiment, the Fc region comprises FcMut220. In an embodiment, the Fc region comprises FcMut221. In an embodiment, the Fc region comprises FcMut222. In an embodiment, the Fc region comprises FcMut223. In an embodiment, the Fc region comprises FcMut224. In an embodiment, the Fc region comprises FcMut225. In an embodiment, the Fc region comprises FcMut226. In an embodiment, the Fc region comprises FcMut227. In an embodiment, the Fc region comprises FcMut228. In an embodiment, the Fc region comprises FcMut229. In an embodiment, the Fc region comprises FcMut230. In an embodiment, the Fc region comprises FcMut231. In an embodiment, the Fc region comprises FcMut232. In an embodiment, the Fc region comprises FcMut233. In an embodiment, the Fc region comprises FcMut234. In an embodiment, the Fc region comprises FcMut242. In an embodiment, the Fc region comprises FcMut243. In an embodiment, the Fc region comprises FcMut244.

Other exemplary Fc mutations are described, e.g., in International Application Publication No. WO2018/052556, US Patent Application Publication No. US2018/0037634, and Booth et al., MAbs. 2018; 10(7):1098-1110, the contents of which are incorporated by reference in their entirety.

In an embodiment, the Fc region is altered to extend half-life. For example, the Fc region can contain one or more of: FcMut183 (T256D-Q311V-A378V), FcMut197 (H285N-T307Q-N315D), FcMut213 (H285D-T307Q-A378V), FcMut215 (T307Q-Q311V-A378V), or FcMut228 (T256D-N286D-T307R-Q311V-A378V) (all according to EU numbering).

In an embodiment, the Fc region is altered to enhance ADCC. For example, the Fc region can contain one or more of: A330L-I332E-S239D, F243L-R292P-Y300L-V305I-P396L, or S298A-E333A-K334A. In an embodiment, afucosylation can be achieved by expression in a cell line such as CHO in which fucosyltransferase (FucT8) is knocked out.

In an embodiment, the Fc region is altered to enhance CDC. For example, the Fc region contains S267E-H268F-S324T.

In an embodiment, the Fc region is altered to enhance antibody-dependent cellular phagocytosis (ADCP). For example, the Fc region contains S239D-I332E-A330L.

In an embodiment, the only amino acids in the antibody molecule are canonical amino acids. In an embodiment, the antibody molecule comprises naturally-occurring amino acids; analogs, derivatives and congeners thereof; amino acid analogs having variant side chains; and/or all stereoisomers of any of any of the foregoing. The antibody molecule may comprise the D- or L-optical isomers of amino acids and peptidomimetics.

A polypeptide of an antibody molecule described herein may be linear or branched, it may comprise modified amino acids, and it may be interrupted by non-amino acids. The antibody molecule may also be modified; for example, by disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The antibody molecule described herein can be used alone in unconjugated form, or can be bound to a substance, e.g., a toxin or moiety (e.g., a therapeutic drug; a compound emitting radiation; molecules of plant, fungal, or bacterial origin; or a biological protein (e.g., a protein toxin) or particle (e.g., a recombinant viral particle, e.g., via a viral coat protein). For example, the anti-CD138 antibody can be coupled to a radioactive isotope such as an α-, β-, or γ-emitter, or a β- and γ-emitter.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a toxin, a pharmaceutical agent, and/or a protein or peptide that can mediate association of the antibody or antibody portion with another molecule (such as a streptavidin core region or a polyhistidine tag).

Some types of derivatized antibody molecule are produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an anti-CD138 antibody molecule may be derivatized (or labeled) to include fluorescent compounds, various enzymes, prosthetic groups, luminescent materials, bioluminescent materials, fluorescent emitting metal atoms, e.g., europium (Eu), and other anthanides, and radioactive materials (described below). Exemplary fluorescent detectable agents include fluorescein, fluorescein isothiocyanate, rhodamine, 5dimethylamine-1-napthalenesulfonyl chloride, phycoerythrin and the like. An antibody may also be derivatized with detectable enzymes, such as alkaline phosphatase, horseradish peroxidase, β-galactosidase, acetylcholinesterase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody molecule may also be derivatized with a prosthetic group (e.g., streptavidin/biotin and avidin/biotin). For example, an antibody may be derivatized with biotin, and detected through indirect measurement of avidin or streptavidin binding. Examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of bioluminescent materials include luciferase, luciferin, and aequorin.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate or cell supernatant) in order to evaluate the abundance and pattern of expression of the protein; (iii) to monitor protein levels in tissue as part of a clinical testing procedure, e.g., to determine the efficacy of a given treatment regimen.

An antibody molecule may be conjugated to another molecular entity, typically a label or a therapeutic (e.g., antimicrobial (e.g., antibacterial or bactericidal), immunomodulatory, immunostimulatory, cytotoxic, or cytostatic) agent or moiety. Radioactive isotopes can be used in diagnostic or therapeutic applications. Radioactive isotopes that can be coupled to the antibody molecules include, but are not limited to α-, β-, or γ-emitters, or β- and γ-emitters. Such radioactive isotopes include, but are not limited to iodine ($^{131}$I or $^{125}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), indium ($^{111}$In), technetium ($^{99}$mTc), phosphorus ($^{32}$P), rhodium ($^{188}$Rh), sulfur ($^{35}$S), carbon ($^{14}$C), tritium ($^{3}$H), chromium ($^{51}$Cr), chlorine ($^{36}$Cl), cobalt ($^{57}$Co or $^{58}$Co), iron ($^{59}$Fe), selenium ($^{75}$Se), or gallium ($^{67}$Ga). Radioisotopes useful as therapeutic agents include yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Radioisotopes useful as labels, e.g., for use in diagnostics, include iodine ($^{131}$I or $^{125}$I), indium ($^{111}$In), technetium ($^{99}$mTc), phosphorus ($^{32}$P), carbon ($^{14}$C), and tritium ($^{3}$H), or one or more of the therapeutic isotopes listed above.

The present disclosure provides radiolabeled antibody molecules and methods of labeling the same. In an embodiment, a method of labeling an antibody molecule is disclosed. The method includes contacting an antibody molecule, with a chelating agent, to thereby produce a conjugated antibody. The conjugated antibody is radiolabeled with a radioisotope, e.g., $^{111}$Indium, $^{90}$Yttrium and $^{177}$Lutetium, to thereby produce a labeled antibody molecule.

In an aspect, this disclosure provides a method of making a humanized antibody molecule disclosed herein. The method includes: providing an antigen, e.g., CD138 or a fragment thereof; obtaining a humanized antibody molecule that specifically binds to the antigen; evaluating efficacy of the antibody molecule in modulating activity of the antigen and/or organism expressing the antigen, e.g., CD138. The method can further include administering the antibody molecule, including a derivative thereof (e.g., a humanized antibody molecule) to a subject, e.g., a human.

This disclosure provides an isolated nucleic acid molecule encoding the above antibody molecule, vectors and host cells thereof. The nucleic acid molecule includes, but is not limited to, RNA, genomic DNA and cDNA.

Amino acid sequences of exemplary antibody molecules are described in Table 1 Amino acid and nucleotide sequences of exemplary VHs and VLs are described in Table 2. Any VH described in Table 2 can be paired with any VL described in Table 2 to form an exemplary humanized anti-CD138 antibody molecule. Antibodies 3820, 3821, 3826, 4221, 4226, 4320, 4321, 4322, 4326, 4421, 4520, 4521, 4526, 3522, 3621, 3822, 3825, or 4422 are also sometimes referred to as mAbs 3820, 3821, 3826, 4221, 4226, 4320, 4321, 4322, 4326, 4421, 4520, 4521, 4526, 3522, 3621, 3822, 3825, or 4422 herein.

Other exemplary antibody molecules are described in PCT Publication No. WO 2019/070726 or U.S. Patent Application Publication No. US 2019/0100588, the contents of which are incorporated by reference in their entirety.

TABLE 1

Exemplary anti-CD138 antibodies. The amino acid sequences of the heavy chain variable region (VH) and light chain variable region (VL) are provided as follows. CDRs, defined according to the Kabat or Chothia system, are indicated.

| Antibody | Chain | Amino Acid Sequence | SEQ ID NO | Chothia CDR | | SEQ ID NO | Kabat CDR | | SEQ ID NO |
|---|---|---|---|---|---|---|---|---|---|
| 2810 | VH | QVQLHQPGTSLVKPGASVKL SCKASGYSFSSYYMHWVKQ RPGQGLEWIGTIHPSDSTTNY NQKFKGKATLTVDKSSRTA YMQLNSLTFEDSAVYYCAN FVYWGQGTSVTVSS | 296 | HCDR1 HCDR2 HCDR3 | GYSFSSY HPSDST FVY | 355 351 508 | HCDR1 HCDR2 HCDR3 | SYYMH TIHPSDSTTNYNQ KFKG FVY | 380 382 508 |

TABLE 1-continued

Exemplary anti-CD138 antibodies. The amino acid sequences
of the heavy chain variable region (VH) and light chain
variable region (VL) are provided as follows.
CDRs, defined according to the Kabat or Chothia system,
are indicated.

| Antibody | Chain | Amino Acid Sequence | SEQ ID NO | Chothia CDR | | SEQ ID NO | Kabat CDR | | SEQ ID NO |
|---|---|---|---|---|---|---|---|---|---|
| | VL | DIVITQDELSNPVTSGDSVSIS CRSSKSLLYKDGKTYLNWFL QRPGQSPQLLIYVVSTRASG VSDRFSGSGSGTDFTLEISRV KAEDVGVYYCQQLVEYPYT FGGGTKLEIK | 292 | LCDR1 | RSSKSLLYKDGK TYLN | 352 | LCDR1 | RSSKSLLYKDGKT YLN | 352 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 3820 | VH | QVQLVQSGAEVKKPGSSVK VSCKASGYSFSSYYMHWVR QAPGQGLEWMGTIHPSDSTA NYNQKFKGRVTITVDKSTST AYMELSSLRSEDTAVYYCA NFVYWGQGTTVTVSS | 466 | HCDR1 | GYSFSSY | 355 | HCDR1 | SYYMH | 380 |
| | | | | HCDR2 | HPSDST | 351 | HCDR2 | TIHPSDSTANYNQ KFKG | 509 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVEYPY TFGQGTKLEIK | 475 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 3821 | VH | QVQLVQSGAEVKKPGSSVK VSCKASGYSFSSYYMHWVR QAPGQGLEWMGTIHPSDSTA NYNQKFKGRVTITVDKSTST AYMELSSLRSEDTAVYYCA NFVYWGQGTTVTVSS | 466 | HCDR1 | GYSFSSY | 355 | HCDR1 | SYYMH | 380 |
| | | | | HCDR2 | HPSDST | 351 | HCDR2 | TIHPSDSTANYNQ KFKG | 509 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVQYPY TFGQGTKLEIK | 476 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 3826 | VH | QVQLVQSGAEVKKPGSSVK VSCKASGYSFSSYYMHWVR QAPGQGLEWMGTIHPSDSTA NYNQKFKGRVTITVDKSTST AYMELSSLRSEDTAVYYCA NFVYWGQGTTVTVSS | 466 | HCDR1 | GYSFSSY | 355 | HCDR1 | SYYMH | 380 |
| | | | | HCDR2 | HPSDST | 351 | HCDR2 | TIHPSDSTANYNQ KFKG | 509 |
| | | | | HCDR3 | FVY | 508 | HCDR3 | FVY | 508 |
| | VL | DIVMTQSPDSLAVSLGERATI NCKSSQSLLYKDGKTYLNW FQQKPGQPPKLLIYVSTRA SGVPDRFSGSGSGTDFTLTIS SLQAEDVAVYYCQQLVEYP YTFGQGTKLEIK | 481 | LCDR1 | KSSQSLLYKDGK TYLN | 512 | LCDR1 | KSSQSLLYKDGKT YLN | 512 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 4221 | VH | QVQLVQSGAEVKKPGASVK VSCKASGYSFSSYYMHWVR QAPGQGLEWMGTIHPSDSTT NYAQKFQGRVTMTRDTSTS TVYMELSSLRSEDTAVYYCA NFVYWGQGTTVTVSS | 470 | HCDR1 | GYSFSSY | 355 | HCDR1 | SYYMH | 380 |
| | | | | HCDR2 | HPSDST | 351 | HCDR2 | TIHPSDSTTNYAQ KFQG | 513 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVQYPY TFGQGTKLEIK | 476 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 4226 | VH | QVQLVQSGAEVKKPGASVK VSCKASGYSFSSYYMHWVR QAPGQGLEWMGTIHPSDSTT NYAQKFQGRVTMTRDTSTS TVYMELSSLRSEDTAVYYCA NFVYWGQGTTVTVSS | 470 | HCDR1 | GYSFSSY | 355 | HCDR1 | SYYMH | 380 |
| | | | | HCDR2 | HPSDST | 351 | HCDR2 | TIHPSDSTTNYAQ KFQG | 513 |
| | | | | HCDR3 | FVY | 508 | HCDR3 | FVY | 508 |

TABLE 1-continued

Exemplary anti-CD138 antibodies. The amino acid sequences
of the heavy chain variable region (VH) and light chain
variable region (VL) are provided as follows.
CDRs, defined according to the Kabat or Chothia system,
are indicated.

| Antibody | Chain | Amino Acid Sequence | SEQ ID NO | Chothia CDR | | SEQ ID NO | Kabat CDR | | SEQ ID NO |
|---|---|---|---|---|---|---|---|---|---|
| | VL | DIVMTQSPDSLAVSLGERATI NCKSSQSLLYKDGKTYLNW FQQKPGQPPKLLIYVVSTRA SGVPDRFSGSGSGTDFTLTIS SLQAEDVAVYYCQQLVEYP YTFGQGTKLEIK | 481 | LCDR1 | KSSQSLLYKDGK TYLN | 512 | LCDR1 | KSSQSLLYKDGKT YLN | 512 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 4320 | VH | QVQLVQSGAEVKKPGASVK VSCKASGYSFSSYYMHWVR QAPGQGLEWMGTIHPSDSTT NYNQKFQGRVTMTVDTSTR TAYMELSSLRSEDTAVYYCA NFVYWGQGTTVTVSS | 471 | HCDR1 | GYSFSSY | 355 | HCDR1 | SYYMH | 380 |
| | | | | HCDR2 | HPSDST | 351 | HCDR2 | TIHPSDSTTNYNQ KFQG | 514 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVEYPY TFGQGTKLEIK | 475 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 4321 | VH | QVQLVQSGAEVKKPGASVK VSCKASGYSFSSYYMHWVR QAPGQGLEWMGTIHPSDSTT NYNQKFQGRVTMTVDTSTR TAYMELSSLRSEDTAVYYCA NFVYWGQGTTVTVSS | 471 | HCDR1 | GYSFSSY | 355 | HCDR1 | SYYMH | 380 |
| | | | | HCDR2 | HPSDST | 351 | HCDR2 | TIHPSDSTTNYNQ KFQG | 514 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVQYPY TFGQGTKLEIK | 476 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 4322 | VH | QVQLVQSGAEVKKPGASVK VSCKASGYSFSSYYMHWVR QAPGQGLEWMGTIHPSDSTT NYNQKFQGRVTMTVDTSTR TAYMELSSLRSEDTAVYYCA NFVYWGQGTTVTVSS | 471 | HCDR1 | GYSFSSY | 355 | HCDR1 | SYYMH | 380 |
| | | | | HCDR2 | HPSDST | 351 | HCDR2 | TIHPSDSTTNYNQ KFQG | 514 |
| | | | | HCDR3 | FVY | 508 | HCDR3 | FVY | 508 |
| | VL | DIQMTQSPSSLSASVGDRVTI TCRASKSLLYKDGKTYLNW YQQKPGKAPKLLIYVSSLQ SGVPSRFSGSGSGTDFTLTIS SLQPEDFATYYCQQLVEYPY TFGQGTKLEIK | 477 | LCDR1 | RASKSLLYKDGK TYLN | 515 | LCDR1 | RASKSLLYKDGKT YLN | 515 |
| | | | | LCDR2 | VVSSLQS | 516 | LCDR2 | VVSSLQS | 516 |
| | | | | LCDR3 | QQLVEYPYT | 354 | LCDR3 | QQLVEYPYT | 354 |
| 4326 | VH | QVQLVQSGAEVKKPGASVK VSCKASGYSFSSYYMHWVR QAPGQGLEWMGTIHPSDSTT NYNQKFQGRVTMTVDTSTR TAYMELSSLRSEDTAVYYCA NFVYWGQGTTVTVSS | 471 | HCDR1 | GYSFSSY | 355 | HCDR1 | SYYMH | 380 |
| | | | | HCDR2 | HPSDST | 351 | HCDR2 | TIHPSDSTTNYNQ KFQG | 514 |
| | | | | HCDR3 | FVY | 508 | HCDR3 | FVY | 508 |
| | VL | DIVMTQSPDSLAVSLGERATI NCKSSQSLLYKDGKTYLNW FQQKPGQPPKLLIYVVSTRA SGVPDRFSGSGSGTDFTLTIS SLQAEDVAVYYCQQLVEYP YTFGQGTKLEIK | 481 | LCDR1 | KSSQSLLYKDGK TYLN | 512 | LCDR1 | KSSQSLLYKDGKT YLN | 512 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 4421 | VH | QVQLVQSGAEVKKPGASVK VSCKASGYTFTSYYMHWVR QAPGQGLEWMGTIHPSDSTT NYNQKFKGRVTMTVDTSTS TAYMELSSLRSEDTAVYYCA NFVYWGQGTTVTVSS | 472 | HCDR1 | GYTFTSY | 322 | HCDR1 | SYYMH | 380 |
| | | | | HCDR2 | HPSDST | 351 | HCDR2 | TIHPSDSTTNYNQ KFKG | 382 |
| | | | | HCDR3 | FVY | 508 | HCDR3 | FVY | 508 |

TABLE 1-continued

Exemplary anti-CD138 antibodies. The amino acid sequences
of the heavy chain variable region (VH) and light chain
variable region (VL) are provided as follows.
CDRs, defined according to the Kabat or Chothia system,
are indicated.

| Antibody | Chain | Amino Acid Sequence | SEQ ID NO | Chothia CDR | | SEQ ID NO | Kabat CDR | | SEQ ID NO |
|---|---|---|---|---|---|---|---|---|---|
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVQYPY TFGQGTKLEIK | 476 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 4520 | VH | QVQLVQSGAEVKKPGASVK VSCKASGYNFASYYMHWVR QAPGQGLEWMGTIHPSDSTT NYNQKFKGRVTMTVDTSTS TAYMELSSLRSEDTAVYYCA NFVYWGQGTTVTVSS | 473 | HCDR1 | GYNFASY | 517 | HCDR1 | SYYMH | 380 |
| | | | | HCDR2 | HPSDST | 351 | HCDR2 | TIHPSDSTTNYNQ KFKG | 382 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVEYPY TFGQGTKLEIK | 475 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 4521 | VH | QVQLVQSGAEVKKPGASVK VSCKASGYNFASYYMHWVR QAPGQGLEWMGTIHPSDSTT NYNQKFKGRVTMTVDTSTS TAYMELSSLRSEDTAVYYCA NFVYWGQGTTVTVSS | 473 | HCDR1 | GYNFASY | 517 | HCDR1 | SYYMH | 380 |
| | | | | HCDR2 | HPSDST | 351 | HCDR2 | TIHPSDSTTNYNQ KFKG | 382 |
| | | | | HCDR3 | FVY | 508 | HCDR3 | FVY | 508 |
| | VL | DIVMTQTPLSLSVTPGQPASI SCKSSKSLLYKDGKTYLNWF LQKPGQSPQLLIYVVSTRAS GVPDRFSGSGSGTDFTLKISR VEAEDVGVYYCQQLVQYPY TFGQGTKLEIK | 476 | LCDR1 | KSSKSLLYKDGK TYLN | 510 | LCDR1 | KSSKSLLYKDGKT YLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 4526 | VH | QVQLVQSGAEVKKPGASVK VSCKASGYNFASYYMHWVR QAPGQGLEWMGTIHPSDSTT NYNQKFKGRVTMTVDTSTS TAYMELSSLRSEDTAVYYCA NFVYWGQGTTVTVSS | 473 | HCDR1 | GYNFASY | 517 | HCDR1 | SYYMH | 380 |
| | | | | HCDR2 | HPSDST | 351 | HCDR2 | TIHPSDSTTNYNQ KFKG | 382 |
| | | | | HCDR3 | FVY | 508 | HCDR3 | FVY | 508 |
| | VL | DIVMTQSPDSLAVSLGERATI NCKSSQSLLYKDGKTYLNW FQQKPGQPPKLLIYVSTRA SGVPDRFSGSGSGTDFTLTIS SLQAEDVAVYYCQQLVEYP YTFGQGTKLEIK | 481 | LCDR1 | KSSQSLLYKDGK TYLN | 512 | LCDR1 | KSSQSLLYKDGKT YLN | 512 |
| | | | | LCDR2 | VVSTRAS | 353 | LCDR2 | VVSTRAS | 353 |
| | | | | LCDR3 | QQLVEYPYT | 354 | LCDR3 | QQLVEYPYT | 354 |
| 3522 | VH | QVQLVQSGAEVKKPGSSVK VSCKASGYTFSSYYIHWVRQ APGQGLEWMGTIHPSDSTTN YNQKFQGRVTITVDESTSTA YMELSSLRSEDTAVYYCANF VYWGQGTTVTVSS | 463 | HCDR1 | GYTFSSY | 356 | HCDR1 | SYYIH | 518 |
| | | | | HCDR2 | HPSDST | 351 | HCDR2 | TIHPSDSTTNYNQ KFQG | 514 |
| | | | | HCDR3 | FVY | 508 | HCDR3 | FVY | 508 |
| | VL | DIQMTQSPSSLSASVGDRVTI TCRASKSLLYKDGKTYLNW YQQKPGKAPKLLIYVVSSLQ SGVPSRFSGSGSGTDFTLTIS SLQPEDFATYYCQQLVEYPY TFGQGTKLEIK | 477 | LCDR1 | RASKSLLYKDGK TYLN | 515 | LCDR1 | RASKSLLYKDGKT YLN | 515 |
| | | | | LCDR2 | VVSSLQS | 516 | LCDR2 | VVSSLQS | 516 |
| | | | | LCDR3 | QQLVEYPYT | 354 | LCDR3 | QQLVEYPYT | 354 |
| 3621 | VH | QVQLVQSGAEVKKPGSSVK VSCKASGYSFSSYYIHWVRQ APGQGLEWMGTIHPSDSTAN YAQKFQGRVTITADKSTSTA YMELSSLRSEDTAVYYCANF VYWGQGTTVTVSS | 464 | HCDR1 | GYSFSSY | 355 | HCDR1 | SYYIH | 518 |
| | | | | HCDR2 | HPSDST | 351 | HCDR2 | TIHPSDSTANYAQ KFQG | 519 |
| | | | | HCDR3 | FVY | 508 | HCDR3 | FVY | 508 |

TABLE 1-continued

Exemplary anti-CD138 antibodies. The amino acid sequences of the heavy chain variable region (VH) and light chain variable region (VL) are provided as follows. CDRs, defined according to the Kabat or Chothia system, are indicated.

| Antibody | Chain | Amino Acid Sequence | SEQ ID NO | | Chothia CDR | SEQ ID NO | | Kabat CDR | SEQ ID NO |
|---|---|---|---|---|---|---|---|---|---|
| | VL | DIVMTQTPLSLSVTPGQPASISCKSSKSLLYKDGKTYLNWFLQKPGQSPQLLIYVVSTRASGVPDRFSGSGSGTDFTLKISRVEAEDVGVYYCQQLVQYPYTFGQGTKLEIK | 476 | LCDR1 | KSSKSLLYKDGKTYLN | 510 | LCDR1 | KSSKSLLYKDGKTYLN | 510 |
| | | | | LCDR2 | VVSTRAS | 353 | LCDR2 | VVSTRAS | 353 |
| | | | | LCDR3 | QQLVQYPYT | 511 | LCDR3 | QQLVQYPYT | 511 |
| 3822 | VH | QVQLVQSGAEVKKPGSSVKVSCKASGYSFSSYYMHWVRQAPGQGLEWMGTIHPSDSTANYNQKFKGRVTITVDKSTSTAYMELSSLRSEDTAVYYCANFVYWGQGTTVTVSS | 466 | HCDR1 | GYSFSSY | 355 | HCDR1 | SYYMH | 380 |
| | | | | HCDR2 | HPSDST | 351 | HCDR2 | TIHPSDSTANYNQKFKG | 509 |
| | | | | HCDR3 | FVY | 508 | HCDR3 | FVY | 508 |
| | VL | DIQMTQSPSSLSASVGDRVTITCRASKSLLYKDGKTYLNWYQQKPGKAPKLLIYVVSSLQSGVPSRFSGSGSGTDFTLTISSLQPEDFATYYCQQLVEYPYTFGQGTKLEIK | 477 | LCDR1 | RASKSLLYKDGKTYLN | 515 | LCDR1 | RASKSLLYKDGKTYLN | 515 |
| | | | | LCDR2 | VVSSLQS | 516 | LCDR2 | VVSSLQS | 516 |
| | | | | LCDR3 | QQLVEYPYT | 354 | LCDR3 | QQLVEYPYT | 354 |
| 3825 | VH | QVQLVQSGAEVKKPGSSVKVSCKASGYSFSSYYMHWVRQAPGQGLEWMGTIHPSDSTANYNQKFKGRVTITVDKSTSTAYMELSSLRSEDTAVYYCANFVYWGQGTTVTVSS | 466 | HCDR1 | GYSFSSY | 355 | HCDR1 | SYYMH | 380 |
| | | | | HCDR2 | HPSDST | 351 | HCDR2 | TIHPSDSTANYNQKFKG | 509 |
| | | | | HCDR3 | FVY | 508 | HCDR3 | FVY | 508 |
| | VL | DIVMTQTPLSLPVTPGEPASISCRSSQSLLYKDGKTYLNWFLQKPGQSPQLLIYVLSTRASGVPDRFSGSGSGTDFTLKISRVEAEDVGVYYCQQLVEYPYTFGQGTKLEIK | 480 | LCDR1 | RSSQSLLYKDGKTYLN | 520 | LCDR1 | RSSQSLLYKDGKTYLN | 520 |
| | | | | LCDR2 | VLSTRAS | 521 | LCDR2 | VLSTRAS | 521 |
| | | | | LCDR3 | QQLVEYPYT | 354 | LCDR3 | QQLVEYPYT | 354 |
| 4422 | VH | QVQLVQSGAEVKKPGASVKVSCKASGYTFTSYYMHWVRQAPGQGLEWMGTIHPSDSTTNYNQKFKGRVTMTVDTSTSTAYMELSSLRSEDTAVYYCANFVYWGQGTTVTVSS | 472 | HCDR1 | GYTFTSY | 322 | HCDR1 | SYYMH | 380 |
| | | | | HCDR2 | HPSDST | 351 | HCDR2 | TIHPSDSTTNYNQKFKG | 382 |
| | | | | HCDR3 | FVY | 508 | HCDR3 | FVY | 508 |
| | VL | DIQMTQSPSSLSASVGDRVTITCRASKSLLYKDGKTYLNWYQQKPGKAPKLLIYVVSSLQSGVPSRFSGSGSGTDFTLTISSLQPEDFATYYCQQLVEYPYTFGQGTKLEIK | 477 | LCDR1 | RASKSLLYKDGKTYLN | 515 | LCDR1 | RASKSLLYKDGKTYLN | 515 |
| | | | | LCDR2 | VVSSLQS | 516 | LCDR2 | VVSSLQS | 516 |
| | | | | LCDR3 | QQLVEYPYT | 354 | LCDR3 | QQLVEYPYT | 354 |

TABLE 2

Amino acid and nucleotide sequences of exemplary heavy chain variable regions (VH) and light chain variable regions (VL). CDRs, as defined according to the Kabat system, are underlined and bolded, while CDRs defined according to the Chothia system are italicized.

| Antibody | Chain | Amino Acid Sequence | SEQ ID NO | Exemplary Nucleotide Sequence | SEQ ID NO |
|---|---|---|---|---|---|
| VH30 | VH | QVQLVESGGGVVQPGRSLRLSCAA*SGYNFA***SYYMHWVRQAPGKGLEWVA*TIHPSDSTKNYADSVKGRFTISRDNSKNTLYLQMNSLRAEDTAVYCANFVY**WGQGTTVTVSS | 458 | TCTGCTCTGCCTGGCCGGGCGCGCCTTGGCCCAGGTCCAGCTTGTGGAATCTGGGGGAGGAGTTGTGCAACCGGGCAGAAGCCTCCGACTGTCTTGCGCTGCCGTCCGGTTACAATTTTGCTTCATACTATATGCATTGGGTCCGCCAAGCGCCCGGTAAAGGGTTGGAATGGGTTGCAACTATTCACCCGTCTGATAGTACCAAAAATTACGCAGATTCTGTGAAAGGCAGATTACCATTTCAAGGGATAATTCCAAGAATACTCTCTAC | 483 |

TABLE 2-continued

Amino acid and nucleotide sequences of
exemplary heavy chain variable regions (VH) and
light chain variable regions (VL). CDRs, as
defined according to the Kabat system, are underlined
and bolded, while CDRs defined according to the
Chothia system are italicized.

| Antibody | Chain | Amino Acid Sequence | SEQ ID NO | Exemplary Nucleotide Sequence | SEQ ID NO |
|---|---|---|---|---|---|
| | | | | CTCCAAATGAACTCATTGCGGGCTGAGGAT ACAGCGGTGTATTACTGCGCTAATTTTGTC TATTGGGGACAGGGTACAACTGTGACAGTC AGCTCTGCGAGCACCAAGGGCCCCTCCGTG TTCCCGTTGGCGCC | |
| VH31 | VH | QVQLVESGGGVVQPGRSLRLSCAA *SGYSFSSYYMHWVRQAPGKGLEW VGTIHPSDSTKNYNQKVKGRFTIS RDNSKNTLYLQMNSLRAEDTAVY YCANFVY**WGQGTTVTVSS | 459 | TCTGCTCTGCCTGGCCGGGCGCGCCTTGGC CCAAGTTCAGCTCGTTGAATCCGGTGGTGG GGTGGTTCAACCGGGCAGAAGTTTGCGACT GAGTTGCGCAGCTTCTGGATATTCATTCTC CTCATACTATATGCACTGGGTACGACAGGC CCCCGGAAAGGGCTTGGAATGGGTTGGTAC AATTCACCCAAGCGATTCTACGAAGAATTA CAACCAAAAAGTTAAGGGGAGATTTACTAT AAGCCGAGACAATAGCAAGAATACTCTTTA TCTTCAGATGAATAGTCTCCGCGCTGAGGA TACAGCGGTGTATTATTGTGCGAATTTCGT ATATTGGGGTCAAGGCACTACCGTAACCGT TTCATCCGCGAGCACCAAGGGCCCCTCCGT GTTCCCGTTGGCGCC | 484 |
| VH32 | VH | QVQLVESGGGVVQPGRSLRLSCAA *SGYSFSSYYMHWVRQAPGKGLEW VAVIHPSDSTKNYADSVKGRFTIS VDKSSRTAYLQMNSLRAEDTAVY YCANFVY**WGQGTTVTVSS | 460 | TCTGCTCTGCCTGGCCGGGCGCGCCTTGGC CCAGGTACAGTTGGTTGAGTCTGGCGGAGG GGTTGTCCAGCCTGGCAGGAGCTTGCGACT CAGTTGTGCCGCTTCAGGGTATAGTTTTAG CAGCTACTACATGCACTGGGTACGGCAGGC ACCAGGGAAGGGACTTGAGTGGGTCGCAG TTATCCATCCATCTGACTCAACTAAAAACT ACGCAGATTCTGTCAAGGGCAGATTTACCA TATCAGTTGACAAGTCATCCCGGACGGCTT ACCTGCAGATGAACTCACTCCGCGCGGAGG ATACAGCGGTTTACTACTGCGCCAATTTTG TTTACTGGGGCCAAGGTACGACCGTGACGG TGAGCAGTGCGAGCACCAAGGGCCCCTCC GTGTTCCCGTTGGCGCC | 485 |
| VH33 | VH | QVQLVESGGGVVQPGRSLRLSCAA *SGYTFSSYYMHWVRQAPGKGLEW VGTIHPSDSTKNYADSVKGRFTIS VDKSSRTAYLQMNSLRAEDTAVY YCANFVY**WGQGTTVTVSS | 461 | TCTGCTCTGCCTGGCCGGGCGCGCCTTGGC CCAAGTCCAGCTCGTCGAATCAGGTGGAGG AGTTGTTCAGCCAGGAAGGAGCTTGCGGCT TAGCTGTGCGGCCAGCGGCTATACGTTTTC ATCTTATTATATGCACTGGGTGCGCCAAGC CCCAGGAAAGGGCCTCGAATGGGTTGGCA CAATTCATCCATCAGATAGCACAAAGAACT ACGCGGATTCCGTTAAAGGTCGATTTACTA TATCCGTCGATAAGAGCTCACGGACGGCAT ACCTCCAGATGAACAGCTTGAGGGCGGAA GACACCGCCGTCTACTACTGTGCCAATTTC GTCTATTGGGGCCAGGGCACCACCGTCACA GTGTCTTCTGCGAGCACCAAGGGCCCCTCC GTGTTCCCGTTGGCGCC | 486 |
| VH34 | VH | QVQLVESGGGVVQPGRSLRLSCAA *SGFTFSSYYMHWVRQAPGKGLEW VATIHPSDSTTNYNQKFKGRFTIS RDNSKNTAYLQMNSLRAEDTAVY YCANFVY**WGQGTTVTVSS | 462 | TCTGCTCTGCCTGGCCGGGCGCGCCTTGGC CCAGGTCCAACTGGTAGAATCAGGAGGTG GGGTGGTGCAACCGGGCAGGTCTCTCCGGT TGTCATGTGCAGCTTCCGGGTTCACCTTTA GCTCTTATTACATGCATTGGGTACGCCAGG CGCCAGGTAAAGGTCTTGAATGGGTTGCTA CGATCCACCCCTCTGATTCCACTACCAATT ACAACCAAAAATTTAAGGGACGCTTCACCA TTTCCCGCGACAACAGCAAAAACACGGCAT ATTTGCAAATGAATAGCCTCCGCGCCGAAG ACACTGCGGTATATTATTGCGCCAATTTTG TTTACTGGGGACAAGGGACAACGGTTACA GTATCCAGTGCGAGCACCAAGGGCCCCTCC GTGTTCCCGTTGGCGCC | 487 |

TABLE 2-continued

Amino acid and nucleotide sequences of exemplary heavy chain variable regions (VH) and light chain variable regions (VL). CDRs, as defined according to the Kabat system, are underlined and bolded, while CDRs defined according to the Chothia system are italicized.

| Antibody | Chain | Amino Acid Sequence | SEQ ID NO | Exemplary Nucleotide Sequence | SEQ ID NO |
|---|---|---|---|---|---|
| VH35 | VH | QVQLVQSGAEVKKPGSSVKVSCK ASGYTFSSYYIHWVRQAPGQGLEW MG*TIHPSDSTTNYNQKFQGRVTIT VDESTSTAYMELSSLRSEDTAVYY CAN*FVY*WGQGTTVTVSS | 463 | TCTGCTCTGCCTGGCCGGGCGCGCCTTGGC CCAAGTTCAGTTGGTACAGAGTGGGGCTGA AGTCAAGAAGCCCGGTTCAAGCGTTAAAGT TTCTTGCAAGGCGAGTGGGTACACTTTCAG CAGTTATTATATCCACTGGGTCAGGCAGGC ACCGGGGCAGGGTCTTGAGTGGATGGGGA CGATACATCCATCAGACTCAACTACAAATT ACAATCAGAAGTTCCAGGGACGGGTGACG ATCACAGTAGACGAGTCTACGAGTACAGCC TATATGGAACTTTCATCCCTCAGGAGCGAA GATACAGCCGTTTACTATTGTGCTAACTTT GTCTATTGGGGGCAAGGAACCACAGTCACC GTCTCATCCGCGAGCACCAAGGGCCCCTCC GTGTTCCCGTTGGCGCC | 488 |
| VH36 | VH | QVQLVQSGAEVKKPGSSVKVSCK ASGYSFSSYYIHWVRQAPGQGLEW MG **TI*HPSDSTANYAQKFQG*RVTIT ADKSTSTAYMELSSLRSEDTAVYY CAN*FVY***WGQGTTVTVSS | 464 | TCTGCTCTGCCTGGCCGGGCGCGCCTTGGC CCAAGTCCAGTTGGTCCAATCCGGCGCGGA AGTGAAGAAGCCCGGTAGCATCTGTAAAAG TTTCATGTAAGGCGTCTGGATATTCCTTCA GTTCATATTATATCCACTGGGTACGCCAGG CCCCTGGACAAGGTTTGGAATGGATGGGA ACCATACATCCAAGCGACAGTACCGCAAA CTATGCGCAAAAATTCCAGGGGCGGGTGA CTATTACTGCGGATAAAAGCACAAGCACTG CTTACATGGAGCTGTCCTCCCTGCGATCAG AGGACACCGCTGTCTACTACTGCGCTAATT TTGTGTATTGGGGCCAAGGAACTACCGTGA CGGTTAGTTCTGCGAGCACCAAGGGCCCCT CCGTGTTCCCGTTGGCGCC | 489 |
| VH37 | VH | QVQLVQSGAEVKKPGSSVKVSCK ASGYNFASYYIHWVRQAPGQGLE WMG*TIHPSDSTANYAQKFQGRVT ITADKSTSTAYMELSSLRSEDTAVY YCAN*FVY***WGQGTTVTVSS | 465 | TCTGCTCTGCCTGGCCGGGCGCGCCTTGGC CCAAGTACAACTGGTGCAATCTGGAGCCGA GGTTAAAAAGCCCGGCAGTTCCGTTAAAGT GTCTTGCAAGGCATCTGGCTATAACTTCGC CAGTTATTACATCCATTGGGTCAGACAGGC GCCTGGACAAGGTCTGGAATGGATGGGGA CGATCCATCCTTCCGACTCAACGGCGAATT ATGCCCAGAAGTTTCAGGGTAGGGTGACTA TCACAGCCGATAAGTCTACCAGCACCGCTT ATATGGAGTTGTCCAGTCTGAGAAGCGAAG ATACCGCTGTCTATTATTGCGCCAACTTCGT GTATTGGGGCAAGGAACCACCGTCACTGT GTCATCAGCGAGCACCAAGGGCCCCTCCGT GTTCCCGTTGGCGCC | 490 |
| VH38 | VH | QVQLVQSGAEVKKPGSSVKVSCK ASGYSFSSYYMHWVRQAPGQGLE WMG **TI*HPSDSTANYNQKFKQ*RVT ITVDKSTSTAYMELSSLRSEDTAVY YCAN*FVY***WGQGTTVTVSS | 466 | TCTGCTCTGCCTGGCCGGGCGCGCCTTGGC CCAAGTCCAGTTGGTCCAGTCTGGGGCGGA GGTGAAAAAGCCAGGTAGTAGCGTTAAAG TTTCCTGTAAAGCGTCCGGTTATTCCTTTAG CTCCTACTATATGCACTGGGTCCGGCAGGC CCCAGGACAGGGGCTTGAGTGGATGGGAA CCATTCATCCTTCAGACTCCACTGCTAACT ATAATCAGAAATTTAAAGGCCGCGTTACCA TCACAGTTGACAAAAGCACCTCTACGGCCT ATATGGAGCTTTCTTCTTTGCGATCCGAGG ACACCGCGGTGTATTATTGCGCTAACTTTG TATATTGGGGCCAGGGGACGACAGTTACTG TCAGTTCAGCGAGCACCAAGGGCCCCTCCG TGTTCCCGTTGGCGCC | 491 |
| VH39 | VH | EVQLLESGGGLVQPGGSLRLSCAA SGYNFASYYMHWVRQAPGKGLEW V*STIHPSDSTTNYADSVKGRFTISR DNSKNTLYLQMNSLRAEDTAVYY CAN*FVY*WGQGTTVTVSS | 467 | TCTGCTCTGCCTGGCCGGGCGCGCCTTGGC CGAGGTTCAACTCTTGGAATCAGGGGGCGG TTTGGTTCAGCCCGGCGGATCACTCAGGCT TTCCTGTGCGGCATCTGGGTACAATTTCGC ATCTTACTACATGCATTGGGTCAGACAAGC TCCAGGTAAAGGTTTGGAATGGGTTTCCAC GATCCATCCTTCCGACAGTACGACGAATTA CGCTGACAGCGTTAAGGGCAGGTTTACTAT CAGTCGCGATAATAGCAAGAATACCCTTTA | 492 |

TABLE 2-continued

Amino acid and nucleotide sequences of exemplary heavy chain variable regions (VH) and light chain variable regions (VL). CDRs, as defined according to the Kabat system, are underlined and bolded, while CDRs defined according to the Chothia system are italicized.

| Antibody | Chain | Amino Acid Sequence | SEQ ID NO | Exemplary Nucleotide Sequence | SEQ ID NO |
|---|---|---|---|---|---|
| | | | | TCTTCAAATGAACTCCCTTAGAGCCGAGGA TACCGCTGTCTATTATTGTGCGAACTTCGTC TACTGGGGCCAGGGTACTACGGTCACCGTG AGTTCAGCGAGCACCAAGGGCCCCTCCGTG TTCCCGTTGGCGCC | |
| VH40 | VH | EVQLLESGGGLVQPGGSLRLSCAA SGFTFSSYYMHWRQAPGKGLEW VSTI*HPSDSTTNYNQKFKG*RFTISR DNSKNTAYLQMNSLRAEDTAVYY CAN*FVY*WGQGTTVTVSS | 468 | TCTGCTCTGCCTGGCCGGGCGCGCCTTGGC CGAAGTCCAGCTTTTGGAGAGCGGTGGTGG ACTGGTGCAGCCAGGGGGATCTCTTCGCTT GTCCTGTGCTGCCTCTGGCTTTACATTTTCA TCTTATTACATGCATTGGGTTCGGCAAGCT CCTGGGAAGGGCTTGGAGTGGGTTTCCACA ATTCATCCAAGCGATAGCACGACGAACTAT AACCAAAAGTTCAAGGGACGCTTCACTATC TCAAGAGACAACTCTAAAAACACCGCATA CTTGCAAATGAACAGCTTGAGAGCTGAAG ATACAGCAGTGTACTATTGTGCAAATTTCG TGTACTGGGGCCAGGGGACTACTGTCACTG TATCATCAGCGAGCACCAAGGGCCCCTCCG TGTTCCCGTTGGCGCC | 493 |
| VH41 | VH | QVQLVESGGGLVKPGGSLRLSCAA SGFTFSSYYMHWIRQAPGKGLEW VSTI*HPSDSTTNYNQKFKG*RFTIS VDNAKNSAYLQMNSLRAEDTAVY YCAN*FVY*WGQGTTVTVSS | 469 | TCTGCTCTGCCTGGCCGGGCGCGCCTTGGC CCAAGTTCAACTGGTGGAGTCCGGAGGCG GTCTGGTTAAGCCTGGTGGCTCTCTCCGCC TTAGTTGTGCAGCTTCTGGTTTTACCTTCAG CTCCTATTATATGCACTGGATCAGACAAGC TCCGGGCAAGGGTCTTGAATGGGTCAGTAC CATACACCCCTCTGACTCAACCACTAATTA CAACCAGAAGTTTAAAGGACGCTTCACCAT CAGCGTCGATAACGCGAAAAATTCAGCTTA TCTCCAGATGAACTCCCTGCGGGCTGAAGA TACAGCAGTCTACTATTGTGCCAACTTCGT TTATTGGGACAAGGCACAACTGTTACTGT CAGTTCTGCGAGCACCAAGGGCCCCTCCGT GTTCCCGTTGGCGCC | 494 |
| VH42 | VH | QVQLVQSGAEVKKPGASVKVSCK ASGYSFSSYYMHVRQAPGQGLE WMG TI*HPSDSTTNYAQKFQG*RVT MTRDTSTSTVYMELSSLRSEDTAV YYCANFVYWGQGTTVTVSS | 470 | TCTGCTCTGCCTGGCCGGGCGCGCCTTGGC CCAAGTCCAACTTGTGCAGAGTGGAGCGG AGGTCAAGAAACCCGGCGCTTCCGTTAAAG TCTCTGCCAAAGCCTCAGGTTATTCTTTCTC CTCATACTATATGCACTGGGTGCGCCAAGC TCCTGGCCAAGGTTTGGAATGGATGGGAAC TATTCACCCCAGCGACTCCACTACGAACTA CGCACAGAAGTTTCAAGGCAGAGTTACGAT GACACGCGATACAAGCACTTCAACTGTTTA TATGGAACTGTCTTCTTTGAGAAGTGAAGA CACAGCCGTCTATTATTGCGCGAACTTCGT CTATTGGGGACAGGGCACCACAGTTACCGT TTCAAGCGCGAGCACCAAGGGCCCCTCCGT GTTCCCGTTGGCGCC | 495 |
| VH43 | VH | QVQLVQSGAEVKKPGASVKVSCK ASGYSFSSYYMHWRQAPGQGLE WMG TI*HPSDSTTNYNQKFQG*RVT MTVDTSTRTAYMELSSLRSEDTAV YYCAN*FVY*WGQGTTVTVSS | 471 | TCTGCTCTGCCTGGCCGGGCGCGCCTTGGC CCAAGTACAGCTTGTCCAGTCAGGTGCAGA GGTAAAAAAGCCCGGCGCATCAGTGAAGG TATCTTGTAAAGCGTCCGGTTATTCATTTTC ATCTTACTACATGCATTGGGTTCGGCAGGC ACCGGGACAGGGCCTGGAATGGATGGGGA CGATCCATCCATCTGACAGCACAACAAATT ACAATCAGAAATTTCAAGGTCGGGTCACAA TGACCGTGGATACAAGCACAAGAACAGCA TATATGGAACTGAGCTCACTTCGGAGTGAA GATACGCCGTGTATTATTGTGCTAATTTCG TCTATTGGGGCAGGGGACGACGGTGACA GTAAGTAGTGCGAGCACCAAGGGCCCCTCC GTGTTCCCGTTGGCGCC | 496 |

TABLE 2-continued

Amino acid and nucleotide sequences of exemplary heavy chain variable regions (VH) and light chain variable regions (VL). CDRs, as defined according to the Kabat system, are underlined and bolded, while CDRs defined according to the Chothia system are italicized.

| Antibody | Chain | Amino Acid Sequence | SEQ ID NO | Exemplary Nucleotide Sequence | SEQ ID NO |
|---|---|---|---|---|---|
| VH44 | VH | QVQLVQSGAEVKKPGASVKVSCK ASGYTF*T*SYYMHWVRQAPGQGLE WMG **TI*HPSDSTTNYNQKFKG*RVT MTVDTSTSTAYMELSSLRSEDTAV YYCAN*FVY***WGQGTTVTVSS | 472 | TCTGCTCTGCCTGGCCGGGCGCGCCTTGGC CCAGGTCCAACTCGTGCAAAGTGGTGCCGA GGTAAAAAGCCCGGCGCATCAGTAAAGG TGAGTTGCAAGGCGTCCGGTTACACATTCA CTTCATATTACATGCACTGGGTGAGACAAG CGCCTGGGCAGGGCCTGGAGTGGATGGGG ACAATCCACCCGTCCGACTCAACCACGAAC TACAACCAGAAATTCAAGGGTCGCGTGACC ATGACAGTTGACACATCAACAAGCACGGC GTATATGGAACTTTCTTCCCTCAGAAGTGA GGACACCGCTGTATACTATTGTGCAAACTT TGTGTATTGGGGGCAAGGCACTACCGTCAC AGTATCATCCGCGAGCACCAAGGGCCCCTC CGTGTTCCCGTTGGCGCC | 497 |
| VH45 | VH | QVQLVQSGAEVKKPGASVKVSCK ASGYNFA*S*YYMHWVRQAPGQGLE WMG **TI*HPSDSTTNYNQKFKG*RVT MTVDTSTSTAYMELSSLRSEDTAV YYCAN*FVY***WGQGTTVTVSS | 473 | TCTGCTCTGCCTGGCCGGGCGCGCCTTGGC CCAAGTGCAGTTGGTACAATCTGGAGCCGA GGTAAAGAAGCCAGGAGCCTCCGTCAAAG TGAGTTGTAAGGCATCTGGCTACAATTTTG CTTCTTACTATATGCATTGGGTTCGGCAGG CACCCGGGTCAGGGGCTTGAGTGGATGGGG ACTATTCATCCGTCAGATAGCACGACTAAC TATAACCAGAAGTTTAAGGGACGGGTAAC CATGACTGTTGACACCTCCACGTCTACAGC GTACATGGAACTCTCCAGTCTTCGGAGCGA AGACACAGCGGTCTACTACTGCGCTAACTT TGTCTACTGGGGGCAAGGCACGACCGTTAC AGTATCTTCTGCGAGCACCAAGGGCCCCTC CGTGTTCCCGTTGGCGCC | 498 |
| VH46 | VH | EVQLVESGGGLVKPGGSLRLSCAA SGYSFS*S*YYMHWVRQAPGKGLEW VG **TI*HPSDSTTNYAAPVKG*RFTIS RDDSKNTAYLQMNSLKTEDTAVY YCAN*FVY***WGQGTTVTVSS | 474 | TCTGCTCTGCCTGGCCGGGCGCGCCTTGGC CGAGGTACAGCTTGTCGAGTCCGGCGGTGG ACTTGTAAAACCTGGAGGTTCACTTAGGTT GAGTTGTGCTGCTTCCGGGTATAGTTTCAG TTCTTATTACATGCATTGGGTACGACAGGC TCCAGGAAAGGGTTGGAGTGGTGGGCA CAATACATCCTAGCGATTCTACTACCAATT ATGCCGCTCCGGTGAAAGGACGCTTTACGA TAAGCCGAGACGATAGCAAGAACACTGCA TACTTGCAAATGAATAGTTTGAAGACCGAG GACACGGCGGTGTACTACTGCGCAAATTTT GTGTACTGGGGACAGGGAACGACAGTCAC CGTCTCTAGTGCGAGCACCAAGGGCCCCTC CGTGTTCCCGTTGGCGCC | 499 |
| VL20 | VL | DIVMTQTPLSLSVTPGQPASISC KSS KSLLYKDGKTYLNWFLQKPGQSPQ LLI *YVSTRAS*GVPDRFSGSGSGTD FTLKISRVEAEDVGVYYC QQLVEY PYTFGQGTKLEIK | 475 | TCTGCTCTGCCTGGCCGGGCGCGCCTTGGC CGATATTGTCATGACACAAACCCCCCTGAG TCTTAGCGTCACCCCTGGGCAGCCCGCTTC AATAAGTTGTAAGTCCTCTAAATCATTGCT GTATAAAGATGGGAAGACCTATCTTAACTG GTTTCTCCAAAAGCCAGGGCAGTCACCACA ACTGTTGATCTACGTTGTAAGCACCAGGGC GAGTGGAGTCCCCGACAGATTCAGTGGTAG CGGCTCTGGTACAGATTTTACCTTGAAAAT ATCTAGGGTGGAAGCGGAGGATGTCGGTG TCTACTACTGTCAGCAGCTCGTAGAATATC CATACACATTTGGACAAGGTACGAAACTGG AGATAAAACGTACGGTGGCAGCGCCTTCCG TGTTC | 500 |
| VL21 | VL | DIVMTQTPLSLSVTPGQPASISC KSS KSLLYKDGKTYLNWFLQKPGQSPQ LLI *YVSTRAS*GVPDRFSGSGSGTD FTLKISRVEAEDVGVYYC QQLVQY PYTFGQGTKLEIK | 476 | TCTGCTCTGCCTGGCCGGGCGCGCCTTGGC CGACATTGTCATGACTCAAACACCGCTCTC TCTGTCAGTGACTCCGGGACAACCTGCATC TATAAGCTGTAAATCTAGTAAATCTCTGCT CTACAAAGATGGTAAAACTTACCTGAATTG GTTCCTTCAAAAACCAGGCCAAAGTCCACA ACTTCTCATCTATGTTGTCTACTCGCGCA AGTGGCGTACCCGACAGGTTTTCCGGTAGC GGCTCAGGTACCGACTTCACTCTCAAAATT TCTCGAGTAGAAGCTGAGGATGTCGGCGTC | 501 |

TABLE 2-continued

Amino acid and nucleotide sequences of
exemplary heavy chain variable regions (VH) and
light chain variable regions (VL). CDRs, as
defined according to the Kabat system, are underlined
and bolded, while CDRs defined according to the
Chothia system are italicized.

| Antibody | Chain | Amino Acid Sequence | SEQ ID NO | Exemplary Nucleotide Sequence | SEQ ID NO |
|---|---|---|---|---|---|
| | | | | TACTATTGCCAACAACTCGTACAATATCCA TACACCTTCGGGCAGGGAACTAAACTCGAA ATAAAGCGTACGGTGGCAGCGCCTTCCGTG TTC | |
| VL22 | VL | DIQMTQSPSSLSASVGDRVTITC RA SKSLLYKDGKTYLNWYQQKPGKAP KLLIY***VV*SSLQS**GVPSRFSGSGSGT DFTLTISSLQPEDFATYYC **QQ*LVEY PYT***FGQGTKLEIK | 477 | TCTGCTCTGCCTGGCCGGGCGCGCCTTGGC CGACATCCAAATGACTCAAAGTCCAAGCA GCCTGTCAGCATCTGTGGGGACAGAGTCA CGATAACCTGCCGCGCGAGTAAGAGTCTGC TCTACAAGGACGGGAAAACGTACCTGAATT GGTATCAGCAGAAGCCAGGGAAAGCACCG AAGTTGCTGATTTACGTTGTGAGTTCCCTCC AATCCGGCGTCCCGAGCAGATTCAGTGGGA GCGGCAGCGGAACTGACTTTACGCTTACCA TCTCCTCACTTCAACCGGAAGACTTCGCCA CTTACTACTGTCAACAGCTTGTTGAGTACC CATACACTTTCGGTCAGGGGACGAAACTGG AAATCAAACGTACGGTGGCAGCGCCTTCCG TGTTC | 502 |
| VL23 | VL | DIQMTQSPSSLSASVGDRVTITC RA SQSISSYLNWFQQKPGKAPKWY*V VSSLQS*GVPSRFSGSGSGTDFTLTIS SLQPEDFATYYC **QQ*LVEYPYT***FGQ GTKLEIK | 478 | TCTGCTCTGCCTGGCCGGGCGCGCCTTGGC CGACATACAGATGACTCAGAGCCCGTCCAG CCTCTCTGCGTCAGTCGGTGATAGGGTCAC GATCACATGTCGCGCCAGTCAAAGCATATC CAGCTACTTGAACTGGTTCCAGCAAAAGCC AGGGAAGGCACCGAAGCTCCTTATATACGT GGTCAGTAGTCTCCAAAGTGGTGTTCCTTC ACGCTTTAGCGGTAGCGGCAGTGGTACTGA CTTTACACTTACGATTAGCAGTCTTCAGCC AGAGGATTTTGCAACCTACTACTGCCAGCA GCTCGTCGAGTATCCGTATACGTTTGGTCA GGGAACGAAGCTGGAGATCAAGCGTACGG TGGCAGCGCCTTCCGTGTTC | 503 |
| VL24 | VL | DIVMTQSPLSLPVTPGEPASISC RSS QSLLDSDDGNTYLNWFLQKPGQSP QLLIY*VLSNRAS*GVPDRFSGSGSGT DFTLKISRVEAEDVGVYYC **QQ*LVE YPYT***FGQGTKLEIK | 479 | TCTGCTCTGCCTGGCCGGGCGCGCCTTGGC CGACATCGTTATGACTCAAAGCCCGCTCAG CCTTCCCGTGACCCCTGGCGAGCCGGCGTC TATATCCTGTCGGTCTTCTCAATCTTTGTTG GATTCCGATGACGGTAACACATACCTGAAT TGGTTCCTTCAGAAACCGGGCCAGTCCCCA CAACTTCTCATATACGTGTTGAGCAACAGG GCTTCAGGCGTACCCGATAGGTTTTCCGGT AGTGGATCAGGAACCGATTTCACATTGAAA ATCAGCAGAGTAGAAGCCGAGGACGTAGG TGTTTACTATTGTCAGCAACTTGTAGAGTA CCCATACACCTTCGGTCAGGGCACCAAATT GGAAATTAAGCGTACGGTGGCAGCGCCTTC CGTGTTC | 504 |
| VL25 | VL | DIVMTQTPLSLPVTPGEPASISC RSS QSLLYKDGKTYLNWFLQKPGQSPQ LLIY*VLSTRAS*GVPDRFSGSGSGTD FTLKISRVEAEDVGVYYC **QQ*LVEY PYT***FGQGTKLEIK | 480 | TCTGCTCTGCCTGGCCGGGCGCGCCTTGGC CGACATTGTGATGACGCAGACCCCATTGTC ACTGCCCGTTACCCCAGGGGAACCGGCAA GCATATCATGTCGATCAAGTCAATCTCTTTT GTACAAGGACGGGAAAACATATCTGAATT GGTTCTTGCAGAAGCCTGGTCAATCTCCGC AGTTGTTGATTTATGTGCTCTCAACAAGGG CGTCCGGGGTACCCGACAGATTTAGTGGA GCGGTTCTGGCACGGATTTCACTTTGAAAA TATCAGGGTTGAAGCCGAAGATGTCGGA GTCTATTATTGTCAGCAACTCGTAGAGTAT CCCTACACTTTCGGGCAGGGCACAAAACTT GAGATTAAGCGTACGGTGGCAGCGCCTTCC GTGTTC | 505 |

TABLE 2-continued

Amino acid and nucleotide sequences of exemplary heavy chain variable regions (VH) and light chain variable regions (VL). CDRs, as defined according to the Kabat system, are underlined and bolded, while CDRs defined according to the Chothia system are italicized.

| Antibody | Chain | Amino Acid Sequence | SEQ ID NO | Exemplary Nucleotide Sequence | SEQ ID NO |
|---|---|---|---|---|---|
| VL26 | VL | DIVMTQSPDSLAVSLGERATINC KS SQSLLYKDGKTYLNWFQQKPGQPP KLLIYVVSTRASGVPDRFSGSGSGT DFTLTISSLQAEDVAVYYC QQLVE YPYTFGQGTKLEIK | 481 | TCTGCTCTGCCTGGCCGGGCGCGCCTTGGC CGACATTGTCATGACACAGTCACCGGATAG TTTGGCCGTCTCCCTGGGTGAACGGGCCAC GATAAACTGCAAATCCAGTCAGTCCCTGCT CTATAAGGACGGGAAGACCTACTTGAACTG GTTCCAACAGAAGCCAGGCCAGCCTCCCAA ATTGCTCATTTACGTCGTAAGCACAAGGGC AAGTGGAGTACCAGACAGGTTCTCAGGAA GTGGGAGCGGCACAGACTTCACGCTTACCA TCTCCAGTCTGCAGGCAGAGGATGTAGCTG TGTACTATTGCCAACAACTTGTAGAATACC CTTACACGTTCGGACAGGGGACCAAACTTG AGATAAAGCGTACGGTGGCAGCGCCTTCCG TGTTC | 506 |
| VL27 | VL | DIVMTQSPDSLAVSLGERATINC KS SQSVLYSSNNKNYLNWFQQKPGQP PKLLIYVVSTRASGVPDRFSGSGSG TDFTLTISSLQAEDVAVYYC QQLV EYPYTFGQGTKLEIK | 482 | TCTGCTCTGCCTGGCCGGGCGCGCCTTGGC CGATATTGTGATGACTCAATCACCGGACAG CTTGGCAGTAAGCCTCGGGGAGCGAGCCA CAATAAACTGCAAATCCTCCCAAAGTGTTC TCTATAGCAGTAACAATAAGAATTACCTTA ATTGGTTCCAACAAAAACCCGGTCAGCCAC CAAAACTGCTCATATATGTGGTGTCCACAA GGGCTTCAGGAGTTCCCGACCGATTCAGCG GAAGCGGGAGTGGCACGGATTTTACACTTA CCATCTCTTCCCTTCAAGCGGAAGACGTCG CGGTGTACTACTGTCAACAACTTGTAGAAT ACCCTTACACGTTCGGGCAGGGCACCAAAC TGGAGATTAAGCGTACGGTGGCAGCGCCTT CCGTGTTC | 507 |

In an embodiment, the antibody molecule comprises one, two, or three CDRs of the VH region of an antibody molecule described herein, e.g., in Table 1 or 2, using the Kabat or Chothia definitions of CDRs. In an embodiment, the antibody molecule comprises one, two, or three CDRs of the VL region of an antibody molecule described herein, e.g., in Table 1 or 2, using the Kabat or Chothia definitions of CDRs. In an embodiment, the antibody molecule comprises one or more (e.g., two or three) CDRs of the VH region and one or more (e.g., two or three) CDRs of the VL region of an antibody molecule described herein, e.g., in Table 1 or 2, using the Kabat or Chothia definitions of CDRs.

In an embodiment, the antibody molecule comprises one, two, or three HCDRs described in Table 1 or 2. In an embodiment, the antibody molecule comprises one, two, or three LCDRs described in Table 1 or 2. In an embodiment, the antibody molecule comprises one or more (e.g., two or three) HCDRs and one or more (e.g., two or three) LCDRs described in Table 1 or 2.

In an embodiment, the antibody molecule comprises one, two, three, or four frameworks of the VH region of an antibody molecule described in Table 1 or 2. In an embodiment, the antibody molecule comprises one, two, three, or four frameworks of the VL region of an antibody molecule described in Table 1 or 2. In an embodiment, the antibody molecule comprises one or more (e.g., two, three, or four) frameworks of the VH region and one or more (e.g., two, three, or four) frameworks of the VL region of an antibody molecule described in Table 1 or 2.

In an embodiment, the antibody molecule comprises a VH of an antibody molecule described herein, e.g., in Table 1 or 2. In an embodiment, the antibody molecule comprises a VL of an antibody molecule described herein, e.g., in Table 1 or 2. In an embodiment, the antibody molecule comprises a VH and a VL of an antibody molecule described herein, e.g., in Table 1 or 2.

In an embodiment, the antibody molecule comprises a VH having an amino acid sequence described in Table 1 or 2, or an amino acid sequence substantially identical thereof (e.g., differing by no more than 1, 2, 3, 4, 5, 6, 7, 8, 9, 10, 11, 12, 13, 14, or 15 amino acid residues therefrom, or at least 85, 90, 95, or 99% identical thereto). In an embodiment, the antibody molecule comprises a VL having an amino acid sequence described in Table 1 or 2, or an amino acid sequence substantially identical thereof (e.g., differing by no more than 1, 2, 3, 4, 5, 6, 7, 8, 9, 10, 11, 12, 13, 14, or 15 amino acid residues therefrom, or at least 85, 90, 95, or 99% identical thereto). In an embodiment, the antibody molecule comprises a VH having an amino acid sequence described in Table 1 or 2 (or an amino acid sequence substantially identical thereof) and a VL having an amino acid sequences described in Table 1 or 2 (or an amino acid sequence substantially identical thereof).

In an embodiment, the antibody molecule comprises a VH encoded by a nucleotide sequence described in Table 2, or a nucleotide sequence substantially identical thereof (e.g., differing by no more than 3, 6, 15, 30, or 45 nucleotides therefrom, or at least about 85%, 90%, 95%, or 99% identical thereto). In an embodiment, the antibody molecule comprises a VL encoded by a nucleotide sequence described in Table 2, or a nucleotide sequence substantially identical thereof (e.g., differing by no more than 3, 6, 15, 30, or 45 nucleotides therefrom, or at least about 85%, 90%, 95%, or 99% identical thereto). In an embodiment, the antibody molecule comprises a VH encoded by a nucleotide sequence described in Table 2 (or a nucleotide sequence substantially identical thereof) and a VL encoded by a nucleotide sequence described in Table 2 (or a nucleotide sequence substantially identical thereof).

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 466. In an embodiment, the VL comprises the amino acid sequence of SEQ ID NO: 475. In an embodiment, the VH comprises the amino acid sequence of SEQ ID NO: 466 and the VL comprises the amino acid sequence of SEQ ID NO: 475.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 466. In an embodiment, the VL comprises the amino acid sequence of SEQ ID NO: 476. In an embodiment, the VH comprises the amino acid sequence of SEQ ID NO: 466 and the VL comprises the amino acid sequence of SEQ ID NO: 476.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 466. In an embodiment, the VL comprises the amino acid sequence of SEQ ID NO: 481. In an embodiment, the VH comprises the amino acid sequence of SEQ ID NO: 466 and the VL comprises the amino acid sequence of SEQ ID NO: 481.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYAQKFQG (SEQ ID NO: 513); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYMH (SEQ ID NO: 380); (ii) an HCDR2 comprising an amino acid sequence of TIHPSDSTTNYAQKFQG (SEQ ID NO: 513); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 470. In an embodiment, the VL comprises the amino acid sequence of SEQ ID NO: 476. In an embodiment, the VH comprises the amino acid sequence of SEQ ID NO: 470 and the VL comprises the amino acid sequence of SEQ ID NO: 476.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYAQKFQG (SEQ ID NO: 513); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYAQKFQG (SEQ ID NO: 513); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 470. In an embodiment, the VL comprises the amino acid sequence of SEQ ID NO: 481. In an embodiment, the VH comprises the amino acid sequence of SEQ ID NO: 470 and the VL comprises the amino acid sequence of SEQ ID NO: 481.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 471. In an embodiment, the VL comprises the amino acid sequence of SEQ ID NO: 475. In an embodiment, the VH comprises the amino acid sequence of SEQ ID NO: 471 and the VL comprises the amino acid sequence of SEQ ID NO: 475.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 471. In an embodiment, the VL comprises the amino acid sequence of SEQ ID NO: 476. In an embodiment, the VH comprises the amino acid sequence of SEQ ID NO: 471 and the VL comprises the amino acid sequence of SEQ ID NO: 476.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises the amino acid sequence of SEQ ID NO: 471. In an embodiment, the VL comprises the amino acid sequence of SEQ ID NO: 477. In an embodiment, the VH comprises the amino acid sequence of SEQ ID NO: 471 and the VL comprises the amino acid sequence of SEQ ID NO: 477.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFQG (SEQ ID NO: 514); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 471. In an embodiment, the VL comprises the amino acid sequence of SEQ ID NO: 481. In an embodiment, the VH comprises the amino acid sequence of SEQ ID NO: 471 and the VL comprises the amino acid sequence of SEQ ID NO: 481.

In an embodiment, the VH comprises one, two, or all of: (i) an HCDR1 comprising an amino acid sequence of GYTFTSY (SEQ ID NO: 322); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYTFTSY (SEQ ID NO: 322); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 472. In an embodiment, the VL comprises the amino acid sequence of SEQ ID NO: 476. In an embodiment, the VH comprises the amino acid sequence of SEQ ID NO: 472 and the VL comprises the amino acid sequence of SEQ ID NO: 476.

In an embodiment, the VH comprises one, two, or all of: (i) an HCDR1 comprising an amino acid sequence of GYNFASY (SEQ ID NO: 517); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYNFASY (SEQ ID NO: 517); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 473. In an embodiment, the VL comprises the amino acid sequence of SEQ ID NO: 475. In an embodiment, the VH comprises the amino acid sequence of SEQ ID NO: 473 and the VL comprises the amino acid sequence of SEQ ID NO: 475.

In an embodiment, the VH comprises one, two, or all of: (i) an HCDR1 comprising an amino acid sequence of GYNFASY (SEQ ID NO: 517); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYNFASY (SEQ ID NO: 517); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 473. In an embodiment, the VL comprises the amino acid sequence of SEQ ID NO: 476. In an embodiment, the VH comprises the amino acid sequence of SEQ ID NO: 473 and the VL comprises the amino acid sequence of SEQ ID NO: 476.

In an embodiment, the VH comprises one, two, or all of: (i) an HCDR1 comprising an amino acid sequence of GYNFASY (SEQ ID NO: 517); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of GYNFASY (SEQ ID NO: 517); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY (SEQ ID NO: 508); and the VL comprises one, two, or all of: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY (SEQ ID NO: 508); and the VL comprises: (i) an LCDR1 comprising an amino acid sequence of KSSQSLLYKDGKTYLN (SEQ ID NO: 512); (ii) an LCDR2 comprising an amino acid sequence of VVSTRAS (SEQ ID NO: 353); and (iii) an LCDR3 comprising an amino acid sequence of QQLVEYPYT (SEQ ID NO: 354).

In an embodiment, the VH comprises the amino acid sequence of SEQ ID NO: 473. In an embodiment, the VL comprises the amino acid sequence of SEQ ID NO: 481. In an embodiment, the VH comprises the amino acid sequence of SEQ ID NO: 473 and the VL comprises the amino acid sequence of SEQ ID NO: 481.

In an embodiment, the VH comprises one, two, or all of: (i) an HCDR1 comprising an amino acid sequence of GYTFSSY (SEQ ID NO: 356); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of GYTFSSY (SEQ ID NO: 356); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYIH (SEQ ID NO: 518); (ii) an HCDR2 comprising an amino acid sequence of TIHPSDSTTNYNQKFQG (SEQ ID NO: 514); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of SYYIH (SEQ ID NO: 518); (ii) an HCDR2 comprising an amino acid sequence of TIHPSDSTTNYNQKFQG (SEQ ID NO: 514); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises the amino acid sequence of SEQ ID NO: 463. In an embodiment, the VL comprises the amino acid sequence of SEQ ID NO: 477. In an embodiment, the VH comprises the amino acid sequence of SEQ ID NO: 463 and the VL comprises the amino acid sequence of SEQ ID NO: 477.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises one, two, or all of: (i) an HCDR1 comprising an amino acid sequence of SYYIH (SEQ ID NO: 518); (ii) an HCDR2 comprising an amino acid sequence of TIHPSDSTANYAQKFQG (SEQ ID NO: 519); or (iii) an HCDR3 comprising an amino acid sequence of FVY (SEQ ID NO: 508); and the VL comprises one, two, or all of: (i) an LCDR1 comprising an amino acid sequence of KSSKSLLYKDGKTYLN (SEQ ID NO: 510); (ii) an LCDR2 comprising an amino acid sequence of VVSTRAS (SEQ ID NO: 353); or (iii) an LCDR3 comprising an amino acid sequence of QQLVQYPYT (SEQ ID NO: 511). In an embodiment, the VH comprises: (i) an HCDR1 comprising an amino acid sequence of SYYIH (SEQ ID NO: 518); (ii) an HCDR2 comprising an amino acid sequence of TIHPSDSTANYAQKFQG (SEQ ID NO: 519); and (iii) an HCDR3 comprising an amino acid sequence of FVY (SEQ ID NO: 508); and the VL comprises: (i) an LCDR1 comprising an amino acid sequence of KSSKSLLY-KDGKTYLN (SEQ ID NO: 510); (ii) an LCDR2 comprising an amino acid sequence of VVSTRAS (SEQ ID NO: 353); and (iii) an LCDR3 comprising an amino acid sequence of QQLVQYPYT (SEQ ID NO: 511).

In an embodiment, the VH comprises the amino acid sequence of SEQ ID NO: 464. In an embodiment, the VL comprises the amino acid sequence of SEQ ID NO: 476. In an embodiment, the VH comprises the amino acid sequence of SEQ ID NO: 464 and the VL comprises the amino acid sequence of SEQ ID NO: 476.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); and (iii) an HCDR3 comprising an amino acid sequence of FVY (SEQ ID NO: 508); and the VL comprises: (i) an LCDR1 comprising an amino acid sequence of RASKSL-LYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises the amino acid sequence of SEQ ID NO: 466. In an embodiment, the VL comprises the amino acid sequence of SEQ ID NO: 477. In an embodiment, the VH comprises the amino acid sequence of SEQ ID NO: 466 and the VL comprises the amino acid sequence of SEQ ID NO: 477.

In an embodiment, the VH comprises one, two, or all of: (i) an HCDR1 comprising an amino acid sequence of GYSFSSY (SEQ ID NO: 355); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of RSSQSLLYKDGKTYLN (SEQ ID NO: 520); (ii) an LCDR2 comprising an amino acid sequence of VLSTRAS (SEQ ID NO: 521); or (iii) an LCDR3 comprising an amino acid sequence of QQLVEYPYT (SEQ ID NO: 354). In an embodiment, the VH comprises: (i) an HCDR1 comprising an amino acid sequence of GYSFSSY (SEQ ID NO: 355); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of RSSQSLLYKDGKTYLN (SEQ ID NO: 520); (ii) an LCDR2 comprising an amino acid sequence of VLSTRAS (SEQ ID NO: 521); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); or (iii) an HCDR3 comprising an amino acid sequence of FVY (SEQ ID NO: 508); and the VL comprises one, two, or all of: (i) an LCDR1 comprising an amino acid sequence of RSSQSLLYKDGKTYLN (SEQ ID NO: 520); (ii) an LCDR2 comprising an amino acid sequence of VLSTRAS (SEQ ID NO: 521); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTANYNQKFKG (SEQ ID NO: 509); and (iii) an HCDR3 comprising an amino acid sequence of FVY (SEQ ID NO: 508); and the VL comprises: (i) an LCDR1 comprising an amino acid sequence of RSSQSL-LYKDGKTYLN (SEQ ID NO: 520); (ii) an LCDR2 comprising an amino acid sequence of VLSTRAS (SEQ ID NO: 521); and (iii) an LCDR3 comprising an amino acid sequence of QQLVEYPYT (SEQ ID NO: 354).

In an embodiment, the VH comprises the amino acid sequence of SEQ ID NO: 466. In an embodiment, the VL comprises the amino acid sequence of SEQ ID NO: 480. In an embodiment, the VH comprises the amino acid sequence of SEQ ID NO: 466 and the VL comprises the amino acid sequence of SEQ ID NO: 480.

In an embodiment, the VH comprises one, two, or all of: (i) an HCDR1 comprising an amino acid sequence of GYTFTSY (SEQ ID NO: 322); (ii) an HCDR2 comprising an amino acid sequence of HPSDST (SEQ ID NO: 351); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of GYTFTSY (SEQ ID NO: 322); (ii) an HCDR2 comprising an amino acid sequence of HPSDST (SEQ ID NO: 351); and (iii) an HCDR3 comprising an amino acid sequence of FVY (SEQ ID NO: 508); and the VL comprises: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises one, two, or all of: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); or (iii) an HCDR3 comprising an amino acid sequence of FVY (SEQ ID NO: 508); and the VL comprises one, two, or all of: (i) an LCDR1 comprising an amino acid sequence of RASKSLLYKDGKTYLN (SEQ ID NO: 515); (ii) an LCDR2 comprising an amino acid sequence of VVSSLQS (SEQ ID NO: 516); or (iii) an LCDR3 comprising an amino acid sequence of QQLVEYPYT (SEQ ID NO: 354). In an embodiment, the VH comprises: (i) an HCDR1 comprising an amino acid sequence of SYYMH (SEQ ID NO: 380); (ii) an HCDR2 comprising an amino acid sequence of TIHPSDSTTNYNQKFKG (SEQ ID NO: 382); and (iii) an HCDR3 comprising an amino acid sequence of FVY (SEQ ID NO: 508); and the VL comprises: (i) an LCDR1 comprising an amino acid sequence of RASKSL-LYKDGKTYLN (SEQ ID NO: 515); (ii) an LCDR2 comprising an amino acid sequence of VVSSLQS (SEQ ID NO: 516); and (iii) an LCDR3 comprising an amino acid sequence of QQLVEYPYT (SEQ ID NO: 354).

In an embodiment, the VH comprises the amino acid sequence of SEQ ID NO: 472. In an embodiment, the VL comprises the amino acid sequence of SEQ ID NO: 477. In an embodiment, the VH comprises the amino acid sequence of SEQ ID NO: 472 and the VL comprises the amino acid sequence of SEQ ID NO: 477.

In an aspect, the disclosure features a humanized anti-CD138 antibody molecule comprising one or both of:

(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH38, VH43, or VH45, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL20; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH43, or VH45. In an embodiment, the antibody molecule the VH comprises the amino acid sequence of VH38, VH43, or VH45.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL20. In an embodiment, the VL comprises the amino acid sequence of VL20.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH43, or VH45; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL20.

In an embodiment, the VH comprises the amino acid sequence of VH38, VH43, or VH45 and the VL comprises the amino acid sequence of VL20.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH38, VH42, VH43, VH44, VH45, or VH36, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or
(b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL21; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH42, VH43, VH44, VH45, or VH36. In an embodiment, the antibody molecule the VH comprises the amino acid sequence of VH38, VH42, VH43, VH44, VH45, or VH36.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL21. In an embodiment, the VL comprises the amino acid sequence of VL21.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH42, VH43, VH44, VH45, or VH36; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL21.

In an embodiment, the VH comprises the amino acid sequence of VH38, VH42, VH43, VH44, VH45, or VH36, and the VL comprises the amino acid sequence of VL21.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH38, VH42, VH43, or VH45, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL26; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:

(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and (b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH42, VH43, or VH45. In an embodiment, the antibody molecule the VH comprises the amino acid sequence of VH38, VH42, VH43, or VH45.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL26. In an embodiment, the VL comprises the amino acid sequence of VL26.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38, VH42, VH43, or VH45; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL26.

In an embodiment, the VH comprises the amino acid sequence of VH38, VH42, VH43, or VH45, and the VL comprises the amino acid sequence of VL26.

In an embodiment, the antibody molecule comprises an Fc region.

In an aspect, the disclosure features a humanized anti-CD138 antibody molecule comprising one or both of:

(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH43, VH35, VH38, or VH44, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL22; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH43, VH35, VH38, or VH44. In an embodiment, the antibody molecule the VH comprises the amino acid sequence of VH43, VH35, VH38, or VH44.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL22. In an embodiment, the VL comprises the amino acid sequence of VL22.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH43, VH35, VH38, or VH44; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL22.

In an embodiment, the VH comprises the amino acid sequence of VH43, VH35, VH38, or VH44, and the VL comprises the amino acid sequence of VL22.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH38, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or
(b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL20, VL21, or VL26; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38. In an embodiment, the antibody molecule the VH comprises the amino acid sequence of VH38.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL20, VL21, or VL26. In an embodiment, the VL comprises the amino acid sequence of VL20, VL21, or VL26.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL20, VL21, or VL26.

In an embodiment, the VH comprises the amino acid sequence of VH38, and the VL comprises the amino acid sequence of VL20, VL21, or VL26.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH42, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or
(b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL21 or VL26; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH42. In an embodiment, the antibody molecule the VH comprises the amino acid sequence of VH42.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL21 or VL26. In an embodiment, the VL comprises the amino acid sequence of VL21 or VL26.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH42; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL21 or VL26.

In an embodiment, the VH comprises the amino acid sequence of VH42, and the VL comprises the amino acid sequence of VL21 or VL26.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH43, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or
(b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL20, VL21, VL26, or VL22; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and (b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH43. In an embodiment, the antibody molecule the VH comprises the amino acid sequence of VH43.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL20, VL21, VL26, or VL22. In an embodiment, the VL comprises the amino acid sequence of VL20, VL21, VL26, or VL22.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH43; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL20, VL21, VL26, or VL22.

In an embodiment, the VH comprises the amino acid sequence of VH43, and the VL comprises the amino acid sequence of VL20, VL21, VL26, or VL22.

In an embodiment, the antibody molecule comprises an Fc region.

In an aspect, the disclosure features a humanized anti-CD138 antibody molecule comprising one or both of:

(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH45, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or (b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL20, VL21, or VL26; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and
(b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH45. In an embodiment, the antibody molecule the VH comprises the amino acid sequence of VH45.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL20, VL21, or VL26. In an embodiment, the VL comprises the amino acid sequence of VL20, VL21, or VL26.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH45; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL20, VL21, or VL26.

In an embodiment, the VH comprises the amino acid sequence of VH45, and the VL comprises the amino acid sequence of VL20, VL21, or VL26.

In an embodiment, the antibody molecule comprises an Fc region.

In an aspect, the disclosure features a humanized anti-CD138 antibody molecule comprising one or both of:
(a) a heavy chain variable region (VH), wherein the VH comprises three heavy chain complementarity determining regions (HCDR1, HCDR2, and HCDR3), wherein the VH comprises one, two, or all of the following: (i) an HCDR1 comprising an amino acid sequence that differs by no more than 1, 2, or 3 amino acid residues from, or has at least 85, 90, 95, 99 or 100% homology with, the amino acid sequence of the HCDR1 of VH38, e.g., as listed in Table 1 or 2); (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH; or
(b) a light chain variable region (VL), wherein the VL comprises three light chain complementarity determining regions (LCDR1, LCDR2, and LCDR3), wherein the VL comprises one, two, or all of the following: (i) an LCDR1 comprising an amino acid sequence that differs by no more than 1, 2, or 3 amino acid residues from, or has at least 85, 90, 95, 99 or 100% homology with, the amino acid sequence of the LCDR1 of VL22 or VL25; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; or (iii) an LCDR3 comprising an amino acid sequence that differs by no more than 1, 2, or 3 amino acid residues from, or has at least 85, 90, 95, 99 or 100% homology with, the amino acid sequence of the VL.

In an embodiment, the VH comprises: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH.

In an embodiment, the VH comprises: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH.

In an embodiment, the VL comprises: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the VL comprises: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the antibody molecule comprises:
(a) a VH comprising: (i) an HCDR1 comprising an amino acid sequence that differs by no more than 1, 2, or 3 amino acid residues from, or has at least 85, 90, 95, 99 or 100% homology with, the amino acid sequence of the HCDR1 of the VH; (ii) an HCDR2 comprising an amino acid sequence that differs by no more than 1, 2, or 3 amino acid residues from, or has at least 85, 90, 95, 99 or 100% homology with, the amino acid sequence of the HCDR2 of the VH; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the VH, and (b) a VL comprising: (i) an LCDR1 comprising an amino acid sequence that differs by no more than 1, 2, or 3 amino acid residues from, or has at least 85, 90, 95, 99 or 100% homology with, the amino acid sequence of the LCDR1 of the VL; (ii) an LCDR2 comprising an amino acid sequence that differs by no more than 1, 2, or 3 amino acid residues from, or has at least 85, 90, 95, 99 or 100% homology with, the amino acid sequence of the LCDR2 of the VL; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the VL.

In an embodiment, the antibody molecule comprises: (a) a VH comprising: (i) an HCDR1 comprising the amino acid sequence of the HCDR1 of the VH; (ii) an HCDR2 comprising the amino acid sequence of the HCDR2 of the VH; and (iii) an HCDR3 comprising the amino acid sequence of the HCDR3 of the VH, and (b) a VL comprising: (i) an LCDR1 comprising the amino acid sequence of the LCDR1 of the VL; (ii) an LCDR2 comprising the amino acid sequence of the LCDR2 of the VL; and (iii) an LCDR3 comprising the amino acid sequence of the LCDR3 of the VL.

In an embodiment, the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38. In an embodiment, the antibody molecule the VH comprises the amino acid sequence of VH38.

In an embodiment, the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VL22 or VL25. In an embodiment, the VL comprises the amino acid sequence of VL22 or VL25.

In an embodiment, (a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of VH38; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL22 or VL25.

In an embodiment, the VH comprises the amino acid sequence of VH38, and the VL comprises the amino acid sequence of VL22 or VL25.

In an embodiment, the antibody molecule comprises an Fc region.

In an embodiment, the anti-CD138 antibody molecule comprises:
(a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of G-Y-N/S/T-F-A/S/T-S-Y (SEQ ID NO: 438); (ii) an HCDR2 comprising an amino acid sequence of H-P-S-D-S-T (SEQ ID NO: 351); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524).

In an embodiment, the anti-CD138 antibody molecule comprises:
(a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of S-Y-Y-I/M-H (SEQ ID NO: 525); (ii) an HCDR2 comprising an amino acid sequence of T-I-H-P-S-D-S-T-A/T-N-Y-A/N-Q-K-F-K/Q-G (SEQ ID NO: 526); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524).

In an embodiment, the antibody molecule comprises: (a) a VH comprising: (i) an HCDR1 comprising the consensus amino acid sequence of the HCDR1 sequences of antibodies 3820, 3821, 3826, 4221, 4226, 4320, 4321, 4322, 4326, 4421, 4520, 4521, 4526, 3522, 3621, 3822, 3825, and 4422, or a subset thereof; (ii) an HCDR2 comprising the consensus amino acid sequence of the HCDR2 sequences of the same antibodies; and (iii) an HCDR3 comprising the consensus amino acid sequence of the HCDR3 sequences of the same antibodies, and (b) a VL comprising: (i) an LCDR1 comprising the consensus amino acid sequence of the LCDR1 sequences of the same antibodies; (ii) an LCDR2 comprising the consensus amino acid sequence of the HCDR2 sequences of the same antibodies; and (iii) an LCDR3 comprising the consensus amino acid sequence of the HCDR3 sequences of the same antibodies.

In an embodiment, the antibody molecule comprises: (a) a VH comprising: (i) an HCDR1 comprising the consensus amino acid sequence of the HCDR1 sequences of antibodies 3820, 3821, 3826, 4221, 4226, 4320, 4321, 4322, 4326, 4421, 4520, 4521, 4526, 3522, 3621, 3822, 3825, and 4422; (ii) an HCDR2 comprising the consensus amino acid sequence of the HCDR2 sequences of the same antibodies; and (iii) an HCDR3 comprising the consensus amino acid sequence of the HCDR3 sequences of the same antibodies, and (b) a VL comprising: (i) an LCDR1 comprising the consensus amino acid sequence of the LCDR1 sequences of the same antibodies; (ii) an LCDR2 comprising the consensus amino acid sequence of the HCDR2 sequences of the same antibodies; and (iii) an LCDR3 comprising the consensus amino acid sequence of the HCDR3 sequences of the same antibodies.

In an embodiment, the antibody molecule comprises: (a) a VH comprising: (i) an HCDR1 comprising the amino acid sequence of the HCDR1 of an anti-CD138 antibody described herein, e.g., chosen from antibodies 3820, 3821, 3826, 4221, 4226, 4320, 4321, 4322, 4326, 4421, 4520, 4521, 4526, 3522, 3621, 3822, 3825, or 4422, or as listed in Table 1; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment the anti-CD138 antibody molecule comprises:

(a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises one, two, or all of: (i) an HCDR1 comprising an amino acid sequence of G-Y-N/S/T-F-A/S/T-S-Y (SEQ ID NO: 438); (ii) an HCDR2 comprising an amino acid sequence of H-P-S-D-S-T (SEQ ID NO: 351); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524).

In an embodiment, the HCDR1 comprises an amino acid sequence of SEQ ID NOS: 355, 322, 517, or 356, the HCDR2 comprises the amino acid sequence of SEQ ID NO: 351, and the HCDR3 comprises the amino acid sequence of F-V-Y (SEQ ID NO: 508). In an embodiment, the LCDR1 comprises the amino acid sequence of SEQ ID NO: 352, 510, 512, 515, or 520; the LCDR2 comprises the amino acid sequence of SEQ ID NO: 353, 516, or 521; and the LCDR3 comprises the amino acid sequence of SEQ ID NO: 354 or 511. In an embodiment, the HCDR1 comprises an amino acid sequence of SEQ ID NOS: 355, 322, 517, or 356, the HCDR2 comprises the amino acid sequence of SEQ ID NO: 351, the HCDR3 comprises the amino acid sequence of F-V-Y (SEQ ID NO: 508), the LCDR1 comprises the amino acid sequence of SEQ ID NO: 352, 510, 512, 515, or 520, the LCDR2 comprises the amino acid sequence of SEQ ID NO: 353, 516, or 521, and the LCDR3 comprises the amino acid sequence of SEQ ID NO: 354 or 511.

In an embodiment, the anti-CD138 antibody molecule comprises:

(a) a heavy chain variable region (VH), wherein the VH comprises three heavy chain complementarity determining regions (HCDR1, HCDR2, and HCDR3), wherein the VH comprises three heavy chain complementarity determining regions (HCDR1, HCDR2, and HCDR3), wherein the VH comprises one, two, or all of: (i) an HCDR1 comprising an amino acid sequence of S-Y-Y-I/M-H (SEQ ID NO: 525); (ii) an HCDR2 comprising an amino acid sequence of T-I-H-P-S-D-S-T-A/T-N-Y-A/N-Q-K-F-K/Q-G (SEQ ID NO: 526); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524).

In an embodiment, the HCDR1 comprises an amino acid sequence of SEQ ID NO: 380 or 518, the HCDR2 comprises the amino acid sequence of SEQ ID NO: 382, 509, 513, 514, or 519, and the HCDR3 comprises the amino acid sequence of F-V-Y (SEQ ID NO: 508). In an embodiment, the LCDR1 comprises the amino acid sequence of SEQ ID NO: 352, 510, 512, 515, or 520; the LCDR2 comprises the amino acid sequence of SEQ ID NO: 353, 516, or 521; and the LCDR3 comprises the amino acid sequence of SEQ ID NO: 354 or 511. In an embodiment, the HCDR1 comprises an amino acid sequence of SEQ ID NO: 380 or 518, the HCDR2 comprises the amino acid sequence of SEQ ID NO: 382, 509, 513, 514, or 519, the HCDR3 comprises the amino acid sequence of F-V-Y (SEQ ID NO: 508), the LCDR1 comprises the amino acid sequence of SEQ ID NO: 352, 510, 512, 515, or 520, the LCDR2 comprises the amino acid sequence of SEQ ID NO: 353, 516, or 521, and the LCDR3 comprises the amino acid sequence of SEQ ID NO: 354 or 511.

In an embodiment, the antibody molecule comprises: (a) a VH comprising: (i) an HCDR1 comprising the amino acid sequence of the HCDR1 of an anti-CD138 antibody described herein, e.g., chosen from antibodies 3820, 3821, 3826, 4221, 4226, 4320, 4321, 4322, 4326, 4421, 4520, 4521, 4526, 3522, 3621, 3822, 3825, or 4422; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

In an embodiment, the VH comprises the amino acid sequence of the VH of the anti-CD138 antibody and the VL comprises the amino acid sequence of the VL of the anti-CD138 antibody.

In an embodiment, the antibody molecule comprises two VHs and two VLs.

In an embodiment, the antibody molecule is a synthetic antibody molecule. In an embodiment, the antibody molecule is an isolated antibody molecule. In an embodiment, the antibody molecule is a humanized antibody molecule. In an embodiment, the antibody molecule comprises one or more framework regions derived from human framework germline sequence.

In an embodiment, the antibody molecule comprises a VH region comprising one or more mutations relative to an anti-CD138 antibody described herein (e.g., antibody 2810, 3820, 3821, 3826, 4221, 4226, 4320, 4321, 4322, 4326, 4421, 4520, 4521, 4526, 3522, 3621, 3822, 3825, or 4422).

In an embodiment, the antibody molecule binds to the extracellular domain of CD138. In an embodiment, the antibody molecule binds to an extracellular region of CD138 proximal to the transmembrane domain. In an embodiment, the antibody molecule is capable of binding to one or more (e.g., two, three, or all) of the following peptides: a peptide comprising the amino acid sequence of ENTAVVAVEPDRRNQSPVDQGATGASQGLLDRKEVLG (SEQ ID NO: 440), a peptide comprising the amino acid sequence of TAVVAVEPDRRNQSPVDQGATGASQ (SEQ ID NO: 441), a peptide comprising the amino acid sequence of ENTAVVAVEPDRRNQSPVDQGATG (SEQ ID NO: 442), or a peptide comprising the amino acid sequence of ENTAVVAVEPDRRNQ (SEQ ID NO: 443). In an embodiment, the antibody molecule is capable of binding to one or more (e.g., two or all) of the following peptides: a peptide comprising the amino acid sequence of ENTAVVAVEPDRRNQSPVDQGATGASQGLLDRKEVLG (SEQ ID NO: 440), a peptide comprising the amino acid sequence of RNQSPVDQGATGASQGLLDRKEVLG (SEQ ID NO: 444), or a peptide comprising the amino acid sequence of ENTAVVAVEPDRRNQ (SEQ ID NO: 443).

In an embodiment, the antibody molecule further binds to an extracellular region of CD138 distal to the transmembrane domain, e.g., a region corresponding to or proximal to the integrin binding domain (IBD) of CD138. In an embodiment, the antibody molecule is capable of binding to one or both the following peptides: a peptide comprising the amino acid sequence of ASTSTLPAGEGPKEGEAVVLPEVEPGLTAREQEA (SEQ ID NO: 10) or a peptide comprising the amino acid sequence of GEAVVLPEVEPGLTA (SEQ ID NO: 445).

In an embodiment, the antibody molecule is a synthetic antibody molecule. In an embodiment, the antibody molecule is an isolated antibody molecule. In an embodiment, the antibody molecule is a humanized antibody molecule. In an embodiment, the antibody molecule comprises one or more framework regions derived from human framework germline sequence.

In an embodiment, the antibody molecule is an IgG antibody. In an embodiment, the antibody molecule comprises a heavy chain constant region of IgG chosen from IgG1, IgG2, IgG3, or IgG4. In an embodiment, the antibody molecule comprises a light chain constant region of kappa or lambda light chain.

In an embodiment, the antibody molecule comprises an Fc region comprising one or more mutations to increase the binding affinity to neonatal receptor FcRn and/or the half-life of the antibody molecule. In an embodiment, the antibody molecule comprises an Fc region comprising one or more mutations described herein, e.g., to increase one or more of half-life, ADCC, CDC, or ADCP.

In an embodiment, the antibody molecule is an IgG antibody. In an embodiment, the antibody molecule comprises a heavy chain constant region of IgG chosen from IgG1, IgG2, IgG3, or IgG4. In an embodiment, the antibody molecule comprises a light chain constant region of kappa or lambda light chain.

In an embodiment, the antibody molecule comprises an Fc region comprising one or more mutations to increase the binding affinity to neonatal receptor FcRn and/or the half-life of the antibody molecule. In an embodiment, the antibody molecule comprises an Fc region comprising one or more mutations described herein, e.g., to increase one or more of half-life, ADCC, CDC, or ADCP. In an embodiment, the antibody molecule induces at least 10% (e.g., at least 15%, 20%, 25%, 30%, 35%, or 40%) greater ADCC activity relative to a reference anti-CD138 antibody (e.g., antibody BB4), e.g., as determined by a method described herein.

In an embodiment, the antibody molecule further comprises a heavy chain constant region. In an embodiment, the heavy chain constant region is an IgG1 constant region or a functional portion thereof. In another embodiment, the heavy chain constant region is an IgG2 constant region or a functional portion thereof. In an embodiment, the antibody molecule further comprises a light chain constant region. In an embodiment, the antibody molecule further comprises a heavy chain constant region and a light chain constant region. In an embodiment, the antibody molecule comprises a heavy chain constant region, a light chain constant region, and heavy and light chain variable regions of an antibody molecule described in Table 1 or 2. In certain embodiments, the antibody molecule comprises a heavy chain constant region, a light chain constant region, and variable regions that comprise one, two, three, four, five, or six CDRs of an antibody molecule described in Table 1 or 2.

Exemplary heavy chain constant regions are described below.

IgG1 HC constant region:
(SEQ ID NO: 446)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

-continued

RVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREE

MTKNQVSLTCLVKGFYPSDIAVEWESNGQPENNYKTTPPVLDSDGSFF

LYSKLTVDKSRWQQGNVFSCSVMHEALHNHYTQKSLSLSPGK

IgG2 HC constant region:
(SEQ ID NO: 447)
ASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDK

TVERKCCVECPPCPAPPVAGPSVFLFPPKPKDTLMISRTPEVTCVVVD

VSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSK

LTVDKSRWQQGNVFSCSVMHEALHNHYTQKSLSLSPGK

In an embodiment, the antibody molecule comprises the heavy chain sequence listed in Table 6 (or an amino acid sequence having at least 75%, 80%, 85%, 90%, 95%, 96%, 97%, 98%, 99%, or 100% sequence identity thereto). In an embodiment, the antibody molecule comprises a heavy chain comprising one or more (e.g., 1, 2, 3, 4, or 5) of the sequences listed in Table B, or one or more amino acid sequences having at least 75%, 80%, 85%, 90%, 95%, 96%, 97%, 98%, 99%, or 100% sequence identity thereto. In an embodiment, the antibody molecule comprises the light chain sequence listed in Table 6 (or an amino acid sequence having at least 75%, 80%, 85%, 90%, 95%, 96%, 97%, 98%, 99%, or 100% sequence identity thereto). In an embodiment, the antibody molecule comprises a light chain comprising one or more (e.g., 1, 2, or 3) of the sequences listed in Table 8, or one or more amino acid sequences having at least 75%, 80%, 85%, 90%, 95%, 96%, 97%, 98%, 99%, or 100% sequence identity thereto.

In an embodiment, the antibody molecule comprises one, two, or all of the heavy chain constant region sequences (e.g., CH1, CH2, or CH3) listed in Table 7 (or an amino acid sequence having at least 75%, 80%, 85%, 90%, 95%, 96%, 97%, 98%, 99%, or 100% sequence identity thereto). In an embodiment, the antibody molecule comprises all of the CH1, CH2, and CH3 sequences listed in Table 7 (or an amino acid sequence having at least 75%, 80%, 85%, 90%, 95%, 96%, 97%, 98%, 99%, or 100% sequence identity thereto). In an embodiment, the antibody molecule further comprises the heavy chain constant hinge region sequence list in Table 7 (or an amino acid sequence having at least 75%, 80%, 85%, 90%, 95%, 96%, 97%, 98%, 99%, or 100% sequence identity thereto).

In an embodiment, the antibody molecule comprises the light chain constant region sequence (e.g., CL) listed in Table 8 (or an amino acid sequence having at least 75%, 80%, 85%, 90%, 95%, 96%, 97%, 98%, 99%, or 100% sequence identity thereto). In an embodiment, the antibody molecule further comprises the light chain constant hinge region sequence list in Table 8 (or an amino acid sequence having at least 75%, 80%, 85%, 90%, 95%, 96%, 97%, 98%, 99%, or 100% sequence identity thereto).

In an embodiment, the antibody molecule comprises one, two, or all of the heavy chain constant region sequences (e.g., CH1, CH2, or CH3) listed in Table 7 (or an amino acid sequence having at least 75%, 80%, 85%, 90%, 95%, 96%, 97%, 98%, 99%, or 100% sequence identity thereto) and the light chain constant region sequence (e.g., CL) listed in Table 8 (or an amino acid sequence having at least 75%, 80%, 85%, 90%, 95%, 96%, 97%, 98%, 99%, or 100% sequence identity thereto). In an embodiment, the antibody molecule comprises all of the CH1, CH2, and CH3 sequences listed in Table 7 (or an amino acid sequence having at least 75%, 80%, 85%, 90%, 95%, 96%, 97%, 98%, 99%, or 100% sequence identity thereto) and the light chain constant hinge region sequence list in Table 8 (or an amino acid sequence having at least 75%, 80%, 85%, 90%, 95%, 96%, 97%, 98%, 99%, or 100% sequence identity thereto). In an embodiment, the antibody molecule further comprises the heavy chain constant hinge region sequence list in Table 7 (or an amino acid sequence having at least 75%, 80%, 85%, 90%, 95%, 96%, 97%, 98%, 99%, or 100% sequence identity thereto) and/or the light chain constant hinge region sequence list in Table 8 (or an amino acid sequence having at least 75%, 80%, 85%, 90%, 95%, 96%, 97%, 98%, 99%, or 100% sequence identity thereto).

In an embodiment, the antibody molecule comprises one, two, or all of the amino acid sequences of SEQ ID NOs: 529, 531, or 532 (or an amino acid sequence having at least 75%, 80%, 85%, 90%, 95%, 96%, 97%, 98%, 99%, or 100% sequence identity thereto). In an embodiment, the antibody molecule comprises all of the amino acid sequences of SEQ ID NOs: 529, 531, and 532 (or an amino acid sequence having at least 75%, 80%, 85%, 90%, 95%, 96%, 97%, 98%, 99%, or 100% sequence identity thereto). In an embodiment, the antibody molecule further comprises the amino acid sequence of SEQ ID NO: 530 (or an amino acid sequence having at least 75%, 80%, 85%, 90%, 95%, 96%, 97%, 98%, 99%, or 100% sequence identity thereto).

In an embodiment, the antibody molecule comprises the amino acid sequence of SEQ ID NO: 534 (or an amino acid sequence having at least 75%, 80%, 85%, 90%, 95%, 96%, 97%, 98%, 99%, or 100% sequence identity thereto). In an embodiment, the antibody molecule further comprises the amino acid sequence of SEQ ID NO: 533 (or an amino acid sequence having at least 75%, 80%, 85%, 90%, 95%, 96%, 97%, 98%, 99%, or 100% sequence identity thereto).

In an embodiment, the antibody molecule comprises one, two, or all of the amino acid sequences of SEQ ID NOs: 529, 531, or 532 (or an amino acid sequence having at least 75%, 80%, 85%, 90%, 95%, 96%, 97%, 98%, 99%, or 100% sequence identity thereto) and the amino acid sequence of SEQ ID NO: 534 (or an amino acid sequence having at least 75%, 80%, 85%, 90%, 95%, 96%, 97%, 98%, 99%, or 100% sequence identity thereto). In an embodiment, the antibody molecule comprises all of the amino acid sequences of SEQ ID NOs: 529, 531, and 532 (or an amino acid sequence having at least 75%, 80%, 85%, 90%, 95%, 96%, 97%, 98%, 99%, or 100% sequence identity thereto) and the amino acid sequence of SEQ ID NO: 534 (or an amino acid sequence having at least 75%, 80%, 85%, 90%, 95%, 96%, 97%, 98%, 99%, or 100% sequence identity thereto). In an embodiment, the antibody molecule further comprises the amino acid sequence of SEQ ID NO: 530 (or an amino acid sequence having at least 75%, 80%, 85%, 90%, 95%, 96%, 97%, 98%, 99%, or 100% sequence identity thereto) and/or the amino acid sequence of SEQ ID NO: 533 (or an amino acid sequence having at least 75%, 80%, 85%, 90%, 95%, 96%, 97%, 98%, 99%, or 100% sequence identity thereto).

In an embodiment, the antibody molecule comprises one, two, three, four, five, or all of the amino acid sequences of SEQ ID NOs: 529-534. In an embodiment, the antibody molecule comprises the amino acid sequences of SEQ ID NOs: 529-534.

TABLE 6 mAb 4320 heavy chain and light chain sequences

| | Amino Acid Sequence |
|---|---|
| Heavy Chain | QVQLVQSGAEVKKPGASVKVSCKASGYSFSSYYM HWVRQAPGQGLEWMGTIHPSDSTTNYNQKFQGRV TMTVDTSTRTAYMELSSLRSEDTAVYYCANFVYW GQGTTVTVSSASTKGPSVFPLAPSSKSTSGGTAA LGCLVKDYFPEPVTVSWNSGALTSGVHTFPAVLQ SSGLYSLSSVVTVPSSSLGTQTYICNVNHKPSNT KVDKRVEPKSCDKTHTCPPCPAPELLGGPSVFLF PPKPKDTLMISRTPEVTCVVVDVSHEDPEVKFNW YVDGVEVHNAKTKPREEQYNSTYRVVSVLTVLHQ DWLNGKEYKCKVSNKALPAPIEKTISKAKGQPRE PQVYTLPPSREEMTKNQVSLTCLVKGFYPSDIAV EWESNGQPENNYKTTPPVLDSDGSFFLYSKLTVD KSRWQQGNVFSCSVMHEALHNHYTQKSLSLSPGK (SEQ ID NO: 527) |
| Light Chain | DIVMTQTPLSLSVTPGQPASISCKSSKSLLYKDG KTYLNWFLQKPGQSPQLLIYVVSTRASGVPDRFS GSGSGTDFTLKISRVEAEDVGVYYCQQLVEYPYT FGQGTKLEIKRTVAAPSVFIFPPSDEQLKSGTAS VVCLLNNFYPREAKVQWKVDNALQSGNSQESVTE QDSKDSTYSLSSTLTLSKADYEKHKVYACEVTHQ GLSSPVTKSFNRGEC (SEQ ID NO: 528) |

TABLE 7

Annotation of mAb 4320 heavy chain sequence

| Feature | Position | Sequence |
|---|---|---|
| Leader Sequence | — | N/A |
| Variable (VH) | 1-112 | QVQLVQSGAEVKKPGASVKVSCKAS<u>GYS FSSY</u>YMHWVRQAPGQGLEWMGT<u>IHPSDS TTNYNQKFQGR</u>VTMTVDTSTRTA<u>YMELS SLRSEDTAVYYCAN</u><u>FVY</u>WGQGTTVTVSS (SEQ ID NO: 471) |
| Constant-CH1 | 113-210 | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKRV (SEQ ID NO: 529) |
| Constant-Hinge | 211-225 | EPKSCDKTHTCPPCP (SEQ ID NO: 530) |
| Constant-CH2 | 226-335 | APELLGGPSVFLFPPKPKDTLMISRTPE VTCVVVDVSHEDPEVKFNWYVDGVEVHN AKTKPREEQYNSTYRVVSVLTVLHQDWL NGKEYKCKVSNKALPAPIEKTISKAK (SEQ ID NO: 531) |
| Constant-CH3 | 336-442 | GQPREPQVYTLPPSREEMTKNQVSLTCL VKGFYPSDIAVEWESNGQPENNYKTTPP VLDSDGSFFLYSKLTVDKSRWQQGNVFS CSVMHEALHNHYTQKSLSLSPGK (SEQ ID NO: 532) |

CDRs in variable region (VH) and as defined by Chothia are underlined. Heavy chain constant region is *Homo sapiens* immunoglobulin heavy constant gamma 1 (m3 allotype). Any of the humanized anti-CD138 antibody molecules described herein (e.g., antibodies 3820, 3821, 3826, 4221, 4226, 4320, 4321, 4322, 4326, 4421, 4520, 4521, 4526, 3522, 3621, 3822, 3825, or 4422) can comprise the constant CH1, hinge, CH2, and/or CH3 sequences described in Table 7.

TABLE 8

Annotation of mAb 4320 light chain sequence

| Feature | Position | Sequence |
|---|---|---|
| Leader Sequence | — | N/A |
| Variable (VK) | 1-112 | DIVMTQTPLSLSVTPGQPASISC<u>KSSK SLLYKDGKTYLN</u>WFLQKPGQSPQLLIY <u>VVSTRAS</u>GVPDRFSGSGSGTDFTLKIS RVEAEDVGVYYC<u>QQLVEYPYT</u>FGQGTK LEIK (SEQ ID NO: 475) |
| Constant-Hinge | 113-118 | RTVAAP (SEQ ID NO: 533) |
| Constant-CL | 119-219 | SVFIFPPSDEQLKSGTASVVCLLNNFY PREAKVQWKVDNALQSGNSQESVTEQD SKDSTYSLSSTLTLSKADYEKHKVYAC EVTHQGLSSPVTKSFNRGEC (SEQ ID NO: 534) |

CDRs in variable region (VL) and as defined by Chothia are underlined. Light chain is *Homo sapiens* kappa constant*01. Any of the humanized anti-CD138 antibody molecules described herein (e.g., antibodies 3820, 3821, 3826, 4221, 4226, 4320, 4321, 4322, 4326, 4421, 4520, 4521, 4526, 3522, 3621, 3822, 3825, or 4422) can comprise the constant CL and/or hinge sequences described in Table 8.

In an embodiment, the antibody molecule is a multivalent (e.g., bivalent, trivalent, or tetravalent) antibody molecule. In an embodiment, the antibody molecule binds to two or more (e.g., three or four) different regions in CD138. For example, the antibody molecule can comprise two or more sets of identical, or substantially identical, VH-VL pairs, wherein each VH-VL pair binds to two or more different regions in CD138. As another example, the antibody molecule can comprise two or more sets of different VH-VL pairs, wherein each VH-VL pair binds to a different region in CD138.

In an embodiment, the antibody molecule is a multispecific (e.g., bispecific, trispecific, or tetraspecific) antibody molecule. In an embodiment, the antibody molecule has a first binding specificity to CD138 and a second binding specificity other than CD138. For example, the antibody molecule can comprise two or more sets of identical, or substantially identical, VH-VL pairs, wherein each VH-VL pair has both the first binding specificity and the second binding specificity. As another example, the antibody molecule can comprise two or more sets of different VH-VL pairs, wherein each VH-VL pair has a different binding specificity.

In an embodiment, the humanized antibody molecule is at least 10%, 20%, 30%, 40%, 50%, 60%, 70%, 80%, or 90%, or at least 1, 2, 3, 4, 5, 6, 7, 8, 9, or 10-fold, more stable in vitro, than a reference antibody molecule, e.g., a related non-humanized antibody molecule, as determined by a method described herein. In an embodiment, the humanized antibody molecule has a first thermal transition temperature of at least about 62° C., e.g., between about 65° C. and about 70° C. (e.g., at about 65° C., 66° C., 67° C., 68° C., 69° C., or 70° C.), e.g., as determined by differential scanning fluorescence (DSF). In an embodiment, the humanized antibody molecule has a second thermal transition temperature of at least about 70° C., e.g., between about 75° C. and about 80° C. (e.g., at about 75° C., 76° C., 77° C., 78° C., 79° C., or 80° C.), e.g., as determined by DSF.

In an embodiment, the humanized antibody molecule is at least 10%, 20%, 30%, 40%, 50%, 60%, 70%, 80%, or 90%, or at least 1, 2, 3, 4, 5, 6, 7, 8, 9, or 10-fold, more stable in vivo, than a reference antibody molecule, e.g., a related non-humanized antibody molecule, as determined by a method described herein. In an embodiment, the antibody molecule has a serum half-life (in human or in an animal model) that is at least 10%, 20%, 30%, 40%, 50%, 60%, 70%, 80%, or 90%, or at least 1, 2, 3, 4, 5, 6, 7, 8, 9, or 10-fold, higher than a related non-humanized antibody molecule, e.g., as determined by ELISA.

Antibody Molecule-Drug Conjugates

As used herein, the term "antibody molecule-drug conjugate" or ADC refers to an antibody molecule that is coupled to a non-antibody moiety, e.g., a therapeutic agent or label, e.g., a cytotoxic agent. The antibody molecule can be coupled to the non-antibody moiety directly, or indirectly, e.g., through a linker.

In an embodiment, the antibody molecule is coupled to the non-antibody moiety by a covalent bond. In an embodiment, the antibody molecule is coupled to the non-antibody moiety by a peptide bond. In an embodiment, the antibody molecule is coupled to the non-antibody moiety by a non-peptide bond. In an embodiment, the antibody molecule is not coupled to the non-antibody moiety by a non-peptide bond. In an embodiment, a non-antibody moiety is also referred to as a "payload."

In an embodiment, the non-antibody moiety is coupled to the backbone of the antibody molecule. In another embodiment, the non-antibody moiety is coupled to a side chain of the antibody molecule. In an embodiment, two or more (e.g., three, four, five, six, seven, eight, or more) non-antibody moieties are coupled to the antibody molecule.

In an embodiment, the ADC comprises an antibody molecule that binds to CD138, e.g., a humanized anti-CD138 antibody molecule described herein.

In an embodiment, the ADC comprises one, two, or three CDRs of the VH region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422), using the Kabat or Chothia definitions of CDRs. In an embodiment, the ADC comprises one, two, or three CDRs of the VL region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422), using the Kabat or Chothia definitions of CDRs. In an embodiment, the ADC comprises one or more (e.g., two or three) CDRs of the VH region and/or one or more (e.g., two or three) CDRs of the VL region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422), using the Kabat or Chothia definitions of CDRs.

In an embodiment, the ADC comprises one, two, or three VH CDRs described in Table 1 or 2. In an embodiment, the ADC comprises one, two, or three VL CDRs described in Table 1 or 2. In an embodiment, the ADC comprises one or more (e.g., two or three) VH CDRs and/or one or more (e.g., two or three) VL CDRs described in Table 1 or 2.

In an embodiment, the ADC comprises one, two, three, or four frameworks of the VH region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422). In an embodiment, the ADC comprises one, two, three, or four frameworks of the VL region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422). In an embodiment, the ADC comprises one or more (e.g., two, three, or four) frameworks of the VH region and/or one or more (e.g., two, three, or four) frameworks of the VL region 3820, 3821, 3826, 4221, 4226, 4320, 4321, 4322, 4326, 4421, 4520, 4521, 4526, 3522, 3621, 3822, 3825, or 4422).

In an embodiment, the ADC comprises a heavy chain variable region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422). In an embodiment, the ADC comprises a light chain variable region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422). In an embodiment, the ADC comprises a heavy chain variable region and a light chain variable region of an antibody molecule described in Table 1 or 2 (e.g., any of antibodies 3820, 3821, 3826, 4221, 4226, 4320, 4321, 4322, 4326, 4421, 4520, 4521, 4526, 3522, 3621, 3822, 3825, or 4422).

In an embodiment, the ADC comprises a heavy chain variable region having an amino acid sequence described in Table 1 or 2. In an embodiment, the ADC comprises a light chain variable region having an amino acid sequence described in Table 1 or 2. In an embodiment, the ADC comprises a heavy chain variable region having an amino acid sequence described in Table 1 or 2 and a light chain variable region having an amino acid sequence described in Table 1 or 2.

In an embodiment, the antibody molecule comprises a heavy chain variable region encoded by a nucleotide sequence described in Table 2. In an embodiment, the antibody molecule comprises a light chain variable region encoded by a nucleotide sequence described in Table 2. In an embodiment, the antibody molecule comprises a heavy chain variable region encoded by a nucleotide sequence described in Table 2 and a light chain variable region encoded by a nucleotide sequence described in Table 2.

In an embodiment, the ADC comprises a heavy chain constant region. In an embodiment, the ADC comprises a light chain constant region. In an embodiment, the ADC comprises a heavy chain constant region and a light chain constant region. In an embodiment, the ADC comprises a heavy chain constant region, a light chain constant region, and heavy and light chain variable regions of an antibody molecule described in Table 1 or 2. In certain embodiments, the ADC comprises a heavy chain constant region, a light chain constant region, and variable regions that comprise one, two, three, four, five, or six CDRs of antibody molecule described in Table 1 or 2.

In an embodiment, the ADC comprises one, two, or all of the heavy chain constant region sequences (e.g., CH1, CH2, or CH3) listed in Table 7. In an embodiment, the ADC comprises all of the CH1, CH2, and CH3 sequences listed in Table 7. In an embodiment, the ADC further comprises the heavy chain constant hinge region sequence list in Table 7. In an embodiment, the ADC comprises the light chain constant region sequence (e.g., CL) listed in Table 8. In an embodiment, the ADC further comprises the light chain constant hinge region sequence list in Table 8.

In an embodiment, the ADC comprises one, two, or all of the heavy chain constant region sequences (e.g., CH1, CH2, or CH3) listed in Table 7 and the light chain constant region sequence (e.g., CL) listed in Table 8. In an embodiment, the ADC comprises all of the CH1, CH2, and CH3 sequences listed in Table 7 and the light chain constant hinge region sequence list in Table 8. In an embodiment, the ADC further comprises the heavy chain constant hinge region sequence list in Table 7 and/or the light chain constant hinge region sequence list in Table 8.

In an embodiment, the ADC comprises a heavy chain comprising an amino acid sequence described in Table 6 or 8. In an embodiment, the ADC comprises a light chain comprising an amino acid sequence described in Table 6 or 7. In an embodiment, the ADC comprises a heavy chain comprising an amino acid sequence described in Table 6 or 8 and a light chain comprising an amino acid sequence described in Table 6 or 7.

In an embodiment, the non-antibody molecule comprises a cytotoxic agent (e.g., any cytotoxic agent that is active against a cancer). In an embodiment, the cytotoxic agent is chosen from a tubulin polymerase inhibitor (e.g., an auristatin), an agent associated with tubulin depolymerization (e.g., a maytansine), an agent associated with DNA cleavage (e.g., a calicheamicin), a DNA minor groove alkylating agent (e.g., a duocarymycin), a DNA minor groove cross-linker (e.g., a PBD dimers), or an RNA polymerase II inhibitor (e.g., α-amanitin).

In an embodiment, the cytotoxic agent is α-amanitin. α-amanitin is a bicyclic octapeptide which belongs to a large group of protoplasmic mushroom toxins known as amatoxins. α-Amanitin binds to the bridging helix of RNA polymerase II inhibiting the translocation of RNA and DNA needed to empty the site for the next round of synthesis, thereby reducing the rate of transcription. α-amanitin and its use in ADCs are described, e.g., in Moldenhauer et al. *J Natl Cancer Inst.* 2012; 104(8): 622-634. The structure of α-amanitin is as follows:

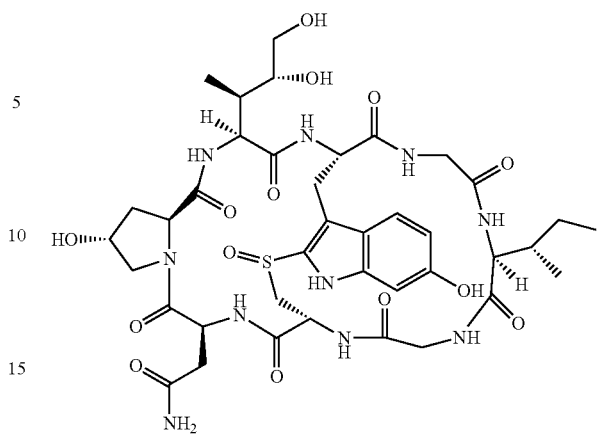

In an embodiment, the cytotoxic agent is a cryptophycin analog. The cryptophycins are a group of cyanobacterial depsipeptides with a remarkable biological activity against multi-drug-resistant (MDR) cancer cells. Cryptophycins deplete microtubules through interaction with tubulin, thereby preventing cell division. They are capable of inducing apoptosis, possibly through other mechanisms in addition to that mediated by microtubule inhibition. Cryptophycin, analogues, and their uses in ADCs are described, e.g., in Shih & Teicher. *Curr Pharm Des.* 2001; 7(13): 1259-1276; Eggen & Georg. *Med Res Rev.* 2002; 22(2): 85-101. The structure of a cryptophycin analog is as follows:

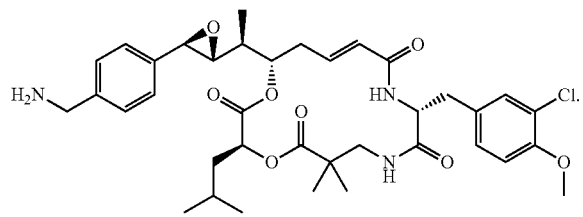 [SMILES: COc1ccc(C[C@H]2NC(=O)/C=C/C[C@@H]([C@H](C)[C@H]3O[C@@H]3c3ccc(CN)cc3)OC(=O)[C@H](CC(C)C)OC(=O)C(C)(C)CNC2=O)cc1Cl]

In an embodiment, the cytotoxic agent is calicheamicin (also known as LL-E33288). Calicheamicin contacts DNA and causes the Bergman cyclization, which results in cleaving the DNA and thus destroying cells. Calicheamicin and its use in ADCs is described, e.g., in Maiese et al. *J Antibiot (Tokyo).* 1989; 42(4): 558-563; Watanabe et al. *Chem Biol.* 2002; 9(2): 245-251; Ricart & Tolcher. *Nat Clin Pract Oncol.* 2007; 4: 245-255. The structure of calicheamicin is as follows.

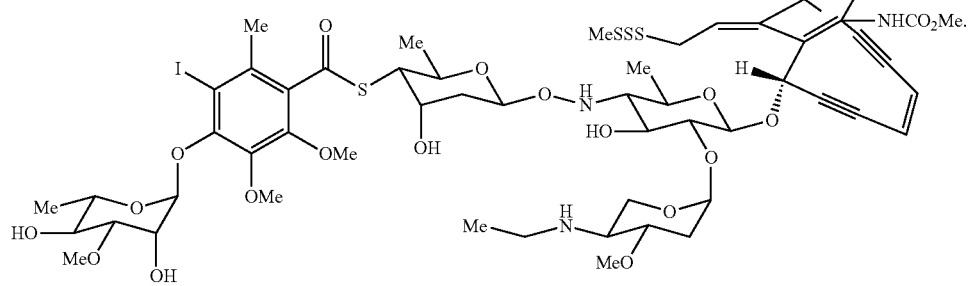

In an embodiment, the cytotoxic agent is centanamycin. Centanamycin is also known as ML-970, AS-I-145, NSC 716970, or N-[4-Amino-1-(2-chloroethyl)-2-naphthyl]-5,6,7-trimethoxy-1H-indole-2-carboxamide). Centanamycin binds the A-T-rich DNA minor groove and alkylates DNA. Centanamycin and its use in ADCs is described, e.g., in Rayburn et al. *Cancer Chemother Pharmacol.* 2012; 69(6): 1423-31.

In an embodiment, the cytotoxic agent is a dolastatin. In an embodiment, the dolastatin is dolastatin 10 or dolastatin 15. Dolastatins noncompetitively inhibit binding of vincristine to tubulin at the *vinca*/peptide region). Analogues of dolastatins include, e.g., symplostatin 1, symplostatin 3, and auristatin. Dolastatins, analogues, and their uses are described, e.g., in Amador et al. *Annals of Oncology.* 2003; 14: 1607-1615; Kijjoa & Sawangwong. *Mar Drugs.* 2004; 2(2): 73-82; Luesch et al. *J Nat Prod.* 2001; 64(7): 907-910; Luesch et al. *J Nat Prod.* 2002; 65(1): 16-20. The structure of dolastatin 10 is as follows:

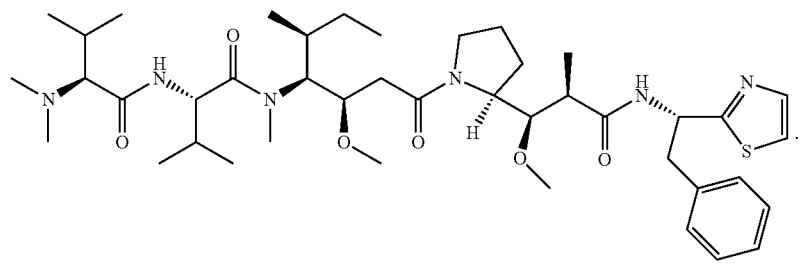 [SMILES: CC[C@H](C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@H](C(C)C)N(C)C)C(C)C]

The structure of dolastatin 15 is as follows:

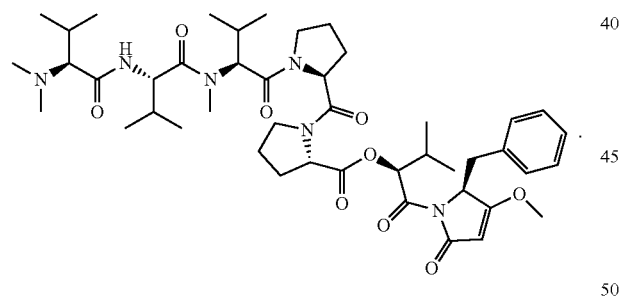

In an embodiment, the cytotoxic agent is a duocarmycin analogue. Duocarmycin analogues are DNA minor groove, AT-sequence selective, and adenine-N3 alkylating agents. Duocarmycin, analogues, and their uses in ADCs are described, e.g., in Tietze & Krewer. *Chem Biol Drug Des.* 2009; 74(3):205-211; Cacciari et al. *Expert Opinion on Therapeutic Patients.* 2000; 10 (12): 1853-1871; Tercel et al. *Angew Chem Int Ed Engl.* 2013; 52(21): 5442-5446. Exemplary duocarmycin and analogues include, e.g., duocarmycin A, duocarmycin B1, duocarmycin B2, duocarmycin C1, duocarmycin C2, duocarmycin D, duocarmycin SA, and CC-1065. The structure of duocarymycin A is as follows:

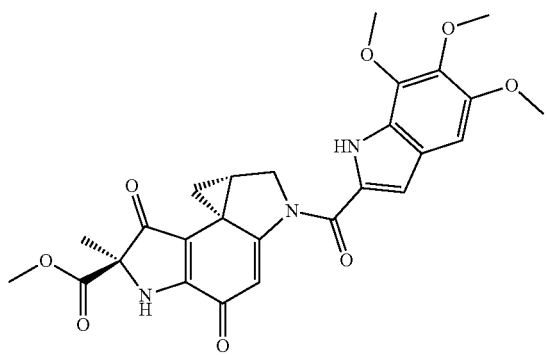

In an embodiment, the cytotoxic agent is maytansine. Maytansine, a benzoansamacrolide, is a highly potent microtubule-targeted compound that induces mitotic arrest and kills tumor cells at subnanomolar concentrations. Maytansine and its analogs (maytansinoids DM1 and DM4) are potent microtubule-targeted compounds that inhibit proliferation of cells at mitosis. Maytansine is described, e.g., in Lopus et al. *Mol Cancer Ther.* 2010; 9(10): 2689-2699; Widdison et al. *J Med Chem.* 2006; 49(14): 4392-4408; Liu et al. *J Mass Spectrom.* 2005; 40(3): 389-399; Tassone et al. *Cancer Res.* 2004; 64(13): 4629-4636; Sawada et al. *Bioconjug Chem.* 1993; 4(4):284-289. The structure of maytansine is as follows:

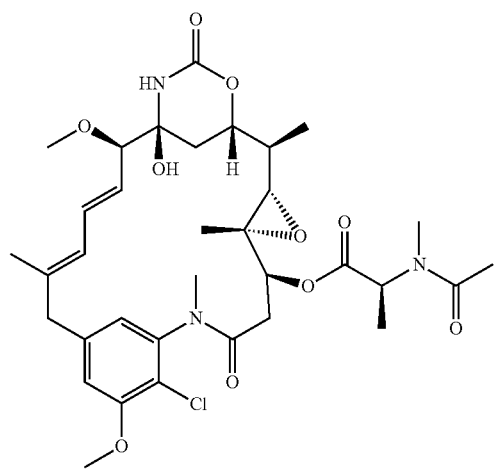

In an embodiment, the cytotoxic agent is monomethyl auristatin E (MMAE, vedotin). MMAE is a highly potent antimitotic agent that inhibits cell division by blocking the polymerization of tubulin. MMAE and its use in ADCs are described, e.g., in Francisco et al. *Blood.* 2003; 102(4):1458-1465; Junutula et al. *Nat Biotechnol.* 2008; 26(8):925-932; Asundi et al. *Clin Cancer Res.* 2011; 17(5): 965-975; Younes et al. *J Clin Oncol.* 2012; 30(18):2183-2189; Pettit et al. *Anticancer Drug Des.* 1995; 10(7): 529-544; Doronina et al. *Nat Biotechnol.* 2003; 21(7): 778-784. The structure of MMAE is as follows:

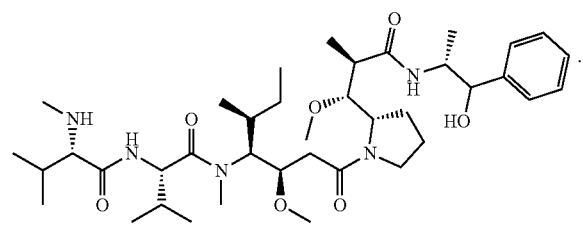 [SMILES: CC[C@H](C)[C@@H]([C@@H](CC(=O)N1CCC[C@H]1[C@H](OC)[C@@H](C)C(=O)N[C@H](C)C(O)c1ccccc1)OC)N(C)C(=O)[C@@H](NC(=O)[C@@H](NC)C(C)C)C(C)C]

In an embodiment, the cytotoxic agent is monomethyl auristatin F (MMAF). MMAF is an antitubulin agent that inhibits cell division by blocking the polymerization of tubulin. It is an auristatin derivative with a charged C-terminal phenylalanine that attenuates its cytotoxic activity compared to its uncharged counterpart, monomethyl auristatin E (MMAE). MMAF can induce potent antitumor effects when conjugated via protease cleavable linkers to a monoclonal antibody targeting internalizing, tumor-specific cell surface antigens. For example, the linker to the monoclonal antibody is stable in extracellular fluid, but can be cleaved by cathepsin once the conjugate has entered a tumor cell, thus activating the anti-mitotic mechanism. MMAF and its use in ADCs are described, e.g., in Smith et al. *Mol Cancer Ther.* 2006 5; 1474-1482; Doronina et al., *Bioconjug Chem.* 2006; 17(1):114-24; Oflazoglu et al. *Clin Cancer Res.* 2008; 14(19): 6171-6180; Nilsson et al. *Cancer.* 2010; 116(4 Suppl): 1033-1042. The structure of MMAF is as follows:

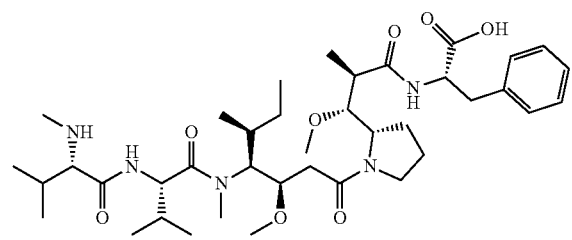

In an embodiment, the cytotoxic agent is a pyrrolobenzodiazepine (PBD). PBDs are a class of sequence-selective DNA minor-groove binding crosslinking agents. The mechanism of action of the PBDs is associated with their ability to form an adduct in the minor groove, thus interfering with DNA processing. Exemplary agents that belong to the pyrrolobenzodiazepine antibiotic group include, but are not limited to, anthramycin. abbeymycin, chicamycin, DC-81, mazethramycin, neothramycin A, neothramycin B, porothramycin, prothracarcin, sibanomicin (DC-102), sibiromycin, and tomamycin. PBDs and their use in ADCs are described, e.g., in Antonow & Thurston D E. *Chem Rev.* 2011; 111: 2815-2864; Cipolla et al. *Anticancer Agents Med Chem.* 2009; 9: 1-31; Gerratana. *Med Res Rev.* 2012; 32: 254-293; Li et al. *Appl Environ Microbiol.* 2009; 75(9): 2869-2878; Rahman et al. Org. Biomol. Chem. 2011; 9: 1632-1641; Saunders et al. Sci Transl Med. 2015; 7(302): 302ra136; Hu et al. *Chem Biol.* 2007; 14(6):691-701. The structure of PBD is as follows:

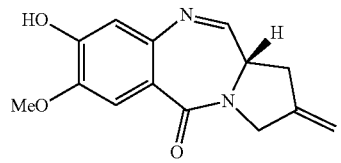

In an embodiment, the ADC further comprises a linker, e.g., a linker that couples an antibody molecule to a non-antibody moiety. In an embodiment, the linker comprises a hydrazone, a disulfide bond, a peptide, or a thioether bond.

In an embodiment, the linker is a non-cleavable linker. Exemplary non-cleavable linkers include, e.g., a non-cleavable thioether linker (e.g., N-succinimidyl-4-(N-maleimidomethyl)cyclohexane-1-carboxylate (SMCC)) or a non-cleavable maleimidocaproyl linker.

In an embodiment, the liner is a cleavable linker. In an embodiment, the cleavable linker is a chemically labile linker, e.g., an acid-cleavable linker (e.g., an acid-cleavable hydrazone) or a reducible linker (e.g., a disulfide linker). In an embodiment, the cleavable linker is an enzyme cleavable linker, e.g., a peptide-based linker (e.g., a dipeptide linker (e.g., a valine-citrulline (Val-Cit) linker or a phenylalanine-lysine (Phe-Lys) dipeptide linker)) or a β-glucuronide linker. Other linkers and their use in ADCs are described, e.g., in Lu et al. *Int J Mol Sci.* 2016; 17(4): 561, the content of which is incorporated by reference in its entirety.

In an embodiment, the linker is a poly(ethylene glycol) (PEG) linker.

Animal Models

The humanized anti-CD138 antibody molecules described herein can be evaluated in vivo, e.g., using various animal models. For example, an animal model can be used to test the efficacy of an antibody molecule described herein in inhibiting CD138 and/or in treating or preventing a disorder described herein, e.g., a myeloma (e.g., multiple myeloma) Animal models can also be used, e.g., to investigate for side effects, measure concentrations of antibody molecules in situ, demonstrate correlations between a CD138 function and a disorder described herein, e.g., a myeloma (e.g., multiple myeloma). Exemplary types of animals that can be used to evaluate the antibody molecules described herein include, but are not limited to, mice, rats, rabbits, guinea pigs, and monkeys.

Exemplary animal models for myelomas (e.g., multiple myeloma) that can be used for evaluating an antibody molecule described herein include, but are not limited to, immunocompetent murine models, e.g., STMM (5T Radl), 5T2, 5T33, and STGMA models (Radl et al. *Am J Pathol.* 1988; 132: 593-597); immunocompromised murine models, e.g., RAG-2 model (Fowler et al. *Dis Model Mech.* 2009; 2: 604-611), xenograft murine myeloma models, e.g., SCID and NOD/SCID models (Huang et al. *Cancer Res.* 1993; 53: 1392-1396; Tsunenari et al. *Blood.* 1997; 90: 2437-2444; Torcia et al. *Exp Hematol.* 1996; 24: 868-874; Hjorth-Hansen et al. *J Bone Miner Res.* 1999; 14: 256-263); SCID-Hu and SCID-Rab models (Urashima et al. *Blood.* 1997; 90: 754-765; Yaccoby et al. *Blood.* 1998; 92: 2908-2913; Yata & Yaccoby. *Leukemia.* 2004; 18: 1891-1897); genetically engineered models, e.g., IL-6- and MYC-driven models (Kovalchuk et al. *Proc Natl Acad Sci USA.* 2002; 99: 1509-1514; Adams et al. *Nature.* 1985; 318: 533-538; Chesi et al. *Blood.* 2012; 120: 376-385); Eμ-xbp-1s model (Carrasco et al. *Cancer Cell.* 2007; 11(4):349-360); L-GP130 model (Dechow et al. *J Clin Invest.* 2014; 124(12): 5263-5274).

Various murine and human myeloma cell lines and primary human myeloma cells can be used in preclinical in vivo models. Exemplary murine and human myeloma cell lines that can be used for engraftment include, but are not limited to, 5T myeloma cells (Radl et al. *Am J Pathol.* 1988; 132: 593-597), human lymphoblastoid ARH-77 cells (Huang et al. *Cancer Res.* 1993; 53(6):1392-1396), the human JJN3 myeloma cell line (Hjorth-Hansen et al. *J Bone Miner Res.* 1999; 14(2): 256-263), and IL-6-dependent myeloma cell lines (Tsunenari et al. *Blood.* 1997; 90(6): 2437-2444). A desired cell line can be selected based on, e.g., the pace of tumor engraftment, characteristics of the particular tumor type (e.g., propensity to develop lytic bone lesions), or the type of monoclonal protein that is produced.

Other animal models for myelomas (e.g., multiple myeloma) are described, e.g., in Lwin et al. *Bonekey Rep.* 2016; 5: 772; Libouban et al. *Morphologic.* 2015; 99(325): 63-72; Campbell et al. *Curr Protoc Pharmacol.* 2008; Chapter 14: Unit 14.9.

Pharmaceutical Compositions and Kits

In an aspect, this disclosure provides compositions, e.g., pharmaceutically acceptable compositions, which include a humanized anti-CD138 antibody molecule described herein or an ADC comprising a humanized anti-CD138 antibody molecule described herein, formulated together with a pharmaceutically acceptable carrier.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion). In certain embodiments, less than about 5%, e.g., less than about 4%, 3%, 2%, or 1% of the antibody molecules in the pharmaceutical composition are present as aggregates. In other embodiments, at least about 95%, e.g., at least about 96%, 97%, 98%, 98.5%, 99%, 99.5%, 99.8%, or more of the antibody molecules in the pharmaceutical composition are present as monomers. In some embodiments, the level of aggregates or monomers is determined by chromatography, e.g., high performance size exclusion chromatography (HP-SEC).

The compositions set out herein may be in a variety of forms. These include, for example, liquid, semi-solid and solid dosage forms, such as liquid solutions (e.g., injectable and infusible solutions), dispersions or suspensions, liposomes, and suppositories. A suitable form depends on the intended mode of administration and therapeutic application. Typical suitable compositions are in the form of injectable or infusible solutions. One suitable mode of administration is parenteral (e.g., intravenous, subcutaneous, intraperitoneal, intramuscular). In some embodiments, the antibody molecule is administered by intravenous infusion or injection. In certain embodiments, the antibody is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high antibody concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antibody molecules described herein can be administered by a variety of methods. Several are known in the art, and for many therapeutic, prophylactic, or diagnostic applications, an appropriate route/mode of administration is intravenous injection or infusion. For example, the antibody molecules can be administered by intravenous infusion at a rate of less than 10 mg/min; preferably less than or equal to 5 mg/min to reach a dose of about 1 to 100 mg/m$^2$, preferably about 5 to 50 mg/m$^2$, about 7 to 25 mg/m$^2$ and more preferably, about 10 mg/m$^2$. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems,* J. R. Robinson, ed., Marcel Dekker, Inc., New York, 1978.

In certain embodiments, an antibody molecule can be orally administered, for example, with an inert diluent or an assimilable edible carrier. The antibody molecule (and other ingredients, if desired) may also be enclosed in a hard or soft shell gelatin capsule, compressed into tablets, or incorporated directly into the subject's diet. For oral therapeutic administration, the antibody molecule may be incorporated with excipients and used in the form of ingestible tablets, buccal tablets, troches, capsules, elixirs, suspensions, syrups, wafers, and the like. To administer an antibody molecule by other than parenteral administration, it may be necessary to coat the compound with, or co-administer the compound with, a material to prevent its inactivation. Therapeutic, prophylactic, or diagnostic compositions can also be administered with medical devices, and several are known in the art.

Dosage regimens are adjusted to provide the desired response (e.g., a therapeutic, prophylactic, or diagnostic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms are dictated by and directly dependent on (a) the unique characteristics of the antibody molecule and the particular therapeutic, prophylactic, or diagnostic effect to be achieved, and (b) the limitations inherent in the art of compounding such an antibody molecule for the treatment of sensitivity in individuals.

An exemplary, non-limiting range for a therapeutically, prophylactically, or diagnostically effective amount of an antibody molecule is about 0.1-50 mg/kg body weight of a subject, e.g., about 0.1-30 mg/kg, e.g., about 1-30, 1-15, 1-10, 1-5, 5-10, or 1-3 mg/kg, e.g., about 1, 2, 3, 4, 5, 6, 7, 8, 9, 10, 15, 20, 30, 40, or 50 mg/kg. The antibody molecule can be administered by intravenous infusion at a rate of less than 10 mg/min, e.g., less than or equal to 5 mg/min to reach a dose of about 1 to 100 mg/m$^2$, e.g., about 5 to 50 mg/m$^2$, about 7 to 25 mg/m$^2$, e.g., about 10 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed compositions.

The pharmaceutical compositions herein may include a "therapeutically effective amount," "prophylactically effective amount," or "diagnostically effectively amount" of an antibody molecule described herein.

A "therapeutically effective amount" refers to an amount effective, at dosages and for periods of time necessary, to achieve the desired therapeutic result. A therapeutically effective amount of the antibody molecule may vary according to factors such as the disease state, age, sex, and weight of the individual, and the ability of the antibody or antibody portion to elicit a desired response in the individual. A therapeutically effective amount is also one in which any toxic or detrimental effect of the antibody molecule is outweighed by the therapeutically beneficial effects. A "therapeutically effective dosage" typically inhibits a measurable parameter by at least about 20%, e.g., by at least about 40%, by at least about 60%, or by at least about 80% relative to untreated subjects. The measurable parameter may be, e.g., hematuria, colored urine, foamy urine, pain, swelling (edema) in the hands and feet, or high blood pressure. The ability of an antibody molecule to inhibit a measurable parameter can be evaluated in an animal model system predictive of efficacy in treating or preventing a myeloma. Alternatively, this property of a composition can be evaluated by examining the ability of the antibody molecule to inhibit CD138, e.g., by an in vitro assay.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

A "diagnostically effective amount" refers to an amount effective, at dosages and for periods of time necessary, to achieve the desired diagnostic result. Typically, a diagnostically effective amount is one in which a disorder, e.g., a disorder described herein, e.g., A myeloma, can be diagnosed in vitro, ex vivo, or in vivo.

Also within this disclosure is a kit that comprises an antibody molecule, described herein. The kit can include one or more other elements including: instructions for use; other reagents, e.g., a label, a therapeutic agent, or an agent useful for chelating, or otherwise coupling, an antibody molecule to a label or therapeutic agent, or a radioprotective composition; devices or other materials for preparing the antibody molecule for administration; pharmaceutically acceptable carriers; and devices or other materials for administration to a subject.

Nucleic Acids

The present disclosure also features nucleic acids comprising nucleotide sequences that encode the humanized anti-CD138 antibody molecules (e.g., heavy and light chain variable regions and CDRs of the antibody molecules), as described herein.

For example, the present disclosure features a first and second nucleic acid encoding heavy and light chain variable regions, respectively, of an antibody molecule chosen from one or more of the antibody molecules disclosed herein, e.g., an antibody molecule of Table 1, 2, or 6, or a portion of an antibody molecule, e.g., the variable regions of Table 1 or 2. The nucleic acid can comprise a nucleotide sequence encoding any one of the amino acid sequences in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein).

In certain embodiments, the nucleic acid can comprise a nucleotide sequence encoding at least one, two, or three CDRs from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, or three CDRs from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding at least one, two, three, four, five, or six CDRs from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding a heavy chain variable region and a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding a heavy chain having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding a light chain having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In some embodiments, the nucleic acid can comprise a nucleotide sequence encoding a heavy chain and a light chain having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs from a heavy chain variable region having the nucleotide sequence as set forth in Table 2, a sequence substantially homologous thereto (e.g., a sequence at least about 85%, 90%, 95%, 99% or more identical thereto, and/or capable of hybridizing under the stringency conditions described herein). In some embodiments, the nucleic acid can comprise a nucleotide sequence encoding at least one, two, or three CDRs from a light chain variable region having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein). In certain embodiments, the nucleic acid can comprise a nucleotide sequence encoding at least one, two, three, four, five, or six CDRs from heavy and light chain variable regions having the nucleotide sequence as set forth in Table 2, or a sequence substantially homologous thereto (e.g., a sequence at least about 85%, 90%, 95%, 99% or more identical thereto, and/or capable of hybridizing under the stringency conditions described herein).

In certain embodiments, the nucleic acid comprises a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). In some embodiments, the nucleic acid comprises a portion of a nucleotide sequence as set forth in Table 2 or a sequence substantially homologous thereto (e.g., a sequence at least about 85%, 90%, 95%, 99% or more identical thereto, and/or capable of hybridizing under the stringency conditions described herein). The portion may encode, for example, a variable region (e.g., VH or VL); one, two, or three or more CDRs; or one, two, three, or four or more framework regions.

The nucleic acids disclosed herein include deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

In an aspect, the application features host cells and vectors containing the nucleic acids described herein. The nucleic acids may be present in a single vector or separate vectors present in the same host cell or separate host cell, as described in more detail below.

Vectors

Further provided herein are vectors that comprise nucleotide sequences encoding an anti-CD138 antibody molecule described herein.

In an embodiment, the vector comprises a nucleotide sequence encoding an antibody molecule described herein, e.g., as described in Table 1, 2, or 6. In another embodiment, the vector comprises a nucleotide sequence described herein, e.g., in Table 2. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

The present disclosure also provides cells (e.g., host cells) comprising a nucleic acid encoding an anti-CD138 antibody molecule as described herein. For example, the host cells may comprise a nucleic acid molecule having a nucleotide sequence described in Table 2, a sequence substantially homologous thereto (e.g., a sequence at least about 85%, 90%, 95%, 99% or more identical thereto, and/or capable of hybridizing under the stringency conditions described herein), or a portion of one of said nucleic acids. Additionally, the host cells may comprise a nucleic acid molecule encoding an amino acid sequence of Table 2, a sequence substantially homologous thereto (e.g., a sequence at least about 80%, 85%, 90%, 95%, 99% or more identical thereto), or a portion of one of said sequences.

In some embodiments, the host cells are genetically engineered to comprise nucleic acids encoding the antibody molecule described herein.

In certain embodiments, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells. In an embodiment, the cell (e.g., host cell) is an isolated cell.

In an embodiment, the humanized antibody molecule is expressed in a cell at a level that is at least 1, 2, 3, 4, 5, 6, 7, 8, 9, or 10-fold higher than a related non-humanized antibody molecule. In an embodiment, the cell is a CHO cell. In an embodiment, the humanized antibody molecule is expressed at about 35 mg/L or more, e.g., about 40 mg/L, 50 mg/L, 60 mg/L, 70 mg/L, 80 mg/L, 90 mg/L, 100 mg/L, 110 mg/L, 120 mg/L, 130 mg/L, 140 mg/L, 150 mg/L, 160 mg/L, 170 mg/L, 180 mg/L, 190 mg/L, 200 mg/L, or more.

Uses of Antibody Molecules

The humanized anti-CD138 antibody molecules disclosed herein, as well as the pharmaceutical compositions disclosed herein, have in vitro, ex vivo, and in vivo therapeutic, prophylactic, and/or diagnostic utilities.

In an embodiment, the antibody molecule causes (e.g., induces or increases) an effector function on a cell expressing CD138. For example, the antibody molecules can be administered to a subject, e.g., a human subject, to cause an antibody-dependent cellular cytotoxicity activity on a diseased cell (e.g., a cancer cell or a precancerous cell) that it binds to. In an embodiment, the antibody molecule causes a complement-dependent cytotoxicity activity on a cell expressing CD138. In an embodiment, the antibody molecule reduces (e.g., inhibits, blocks, or neutralizes) one or more biological activities of a cell expressing CD138. In an embodiment, the antibody molecule inhibits the action of a protease on a membrane-bound CD138, e.g., to reduce shedding of CD138. For example, these antibodies molecules can be administered to cells in culture, in vitro or ex vivo, or to a subject, e.g., a human subject, e.g., in vivo, to reduce (e.g., inhibits, blocks, or neutralizes) one or more biological activities of the cell.

Accordingly, in an aspect, the disclosure provides a method of treating, preventing, or diagnosing a disorder, e.g., a disorder described herein (e.g., multiple myeloma), in a subject, comprising administering to the subject a humanized anti-CD138 antibody molecule described herein, such that the disorder is treated, prevented, or diagnosed. For example, the disclosure provides a method comprising contacting the humanized antibody molecule described herein with cells in culture, e.g. in vitro or ex vivo, or administering the antibody molecule described herein to a subject, e.g., in vivo, to treat, prevent, or diagnose a disorder, e.g., a disorder associated with CD138 (e.g., multiple myeloma).

As used herein, the term "subject" is intended to include human and non-human animals. In some embodiments, the subject is a human subject, e.g., a human patient having a disorder described herein (e.g., multiple myeloma), or at risk of having a disorder described herein (e.g., multiple myeloma). The term "non-human animals" includes mammals and non-mammals, such as non-human primates. In some embodiments, the subject is a human. The methods and compositions described herein are suitable for treating human patients a disorder described herein (e.g., multiple myeloma). Patients having a disorder described herein include, e.g., those who have developed a disorder described herein but are (at least temporarily) asymptomatic, patients who have exhibited a symptom of a disorder described herein, and patients having a disorder related to or associated with a disorder described herein.

Methods of Treating or Preventing Disorders

The humanized antibody molecules described herein can be used to treat or prevent disorders associated with CD138 or symptoms thereof.

Exemplary disorders or conditions that can be associated with CD138 include, but are not limited to cancer (e.g., hematological cancer (e.g., a myeloma, e.g., multiple myeloma) or solid tumors, and precancerous conditions (e.g., smoldering myeloma or monoclonal gammopathy of undetermined significance (MGUS)). In an embodiment, the disorder is associated with aberrant expression of CD138. In an embodiment, the antibody molecule is used to treat a subject having a disorder described herein, or is at risk of developing a disorder described herein. In an embodiment, the antibody molecule is used to reduce progression of the disorder, e.g., to reduce progression of a precancerous condition to cancer.

In an embodiment, the humanized antibody molecule has an increased efficacy for treating a disorder described herein, compared to a reference antibody molecule, e.g., a related non-humanized antibody molecule, e.g., as determined by a method described herein. In an embodiment, the humanized antibody molecule results in at least 10%, 20%, 30%, 40%, 50%, 60%, 70%, 80%, or 90% lower tumor burden, e.g., within a predetermined period of time. In an embodiment, the humanized antibody molecule results in at least 10%, 20%, 30%, 40%, 50%, 60%, 70%, 80%, or 90%, or at least 1, 2, 3, 4, or 5-fold greater overall survival, e.g., the length of time from the date of diagnosis or the start of treatment. In an embodiment, the disorder is a cancer, e.g., a multiple myeloma. In an embodiment, the tumor burden is determined by imaging. In an embodiment, the tumor burden is determined in a tissue, e.g., a skeletal tissue.

The antibody molecules described herein are typically administered at a frequency that keeps a therapeutically effective level of antibody molecules in the patient's system until the patient recovers. For example, the antibody molecules may be administered at a frequency that achieves a serum concentration sufficient for at least about 1, 2, 5, 10, 20, 30, or 40 antibody molecules to bind each CD138 molecule. In an embodiment, the antibody molecules are administered every 1, 2, 3, 4, 5, 6, or 7 days, every 1, 2, 3, 4, 5, or 6 weeks, or every 1, 2, 3, 4, 5, or 6 months.

Methods of administering various antibody molecules are known in the art and are described below. Suitable dosages of the antibody molecules used will depend on the age and weight of the subject and the particular drug used.

In an embodiment, the antibody molecule is administered to the subject (e.g., a human subject) intravenously. In an embodiment, the antibody molecule is administered to the subject at a dose between 0.1 mg/kg and 50 mg/kg, e.g., between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg. In an embodiment, the antibody molecule is administered to the subject at a fixed dose between 10 mg and 1000 mg, e.g., between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg. In an embodiment, the antibody molecule is administered once a week, twice a week, once every two weeks, once every three weeks, once every four weeks, once every eight weeks, once a month, once every two months, or once every three months. In an embodiment, the antibody molecule is administered between 0.5 mg/kg and 3 mg/kg or between 50 mg and 150 mg, once a week, twice a week, once every two weeks, or once every four weeks.

The antibody molecules can be used by themselves or conjugated to a second agent, e.g., a bacterial agent, toxin, or protein, e.g., a second anti-CD138 antibody molecule. This method includes: administering the antibody molecule, alone or conjugated to a second agent, to a subject requiring such treatment. The antibody molecules can be used to deliver a variety of therapeutic agents, e.g., a toxin, or mixtures thereof.

Cancer

The humanized anti-CD138 antibody molecules described herein can be used to treat or prevent a cancer or a precancerous condition.

CD138 expression is dysregulated in many cancers, e.g., prostate cancer, breast cancer, pancreatic cancer, ovarian cancer, colon cancer, lung cancer, and myeloma (Kiviniemi et al. *APMIS*. 2004; 112(2): 89-97; Lendorf et al. *J Histochem Cytochem*. 2011; 59(6): 615-629; Juuti et al. *Oncology*. 2005; 68(2-3): 97-106; Kusumoto et al. *Oncol Rep*. 2010; 23(4): 917-25; Hashimoto et al. *BMC Cancer*. 2008; 8: 185; Joensuu et al. *Cancer Res*. 2002; 62(18):5210-5217; Seidel et al. *Blood*. 2000; 95(2): 388-392). CD138 can modulate several key processes of tumorigenesis, e.g., cancer cell proliferation, apoptosis, and angiogenesis (Teng et al. *Matrix Biol*. 2012; 31(1): 3-16). The molecular and clinical profiles of CD138 in solid and hematological cancers are described, e.g., in Akl et al. *Oncotarget*. 2015; 6(30):28693-28715.

CD138 can affect tumorigenesis by regulating mediators of tumor cell survival and proliferation (e.g., oncogenes or growth factors). For example, Sdc1−/− mice were protected against Wnt-1 induced mammary tumorigenesis (Alexander et al. *Nat Genet*. 2000; 25(3): 329-32). Hepatocyte growth factor (HGF) binds to CD138 on myeloma cells (Derksen et al. *Blood*. 2002; 99(4): 1405-1410). The interaction of HGF with CD138 potentiated Met signaling, which is involved in the growth, survival, and spread of a number of cancers (Birchmeier et al. *Nat Rev Mol Cell Biol*. 2003; 4(12): 915-925; Derksen et al. *Blood*. 2002; 99(4):1405-1410). CD138 expression is elevated in the reactive stroma of breast carcinoma tissue (Stanley et al. *Am J Clin Pathol*. 1999; 112(3): 377-383). MEFs expressing CD138 enhanced the growth of breast cancer cell lines in co-culture and promoted breast carcinoma progression in vivo (Maeda et al. *Cancer Res*. 2004; 64(2):612-621).

CD138 can regulate tumor cell apoptosis. Knock-down of CD138 in myeloma cells induced growth arrest and apoptosis (Khotskaya et al. *J Biol Chem*. 2009; 284(38): 26085-26095). Recombinant CD138 ectodomains induced apoptosis in MCF-7 breast cancer cells and cultured human prostate cancer cells (Sun et al. *Cancer Res*. 2008; 68(8): 2912-2919; Hu et al. *Neoplasia*. 2010; 12(10): 826-836).

CD138 can bind to pro-angiogenic factors (e.g., FGF-2 and VEGF) and present these factors to their respective receptors on endothelial cells to initiate endothelial invasion and budding (Teng et al. *Matrix Biol*. 2012; 31(1): 3-16). Increased CD138 expression in stromal fibroblasts was observed in several carcinomas, such as those of the breast, stomach, and thyroid (Stanley et al. *Am J Clin Pathol*. 1999; 112(3): 377-383; Wiksten et al. *Int J Cancer*. 2001; 95(1): 1-6; Barbareschi et al. *Cancer*. 2003; 98(3): 474-483). In a xenograft model of human breast carcinoma cells and CD138-transfected fibroblasts implantation into mice, stromal CD138 expression was associated with significantly elevated microvessel density and larger vessel area (Maeda et al. *Oncogene*. 2006; 25(9): 1408-1412).

Exemplary cancers that can be treated or prevented by the antibody molecules described herein include, but are not limited to, acute lymphoblastic leukemia (ALL), acute myeloid leukemia (AML), adrenocortical carcinoma, Kaposi sarcoma, an AIDS-related lymphoma, primary central nervous system (CNS) lymphoma, anal cancer, appendix cancer, astrocytoma, atypical teratoid/rhabdoid tumor, basal cell carcinoma, bile duct cancer, bladder cancer, bone cancer (e.g., Ewing sarcoma or osteosarcoma and malignant fibrous histiocytoma), brain tumor (e.g., astrocytomas, brain stem glioma, central nervous system atypical teratoid/rhabdoid tumor, central nervous system embryonal tumor, central nervous system germ cell tumor, craniopharyngioma, or ependymoma), breast cancer, bronchial tumor, Burkitt lymphoma, carcinoid tumor (e.g., gastrointestinal carcinoid tumor), cardiac (heart) tumor, embryonal tumor, germ cell tumor, lymphoma, cervical cancer, cholangiocarcinoma, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma in situ (DCIS), endometrial cancer, ependymoma, esophageal cancer, esthesioneuroblastoma, Ewing sarcoma, extracranial germ cell tumor, extragonadal germ cell tumor, eye cancer (e.g., intraocular melanoma or retinoblastoma), fallopian tube cancer, fibrous histiocytoma of bone, osteosarcoma, gallbladder cancer, gastric (stomach) cancer, gastrointestinal carcinoid tumor, gastrointestinal stromal tumors (GIST), germ cell tumor (e.g., central nervous system tumor, extracranial tumor, extragonadal tumor, ovarian cancer, or testicular cancer), gestational trophoblastic disease, glioma, hairy cell leukemia, head and neck cancer, hepatocellular (liver) cancer, Hodgkin lymphoma, hypopharyngeal cancer, intraocular melanoma, islet cell tumor, pancreatic neuroendocrine tumor, Kaposi sarcoma, kidney cancer (e.g., renal cell cancer or Wilms tumor), Langerhans cell histiocytosis (LCH), laryngeal cancer, leukemia (e.g., acute lymphoblastic leukemia (ALL), acute myeloid leukemia (AML), chronic lymphocytic leukemia (CLL), chronic myelogenous leukemia (CML), or hairy cell leukemia), lip and oral cavity cancer, liver cancer, lung cancer (e.g., non-small cell lung cancer (NSCLC) or small cell lung cancer), lymphoma (e.g., aids-related, Burkitt lymphoma, cutaneous T-cell lymphoma, Hodgkin lymphoma, non-Hodgkin lymphoma, or primary central nervous system (CNS) lymphoma), Waldenström macroglobulinemia, male breast cancer, malignant fibrous histiocytoma of bone and osteosarcoma, melanoma (e.g., intraocular (eye) melanoma), Merkel cell carcinoma, mesothelioma, metastatic squamous neck cancer, midline tract carcinoma, mouth cancer, multiple endocrine neoplasia syndrome, multiple myeloma/plasma cell neoplasm, mycosis fungoides, myelodysplastic syndrome, myelodysplastic/myeloproliferative neoplasm, chronic myeloproliferative neoplasm, nasal cavity and paranasal sinus cancer, nasopharyngeal cancer, neuroblastoma, oral cancer, lip and oral cavity cancer, oropharyngeal cancer, osteosarcoma and malignant fibrous histiocytoma of bone, ovarian cancer (e.g., epithelial ovarian cancer or germ cell ovarian tumor), pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, pleuropulmonary blastoma, peritoneal cancer, prostate cancer, rectal cancer, retinoblastoma, rhabdomyosarcoma, salivary gland cancer, sarcoma (e.g., Ewing sarcoma, Kaposi sarcoma, osteosarcoma, rhabdomyosarcoma, soft tissue sarcoma, or uterine sarcoma), Sezary syndrome, skin cancer (e.g., melanoma, Merkel cell carcinoma, or nonmelanoma skin cancer), small intestine cancer, squamous cell carcinoma, testicular cancer, throat cancer, thymoma and thymic carcinoma, thyroid cancer, transitional cell cancer of the renal pelvis and ureter, urethral cancer, endometrial uterine cancer, vaginal cancer, vulvar cancer, or a metastatic lesion thereof.

In an embodiment, the cancer is a hematological cancer, e.g., a myeloma, lymphoma, or leukemia. In an embodiment, the cancer is a myeloma. In an embodiment, the cancer is a multiple myeloma.

In another embodiment, the cancer is a solid tumor. In an embodiment, the cancer is a cervical cancer (e.g., a cervical squamous cell carcinoma or an endocervical adenocarcinoma), a uterine cancer (e.g., a uterine corpus endometrioid carcinoma), a brain cancer (e.g., a glioblastoma), a lung cancer (e.g., a lung squamous cell carcinoma), or a breast cancer (e.g., a breast invasive carcinoma).

In an embodiment, the cancer is chosen from a bladder cancer, a breast cancer, a cervical cancer, a colorectal cancer, an endometrial cancer, a gallbladder cancer, a gastric cancer, a glioma, a head and neck cancer, a laryngeal cancer, a liver cancer, a lung cancer, a mesothelioma, a nasopharyngeal cancer, an oral cancer, an ovarian cancer, a pancreatic cancer, a prostate cancer, or a thyroid cancer.

In an embodiment, the cancer is a bladder cancer. CD138 is expressed in bladder cancer (Kim & Park. *Hum Pathol.* 2014; 45: 1830-1838). In an embodiment, the bladder cancer is a urothelial carcinoma, a squamous cell carcinoma, or an adenocarcinoma. In an embodiment, the bladder cancer is a noninvasive, non-muscle-invasive, or muscle-invasive. The anti-CD138 antibody molecules described herein can be used alone or in combination with a second therapeutic agent, procedure, or modality to treat a bladder cancer. In an embodiment, the anti-CD138 antibody molecule is used in combination with a surgery (e.g., transurethral resection of bladder tumor (TURBT) or cystectomy), an intravesical therapy (e.g., an intravesical immunotherapy (e.g., *Bacillus* Calmette-Guerin (BCG) therapy) or an intravesical chemotherapy (e.g., mitomycin, valrubicin, docetaxel, thiotepa, or gemcitabine)), a chemotherapy (e.g., an intravesical chemotherapy or a systemic chemotherapy (e.g., cisplatin, fluorouracil (5-FU), mitomycin, gemcitabine, methotrexate, vinblastine, doxorubicin, carboplatin, paclitaxel, docetaxel, ifosfamide, or pemetrexed), a radiation therapy, or an immunotherapy (e.g., intravesical BCG, an immune checkpoint inhibitor (e.g., a PD-L1 inhibitor (e.g., atezolizumab, durvalumab, or avelumab) or a PD-1 inhibitor (e.g., nivolumab or pembrolizumab).

In an embodiment, the cancer is a breast cancer. CD138 is expressed in breast cancer (Akl et al. *Oncotarget.* 2015; 6(30):28693-28715; Barbareschi et al. *Cancer.* 2003; 98: 474-483; Lim et al. *Singapore Med J.* 2014; 55: 468-472; Nguyen et al. *Am J Clin Pathol.* 2013; 140: 468-474; Lendorf et al. *J Histochem Cytochem.* 2011; 59: 615-629; Gotte et al. *Breast Cancer Res.* 2007; 9(1):R8; Tsanou et al. *J Exp Clin Cancer Res.* 2004; 23(4):641-650). In an embodiment, the breast cancer is a ductal carcinoma (e.g., ductal carcinoma in situ (DCIS), or invasive ductal carcinoma (IDC) (e.g., a tubular carcinoma, a medullary carcinoma, a mucinous carcinoma, a papillary carcinoma, or a cribriform carcinoma), a lobular carcinoma (e.g., a lobular carcinoma in situ (LCIS) or an invasive lobular carcinoma (ILC)), or an inflammatory breast cancer. In an embodiment, the breast cancer is ER-positive, PR-positive, HER2-positive, or triple-negative (ER-, PR- and HER2-). The anti-CD138 antibody molecules described herein can be used alone or in combination with a second therapeutic agent, procedure, or modality to treat a bladder cancer. In an embodiment, the anti-CD138 antibody molecule is used in combination with a surgery (e.g., a breast-conserving surgery or a mastectomy), a radiation therapy, a chemotherapy (e.g., an anthracycline (e.g., doxorubicin, liposomal doxorubicin, epirubicin), a taxane (e.g., paclitaxel, albumin-bound paclitaxel (e.g., nab-paclitaxel) or docetaxel), 5-fluorouracil (5-FU), cyclophosphamide, a platinum agent (e.g., cisplatin or carboplatin), vinorelbine, capecitabine, gemcitabine, mitoxantrone, ixabepilone, or eribulin), a hormone therapy (e.g., tamoxifen, toremifene, fulvestrant, an aromatase inhibitor (e.g., letrozole, anastrozole, or exemestane), ovarian ablation (e.g., oophorectomy, a luteinizing hormone-releasing hormone (LHRH) analog, or a chemotherapy drug)), a targeted therapy (e.g., trastuzumab, pertuzumab, ado-trastuzumab emtansine, lapatinib, neratinib, a CDK4/6 inhibitor (e.g., palbociclib or ribociclib), an mTOR inhibitor (e.g., everolimus), or a combination thereof.

In an embodiment, the cancer is a cervical cancer. CD138 is expressed in cervical cancer (Akl et al. *Oncotarget.* 2015; 6(30):28693-28715). In an embodiment, the cervical cancer is a microinvasive cervical cancer or invasive cervical cancer. In an embodiment, the cervical cancer is a squamous cell carcinoma or an adenocarcinoma. The anti-CD138 antibody molecules described herein can be used alone or in combination with a second therapeutic agent, procedure, or modality to treat a cervical cancer. In an embodiment, the anti-CD138 antibody molecule is used in combination with a surgery (e.g., a cryosurgery, a laser surgery, a conization, a simple hysterectomy, a radical hysterectomy, a trachelectomy, or a pelvic exenteration), a radiation therapy, a chemotherapy (e.g., cisplatin, carboplatin, paclitaxel, topotecan, gemcitabine, docetaxel, ifosfamide, 5-fluorouracil (5-FU), irinotecan, or mitomycin), a targeted therapy (e.g., an angiogenesis inhibitor (e.g., bevacizumab)), or a combination thereof.

In an embodiment, the cancer is an endometrial cancer. CD138 is expressed in endometrial cancer (Hasengaowa et al. *Ann Oncol.* 2005; 16:1109-1115). In an embodiment, the endometrial cancer is an endometrioid carcinoma, a serous carcinoma, a clear cell carcinoma, a mucinous carcinoma, a mixed or undifferentiated carcinoma, a squamous cell carcinoma, a transitional cell carcinoma, or an endometrial stromal sarcoma. The anti-CD138 antibody molecules described herein can be used alone or in combination with a second therapeutic agent, procedure, or modality to treat an endometrial cancer. In an embodiment, the anti-CD138 antibody molecule is used in combination with a surgery, a radiation therapy, a hormone therapy (e.g., a progestin (e.g., medroxyprogesterone acetate) or megestrol acetate), tamoxifen, a luteinizing hormone-releasing hormone (LHRH) agonist (e.g., goserelin or leuprolide), an aromatase inhibitor (e.g., letrozole, anastrozole, or exemestane), a chemotherapy (e.g., paclitaxel, carboplatin, doxorubicin, liposomal doxorubicin, or cisplatin), or a combination thereof.

In an embodiment, the cancer is a gallbladder cancer. CD138 is overexpressed in gallbladder cancer (Roh et al. *Eur Surg Res.* 2008; 41(2): 245-250). In an embodiment, the gallbladder cancer is an adenocarcinoma or a papillary adenocarcinoma. The anti-CD138 antibody molecules described herein can be used alone or in combination with a second therapeutic agent, procedure, or modality to treat a gallbladder cancer. In an embodiment, the anti-CD138 antibody molecule is used in combination with a surgery, a radiation therapy, a chemotherapy (e.g., gemcitabine, cisplatin, 5-fluorouracil (5-FU), capecitabine, or oxaliplatin), or a palliative therapy (e.g., a biliary stent, a biliary catheter, a biliary bypass, an alcohol injection, a pain medicine, or a combination thereof.

In an embodiment, the cancer is a gastric cancer. Strong stromal CD138 expression is associated with gastric cancer (Wiksten et al. *Int J Cancer.* 2001; 95(1):1-6). In an embodiment, the gastric cancer is an adenocarcinoma (ACA). The anti-CD138 antibody molecules described herein can be used alone or in combination with a second therapeutic agent, procedure, or modality to treat a gastric cancer. In an embodiment, the anti-CD138 antibody molecule is used in combination with a surgery, a chemotherapy (e.g., 5-FU (fluorouracil), capecitabine, carboplatin, cisplatin, docetaxel, epirubicin, irinotecan, oxaliplatin, or paclitaxel), or a combination thereof.

In an embodiment, the cancer is a brain cancer (e.g., a glioma). CD138 is expressed in glioma (Xu et al. *Mol Biol Rep.* 2012; 39(9): 8979-8985). In an embodiment, the glioma is an astrocytoma, an en ependymoma, or an oligodendroglioma. The anti-CD138 antibody molecules described herein can be used alone or in combination with a second therapeutic agent, procedure, or modality to treat a glioma. In an embodiment, the anti-CD138 antibody molecule is used in combination with a surgery, a radiation therapy, a chemotherapy (e.g., carboplatin, carmustine (BCNU), cisplatin, cyclophosphamide, etoposide, irinotecan, lomustine (CCNU), methotrexate, procarbazine, temozolomide, or vincristine), a targeted therapy (e.g., bevacizumab or everolimus), a corticosteroid (e.g., dexamethasone), an anti-seizure drug, or a hormone, or a combination thereof.

In an embodiment, the cancer is a laryngeal cancer. CD138 expression is in laryngeal cancer (Klatka et al. *Otolaryngol Pol.* 2004; 58: 933-940). In an embodiment, the laryngeal cancer is a squamous cell carcinoma or an adenocarcinoma. The anti-CD138 antibody molecules described herein can be used alone or in combination with a second therapeutic agent, procedure, or modality to treat a laryngeal cancer. In an embodiment, the anti-CD138 antibody molecule is used in combination with a surgery, a radiation therapy, a chemotherapy (e.g., cisplatin, carboplatin, 5-fluorouracil (5-FU), docetaxel, paclitaxel, bleomycin, methotrexate, or ifosfamide), a targeted therapy (e.g., an EGFR inhibitor (e.g., cetuximab)), or a combination thereof. In an embodiment, the cancer is a liver cancer. In an embodiment, the liver cancer is a hepatocellular carcinoma (HCC), a cholangiocarcinoma, an angiosarcoma, or a secondary liver cancer. The anti-CD138 antibody molecules described herein can be used alone or in combination with a second therapeutic agent, procedure, or modality to treat a liver cancer. In an embodiment, the anti-CD138 antibody molecule is used in combination with a surgery, tumor ablation, tumor embolization, a radiation therapy, a targeted therapy (e.g., sorafenib or regorafenib), a chemotherapy (e.g., doxorubicin, 5-fluorouracil (5-FU), or cisplatin), or a combination thereof.

In an embodiment, the cancer is a lung cancer. CD138 is expressed in lung cancer (Anttonen et al. *Lung Cancer.* 2001; 32:297-305). In an embodiment, the lung cancer is a non-small cell lung cancer (NSCLC) (e.g., an adenocarcinoma, a squamous cell carcinoma, a large cell carcinoma, or a large cell neuroendocrine tumor) or a small cell lung cancer (SCLC). The anti-CD138 antibody molecules described herein can be used alone or in combination with a second therapeutic agent, procedure, or modality to treat a lung cancer. In an embodiment, the anti-CD138 antibody molecule is used in combination with a surgery, radiofrequency ablation (RFA), a radiation therapy, a chemotherapy (cisplatin, carboplatin, paclitaxel, albumin-bound paclitaxel (nab-paclitaxel), docetaxel, gemcitabine, vinorelbine, irinotecan, etoposide, vinblastine, or pemetrexed), a targeted therapy (an angiogenesis inhibitor (e.g., bevacizumab or ramucirumab), an EGFR inhibitor (e.g., erlotinib, afatinib, gefitinib, osimertinib, or necitumumab), an ALK inhibitor (e.g., crizotinib, ceritinib, alectinib, or brigatinib), a BRAF inhibitor (e.g., dabrafenib or trametinib), an immunotherapy (e.g., a PD-1 inhibitor (e.g., nivolumab or pembrolizumab) or a PD-L1 inhibitor (e.g., atezolizumab), or a combination thereof, e.g., to treat a non-small cell lung cancer. In an embodiment, the anti-CD138 antibody molecule is used in combination with a surgery, a radiation therapy, a chemotherapy (cisplatin, etoposide, carboplatin, or irinotecan), or a combination thereof, e.g., to treat a small cell lung cancer.

In an embodiment, the cancer is a mesothelioma. CD138 is expressed in mesothelioma (Kumar-singh et al. *J Pathol.* 1998; 186:300-305). In an embodiment, the mesothelioma is an epithelioid mesothelioma, a sarcomatoid mesothelioma, or abiphasic mesothelioma. In an embodiment, the mesothelioma is a pleural mesothelioma, a peritoneal mesothelioma, or a pericardial mesothelioma. The anti-CD138 antibody molecules described herein can be used alone or in combination with a second therapeutic agent, procedure, or modality to treat a mesothelioma. In an embodiment, the anti-CD138 antibody molecule is used in combination with a surgery, a radiation therapy, a chemotherapy (e.g., pemetrexed, cisplatin, carboplatin, gemcitabine, methotrexate, vinorelbine, mitomycin, or doxorubicin), or a combination thereof.

In an embodiment, the cancer is a nasopharyngeal cancer. CD138 is expressed in nasopharyngeal cancer (Kim et al. *Head Neck.* 2011; 33:1458-1466). In an embodiment, the nasopharyngeal cancer is a keratinizing squamous cell carcinoma, a non-keratinizing differentiated carcinoma, or an undifferentiated carcinoma. The anti-CD138 antibody molecules described herein can be used alone or in combination with a second therapeutic agent, procedure, or modality to treat a nasopharyngeal cancer. In an embodiment, the anti-CD138 antibody molecule is used in combination with a surgery, a radiation therapy, a chemotherapy (e.g., carboplatin, doxorubicin, epirubicin, paclitaxel, docetaxel, gemcitabine, bleomycin, or methotrexate), a targeted therapy (e.g., cetuximab), or a combination thereof.

In an embodiment, the cancer is a nasopharyngeal cancer. CD138 is expressed in oral cancer (Al-Otaibi et al. *J Oral Pathol Med.* 2013; 42: 186-193). In an embodiment, the oral cancer is a squamous cell carcinoma, a verrucous carcinoma, or a minor salivary gland carcinoma. The anti-CD138 antibody molecules described herein can be used alone or in combination with a second therapeutic agent, procedure, or modality to treat an oral cancer. In an embodiment, the anti-CD138 antibody molecule is used in combination with a surgery, a radiation therapy, a chemotherapy (e.g., cisplatin, carboplatin, 5-fluorouracil (5-FU), paclitaxel, docetaxel, methotrexate, ifosfamide, or bleomycin), a targeted therapy (e.g., cetuximab), or a combination thereof.

In an embodiment, the cancer is an ovarian cancer. CD138 is expressed in ovarian cancer (Kusumoto et al. *Oncol Rep.* 2010; 23: 917-925; Davies et al. *Clin Cancer Res.* 2004; 10: 5178-5186). In an embodiment, the ovarian cancer is an epithelial cancer, a germ cell carcinoma, a stromal carcinoma, or a small cell carcinoma. The anti-CD138 antibody molecules described herein can be used alone or in combination with a second therapeutic agent, procedure, or modality to treat an ovarian cancer. In an embodiment, the anti-CD138 antibody molecule is used in combination with a surgery, a chemotherapy (e.g., cisplatin, carboplatin, paclitaxel, albumin bound paclitaxel (nab-paclitaxel), docetaxel, altretamine, capecitabine, cyclophosphamide, etoposide, gemcitabine, ifosfamide, irinotecan, liposomal doxorubicin, melphalan, pemetrexed, topotecan, or vinorelbine), a hormone therapy (e.g., a luteinizing-hormone-releasing hormone (LHRH) agonist (e.g., goserelin or leuprolide), tamoxifen, or aromatase inhibitor (e.g., letrozole, anastrozole, or exemestane), a targeted therapy (e.g., an angiogenesis inhibitor (e.g., bevacizumab), a PARP inhibitor (e.g., olaparib, rucaparib, or niraparib), a radiation therapy, or a combination thereof.

In an embodiment, the cancer is a pancreatic cancer. CD138 is expressed in pancreatic cancer (Juuti et al. *Oncology.* 2005; 68: 97-106). In an embodiment, the pancreatic cancer is an exocrine tumor or an endocrine tumor. The anti-CD138 antibody molecules described herein can be used alone or in combination with a second therapeutic agent, procedure, or modality to treat a pancreatic cancer. In an embodiment, the anti-CD138 antibody molecule is used in combination with a surgery, ablation, embolization, a radiation therapy, or a chemotherapy (cemcitabine, 5-fluorouracil (5-FU), irinotecan, oxaliplatin, albumin-bound paclitaxel, capecitabine, cisplatin, paclitaxel, docetaxel, or irinotecan liposome.

In an embodiment, the cancer is a prostate cancer. CD138 is expressed in prostate cancer (Ledezma et al. *Asian J Androl.* 2011; 13: 476-480; Shariat et al. *BJU Int.* 2008; 101:232-237; Kiviniemi et al. *Apmis.* 2004; 112: 89-97; Zellweger et al. *Prostate.* 2003; 55: 20-29). In an embodiment, the prostate cancer is an adenocarcinoma, a transitional cell (or urothelial) cancer, a squamous cell cancer, or a small cell prostate cancer. The anti-CD138 antibody molecules described herein can be used alone or in combination with a second therapeutic agent, procedure, or modality to treat a prostate cancer. In an embodiment, the anti-CD138 antibody molecule is used in combination with a surgery, a radiation therapy, a cryotherapy, a hormone therapy (e.g., orchiectomy, an LHRH agonist (e.g., leuprolide, goserelin, triptorelin, or histrelin), an LHRH antagonist (e.g., degarelix), a CYP17 inhibitor (e.g., abiraterone), an anti-androgen (e.g., flutamide, bicalutamide, nilutamide, or enzalutamide), an estrogen, or ketoconazole), a chemotherapy (e.g., docetaxel, cabazitaxel, mitoxantrone, or estramustine), a vaccine treatment (e.g., Sipuleucel-T), or a bone-directed treatment (e.g., a bisphosphonate (e.g., zoledronic acid), denosumab, a corticosteroid (e.g., prednisone or dexamethasone), an external radiation therapy, a radiopharmaceutical (e.g., Strontium-89, Samarium-153, or Radium-223), or a combination thereof.

In an embodiment, the cancer is a head and neck cancer. CD138 is expressed in head and neck cancer (Anttonen et al. *Br J Cancer.* 1999; 79: 558-564; Inki et al. *Br J Cancer.* 1994; 70: 319-323). In an embodiment, the head and neck cancer is a squamous cell carcinoma. The anti-CD138 antibody molecules described herein can be used alone or in combination with a second therapeutic agent, procedure, or modality to treat a head and neck cancer. In an embodiment, the anti-CD138 antibody molecule is used in combination with a surgery, a radiation therapy, a chemotherapy (e.g., methotrexate, bleomycin, or docetaxel), a targeted therapy (e.g., cetuximab), an immunotherapy (e.g., a PD-1 inhibitor (e.g., nivolumab or pembrolizumab)), or a combination thereof.

In an embodiment, the cancer is a thyroid cancer. CD138 is expressed in thyroid cancer (Oh & Park. *J Korean Med Sci.* 2006; 21: 397-405). In an embodiment, the thyroid cancer is a papillary carcinoma, a follicular carcinoma, a Hürthle cell carcinoma, a medullary thyroid carcinoma, or an anaplastic carcinoma. The anti-CD138 antibody molecules described herein can be used alone or in combination with a second therapeutic agent, procedure, or modality to treat a thyroid cancer. In an embodiment, the anti-CD138 antibody molecule is used in combination with a surgery, a radioactive iodine treatment, a thyroid hormone therapy, a radiation therapy, a chemotherapy, a targeted therapy (e.g., a kinase inhibitor (e.g., sorafenib or lenvatinib), or a combination thereof.

In an embodiment, the cancer is a chronic lymphocytic leukemia (CLL). CD138 is expressed in chronic lymphocytic leukemia cancer (Jilani et al. *Int J Lab Hematol.* 2009; 31:97-105). The anti-CD138 antibody molecules described herein can be used alone or in combination with a second therapeutic agent, procedure, or modality to treat a thyroid cancer. In an embodiment, the anti-CD138 antibody molecule is used in combination with a chemotherapy (e.g., a purine analog (e.g., fludarabine, pentostatin, or cladribine), an alkylating agent (e.g., chlorambucil, cyclophosphamide, or bendamustine), a corticosteroid (e.g., prednisone, methylprednisolone, or dexamethasone), doxorubicin, methotrexate, oxaliplatin, vincristine, etoposide, and cytarabine), an anti-CD20 antibody (rituximab, obinutuzumab, or ofatumumab), an anti-CD52 antibody (e.g., alemtuzumab), a targeted therapy (e.g., ibrutinib, idelalisib, or venetoclax), a stem cell transplant (SCT), or a combination thereof.

In an embodiment, the cancer is a lymphoma (e.g., a diffuse large B-cell lymphoma (DLBCL)). CD138 is expressed in DLBCL (Oh & Park. J Korean Med Sci. 2006; 21: 397-405; Bodoor et al. *Asian Pac J Cancer Prev.* 2012; 13: 3037-3046). The anti-CD138 antibody molecules described herein can be used alone or in combination with a second therapeutic agent, procedure, or modality to treat a DLBCL. In an embodiment, the anti-CD138 antibody molecule is used in combination with a chemotherapy (e.g., an alkylating agent (e.g., cyclophosphamide, chlorambucil, bendamustine, or ifosfamide), a corticosteroid (e.g., prednisone or dexamethasone), a platinum drug (cisplatin, carboplatin, or oxaliplatin), a purine analog (e.g., fludarabine, pentostatin, or cladribine), an anti-metabolite (e.g., cytarabine, gemcitabine, methotrexate, or pralatrexate), vincristine, doxorubicin, mitoxantrone, etoposide, or bleomycin), an immunotherapy (e.g., an anti-CD20 antibody (rituximab, obinutuzumab, or ofatumumab), an anti-CD52 antibody (e.g., alemtuzumab), an anti-CD30 antibody (e.g., brentuximab vedotin), interferon, an immunomodulating drug (e.g., thalidomide or lenalidomide), a targeted therapy (e.g., a proteasome inhibitor (e.g., bortezomib), a histone deacetylase (HDAC) inhibitor (e.g., romidepsin or belinostat), or a kinase inhibitor (e.g., ibrutinib or idelalisib)), a radiation therapy, a stem cell transplant (SCT), or a combination thereof.

In an embodiment, the cancer is a Hodgkin's lymphoma. CD138 is expressed in Hodgkin's lymphoma (Gharbaran et al. *J Hematol Oncol.* 2013; 6:62; Vassilakopoulos et al. *Anticancer Res.* 2005; 25: 4743-4746). The anti-CD138 antibody molecules described herein can be used alone or in combination with a second therapeutic agent, procedure, or modality to treat a Hodgkin's lymphoma. In an embodiment, the anti-CD138 antibody molecule is used in combination with a chemotherapy (e.g., doxorubicin, bleomycin, vinblastine, dacarbazine, etoposide, cyclophosphamide, vincristine, procarbazine, prednisone, mechlorethamine, vincristine, or vinblastine), a radiation therapy, an immunotherapy (e.g., an anti-CD30 antibody (e.g., brentuximab vedotin)), a stem cell transplant, or a combination thereof.

In an embodiment, the antibody molecule is used to treat or prevent a precancerous condition. Precancerous condition, also known as premalignant condition, potentially precancerous condition, or potentially premalignant condition, refers to a state of disordered morphology of cells that is associated with an increased risk of cancer. If left untreated, precancerous conditions may lead to cancer. In an embodiment, the premalignant lesion is morphologically atypical tissue which appears abnormal under microscopic examination, and in which cancer is more likely to occur than in its apparently normal counterpart. In an embodiment, the precancerous condition is smoldering myeloma or asymptomatic myeloma. In an embodiment, the precancerous condition is monoclonal gammopathy of undetermined significance (MGUS). Other examples of precancerous conditions include, but are not limited to, actinic keratosis, Barrett's esophagus, atrophic gastritis, ductal carcinoma in situ, dyskeratosis congenital, sideropenic dysphagia, lichen planus, oral submucous fibrosis, solar elastosis, cervical dysplasia, leukoplakia, and erythroplakia.

Multiple Myeloma

The humanized antibody molecule described herein can be used to treat or prevent multiple myeloma.

Multiple myeloma (MM), also known as plasma cell myeloma, is a cancer of plasma cells, which are normally responsible for producing antibodies (Raab et al. *Lancet.* 2009; 374(9686): 324-39). Multiple myeloma is typically considered as a malignant disorder of uncontrolled proliferation of monoclonal plasma cells (PCs) in the bone marrow. This hematological malignancy is clinically characterized for example, by hyperproduction of monoclonal immunoglobulins, osteolytic bone disease, anemia, immunosuppression and end-organ damage, predominantly occurring in the kidney. Encouraging therapeutic advancements in the treatment of MM patients have occurred over the last several decades. Despite such advances, multiple myeloma remains an incurable disease in most patients due to a high incidence of relapse or treatment resistance. MM represents the second leading hematological cancer (globally) accounting for about 2% of all newly diagnosed cancers and approximately 13% of hematological malignancies in the U.S. with conservative estimates of greater than 30,000 new cases in 2018 leading to approximately 13,000 deaths. There is a high unmet need for developing new approaches for treating, preventing and diagnosing multiple myeloma and other plasma cell disorders that share similar disease mechanisms. Without wishing to be bound by theory, it is believed that in an embodiment, the prospect of earlier intervention in disease treatment through the use of safe and efficacious agents is also an emerging and attractive strategy. Novel targeted therapies, such as the therapies using the anti-CD138 antibody molecules described herein, can be beneficial at least in this respect.

Signs or symptoms of multiple myeloma include, e.g., bone pain, anemia (e.g., normocytic and/or normochromic anemia), kidney failure (e.g., acute or chronical kidney failure), infection (e.g., pneumonias or pyelonephritis), a neurological symptom (e.g., weakness, confusion, fatigue, headache, visual change, retinopathy, radicular pain, loss of bowel or bladder control, carpal tunnel syndrome, or paraplegia).

Risk factors for multiple myeloma include, e.g., smoldering myeloma (also known as asymptomatic myeloma), monoclonal gammopathy of undetermined significance (MGUS), obesity, or familial predisposition. In an embodiment, the anti-CD138 antibody molecules described herein can be used to reduce (e.g., prevent) the progression of smoldering myeloma or MGUS to multiple myeloma.

Diagnostic criteria for symptomatic myeloma, asymptomatic myeloma and MGUS are described, e.g., in Kyle & Rajkumar *Leukemia.* 2009; 23(1): 3-9.

Diagnostic criteria for symptomatic myeloma (all three criteria must be met) include, e.g., clonal plasma cells >10% on bone marrow biopsy or (in any quantity) in a biopsy from other tissues (plasmacytoma), a monoclonal protein (Myeloma protein) in either serum or urine (except in cases of true non-secretory myeloma), and evidence of end-organ damage felt related to the plasma cell disorder (related organ or tissue impairment, commonly referred to by the acronym "CRAB"): hypercalcemia (corrected calcium >2.75 mmol/1, >11 mg/dL), renal insufficiency attributable to myeloma, anemia (hemoglobin <10 g/dl), bone lesions (lytic lesions or osteoporosis with compression fractures). Diagnostic criteria for asymptomatic/smoldering myeloma include, e.g., serum M protein >30 g/l (3 g/dL) and/or clonal plasma cells >10% on bone marrow biopsy and no myeloma-related organ or tissue impairment). Diagnostic criteria for monoclonal gammopathy of undetermined significance (MGUS)

include, e.g., serum paraprotein <30 g/l (3 g/dL) and clonal plasma cells <10% on bone marrow biopsy and no myeloma-related organ or tissue impairment or a related B-cell lymphoproliferative disorder Related conditions include, e.g., solitary plasmacytoma, plasma cell dyscrasia (e.g., AL amyloidosis), and peripheral neuropathy, organomegaly, endocrinopathy, monoclonal plasma cell disorder, and skin changes.

The International Staging System (ISS) for myeloma is described, e.g., in Greipp et al. *J Clin Oncol*. 2005; 23(15): 3412-20. For example, the ISS includes the following: Stage I: β2 microglobulin (β2M)<3.5 mg/L, albumin ≥3.5 g/dL; Stage II: β2M<3.5 mg/L and albumin <3.5 g/dL; or β2M 3.5-5.5 mg/L irrespective of the serum albumin; Stage III: β2M≥5.5 mg/L.

The ISS can be used along with the Durie-Salmon Staging System. The Durie-Salmon Staging System is described, e.g., in Durie & Salmon Cancer. 1975; 36(3):842-54. For example, the Durie-Salmon Staging System include the following: Stage I (all of Hb>10 g/dL, normal calcium, skeletal survey: normal or single plasmacytoma or osteoporosis, serum paraprotein level <5 g/dL if IgG, <3 g/dL if IgA, urinary light chain excretion <4 g/24 h); Stage II (fulfilling the criteria of neither I nor III); Stage III (one or more of Hb<8.5 g/dL, high calcium >12 mg/dL, skeletal survey: three or more lytic bone lesions, serum paraprotein >7 g/dL if IgG, >5 g/dL if IgA, urinary light chain excretion >12 g/24 h). Stages I, II, and III of the Durie-Salmon Staging System can be divided into A or B depending on serum creatinine: A: serum creatinine <2 mg/dL (<177 μmol/L); B: serum creatinine >2 mg/dL (>177 μmol/L).

Other treatments for multiple myeloma that can be used in combination with an anti-CD138 antibody molecule described herein include, e.g., a protease inhibitor (e.g., bortezomib (VELCADE®), carfilzomib (KYPROLIS®), or ixazomib (NINLARO®)), an immunomodulating agent (e.g., thalidomide (THALOMID®), lenalidomide (REVLIMID®), or pomalidomide (POMALYST®)), a chemotherapy (e.g., melphalan, vincristine (ONCOVIN®), cyclophosphamide, etoposide, doxorubicin (ADRIAMYCIN®), liposomal doxorubicin (DOXIL®), or bendamustine (TREANDA®)), a corticosteroid (e.g., prednisone or dexamethasone), a histone deacetylase (HDAC) inhibitor (e.g., panobinostat (FARYDAK®), an anti-CD38 antibody (e.g., daratumumab (DARZALEX®)), an anti-SLAMF7 antibody (e.g., elotuzumab (EMPLICITI®)), an interferon, or a bone marrow transplantation (e.g., autologous stem cell transplantation (ASCT) or allogeneic stem cell transplantation), a bisphosphonate (e.g., pamidronate (AREDIA®) and zoledronic acid (ZOMETA®), a radiation therapy, a surgery, an intravenous immunoglobulin (IVIG), a treatment for low blood cell count (e.g., erythropoietin (PROCRIT®) or darbepoietin (ARANESP®), plasmapheresis, or a combination thereof.

Exemplary combination therapies that can be used in combination with an anti-CD138 antibody molecule described herein for treating multiple myeloma include, but are not limited to, melphalan and prednisone (MP), with or without thalidomide or bortezomib; vincristine, doxorubicin (ADRIAMYCIN®), and dexamethasone (VAD); thalidomide (or lenalidomide) and dexamethasone; bortezomib, doxorubicin, and dexamethasone; bortezomib, dexamethasone, and thalidomide (or lenalidomide); liposomal doxorubicin, vincristine, and dexamethasone; carfilzomib, lenalidomide, and dexamethasone; dexamethasone, cyclophosphamide, etoposide, and cisplatin (DCEP); dexamethasone, thalidomide, cisplatin, doxorubicin, cyclophosphamide, and etoposide (DT-PACE), with or without bortezomib; panobinostat, bortezomib, and dexamethasone; ixazomib, lenalidomide; and dexamethasone, and elotuzumab, lenalidomide, and dexamethasone.

Combination Therapies

The humanized antibody molecules described herein can be used in combination with other therapies. For example, the combination therapy can include an antibody molecule co-formulated with, and/or co-administered with, one or more additional therapeutic agents, e.g., one or more additional therapeutic agents described herein. In other embodiments, the antibody molecules are administered in combination with other therapeutic treatment modalities, e.g., other therapeutic treatment modalities described herein. Such combination therapies may advantageously utilize lower dosages of the administered therapeutic agents, thus avoiding possible toxicities or complications associated with the various monotherapies.

Administered "in combination", as used herein, means that two (or more) different treatments are delivered to the subject before, or during the course of the subject's affliction with a disorder. In an embodiment, two or more treatments are delivered prophylactically, e.g., before the subject has the disorder or is diagnosed with the disorder. In another embodiment, the two or more treatments are delivered after the subject has developed or diagnosed with the disorder. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two or more treatments can be partially additive, wholly additive, or greater than additive. In some embodiments, the effect of the two or more treatments can be synergistic. The delivery can be such that an effect of the first treatment delivered is still detectable when the second is delivered.

In certain embodiments, the additional agent is a second antibody molecule, e.g., an antibody molecule different from a first antibody molecule. Exemplary antibody molecules that can be used in combination include, but are not limited to, any combination of the antibody molecules listed in Table 1, 2, or 6.

In an embodiment, the antibody molecule is administered in combination with a second therapy to treat or prevent a myeloma, e.g., multiple myeloma.

In an embodiment, the antibody molecule is administered in combination with a protease inhibitor. Exemplary protease inhibitors include, e.g., bortezomib (VELCADE®), carfilzomib (KYPROLIS®), and ixazomib (NINLARO®).

In an embodiment, the antibody molecule is administered in combination with an immunomodulating agent. Exemplary immunomodulating agents include, e.g., thalidomide (THALOMID®), lenalidomide (REVLIMID®), and pomalidomide (POMALYST®).

In an embodiment, the antibody molecule is administered in combination with a chemotherapeutic agent. Exemplary chemotherapeutic agents include, e.g., melphalan, vincristine (ONCOVIN®), cyclophosphamide, etoposide, doxorubicin (ADRIAMYCIN®), liposomal doxorubicin (DOXIL®), and bendamustine (TREANDA®).

In an embodiment, the antibody molecule is administered in combination with a corticosteroid, e.g., prednisone and dexamethasone.

In an embodiment, the antibody molecule is administered in combination with a histone deacetylase (HDAC) inhibitor, e.g., panobinostat (FARYDAK®).

In an embodiment, the antibody molecule is administered in combination with an anti-CD38 antibody, e.g., daratumumab (DARZALEX®).

In an embodiment, the antibody molecule is administered in combination with an anti-SLAMF7 antibody, e.g., elotuzumab (EMPLICITI®).

In an embodiment, the antibody molecule is administered in combination with an interferon.

In an embodiment, the antibody molecule is administered in combination with bone marrow transplantation (e.g., autologous stem cell transplantation (ASCT) or allogeneic stem cell transplantation).

In an embodiment, the antibody molecule is administered in combination with a bisphosphonate, e.g., pamidronate (AREDIA®) or zoledronic acid (ZOMETA®).

In an embodiment, the antibody molecule is administered in combination with a radiation therapy.

In an embodiment, the antibody molecule is administered in combination with a surgery.

In an embodiment, the antibody molecule is administered in combination with an intravenous immunoglobulin (IVIG).

In an embodiment, the antibody molecule is administered in combination with a treatment for low blood cell count, e.g., erythropoietin (PROCRIT®) or darbepoietin (ARANESP®).

In an embodiment, the antibody molecule is administered in combination with plasmapheresis.

In an embodiment, the antibody molecule is administered in combination with melphalan and prednisone (MP), with or without thalidomide or bortezomib.

In an embodiment, the antibody molecule is administered in combination with vincristine, doxorubicin (ADRIAMYCIN®), and dexamethasone (VAD).

In an embodiment, the antibody molecule is administered in combination with thalidomide (or lenalidomide) and dexamethasone.

In an embodiment, the antibody molecule is administered in combination with bortezomib, doxorubicin, and dexamethasone.

In an embodiment, the antibody molecule is administered in combination with bortezomib, dexamethasone, and thalidomide (or lenalidomide).

In an embodiment, the antibody molecule is administered in combination with liposomal doxorubicin, vincristine, and dexamethasone;

In an embodiment, the antibody molecule is administered in combination with carfilzomib, lenalidomide, and dexamethasone.

In an embodiment, the antibody molecule is administered in combination with dexamethasone, cyclophosphamide, etoposide, and cisplatin (DCEP).

In an embodiment, the antibody molecule is administered in combination with dexamethasone, thalidomide, cisplatin, doxorubicin, cyclophosphamide, and etoposide (DT-PACE), with or without bortezomib.

In an embodiment, the antibody molecule is administered in combination with panobinostat, bortezomib, and dexamethasone.

In an embodiment, the antibody molecule is administered in combination with ixazomib, lenalidomide, and dexamethasone.

In an embodiment, the antibody molecule is administered in combination with elotuzumab, lenalidomide, and dexamethasone.

In an embodiment, the antibody molecule is administered in combination with a second agent that targets the CD138 pathway. Exemplary agents that target the CD138 pathway include, e.g., an agent that targets the extracellular domain of CD138 (e.g., synstatin, BT-062-DM4 (indatuximab ravtansine), BB4 conjugated to $^{131}$I, OC-46F2, or GLVGLI-FAV (SEQ ID NO: 448)), an agent that targets shed CD138 (e.g., NSC 405020, BB-94, PI-88, PG545, M402, SST00001, or Pentraxin-3), and an agent that targets genetic expression of CD138 (e.g., an all-trans retinoic acid, nimesulide, zoledronic acid, or imatinib) Other agents that target the CD138 pathway are described, e.g., Akl et al. *Oncotarget*. 2015; 6(30):28693-28715, the content of which in incorporated by reference in its entirety.

In an embodiment, the antibody molecule is administered in combination with lenalidomide and/or dexamethasone, e.g., to treat a multiple myeloma (e.g., a relapsed multiple myeloma).

In an embodiment, the antibody molecule is administered in combination with an FGFR2 antagonist (e.g., an anti-FGFR2 antibody, e.g., FPA144) to treat a solid tumor (e.g., an advanced solid tumor).

In an embodiment, the antibody molecule is administered in combination with a $\alpha_v\beta_3$ inhibitor (e.g., an ADC against integrin $\alpha_v\beta_3$, e.g., brentuximab vedotin), e.g., to treat Hodgkin lymphoma (e.g., relapsed or refractory Hodgkin lymphoma).

In an embodiment, the antibody molecule is administered in combination with a heparin or heparanase inhibitor (e.g., roneparstat (SST0001)), e.g., to treat a multiple myeloma (e.g., an advanced multiple myeloma).

In an embodiment, the antibody molecule is administered in combination with a VEGFR inhibitor (e.g., bevacizumab or cediranib), e.g., to treat a cancer (e.g., an advanced cancer).

In an embodiment, the antibody molecule is administered in combination with a Wnt signaling pathway inhibitor (e.g., ipafricept (OMP-54F28)), e.g., to treat a solid tumor.

In an embodiment, the antibody molecule is administered in combination with an FAK inhibitor (e.g., defactinib (VS-6063) or GSK2256098), e.g., to treat a solid tumor, e.g., a lung cancer (e.g., a non-small cell lung cancer, e.g., with a KRAS mutation).

In an embodiment, the antibody molecule is administered in combination with a glysoaminoglycan or heparanase inhibitor (e.g., necuparanib (M402)), optionally, further in combination with a chemotherapeutic agent (e.g., nab-paclitaxel or gemcitabine), e.g., to treat a pancreatic cancer (e.g., a metastatic pancreatic cancer).

In an embodiment, the antibody molecule is administered in combination with a mannose oligosaccharide, or a FGF, heparanase, and/or VEGF inhibitor (e.g., muparfostat (PI-88)), e.g., to treat a cancer (e.g., a melanoma).

In an embodiment, the antibody molecule is administered in combination with a chemically modified heparin sulfate/heparanase inhibitor (e.g., PG545), e.g., to treat a solid tumor (e.g., an advanced solid tumor).

In an embodiment, the antibody molecule is administered in combination with an amino acid or matrix metalloprotease inhibitor (e.g., intrapleural batimastat (BB-94)), e.g., to treat a malignant pleural effusion.

In an embodiment, the antibody molecule is administered in combination with a chimeric anti-CD138 antigen receptor-modified T cells, e.g., to treat a multiple myeloma (e.g., a relapsed and/or refractory multiple myeloma).

In an embodiment, the antibody molecule is administered in combination with a proteasome inhibitor. In an embodiment, the proteasome inhibitor comprises bortezomib. In an embodiment, the proteasome inhibitor comprises a compound having a formula of

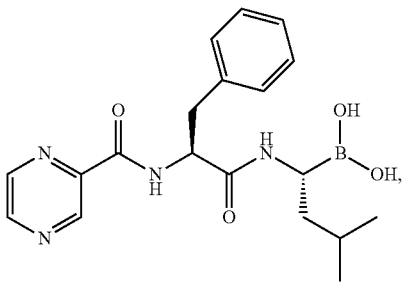 [SMILES: CC(C)C[C@H](NC(=O)[C@H](Cc1ccccc1)NC(=O)c1cnccn1)B(O)O]

or a pharmaceutically acceptable salt, hydrate, solvate, prodrug, stereoisomer, or tautomer thereof.

Bortezomib (also known as VELCADE®, LDP 341, MLN341, or PS-341) is an anti-cancer drug and the first therapeutic proteasome inhibitor to be used in humans. Proteasomes are higher order enzymatic complexes that degrade misfolded, damaged, or potentially toxic proteins and constitute a metabolic and homeostatic mechanism by which cells regulate the concentration and turnover of such proteins. In some cancers, this homeostasis is imbalanced leading to the inappropriate degradation of proteins that normally function to kill cancer cells or control cellular growth (e.g., the immunoproteasome). Bortezomib modulates this process and promotes a pro-apoptotic or immune-based killing of the cancer cells. It does so in part by promoting the unfolded protein response (UPR). In an embodiment, bortezomib has the chemical structure of [(1R)-3-Methyl-1-[[(2S)-1-oxo-3-phenyl-2-[(pyrazinylcarbonyl)amino]propyl]amino]butyl]boronic Acid.

Bortezomib is approved in the U.S. and Europe for treating relapsed multiple myeloma and mantle cell lymphoma. Clinical studies have shown partial benefit in the use of bortezomib as an initial therapy, as maintenance therapy, or as second line therapy for previously treated multiple myeloma. The drug is more typically used in combination with dexamethasone (VD) or as part of a three-drug combination, e.g., VELCADE-REVLIMID (lenalidomide)-dexamethasone (VRD).

Exemplary therapies that can be used in combination with an antibody molecule or composition described herein to treat or prevent other disorders are also described in the section of "Methods of Treating or Preventing Disorders" herein.

Methods of Diagnosis

In an aspect, the present disclosure provides a diagnostic method for detecting the presence of CD138 in vitro (e.g., in a biological sample, such as a biopsy or blood sample) or in vivo (e.g., in vivo imaging in a subject). The method includes: (i) contacting the sample with a humanized anti-CD138 antibody molecule described herein, or administering to the subject, the antibody molecule; (optionally) (ii) contacting a reference sample, e.g., a control sample (e.g., a control biological sample, such as a biopsy or blood sample) or a control subject with an antibody molecule described herein; and (iii) detecting formation of a complex between the antibody molecule and CD138 in the sample or subject, or the control sample or subject, wherein a change, e.g., a statistically significant change, in the formation of the complex in the sample or subject relative to the control sample or subject is indicative of the presence of CD138 in the sample. The antibody molecule can be directly or indirectly labeled with a detectable substance to facilitate detection of the bound or unbound antibody molecule. Suitable detectable substances include various enzymes, prosthetic groups, fluorescent materials, luminescent materials and radioactive materials, as described above and described in more detail below.

The term "sample," as it refers to samples used for detecting a polypeptide (e.g., CD138) or a nucleic acid encoding the polypeptide includes, but is not limited to, cells, cell lysates, proteins or membrane extracts of cells, body fluids such as blood, or tissue samples such as biopsies.

Complex formation between the antibody molecule, and CD138, can be detected by measuring or visualizing either the antibody molecule bound to CD138 or unbound antibody molecule. Any suitable detection assays can be used, and conventional detection assays include an enzyme-linked immunosorbent assays (ELISA), a radioimmunoassay (RIA) or tissue immunohistochemistry. Alternative to labeling the antibody molecule, the presence of CD138 can be assayed in a sample by a competition immunoassay utilizing standards labeled with a detectable substance and an unlabeled antibody molecule. In this assay, the biological sample, the labeled standards and the antibody molecule are combined and the amount of labeled standard bound to the unlabeled binding molecule is determined. The amount of CD138 in the sample is inversely proportional to the amount of labeled standard bound to the antibody molecule.

The anti-CD138 antibody molecules described herein can be used to diagnose disorders that can be treated or prevented by the anti-CD138 antibody molecules described herein. The detection or diagnostic methods described herein can be used in combination with other methods described herein to treat or prevent a disorder described herein.

The present disclosure also includes any of the following numbered paragraphs:

1. An anti-CD138 antibody molecule comprising one or both of:
   (a) a heavy chain variable region (VH), wherein the VH comprises three heavy chain complementarity determining regions (HCDR1, HCDR2, and HCDR3), wherein the VH comprises one, two, or all of the following:
      (i) an HCDR1 comprising an amino acid sequence that differs by no more than 1, 2, or 3 amino acid residues from, or has at least 85, 90, 95, 99 or 100% homology with, the amino acid sequence of the HCDR1 of an anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422, e.g., as listed in Table 1, 2, or 6);

(ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; or (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody; or (b) a light chain variable region (VL), wherein the VL comprises three light chain complementarity determining regions (LCDR1, LCDR2, and LCDR3), wherein the VL comprises one, two, or all of the following:

(i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;

(ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; or (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

2. The antibody molecule of paragraph 1, wherein the VH comprises:

(i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody;

(ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody.

3. The antibody molecule of paragraph 1 or 2, wherein the VH comprises: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody.

4. The antibody molecule of any of paragraphs 1-3, wherein the VL comprises:

(i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;

(ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

5. The antibody molecule of any of paragraphs 1-4, wherein the VL comprises: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

6. The antibody molecule of any of paragraphs 1-5, comprising:

(a) a VH comprising:

(i) an HCDR1 comprising an amino acid sequence that differs by no more than 1, 2, or 3 amino acid residues from, or has at least 85, 90, 95, 99 or 100% homology with, the amino acid sequence of the HCDR1 of the anti-CD138 antibody;

(ii) an HCDR2 comprising an amino acid sequence that differs by no more than 1, 2, or 3 amino acid residues from, or has at least 85, 90, 95, 99 or 100% homology with, the amino acid sequence of the HCDR2 of the anti-CD138 antibody; and (iii) an HCDR3 comprising an amino acid sequence that differs by no more than 1, 2, or 3 amino acid residues from, or has at least 85, 90, 95, 99 or 100% homology with, the amino acid sequence of the HCDR3 of the anti-CD138 antibody, and (b) a VL comprising:

(i) an LCDR1 comprising an amino acid sequence that differs by no more than 1, 2, or 3 amino acid residues from, or has at least 85, 90, 95, 99 or 100% homology with, the amino acid sequence of the LCDR1 of the anti-CD138 antibody;

(ii) an LCDR2 comprising an amino acid sequence that differs by no more than 1, 2, or 3 amino acid residues from, or has at least 85, 90, 95, 99 or 100% homology with, the amino acid sequence of the LCDR2 of the anti-CD138 antibody; and (iii) an LCDR3 comprising an amino acid sequence that differs by no more than 1, 2, or 3 amino acid residues from, or has at least 85, 90, 95, 99 or 100% homology with, the amino acid sequence of the LCDR3 of the anti-CD138 antibody.

7. The antibody molecule of any of paragraphs 1-6, comprising:

(a) a VH comprising: (i) an HCDR1 comprising the amino acid sequence of the HCDR1 of the anti-CD138 antibody; (ii) an HCDR2 comprising the amino acid sequence of the HCDR2 of the anti-CD138 antibody; and (iii) an HCDR3 comprising the amino acid sequence of the HCDR3 of the anti-CD138 antibody, and (b) a VL comprising: (i) an LCDR1 comprising the amino acid sequence of the LCDR1 of the anti-CD138 antibody; (ii) an LCDR2 comprising the amino acid sequence of the LCDR2 of the anti-CD138 antibody; and (iii) an LCDR3 comprising the amino acid sequence of the LCDR3 of the anti-CD138 antibody.

8. The antibody molecule of any of paragraphs 1-7, wherein the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody.

9. The antibody molecule of any of paragraphs 1-8, wherein the VH comprises the amino acid sequence of the VH of the anti-CD138 antibody.

10. The antibody molecule of any of paragraphs 1-9, wherein the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VL of the anti-CD138 antibody.

11. The antibody molecule of any of paragraphs 1-10, wherein the VL comprises the amino acid sequence of the VL of the anti-CD138 antibody.

12. The antibody molecule of any of paragraphs 1-11, wherein:

(a) the VH comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody; and (b) the VL comprises an amino acid sequence that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the VH of the anti-CD138 antibody.

13. The antibody molecule of any of paragraphs 1-12, wherein the VH comprises the amino acid sequence of the VH of the anti-CD138 antibody and the VL comprises the amino acid sequence of the VL of the anti-CD138 antibody.

14. The antibody molecule of any of paragraphs 1-13, comprising an Fc region.

15. The antibody molecule of any of paragraphs 1-14, comprising a heavy chain (HC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the HC of the anti-CD138 antibody.

16. The antibody molecule of paragraph 15, wherein the HC comprises the amino acid sequence of the HC of the anti-CD138 antibody.

17. The antibody molecule of any of paragraphs 1-16, comprising a light chain (LC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the LC of the anti-CD138 antibody.

18. The antibody molecule of paragraph 17, wherein the LC comprises the amino acid sequence of the LC of the anti-CD138 antibody.

19. The antibody molecule of any of paragraphs 1-18, comprising:

(a) a heavy chain (HC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the HC of the anti-CD138 antibody; and (b) a light chain (LC) comprising an amino acid sequence of that differs by no more than 1, 2, 3, 4, 5, 6, 7, 8, 9, 10, 11, 12, 13, 14, or 15 amino acid residues from, or has at least 85, 90, 95, 99 or 100% homology with, the amino acid sequence of the LC of the anti-CD138 antibody.

20. The antibody molecule of paragraph 19, wherein the HC comprises the amino acid sequence of the HC of the anti-CD138 antibody and the LC comprises the amino acid sequence of the LC of the anti-CD138 antibody.

21. An anti-CD138 antibody molecule comprising:

(I) (a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of G-Y-N/S/T-F-A/S/T-S-Y (SEQ ID NO: 438); (ii) an HCDR2 comprising an amino acid sequence of H-P-S-D-S-T (SEQ ID NO: 351); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524); or (II) (a) a heavy chain variable region (VH), wherein the VH comprises three heavy chain complementarity determining regions (HCDR1, HCDR2, and HCDR3), wherein the VH comprises one, two, or all of: (i) an HCDR1 comprising an amino acid sequence of S-Y-Y-I/M-H (SEQ ID NO: 525); (ii) an HCDR2 comprising an amino acid sequence of T-I-H-P-S-D-S-T-A/T-N-Y-A/N-Q-K-F-K/Q-G (SEQ ID NO: 526); or (iii) an HCDR3 comprising an amino acid sequence of F-V-Y (SEQ ID NO: 508); and (b) a light chain variable region (VL), wherein the VL comprises three light chain complementarity determining regions (LCDR1, LCDR2, and LCDR3), wherein the VL comprises one, two, or all of: (i) an LCDR1 comprising an amino acid sequence of K/R-A/S-S-K/Q-S-L-L-Y-K-D-G-K-T-Y-L-N(SEQ ID NO: 522); (ii) an LCDR2 comprising an amino acid sequence of V-L/V-S-S/T-L/R-A/Q-S(SEQ ID NO: 523); or (iii) an LCDR3 comprising an amino acid sequence of Q-Q-L-V-E/Q-Y-P-Y-T (SEQ ID NO: 524).

22. The antibody molecule of any of paragraphs 1-21, comprising two VHs and two VLs.

23. The antibody molecule of any of paragraphs 1-22, which is a synthetic antibody molecule or an isolated antibody molecule.

24. The antibody molecule of any of paragraphs 1-23, which is a monovalent antibody molecule, a multivalent (e.g., bivalent, trivalent, or tetravalent) antibody molecule, a monospecific molecule, or a multispecific (e.g., bispecific, trispecific, or tetraspecific) antibody molecule.

25. The antibody molecule of any of paragraphs 1-24, which is a humanized antibody molecule.

26. The antibody molecule of any of paragraphs 1-25, comprising one or more framework regions derived from human framework germline sequence.

27. The antibody molecule of any of paragraphs 1-26, which is an IgG antibody.

28. The antibody molecule of any of paragraphs 1-27, comprising a heavy chain constant region of IgG chosen from IgG1, IgG2, IgG3, or IgG4.

29. The antibody molecule of any of paragraphs 1-28, comprising a light chain constant region of kappa or lambda light chain.

30. The antibody molecule of any of paragraphs 1-29, comprising an Fc region comprising one or more mutations to increase the binding affinity to neonatal receptor FcRn and/or the half-life of the antibody molecule.

31. The antibody molecule of any of paragraphs 1-30, comprising an Fc region comprising one or more mutations described herein, e.g., to increase one or more of half-life, ADCC, CDC, or ADCP.

32. An antibody molecule, which competes for binding to CD138 with an anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422).

33. An antibody molecule, which binds, or substantially binds, to an epitope that completely or partially overlaps with the epitope of an anti-CD138 monoclonal antibody described herein (e.g., any of antibodies 3820, 3821, 3826, 4221, 4226, 4320, 4321, 4322, 4326, 4421, 4520, 4521, 4526, 3522, 3621, 3822, 3825, or 4422).

34. An antibody-molecule drug conjugate (ADC) comprising an antibody molecule of any of paragraphs 1-33, optionally comprising a cytotoxic agent, further optionally comprising a linker.

35. A composition comprising an antibody molecule of any of paragraphs 1-33, or an ADC of paragraph 34, optionally, wherein the composition is a pharmaceutical composition.

36. The composition of paragraph 35, further comprising a pharmaceutically acceptable carrier.

37. A nucleic acid molecule encoding a heavy chain variable region (VH), a light chain variable region (VL), or both, of an antibody molecule of any of paragraphs 1-33.

38. A vector comprising a nucleic acid molecule of paragraph 37.

39. A cell comprising a nucleic acid molecule of paragraph 37 or a vector of paragraph 38, optionally, wherein the cell is an isolated cell.

40. A kit comprising an antibody molecule of any of paragraphs 1-33, an ADC of paragraph 34, or a composition of paragraph 35 or 36, and instructions to use of the antibody molecule or composition.

41. A container comprising an antibody molecule of any of paragraphs 1-33, an ADC of paragraph 34, or a composition of paragraph 35 or 36.

42. A method of producing an anti-CD138 antibody molecule, the method comprising culturing a cell of paragraph 33 under conditions that allow production of an antibody molecule, thereby producing the antibody molecule.

43. The method of paragraph 36, further comprising isolating or purifying the antibody molecule.

44. An antibody molecule of any of paragraphs 1-33, an ADC of paragraph 34, or a composition of paragraph 35 or 36, for use in a method of treating a cancer in a subject.

45. The antibody molecule, ADC, or composition for use of paragraph 44, wherein the cancer is a hematological cancer.

46. The antibody molecule, ADC, or composition for use of paragraph 44 or 45, wherein the cancer is a multiple myeloma.

47. The antibody molecule, ADC, or composition for use of paragraph 44, wherein the cancer is a solid tumor, e.g., a solid tumor described herein.

48. The antibody molecule, ADC, or composition for use of any of paragraphs 44-47, wherein the antibody molecule, ADC, or composition is administered to the subject intravenously.

49. The antibody molecule, ADC, or composition for use of any of paragraphs 44-48, wherein the antibody molecule, ADC, or composition is administered to the subject at a dose between 0.1 mg/kg and 50 mg/kg, between 0.2 mg/kg and 25 mg/kg, between 0.5 mg/kg and 10 mg/kg, between 0.5 mg/kg and 5 mg/kg, between 0.5 mg/kg and 3 mg/kg, between 0.5 mg/kg and 2.5 mg/kg, between 0.5 mg/kg and 2 mg/kg, between 0.5 mg/kg and 1.5 mg/kg, between 0.5 mg/kg and 1 mg/kg, between 1 mg/kg and 1.5 mg/kg, between 1 mg/kg and 2 mg/kg, between 1 mg/kg and 2.5 mg/kg, between 1 mg/kg and 3 mg/kg, between 1 mg/kg and 2.5 mg/kg, or between 1 mg/kg and 5 mg/kg.

50. The antibody molecule, ADC, or composition for use of any of paragraphs 44-49, wherein the antibody molecule, ADC, or composition is administered to the subject at a fixed dose between 10 mg and 1000 mg, between 10 mg and 500 mg, between 10 mg and 250 mg, between 10 mg and 150 mg, between 10 mg and 100 mg, between 10 mg and 50 mg, between 250 mg and 500 mg, between 150 mg and 500 mg, between 100 mg and 500 mg, between 50 mg and 500 mg, between 25 mg and 250 mg, between 50 mg and 150 mg, between 50 mg and 100 mg, between 100 mg and 150 mg. between 100 mg and 200 mg, or between 150 mg and 250 mg.

51. The antibody molecule, ADC, or composition for use of any of paragraphs 44-50, wherein the antibody molecule, ADC, or composition is administered once a week, twice a week, once every two weeks, once every three weeks, or once every four weeks.

52. The antibody molecule, ADC, or composition for use of any of paragraphs 44-51, further comprising determining the level of CD138 in a sample from the subject.

53. The antibody molecule, ADC, or composition for use of any of paragraphs 44-52, further comprising administering to the subject a second therapy for cancer.

54. An antibody molecule of any of paragraphs 1-33, an ADC of paragraph 34, or a composition of paragraph 35 or 36, for use in a method of treating a precancerous condition or preventing a cancer.

55. The antibody molecule, ADC, or composition for use of paragraph 54, wherein the precancerous condition is smoldering myeloma or monoclonal gammopathy of undetermined significance (MGUS).

56. The antibody molecule, ADC, or composition for use of paragraph 54, wherein the cancer is multiple myeloma.

57. A method of causing an ADCC activity, the method comprising contacting a cell or subject an antibody molecule of any of paragraphs 1-33, an ADC of paragraph 34, or a composition of paragraph 35 or 36, thereby causing the ADCC activity.

58. A method of treating a cancer, the method comprising administering to a subject in need thereof an effective amount of an antibody molecule of any of paragraphs 1-33, an ADC of paragraph 34, or a composition of paragraph 35 or 36, thereby treating the cancer.

59. A method of treating a precancerous condition or preventing a cancer, the method comprising administering to a subject in need thereof an effective amount of an antibody molecule of any of paragraphs 1-33, an ADC of paragraph 34, or a composition of paragraph 35 or 36, thereby treating the precancerous condition or preventing the cancer.

60. A method of detecting an anti-CD138 molecule, the method comprising contacting a cell or a subject with an antibody molecule of any of paragraphs 1-33, thereby detecting the CD138 molecule.

61. The method of paragraph 60, wherein the antibody molecule is coupled with a detectable label.

62. The method of paragraph 60 or 61, wherein the CD138 molecule is detected in vitro, ex vivo, or in vivo.

63. The antibody molecule, ADC, or composition for use of any of paragraphs 44-56, or the method of paragraph 58 or 59, wherein the antibody molecule is used or administered in combination with a second therapeutic agent or modality.

64. The antibody molecule, ADC, or composition for use of paragraph 63, or the method of paragraph 63, wherein the second therapeutic agent or modality comprises a proteasome inhibitor.

65. The antibody molecule, ADC, or composition for use of paragraph 64, or the method of paragraph 64, wherein the proteasome inhibitor comprises bortezomib.

EXAMPLES

Example 1: Humanized Anti-CD138 Antibody Variants

In this example the variable regions of the mouse chimeric anti-CD138 antibody 2810 were humanized for purposes of potential therapeutic use, mitigation of immunogenicity, improvement of biophysical, physicochemical, and pharmaceutical properties and higher recombinant expression in mammalian cell lines used for purposes of antibody production. While immunogenicity is a multifaceted and complex phenomenon, in general for the purposes of humanization, constructs are designed to have the fewest number of changes from a functional human germline in order to most closely resemble a human-derived antibody. Humanization of mAb 2810 was otherwise carried out with the aim of retention of antibody properties of mAb 2810 as described herein and in PCT Publication No. WO 2019/070726 or U.S. Patent Application Publication No. US 2019/0100588 (each of which is incorporated herein by reference in its entirety). Such antibody properties pertained to, but were not limited to, target binding, effector function, cellular cytotoxicity and epitope engagement. In brief, humanization was performed by identifying human germlines proximal to mouse variable heavy (VH) and variable light (VL) sequences. Once identified, the complementarity determining regions (CDRs) from mAb 2810 VH and VL were grafted on to the human VH and VL germline templates respectively using structure-guided design. Additional mutations (including back mutations to the parental residue in the mouse mAb) were selectively introduced based on visual inspection of the structural model. Additional methods were incorporated as appropriate.

The DNA sequences corresponding to the variable regions of these humanized antibody variants and based on these protein designs were chemically synthesized following codon optimization suited for expression in either human and rodent cell lines. Variable regions were cloned into mammalian expression vector pcDNA 3.4 (Thermo Fisher Scientific) using standard molecular cloning methods for construction of recombinant vectors. These vectors included the requisite genetic, translational, and protein signaling elements suitable for the synthesis and secretion of functional monoclonal antibodies following transient or stable transfection of these vectors in mammalian cells such as HEK293 or Chinese Hamster Ovary. In this example, humanized variants of mAb 2810 were produced by the transient co-transfection of separate vectors separately encoding heavy chain (HC) and light chains (LC) for production as full length, human IgG1 kappa antibodies in EXPICHO (Chinese hamster ovary cells) as secreted proteins. DNA transfection was typically performed using lipid-based transfection reagents (e.g., ExpiFectamine CHO Transfection Kit, Thermo Fisher Scientific) and standard protocols as generally recommended by the manufacturer. Cell culture was completed in shake flasks for a period varying between 7-10 days. Secreted antibody was harvested from spent culture media by centrifugation followed by further clarification and sterilization by membrane filtration. Monoclonal antibodies were subsequently purified from cell culture media using protein A affinity capture on Fast Protein Liquid chromatography (FPLC) in accordance with established protocols for the purification of recombinant antibodies. Humanized anti-CD138 antibodies were produced under conditions designed to modify antibody Fc glycosylation, in particular, the reduction of core fucose in the respective N-glycans at position N297, and for the purpose of enhancing Fc-mediated ADCC activity, e.g., as described herein. The absence or substantial reduction of IgG-Fc core fucose vastly increases binding to Fcγ RIII, the Fc receptor present on myeloid and NK cells, thereby improving the efficacy of therapeutic antibodies with respect to Fc mediated effector function such as ADCC mediated by NK cells. Several methods for glycoengineering of cell lines for such a purpose include, for example, genetic approaches (e.g., knockdown or silencing of the alpha 1,6 fucosyltransferase 8, a key cellular enzyme in the glycosylation pathway responsible for the addition of fucose) or metabolic approaches (e.g., transfection of bacterial enzyme GDP-6-deoxy-D-lyxo-4-hexulose reductase (RMD) to block the de novo production of fucose). An alternative method to decrease fucosylation in the Fc regions of IgG involves the use of the decoy substrate 2-deoxy-2-fluoro-1-fucose (2FF). Addition of 2FF to the culture media has been shown to result in reduced incorporation of fucose in the IgG-Fc glycan down to levels less than 20%. In this example, 2FF was added concurrently to the culture media at 0.15 mM at one hour following transient transfection of antibody LC and HC vectors.

Antibody Binding to Membrane CD138 Expressed on a CD138+ Multiple Myeloma Cell Line In one experiment, the humanized variants of monoclonal antibody 2810 were assessed for their capacity to bind to CD138 on the surface of cells. Briefly, the humanized variants of antibody 2810 were produced in HEK 293 cells following transient transfection. The antibodies were then serially diluted three-fold. Antibody binding to membrane CD138 was evaluated using the CD138+ human lymphoblastic myeloma cell line U266 and quantified by flow cytometry. Antibody cell binding was reported as geometric mean fluorescence intensity (MFI). Binding data were plotted using nonlinear regression analysis and a 4-parameter curve fit. As shown in FIG. 1, the humanized variants of antibody 2810 showed dose-dependent binding to CD138+ multiple myeloma cells. The observed binding for the humanized variants was comparable to that observed for the parental 2810 antibody.

ADCC Bioassay

In another experiment, the ADCC activity of the humanized variants of anti-CD138 antibody 2810 was assessed. Briefly, the humanized variant antibodies were produced by transient transfection of HEK 293 cells metabolically altered for purposes of reduced Fc fucosylation. The antibodies were then evaluated for antibody dependent cellular cytotoxicity (ADCC) activity against CD138$^+$ human lymphoblastic myeloma U266 cells in a luciferase based ADCC reporter assay using, as effector cells, engineered Jurkat cells stably transfected with the human FcγRIIIa receptor. U266 cells were incubated with mAbs that were 3-fold serially diluted from a starting concentration of 3 μg/mL and added to effector cells and CD138+U266 multiple myeloma target cells at a cell ratio of effector:target of 10:1. After 16-hour incubation at 37° C., luciferase activity was assessed as a measure of ADCC activity and reported as relative luminescence units (RLU). ADCC data were plotted using nonlinear regression analysis and a 4-parameter curve fit. As shown in FIG. 2, the humanized anti-CD138 antibody variants induced substantial ADCC activity, comparable to that exhibited by antibody 2810.

Example 2: Further Characterization of Humanized Anti-CD138 Variants

In this example, a subset of the humanized variants of anti-CD138 antibody 2810 were further examined for binding to and induction of ADCC in a set of multiple myeloma cell lines.

Figure 3A:
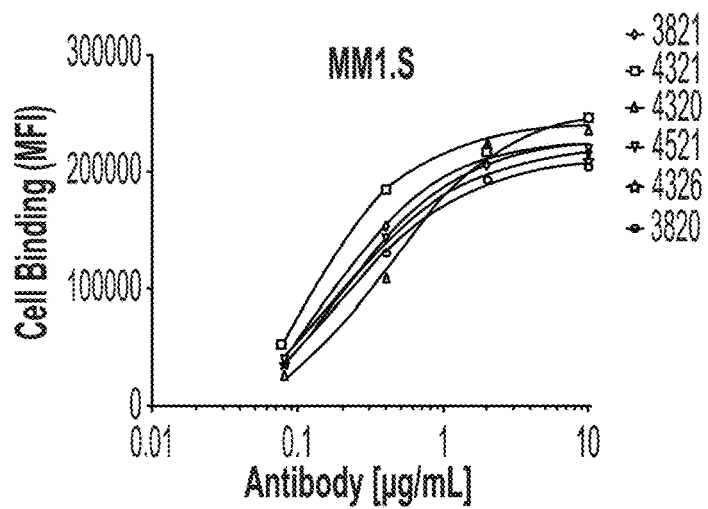
FIGS. 3A-3C are a series of graphs showing dose-dependent binding of humanized anti-CD138 antibodies to three multiple myeloma cell lines: MM1.S, LP-1, and RPMI 8226.
Figure 3B:
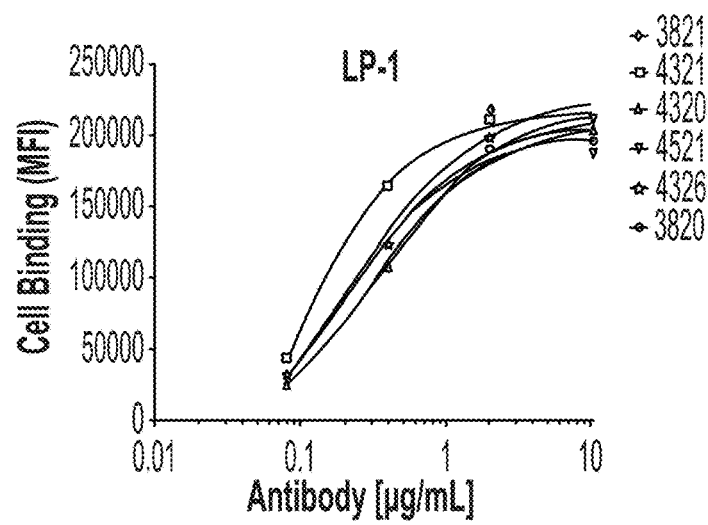
Figure 3C:
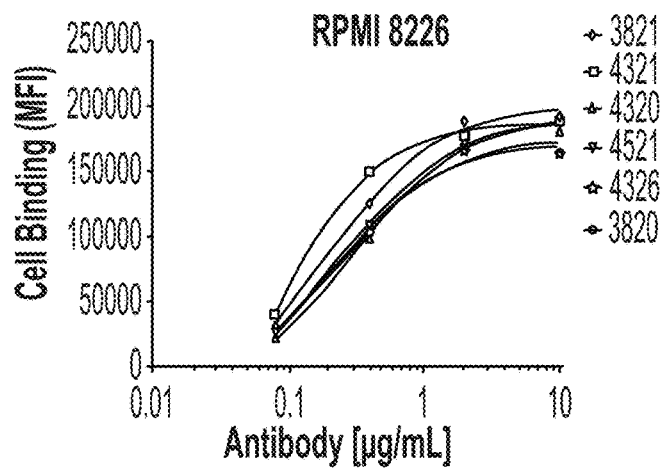
Figure 4A:
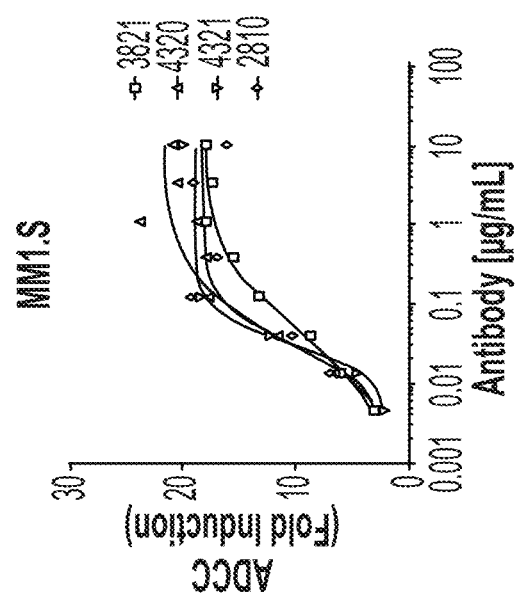
FIGS. 4A-4D are a series of graphs showing that humanized anti-CD138 antibodies induced ADCC in four multiple myeloma cell lines: U266, MM1.S, LP-1, and RPMI 8226.
Figure 4B:
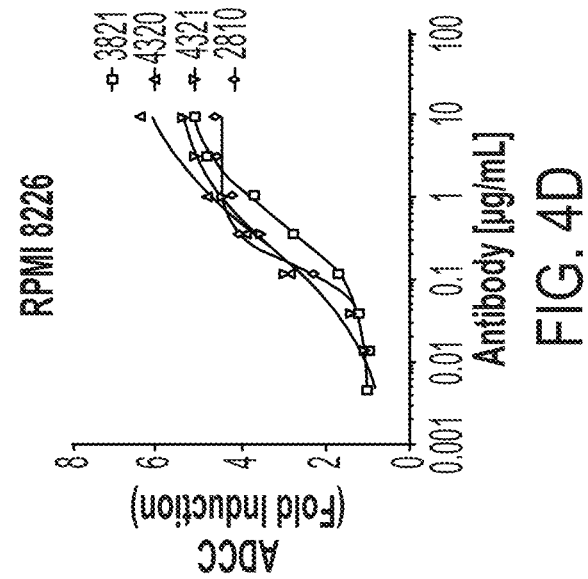
Figure 4C:
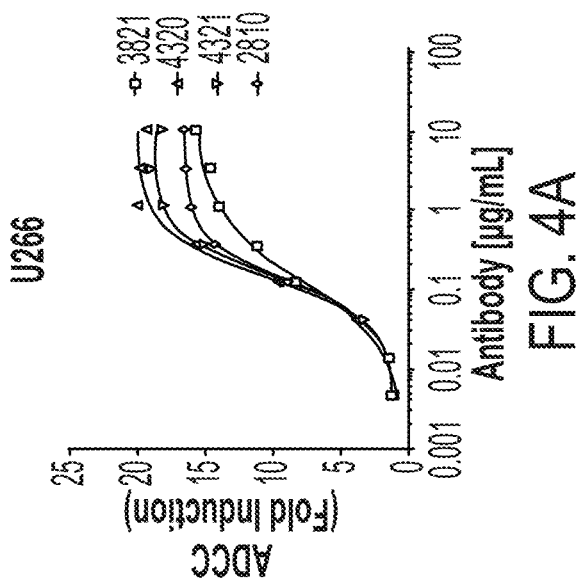
Figure 4D:
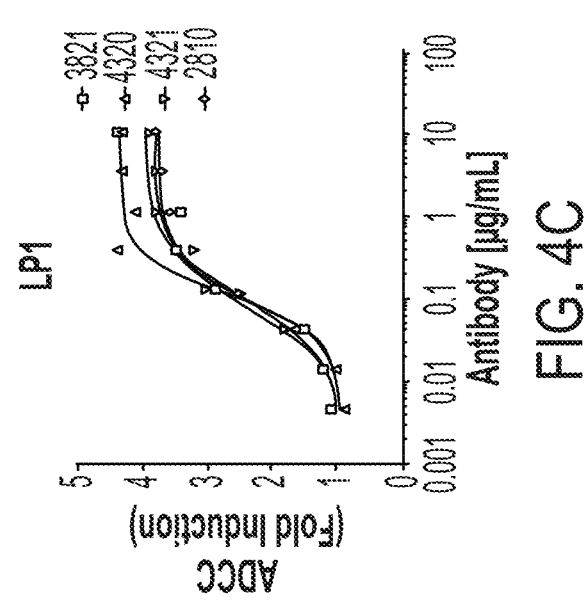

First, humanized anti-CD138 antibody variants 3821, 4321, 4320, 4521, 4326, and 3820 were evaluated for binding to three different CD138+ multiple myeloma related cell lines: MM1.S, LP-1, and RPMI 8226. Antibody binding was measured by flow cytometry as described in Example 15. As shown in FIGS. 3A-3C, the humanized anti-CD138 antibody variants showed dose-dependent binding to each of the three multiple myeloma cell lines.

Second, humanized anti-CD138 antibody variants 3821, 4321, 4320, 4521, 4326, and 3820 were assessed for ADCC activity against U266, MM1.S, LP-1, and RPMI 8226 CD138$^+$ multiple myeloma cell lines using a luciferase based ADCC reporter assay, as described in Example 15. CD138$^+$ target cells were incubated with anti-CD138 antibodies that were serially diluted 3-fold starting at a concentration of 10 μg/mL, and subsequently added to FcγRIIIa effector cells at a cell ratio of effector:target cell (E:T of 10:1). After a 16 hour incubation at 37° C., cellular luciferase levels were quantified as a measure of ADCC activity and reported as relative luminescence units (RLU). As shown in FIGS. 4A-4D, the humanized anti-CD138 antibody variants induced ADCC activity in each of the four multiple myeloma cell lines.

Example 3: In Vivo Efficacy Study of Anti-CD138 Antibody

Figure 5B:
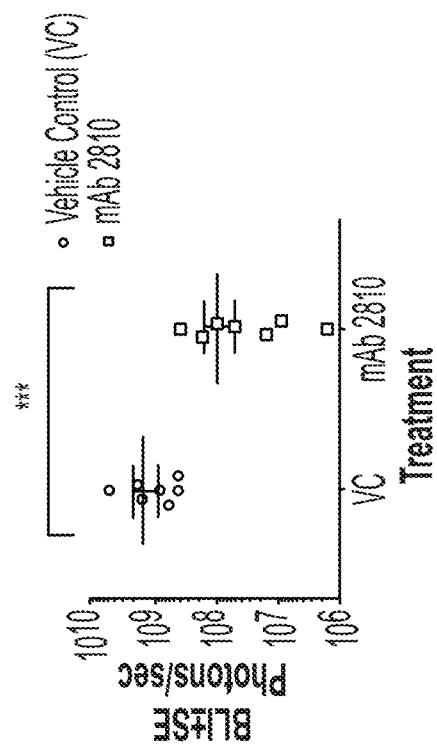
FIGS. 5A-5D are a series of graphs showing in vivo efficacy of monoclonal anti-CD138 antibody 2810. Mean BLI±95% CI of disseminated multiple myeloma tumors quantification from IVIS imaging at specific time points are shown (FIG. 5A). Statistics comparing treatment groups by multiple t-test (Bonferroni-Dunn). Comparison of whole body tumor burden in individual mice in vehicle and mAb 2810 groups (mean plus min max is also shown) (FIG. 5B). Bioluminescence (BLI) of tumor burden in ex vivo imaged skeletal tissues on day 42 post-sacrifice in spine (FIG. 5C) and hind limbs (FIG. 5D). Statistics determined by unpaired t-test. BLI data are plotted on a logarithmic scale.
Figure 5D:
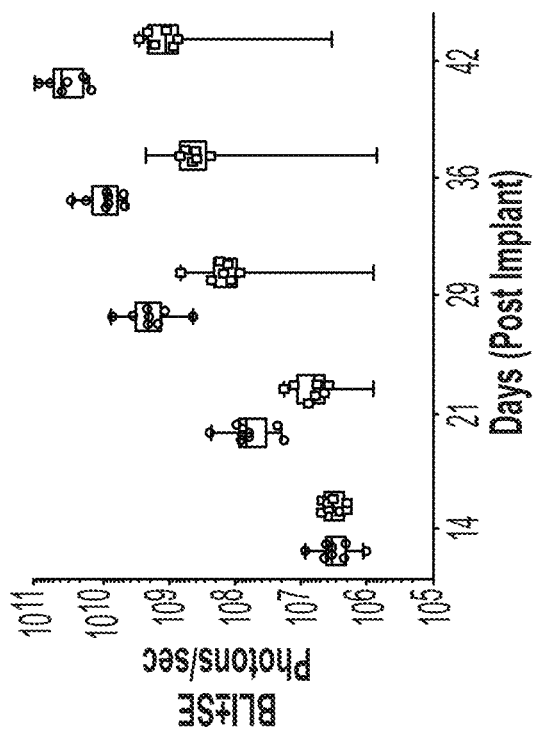
Figure 5A:
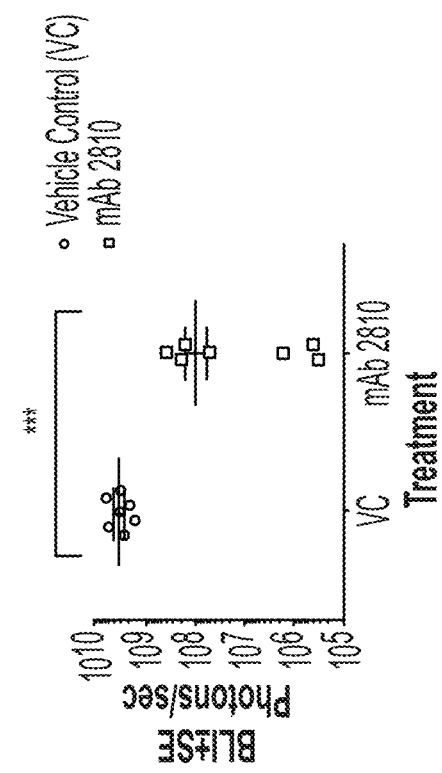
Figure 5C:
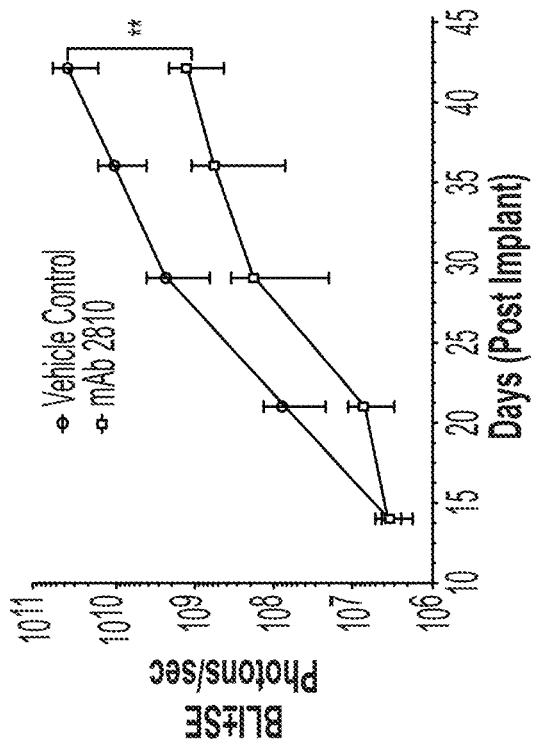

In this example, the in vivo efficacy of monoclonal anti-CD138 antibody 2810 was assessed using a mouse xenograft multiple myeloma model. Briefly, the in vivo efficacy of mAb 2810 was determined in the MM1.S dissemination model in CB17 SCID mice. 4-6 week old mice were injected intravenously with 5.00E+06 MM1.S cells on day 0 and staged for dosing on day 14 (N=8 animals per group) after normalizing the tumor volume between the groups. Monoclonal antibody 2810 was dosed intraperitoneally (Q3Dx2; 3 off) four times at a 4.0 mg/kg dose level, and tumor volume was assessed by bioluminescence once weekly. FIGS. 5A-5B shows the mean BLI±SEM of tumors determined from IVIS imaging at specific time points shown (FIG. 5A), comparison of tumor growth in individual mice in vehicle and mAb2810 groups (FIG. 5B). The effect of anti-CD138 antibody treatment on reduction of myeloma tumor burden in skeletal tissues was also tested. Quantification of tumor volume in ex vivo imaged tumors on Day 42 post euthanasia for spine and hind limbs (FIGS. 5C and 5D, respectively) in both groups.

Example 4. In Vivo Efficacy Study of Humanized Anti-CD138 Antibody

In this example, the in vivo efficacies of humanized monoclonal humanized anti-CD138 antibodies mAb 4320 and 2810 was assessed using a mouse xenograft multiple myeloma model likewise described in Example 3 using bioluminescence imaging (BLI) of luciferase-expressing, human multiple myeloma tumor cell line MM1.S (Luc). Bioluminescence imaging (BLI) allows for a noninvasive determination of site-localized tumor burden. The quantity of emitted light from the tumor after systemic injection of D-luciferin was calibrated to correlate with viable tumor burden. 5-6 week old mice were injected intravenously with 5.0E+06 trypan-excluding MM1.S (Luc) cells on day 0 and staged for dosing on day 14 after normalizing the tumor volume between the groups set by BLI as 2.39E+07p/s (range of group means, 2.35-2.43E+07p/s). The mice (N=8 per group) were distributed to ensure that the mean whole-body tumor burden for all groups was within 10% of the overall mean whole body tumor burden for the study population. For this study, in vivo BLI images were acquired on days 14, 21, 28, 35 and 42.

Anti-CD138 antibodies were dosed intraperitoneally twice weekly (Q3Dx2; 3 off) for five weeks. Study groups included vehicle (PBS), likewise dosed twice weekly by i.p. injection (0.2 mL). mAb 2810 was dosed at a single dose level of 4.0 mg/kg, while humanized mAb 4320 was variably dosed at 4, 8, or 16 mg/kg. BLI was performed using an IVIS Lumina S5 (PerkinElmer, MA). Animals were imaged five at a time under 1-2% isoflurane gas anesthesia. Each mouse was injected IP with 150 mg/kg (15 mg/ml) D-luciferin and imaged in the prone then supine positions 10 minutes after the injection. Large binning of the CCD chip was used, and the exposure time was adjusted (5 seconds to 2 minutes) to obtain at least several hundred counts per image and to avoid saturation of the CCD chip.

Images were analyzed using Living Image 4.3.1 (PerkinElmer, MA) software. Whole body fixed-volume regions of interest were placed on prone and supine images for each individual animal and labeled based on animal identification. The prone and supine images were summed together to estimate whole body tumor burden.

Figures 6A, 6B:
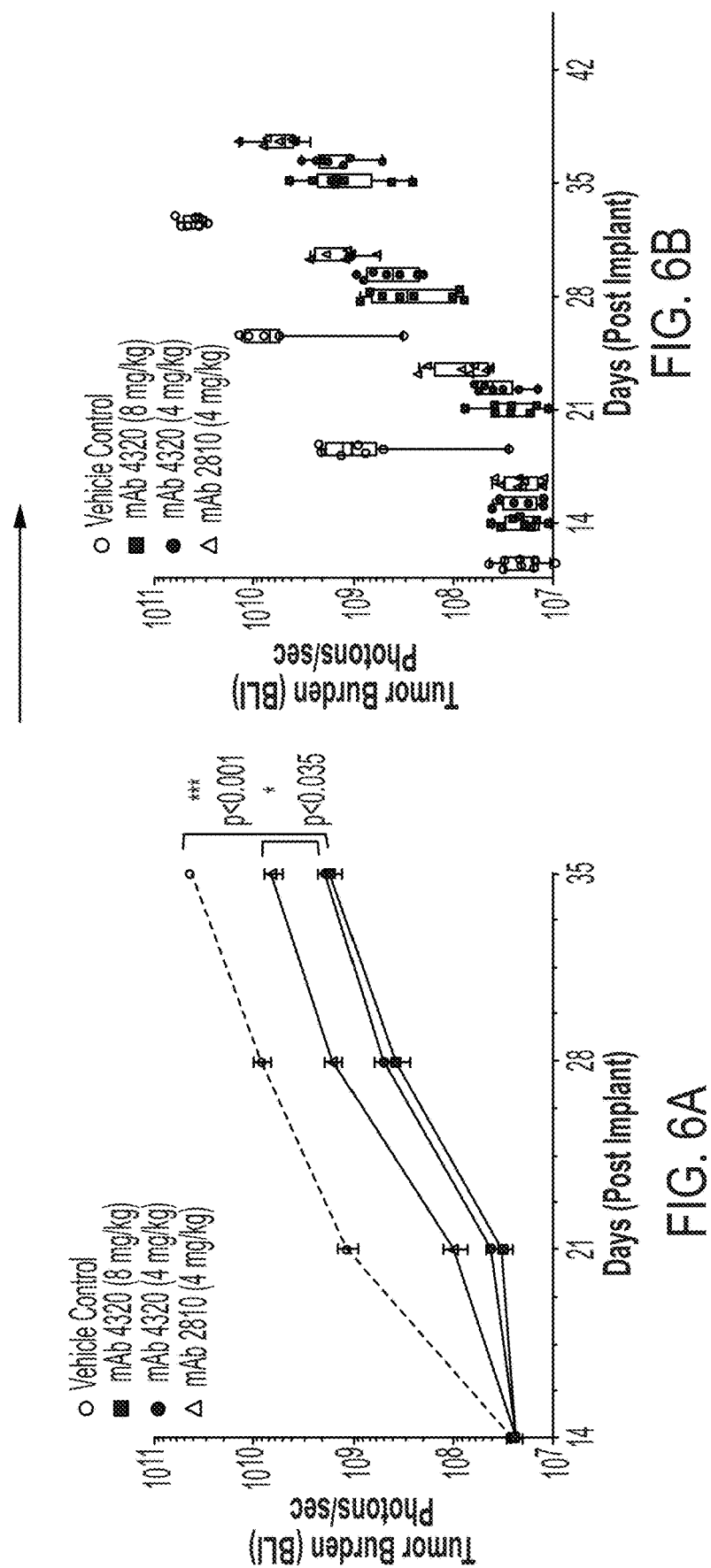
FIGS. 6A-6C are a series of graphs showing in vivo efficacy of monoclonal anti-CD138 antibodies. Mean BLI±standard error of the means of disseminated multiple myeloma tumors quantified from IVIS imaging at specific time points and dose levels are shown (FIG. 6A). Statistical analysis by 2-way ANOVA (Tukey's multiple comparison). Comparison of whole body tumor burden in individual mice in vehicle control humanized anti-CD138 antibody mAb 4320, and mouse chimeric anti-CD138 mAb 2810 treatment groups (FIG. 6B). Mean plus min max is also shown with median values depicted as a bar. BLI data is plotted on a logarithmic scale. Percent survival of animals in vehicle group vs animals treated with anti-CD138 antibodies mAb 2810 and 4320 (FIG. 6C). Percent survival is defined as mice surviving to predetermined euthanasia criteria related to disease-related morbidity such as weight loss greater than 20%, severely impaired CNS function or severely impaired movement or loss of righting reflexes. Log rank test (Mantel-Cox) was used for comparison of survival curves (VC vs. animals treated with anti-CD138 antibodies).
Figure 6C:
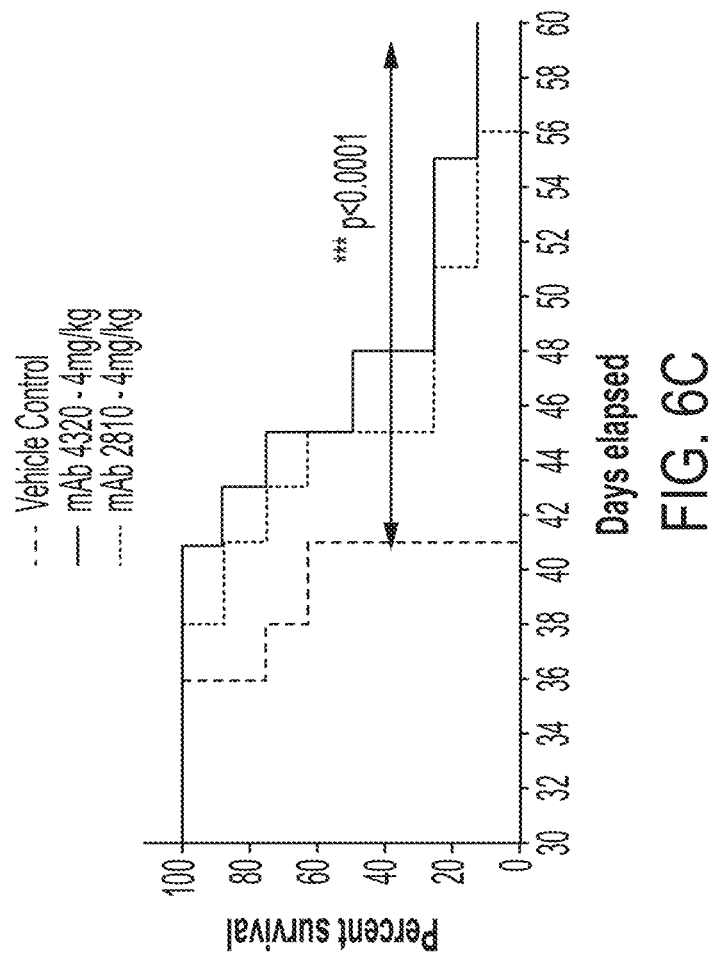

FIGS. 6A-6B summarize the Mean BLI±standard error of the means of disseminated multiple myeloma tumors quantification from IVIS imaging at specific time points and dose levels shown. Efficacy of treatment with antibody mAb 4320 was observed in comparison to animals in the control group receiving vehicle only based on statistical analysis (p<0.001, 2-way ANOVA). Treatment with mAb 4320 did not demonstrate a dose dependency, even at the highest dose level of 16 mg/kg, suggesting a sufficient dose exposure at 4 mg/kg in this study. In this analysis, treatment with humanized anti-CD138 antibody mAb 4320 resulted in a discernibly lower tumor burden and higher efficacy in comparison to mouse-human chimeric anti CD138 antibody mAb 2810. Comparison of whole body tumor burden in individual mice in vehicle, humanized anti-CD138 antibody mAb 4320, and mouse chimeric anti-CD138 mAb 2810 treatment groups is shown in FIG. 6B. FIG. 6C summarizes percent survival of animals in vehicle group versus animals treated with anti-CD138 antibodies mAb 2810 and 4320. Percent survival was defined as mice surviving to a predetermined euthanasia criterium related to disease-related morbidity, defined as weight loss greater than 20%, severely impaired CNS function, or severely impaired movement or loss of righting reflexes. Related aspects of treatment efficacy such as increased life span, overall survival, and time to evaluation (as defined by time to reach tumor burden of 1.00E+09 p/s BLI units) based in treatment of animals with humanized anti-CD138 mAb 4320 relative to vehicle control group were established.

Figure 7:
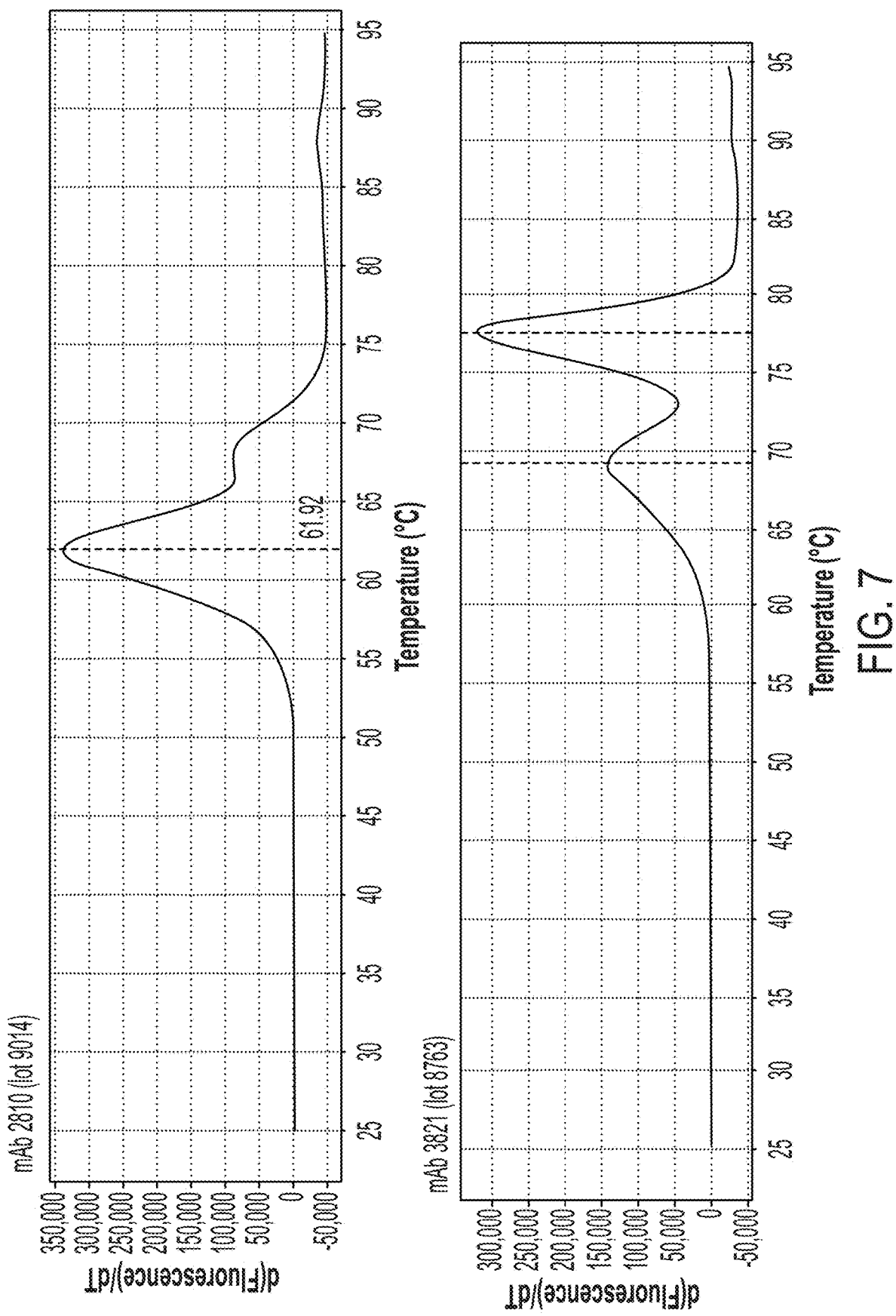
FIG. 7 are a series of graphs evaluating the thermal stabilities of anti-CD138 antibodies as analyzed by differential scanning fluorescence (DSF). Thermal melting profiles are displayed as first derivative transformations (d(fluorescence)/d(temperature)) of thermal scans. Thermal transitions (Tm1 and Tm2) are noted by vertical lines and are summarized in Table 4.
Figure 7:
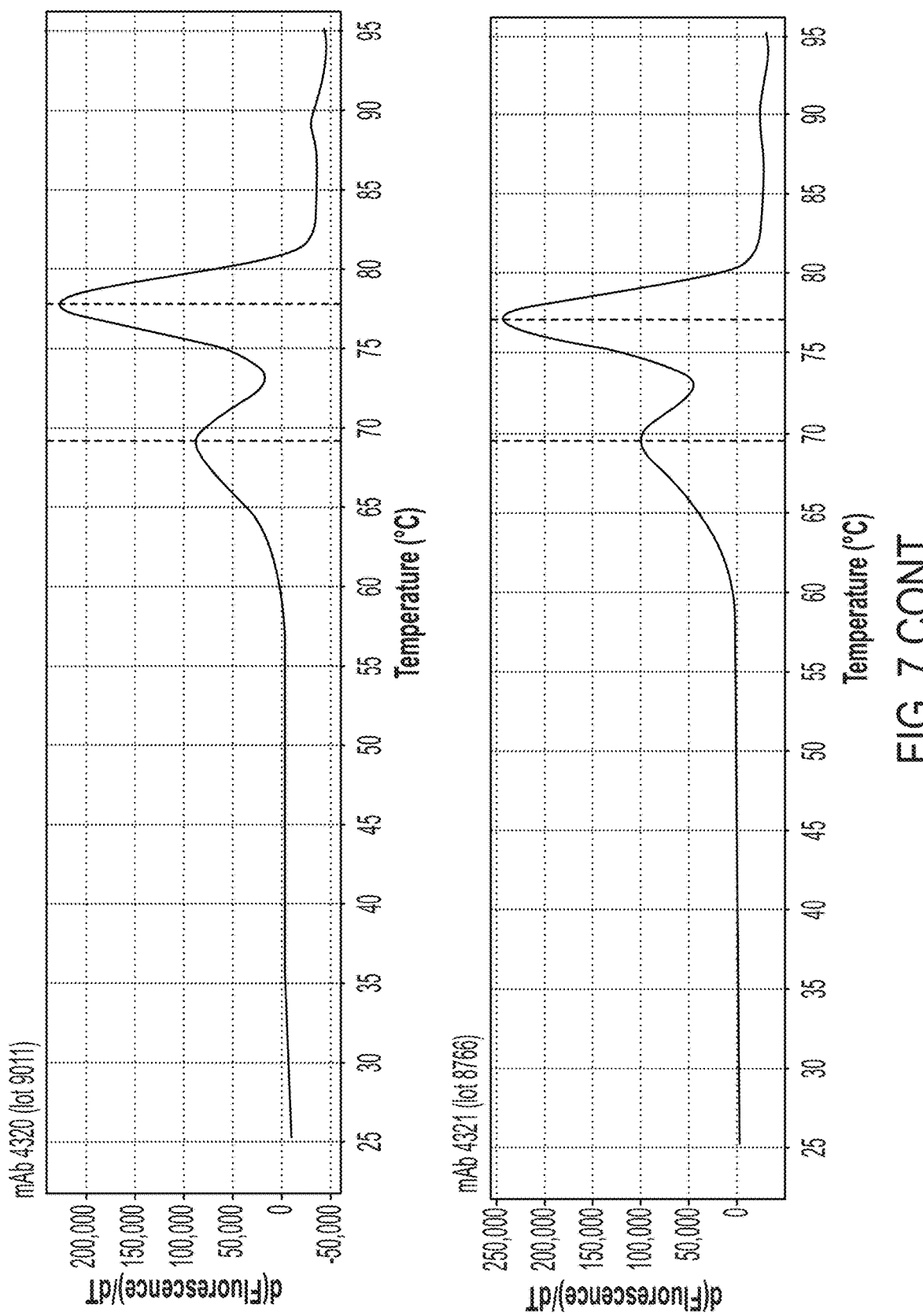

Example 5. Evaluation of Biophysical and Pharmacokinetic Properties of Humanized Anti-CD138 Antibodies Differential Scanning Fluorescence Assay for Determining Antibody Thermal Stability Thermal stability represents an important property of antibodies and is used as a predictive surrogate of pharmaceutical drug stability in humans based on a relative stability profile as characterized by differential thermal melting profiles. Several methods exist for evaluation of product stability based on thermal melting. These include, for example, circular dichroism (CD), differential scanning calorimetry (DSC), and differential scanning fluorescence (DSF), among others. In this example, the thermal stabilities of select humanized anti-CD138 antibodies were evaluated by DSF. DSF was used to monitor the conformational stability of a protein as it was exposed to increasing thermal stress. The dye, SYPRO Orange®, fluoresces in a hydrophobic environment, such as hydrophobic core residues that are exposed during thermally triggered protein unfolding, or denaturation. In brief, SYPRO® Orange Dye (Sigma Chemical) was diluted 1:500 in phosphate buffered saline (PBS), pH 7.4, without addition of any detergents. Antibodies were likewise diluted in PBS to a target concentration of 0.5 mg/mL. 15 μl of diluted antibody and fluorescent dye were added 1:1 (v/v) into a 96 well microtiter plate and thoroughly mixed by repeat pipetting. Thermal scans were carried out using a real-time quantitative PCR (qPCR) thermal cycler with fluorescence detection capabilities. Scans were initiated at 25° C. with incremental increase in well temperature of 1° C. ramp/minute from 25° C. to 95° C. The mid-point (Tm) between native state and the first unfolding event was reported as the transition temperature or melt temperature ($T_M$). $T_M$s were then calculated based on transformation of the data using the first derivative of the fluorescence signal versus time. (dfluoresence/dtime) (FIG. 7). These analyses typically resulted in two thermal transitions reported as $T_M 1$ and $T_M 2$ and corresponding to the local denaturation of Fab and IgG-Fc domains, respectively (Table 4).

TABLE 4

Thermal stability of exemplary anti-CD138 monoclonal antibodies as measured by DSF

| Antibody ID | Lot no. | $T_M 1$ (° C.) | $T_M 2$ (° C.) |
|---|---|---|---|
| 2810 | 9014 | 61.9 | — |
| 3821 | 8763 | 69.1 | 77.7 |
| 4320 | 9013 | 68.9 | 77.7 |
| 4321 | 8766 | 69.3 | 76.9 |

Antibody Pharmacokinetics in Transgenic Tg276 Mice

In addition to changes in relative thermal stabilities of anti-CD138 antibodies that was observed in the process of humanizing mAb 2810, improvement in the biophysical properties of therapeutic antibodies can also result in improved in vivo properties such as pharmacokinetics (PK). In this example, the relative serum titer profiles of 8 humanized anti-CD138 antibodies were evaluated in mice suing the human FcRn transgenic mouse strain (Tg276). Such a transgenic mouse model has been described as a reasonable surrogate for predicting antibody PK profiles based on the transgenic expression of human FcRn, the receptor critically promoting antibody half-life extension through receptor mediated recycling. It can minimally serve as a valuable in vivo tool for assessing the relative PK properties of various antibodies comparatively measured in such a model.

Figure 8:
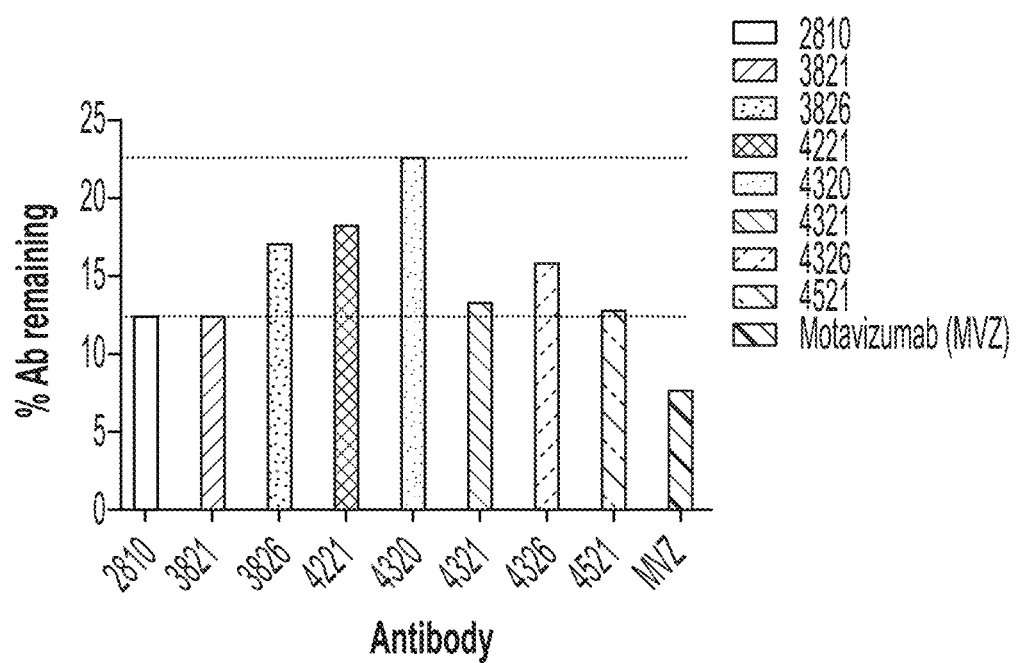
FIG. 8 is a graph showing the relative levels of anti-CD138 antibodies in mouse sera administered as a single dose in transgenic human FcRn hemizygous mouse strain Tg 276. Anti-CD138 monoclonal antibodies were administered intravenously by tail vein injection at a 2.5 mg/kg dose level. Antibody titers from serum samples taken at approximately 65 hours post-injection were determined by ELISA (for detection of human IgG1 Fc) and plotted as percentage of antibody remaining normalized to serum antibody titers measured at an earlier (one hour) post-dosing time point. Levels of chimeric antibody mAb2810 (white bar) and humanized anti-CD138 mAb 4320 (black bar) are noted by dotted lines. Motavizumab, MVZ), an anti-RSV antibody is also included in this analysis for comparative purposes.

In this example, humanized CD138 antibodies were produced in HEK 293 (EXPI 293, Thermo Fisher Scientific) with the inclusion of decoy substrate 2-deoxy-2-fluoro-1-fucose (2FF) to greatly reduce core fucosylation as described in Example 1. Anti-RSV monoclonal antibody motavizumab (MVZ) and parental anti-CD138 antibody mAb 2810 were used for comparative purposes. MVZ was produced separately in HEK 293 without the inclusion of 2FF resulting in normally fucosylated Fc glycans. Antibodies were administered intravenously through tail vein injections. Experimental design included 50 μg dose levels (approximately 2.5 mg/kg), 3 mice/group. Serum samples were processed using standard protocols and following blood collection at approximately 1-hour and 65-hour intervals. Serum levels of human IgG were subsequently quantified by ELISA using the Human IgG Quantitative ELISA Kit (Bethyl Labs) which included affinity purified goat anti-human IgG-Fc coating antibody (for capture) and HRP-conjugated goat secondary anti-human IgG antibody for human IgG-Fc detection. Human reference serum was used for quantification and as an assay control. Serum antibody levels at 65 hours were normalized to the first one-hour time point and reported as percentage of antibody remaining based on OD values (FIG. 8). Based on this analysis, humanized anti-CD138 mAb 4320 was detected at approximately 2-fold higher concentration than parental antibody mAb 2810 under the conditions tested.

Antibody Production Titers in Chinese Hamster Ovary Cell Line

In addition to differential thermal stability and PK profiles, anti-CD138 antibodies mAb 2810 (non-humanized) and mAb 4320 (humanized) exhibited differential production titers when produced in CHO cells. Comparative evaluation of production yields for the two antibodies are listed in Table 5. The yields represent antibody amounts following purification from cell culture media by Protein A affinity chromatography, carried out under identical transfection conditions and culture scale. Differential pre-purification titers based on quantification using Protein-A biosensors (bio-layer interferometry) of antibody in culture media was also noted likewise indicating differential expression levels (antibody titers).

TABLE 5

Expression Levels of anti-CD138 antibodies

| Antibody ID | Lot no. | Expression (mg/L) |
|---|---|---|
| 4320 | 9013 | 106.4 |
| 2810 | 9014 | 30.2 |

Example 6: Study of Comparative CD138 Binding and Effector Function of Anti-CD138 Antibodies Antibody Binding to Membrane CD138 Expressed on a CD138+ Multiple Myeloma Cell Line U266

Figure 9A:
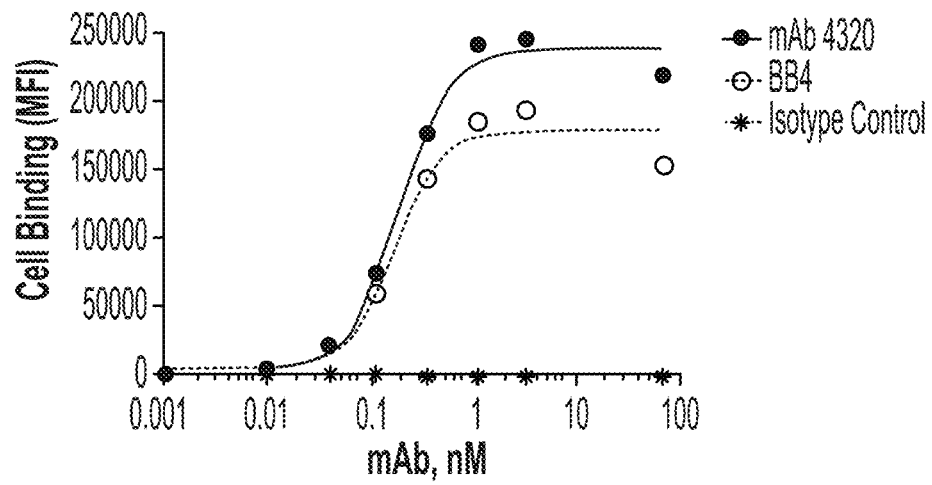
FIGS. 9A-9B are a series of graphs showing comparative dose-dependent cell binding and Fc effector mediated ADCC activities of humanized antibody mAb 4320 and reference antibody BB4. Cell binding to human lymphoblastic cell line U266 (expressing CD138) as measured by flow cytometry (FIG. 9A). Antibody binding to cell surface CD138 is quantified as mean fluorescence intensity. ADCC activity measured using Jurkat reporter bioassay with human FcγIIIa transgene as effector cells (FIG. 9B). Data are normalized as fold-induction relative to minus antibody control.

Humanized anti-CD138 antibody 4320 was compared to the well characterized anti-CD138 monoclonal antibody BB4 used herein as a reference. In one experiment, humanized anti-CD138 mAb 4320 and BB4 were assessed for their relative capacity to bind to CD138 on the surface of CD138+ human lymphoblastic myeloma cell line U266 and quantified by flow cytometry using methods as described in Example 1. Antibody cell binding was reported as geometric mean fluorescence intensity (MFI). Binding data were plotted using nonlinear regression analysis and a 4-parameter curve fit. As shown in FIG. 9A, both anti-CD138 antibodies showed dose-dependent binding to CD138+ multiple myeloma cells with comparable binding affinities based on similar $EC_{50}$ values. Total cell surface binding of mAb 4320 to membrane associated CD138 based on maximal MFI values was approximately 25% greater relative to antibody BB4 as concurrently measured in this assay.

ADCC Bioassay

Figure 9B:
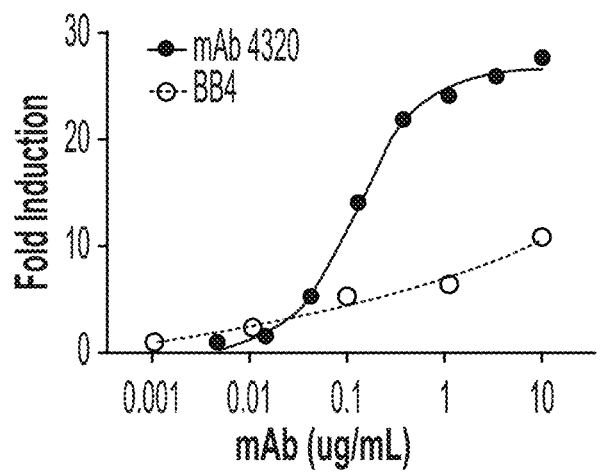

While mAb 4320 and BB4 would appear to have similar CD138 binding profiles based on cell surface staining by flow cytometry, the epitope engagement for the two antibodies is predicted to be differentiated based on the respective biological activities and properties of BB4 in comparison to mAb 2810. In this experiment, the relative antibody dependent cellular cytotoxicity (ADCC) activities of mAb 4320 and BB4 were evaluated. Briefly, the two antibodies were evaluated for ADCC activity against CD138+ human lymphoblastic myeloma U266 cells in a luciferase based ADCC reporter assay using, as effector cells, engineered Jurkat cells stably transfected with the human FcγRIIIa receptor as described in Example 1. This comparison is summarized in FIG. 9B with data normalized as fold-induction of ADCC activity relative to the minus antibody control. The humanized anti-CD138 antibody mAb 4320 induced substantial ADCC activity; in comparison, anti-CD138 antibody BB4 exhibited only modest ADCC activity observed only at the highest antibody concentrations tested. These data show clearly differentiated Fc effector mediated activities of these two anti-CD138 antibodies, but also point to differentiated epitopes and modes of paratope-target engagement for these antibodies, which would be expected to influence this activity.

Binding to CD138 Extracellular Domain and Derivative Peptides

Figure 10:
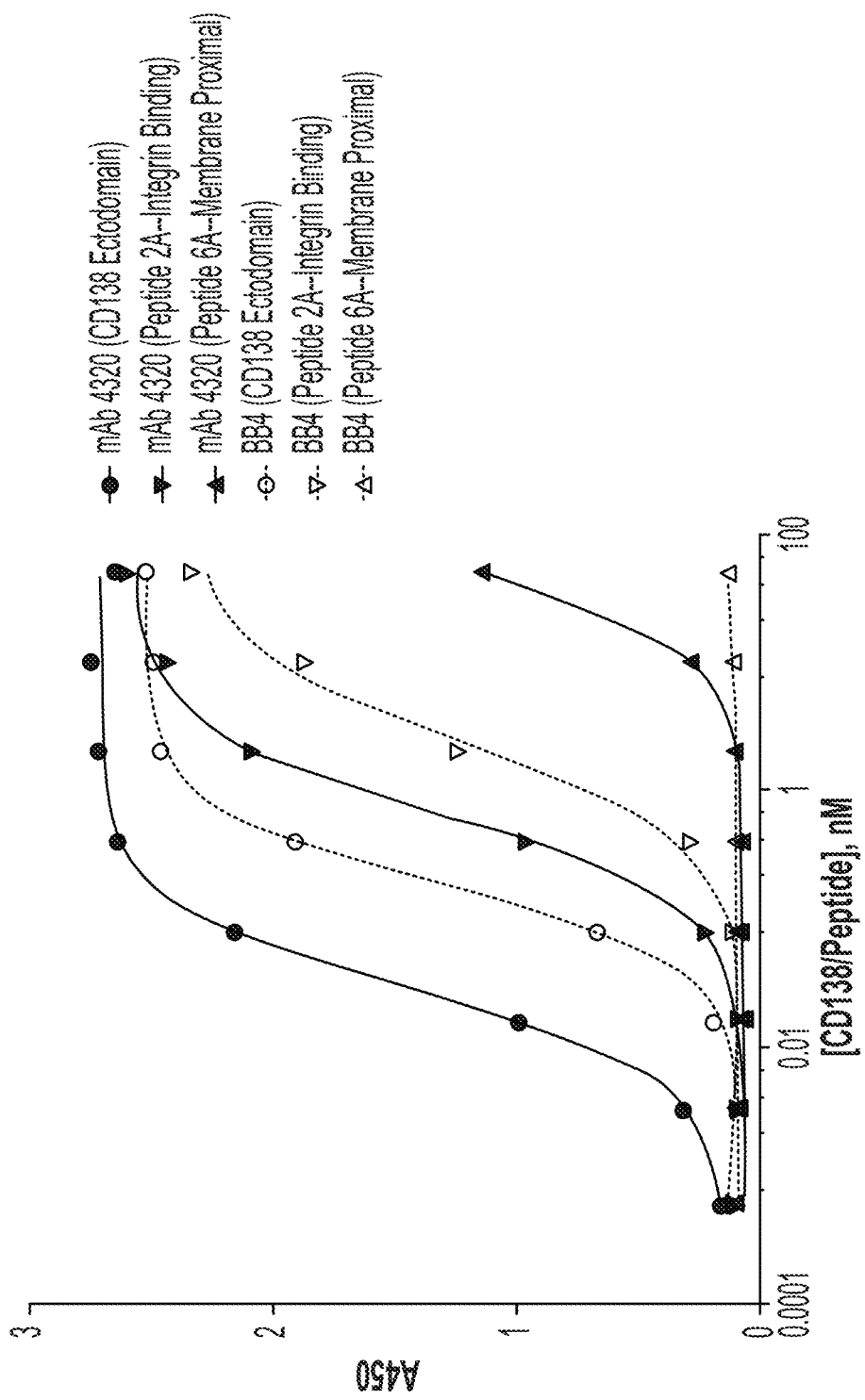
FIG. 10 summarizes the differential binding of humanized anti-CD138 antibody mAb 4320 and reference antibody BB4 to soluble extracellular domain of human CD138 and select CD138-derived peptides at varying concentrations. Protein and peptide binding were quantified by ligand capture ELISA. CD138 peptides corresponding to integrin binding domain (designated as Peptide 2A) or membrane proximal region (designated as Peptide 6A) are noted.

In this experiment, the binding of mAb 4320 and BB4 to the extracellular domain of soluble human CD138 having the sequence of amino acids 18-251, SEQ ID NO. 1 or select human CD138 derived peptides (Table 3) was evaluated by antigen capture ELISA. In brief, MaxiSorp™ plates were first coated with antibodies 4320 or BB4 at a 0.5 µg/ml concentration overnight (12-15 hours) at 2-8° C. The immobilized monoclonal antibodies were tested for binding to biotinylated recombinant CD138 extracellular domain or peptides 2A, peptide 6A in 5-fold serial antigen dilutions starting at starting at a 50 nM concentration. HRP-conjugated Anti-biotin secondary antibody (1:10000 dilution) was used for detection. As shown in FIG. 10, both antibodies 4320 and reference antibody BB4 were able to bind to the CD138 extracellular domain with apparent subnanomolar affinities based on binding EC50 values; mAb 4320 demonstrated an approximately 6-fold higher binding affinity in comparison to BB4. Differential binding to CD138 derived peptides was also noted. mAb 4320 bound to peptide 2A with substantially higher affinity than to 6A which was detected at the higher concentration evaluated. In contrast, BB4 bound to peptide 2A with lower affinity than measured for mAb 4320; no binding of BB4 reference antibody to peptide 6A was observed at any peptide concentration. These data confirm a differential set of epitope(s) for the two antibodies and further indicate that these epitope differences impact their respective Fc effector functions as measured by the ADCC bioassay. These data also indicate that mAb 4320 epitope maps minimally to two peptide regions within CD138, inclusive of a membrane proximal region.

Example 7: Evaluation of Anti-CD138 Efficacy in a Mouse Xenograft Model of Multiple Myeloma This example describes the in vivo evaluation of an exemplary humanized anti-CD138 antibody molecule, mAb 4320, at a dose escalation and in a disseminated human xenograft model of multiple myeloma in C.B-17 SCID mice. Parental anti-CD138 monoclonal antibody 2810 (mouse-human chimera and predecessor to humanized mAb 4320) was included in this evaluation at a single dose level for comparative purposes and for use as positive controls based on previous studies and historical data. The results of this study demonstrate targeting human CD138 with mAb 4320 to be an efficacious treatment for reduction of disease in comparison to vehicle control and based on several endpoints including reduced median tumor burden (disseminated and tissue localized), tumor growth delay and overall survival as measured by disease-related morbidity leading to euthanasia based on predetermined criteria. An analysis of the clinical and necropsy findings demonstrated the mAb 4320 and control groups succumbed to the same apparent myeloma-induced morbidity, albeit with substantially differing rates of disease progression. This observation is in line with mAb 4320 being well tolerated. A general lack of a dose response with respect to biological potency in conjunction with measured serum titers of mAb 4320 (PK analysis) further indicates sufficient exposure at the lowest dose level studied. These data also indicate improvement in biological activity of humanized mAb 4320 in comparison to parental mouse antibody (Mab 2810) from which it was derived.

Methods

Production of mAb 4320

The discovery and humanization of anti-CD138 antibody mAb 4320 are described herein. In brief, humanization was performed by identifying human germlines proximal to mouse variable heavy (VH) and variable light (VL) sequences. Once identified, the complementarity determining regions (CDRs) from parental mouse-derived mAb 2810 were grafted on to the human VH and VL germline templates, respectively, using structure-guided design. Additional mutations (including back mutations to the parental residue in the mouse mAb) were selectively introduced based on visual inspection of the structural model. The resultant constructs (including mAb 4320) were designed to have the fewest number of changes from a functional human germline to most closely resemble a human-derived antibody. Humanization of parental mAb 2810 was otherwise carried out with the aim of retention (or improvement) of antibody properties of mAb 2810 pertaining to but not limited to target binding, effector function, cellular cytotoxicity and epitope engagement.

mAb 4320 was produced by the transient co-transfection of two mammalian expression vectors separately encoding heavy chain (HC) and light chains (LC) for production as full length, human IgG1kappa antibodies in Chinese hamster ovary cells (ExpiCHO, Thermo Fisher Scientific). DNA transfection was performed using lipid-based transfection reagents (e.g., ExpiFectamine CHO Transfection Kit, Thermo Fisher Scientific) and standard protocols as recommended by the manufacturer. mAb 4320 was produced under cell culture conditions designed to reduce core fucose in the respective N-glycans at asparagine 297 and ultimately for the purpose of further enhancing Fc-mediated ADCC activity. Highly-reduced core fucosylation was achieved metabolically through the use of the decoy substrate 2-deoxy-2-fluoro-1-fucose (2FF) which was added concurrently to the culture media at 0.15 mM at four hours following transient transfection. Cell culture was carried out in shake flasks at 600 mL cell culture scale for a period varying 7-10 days without feed supplementation. Secreted monoclonal antibodies were subsequently purified from cell culture media using protein A affinity capture on Fast Protein Liquid chromatography (FPLC). Parental anti-CD138 mAb 2810 was produced in parallel using the same cell culture strategy and purification workflow. Both antibodies were formulated in phosphate buffered saline, pH 7.4. All antibodies were evaluated by flow cytometry for cell binding to lymphoblastic- and multiple myeloma-related cell lines including MM1.S, RPMI8226, LP-1 and U266. The antibodies were also evaluated for ADCC activity against CD138$^+$ human lymphoblastic myeloma U266 cells in a luciferase-based ADCC reporter assay using engineered Jurkat cells stably transfected with the human Fcγ RIIIa receptor (Promega Corporation). All antibodies were also tested for endotoxin and adventitious agents prior to being deemed acceptable for in vivo use in mice.

MM.1S Luc Xenograft Multiple Myeloma Model

Figure 11:
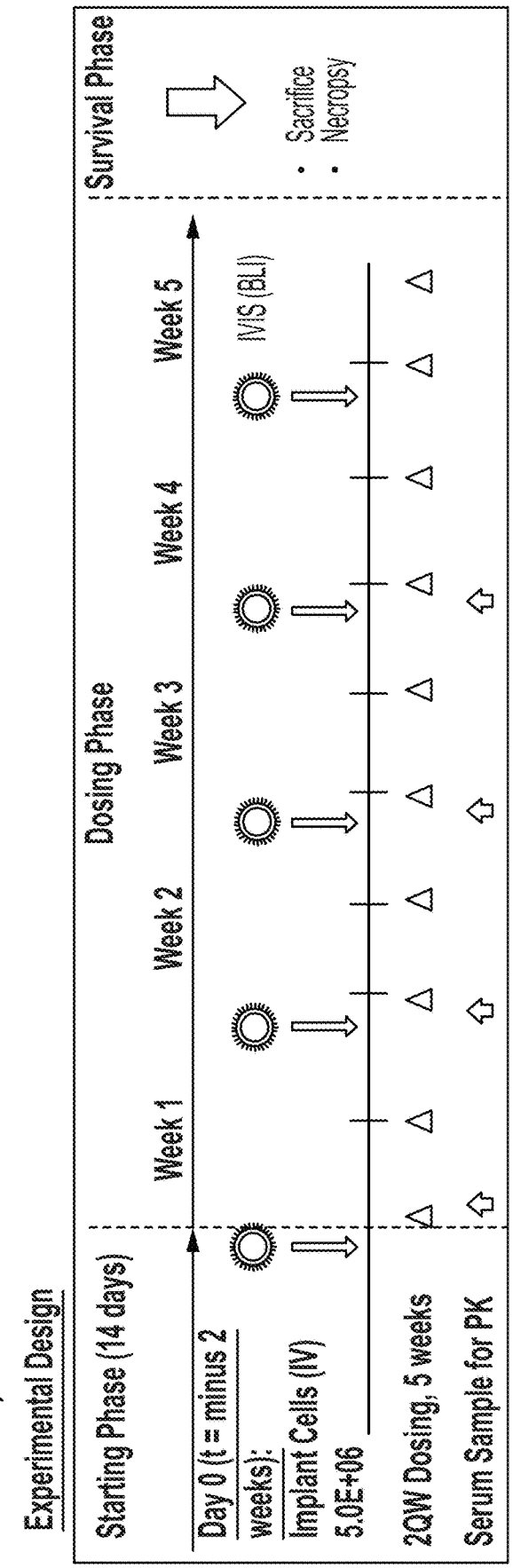
FIG. 11 is a diagram showing an in vivo multiple myeloma tumor dissemination (xenograft) model used for evaluation of mAb 4320 treatment efficacy. The Experimental Overview lists mouse background (CB.17 SCID mice), human MM1.S (Luc) cell line, imaging assay (intravital imaging/whole body luminescence to measure tumor burden), and dosing schedule (i.p. administration, twice weekly, over 8 weeks). Treatment groups (N=8 mice/group) included a vehicle control, mAb 2810 (4 mg/kg), and mAb 4320 variable dosing (4, 8, and 16 mg/kg). In the Experimental Design diagram, three phases are noted: staging phase, dosing phase (with efficacy), and survival phase. BLI, bioluminescence.

The in vivo efficacies of humanized anti-CD138 mAb 4320 and parental mouse/human chimeric antibody mAb 2810 were assessed using a mouse xenograft multiple myeloma model involving the dissemination of myeloma cell line MM.1S implanted by intravenous (i.v.) injection in C.B-17 SCID mice. An outline of the experimental design is summarized in FIG. 11. C.B-17 mice were chosen on the basis of preservation of aspects of innate immunity relevant to antibody mechanism of action, namely NK cell-mediated cytotoxicity of antibody-targeted CD138 positive MM cells. The ability of mouse NK cells to cross bind to human Fc albeit with lower affinity was noted. Whole bioluminescence imaging (BLI) of luciferase-expressing, human multiple myeloma tumor cell line MM1.S (Luc) was used to non-invasively quantify site-specific disease burden, disease progression and therapeutic benefit. The quantity of emitted light from the tumor after systemic injection of D-luciferin was calibrated to correlate with viable tumor burden.

Five-to-six-week-old mice were injected intravenously with $5.0 \times 10^6$ live (trypan-excluding) MM1.S (Luc) cells on day 0 and staged for dosing on day 14 after normalizing the tumor volume between the groups set by BLI as $2.39 \times 10^7$ photons/second (p/s, range of group means, $2.35$-$2.43 \times 10^7$ p/s). The mice (N=8 per group) were distributed to ensure that the mean whole-body tumor burden for all groups was within 10% of the overall mean whole-body tumor burden for the study population.

Anti-CD138 antibodies were dosed intraperitoneally twice weekly (2QW) for up to five weeks. Days of treatment (in relation to the day of MM1.S (Luc) cell infusion) were day 14, 17, 21, 24, 28, 31, 35, 38, 42, and 45 (when appropriate for animals that remained on study). Study groups included vehicle (PBS) likewise dosed twice weekly by i.p. injection (0.2 mL/20 g). mAb 2810 was dosed at a single dose level of 4.0 mg/kg, while humanized mAb 4320 was variably dosed at 4, 8 and 16 mg/kg. BLI was performed using an IVIS Lumina S5 (PerkinElmer, MA). Animals were imaged once weekly for a total of 4 images (at staging on day 14, day 21, day 28, and day 35) Animals were imaged five mice at a time under 1-2% isoflurane gas anesthesia. Each mouse was injected IP with 150 mg/kg (15 mg/mL) D-luciferin and imaged in the prone then supine positions 10 minutes after the injection. Large binning of the CCD chip was used, and the exposure time was adjusted (5 seconds to 2 minutes) to obtain at least several hundred counts per image and to avoid saturation of the CCD chip.

Images were analyzed using Living Image 4.3.1 (PerkinElmer, MA) software. Whole body fixed-volume regions of interest were placed on prone and supine images for each individual animal and labeled based on animal identification. The prone and supine images were summed together to estimate whole body tumor burden (BLI).

Additional measurements included body weights (3× weekly), daily clinical observations and necropsy following euthanasia based on predetermined criteria or end of study at day 59. Euthanasia criteria were related to disease progression and included >20% loss in body weight or disease-related morbidity such as hind limb paralysis, paresthesia, or other signs of severe CNS or musculoskeletal impairment Primary and secondary efficacy endpoints were generated using in vivo whole body BLI and included tumor burden as defined as percentage of T/C (where T=treatment group and C=vehicle control) measured on each imaging day and reported on day 35 and tumor growth delay as measured as time to tumor burden as pre-defined at a BLI signal of $1.0 \times 10^9$ p/s.

Additional efficacy endpoints included survival (median life span) also normalized to vehicle control (% increased life span) based on morbidity and calculated based on the first day of treatment and not day of implant.

Antibody Pharmacokinetics (PK)

Non-terminal blood sampling was taken weekly from 4 mice per group starting on day 14 prior to first dose day 15, 24 hour post-first dose day 20, prior to third dose day 27, prior to fifth dose and day 34, prior to seventh dose (if applicable). Animals chosen for weekly sampling alternated between animals 1-4 and 5-8 in each group to conform to a two-week bleeding schedule for each individual animal One hundred microliters of whole blood were collected via retro-orbital puncture and processed into serum for human antibody titer determination by ELISA. Human IgG1 antibody titers were measured in mouse sera using Human IgG Quantitative ELISA Kit, Bethyl Labs, (Catalog #E80-104) based on the manufacturer's recommendation, incorporating modifications as needed. Sera were diluted from 1:50-1:1350, as needed, to conform to preset limits of assay linearity and quantification (LOQ). Antibody concentrations were extrapolated using both validated human Ig standards provided in the kit, along with purified mAb 4320 for comparative purposes. Both methods of quantification lead to a calculation of comparable antibody serological titers.

Results

Efficacy

Figure 12:
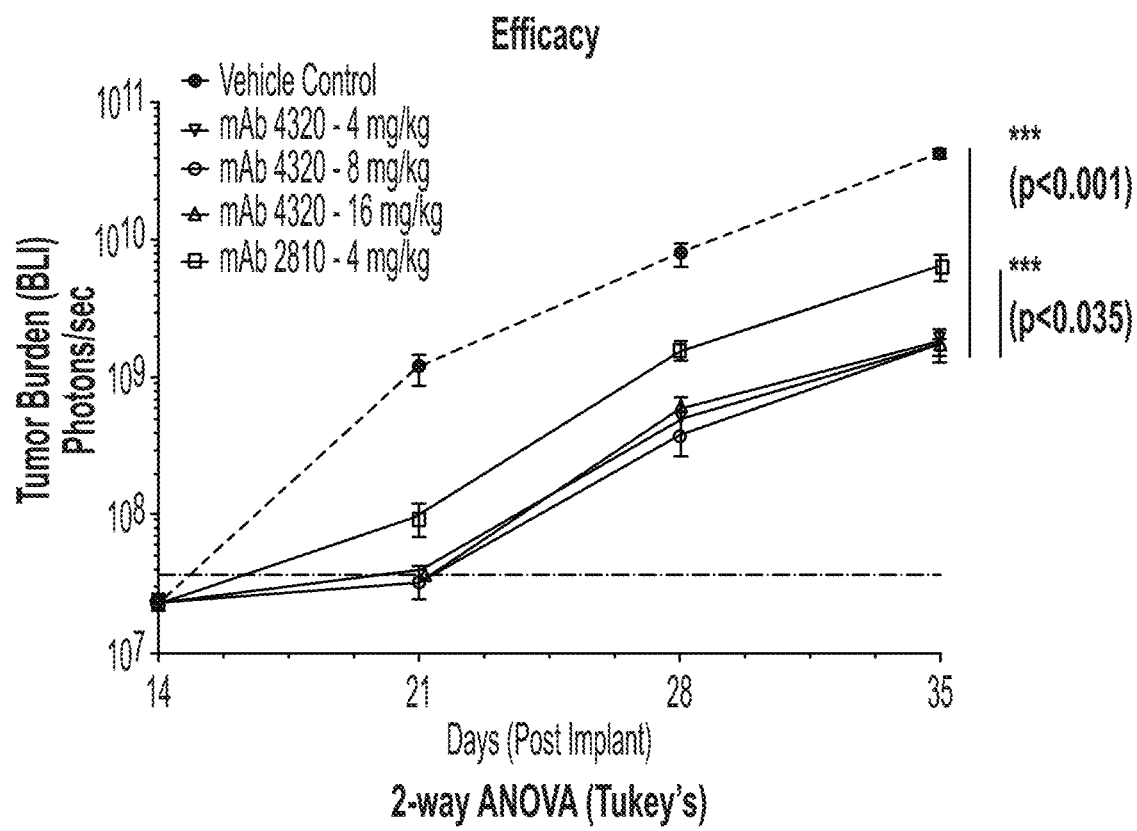
FIG. 12 is a graph showing group efficacy data after treatment of mice in the multiple myeloma xenograft model with the indicated antibody molecules. Disseminated tumor burden is shown as BLI±standard error of the means of disseminated multiple myeloma tumors quantified from IVIS imaging at specific time points and dose levels. Efficacy was defined in part by time to evaluation size (BLI equal to $1 \times 10^9$ p/s) and is depicted by the dashed horizontal line. Statistical analysis by 2-way ANOVA (Tukey's multiple comparison) was performed to compare mAb 4320 treatment to other treatment groups. P-values were calculated based on interaction as source of variance. BLI data are plotted on a logarithmic scale.
Figure 14:
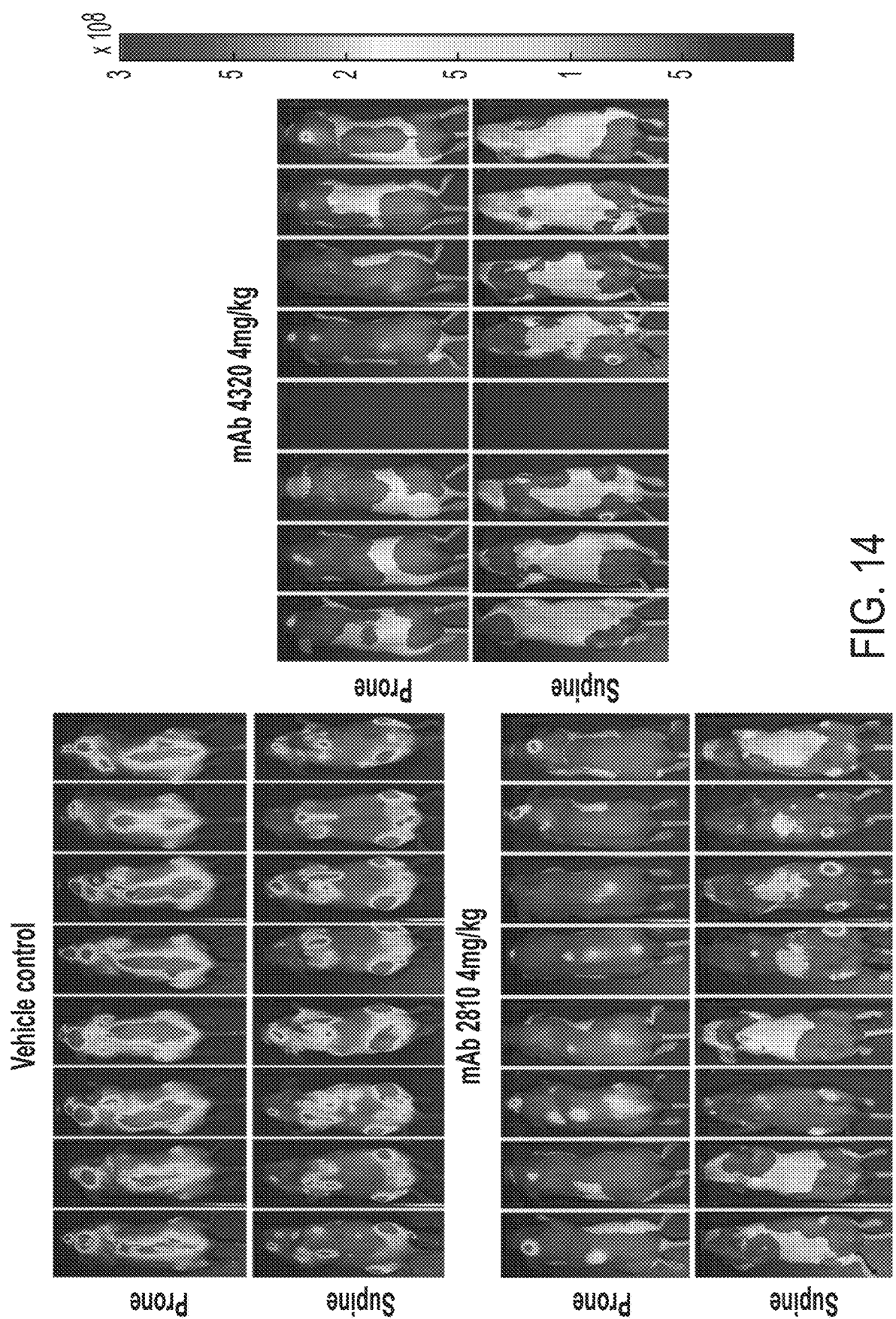
FIG. 14 is a series of images showing bioluminescence (BLI) results from the multiple myeloma xenograft study. BLI Images are shown for individual mice comparing mAb 4320, mAb2810 and vehicle groups, as indicated, on day 35 post-tumor implantation.

Tumor growth was consistent with historical norms (Td range: 1.5-2.2 days) based on prior model data collected from in vivo study. The experiment was judged to be technically satisfactory and the data appropriate for evaluation. Efficacy data is summarized in FIG. 12 (means±SEM of whole body BLI). Corresponding individual animal data (depicted as box and whisker plots with min-max included) are presented in FIG. 13. Representative images (corresponding to mice closest to median BLI at day 35) are depicted in FIG. 14.

Based on these data, animals dosed with mAb 4320 showed clear treatment benefit relative to the vehicle control and as evaluated by tumor growth delay of up to 11.4 days to reach a preset efficacy endpoint of median BLI value of $1.0 \times 10^9$ p/s and median % T/C calculated at each day of imaging but reported at day 35 (3.4-5.1% vs. control). This benefit of treatment met statistical significance in a group analysis by 2-way ANOVA (Tukey multiple t-test).

Mice receiving varying dose levels of mAb 4320 did not produce a clearly differentiated dose response when evaluating either efficacy by whole body signal or hind limb/spine signal Animals receiving parental monoclonal antibody 2810 also demonstrated benefit of treatment with a 6.6-day tumor growth delay and % T/C of 13.1% relative to vehicle control groups. This treatment benefit also met statistical significance at all time points (Bonferroni-Dunn method). A comparison of mAb 2810 and mAb 4320 treatments (i.e., comparison at the same 4 mg/kg dose level) indicated a discernible treatment benefit with statistical significance (Bonferroni-Dunn method), especially at later time points (P<0.007). These results would suggest some improvement of target engagement and/or biological activity in humanizing mAb 2810 to achieve mAb 4320.

Figure 15:
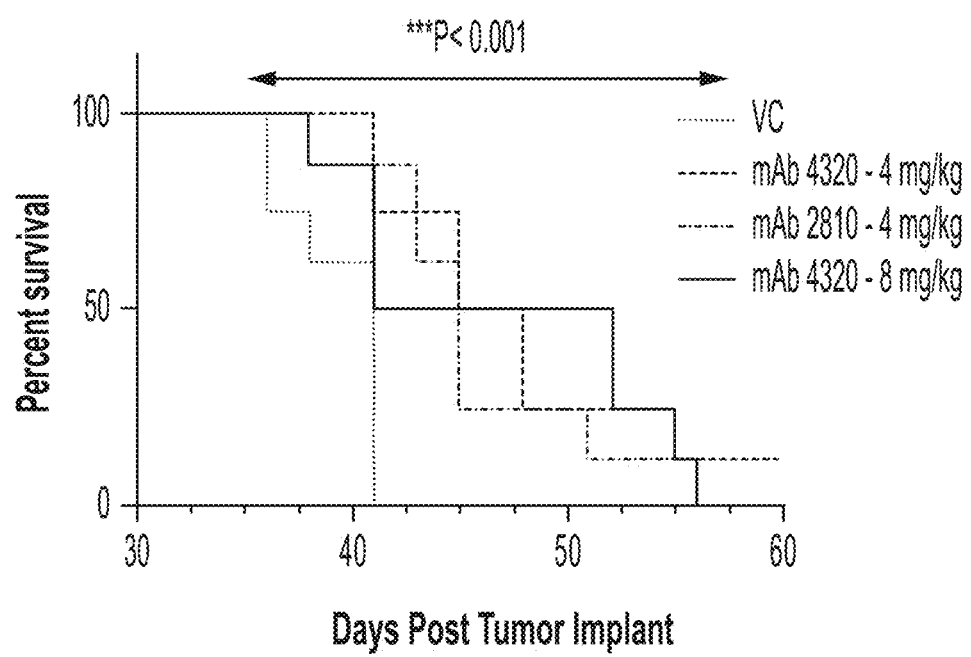
FIG. 15 is a graph showing group survival results from the multiple myeloma xenograft study. Shown are Kaplan-Meier survival curves of animals in vehicle group vs. animals treated with anti-CD138 antibodies mAb 2810 and mAb 4320. Percent survival was defined as mice surviving until reaching a pre-determined euthanasia criteria related to disease-related morbidity, such as weight loss >20%, severely impaired CNS function or severely impaired movement or loss of righting reflexes. P-values for comparison of VC to mAb 4320 treatment (log rank test) was calculated by Mantel-Cox test.

As shown in FIG. 15, treatment of C.B-17 mice with mAb 4320 also provided clear survival benefit in this dissemination model as evidenced by at least a 20% increased median lifespan (e.g., for the 4 mg/kg dosing cohort) in comparison to animals in the control group. As described above, survival was defined as days on study before requirement of euthanasia due to a >20% loss of body weight or disease related morbidity such as hind limb paralysis, parathesis, or other signs of severe CNS or musculoskeletal impairment presumptively due to disease progression and concurrently observed in the control group (as described herein). A log ranking of survival (e.g. based on mantel-Cox test) indicates clear statistical benefit (P<0.001). This observed benefit in overall survival was noteworthy, especially given the high tumor burden at the time of dose initiation and the aggressive rate of disease progression in this xenograft model resulting in accelerated morbidity in the absence of treatment.

None of the animals demonstrated complete regression as defined in this bioluminescence study as a decrease in tumor burden in any mice to less than a declared background BLI signal level.

Tolerability

Figure 16:
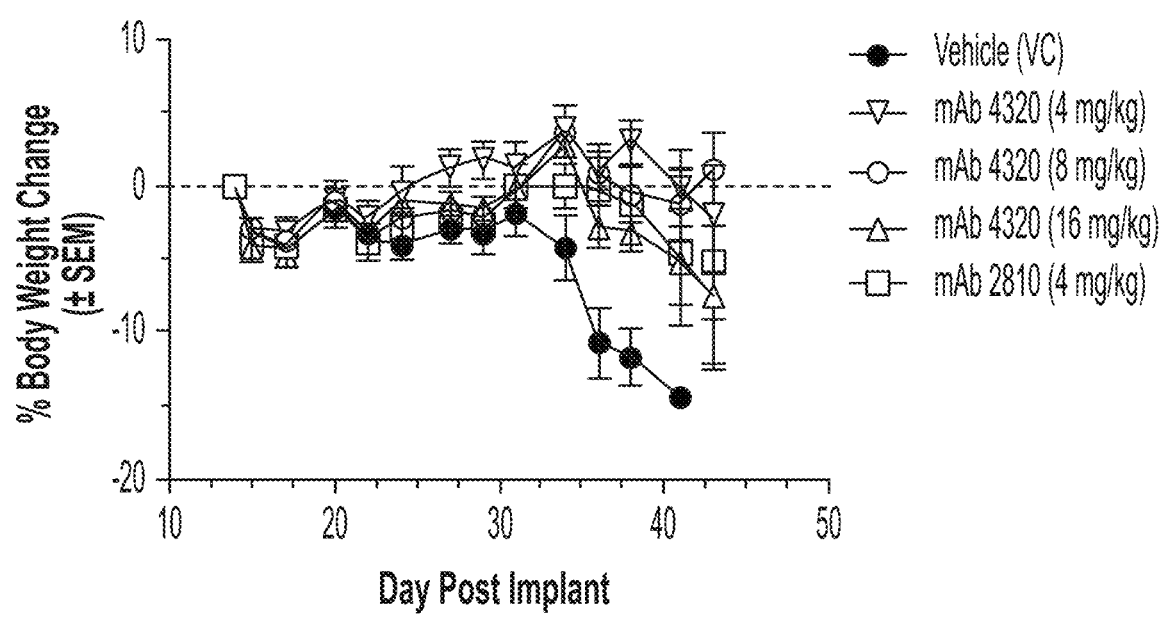
FIG. 16 is a graph showing changes in animal body weight in the multiple myeloma xenograft study. Percent change in body weight was plotted as standard error of the means. Animals corresponding to the mAb 4320 treatment groups are noted in open symbols; animals corresponding to vehicle control (VC) are noted in solid circles. The largest change in body weight was observed for animals in the vehicle control group, indicating correspondence to disease progression.

Treatment with anti-CD138 monoclonal antibody mAb 4320 appears to have been well tolerated. There were no deaths reported related to any infection, sampling or trauma or other morbidities clearly unrelated to disease. Loss of body weight during the first week of treatment was minimal and mean body weight change was likewise minimal (generally <10%) (FIG. 16). The greatest treatment-related weight loss was seen in the vehicle control (VC) group indicating disease progression as the primary cause of weight loss Animals treated with 4 mg/kg mAb 4320 experienced an upward trend in mean body weight in spite of anticipated body weight loss due to disease progression. No animal deaths were reported in any of the mAb 4320 treatment groups. As most clinical signs and necropsy findings described for the antibody treatment groups matched the control group, a causality of disease progression rather than treatment most logically should be ascribed as the primary cause of morbidity. Nothing observed in this study suggested that mice were adversely affected by administration of mAb 4320.

Figure 17:
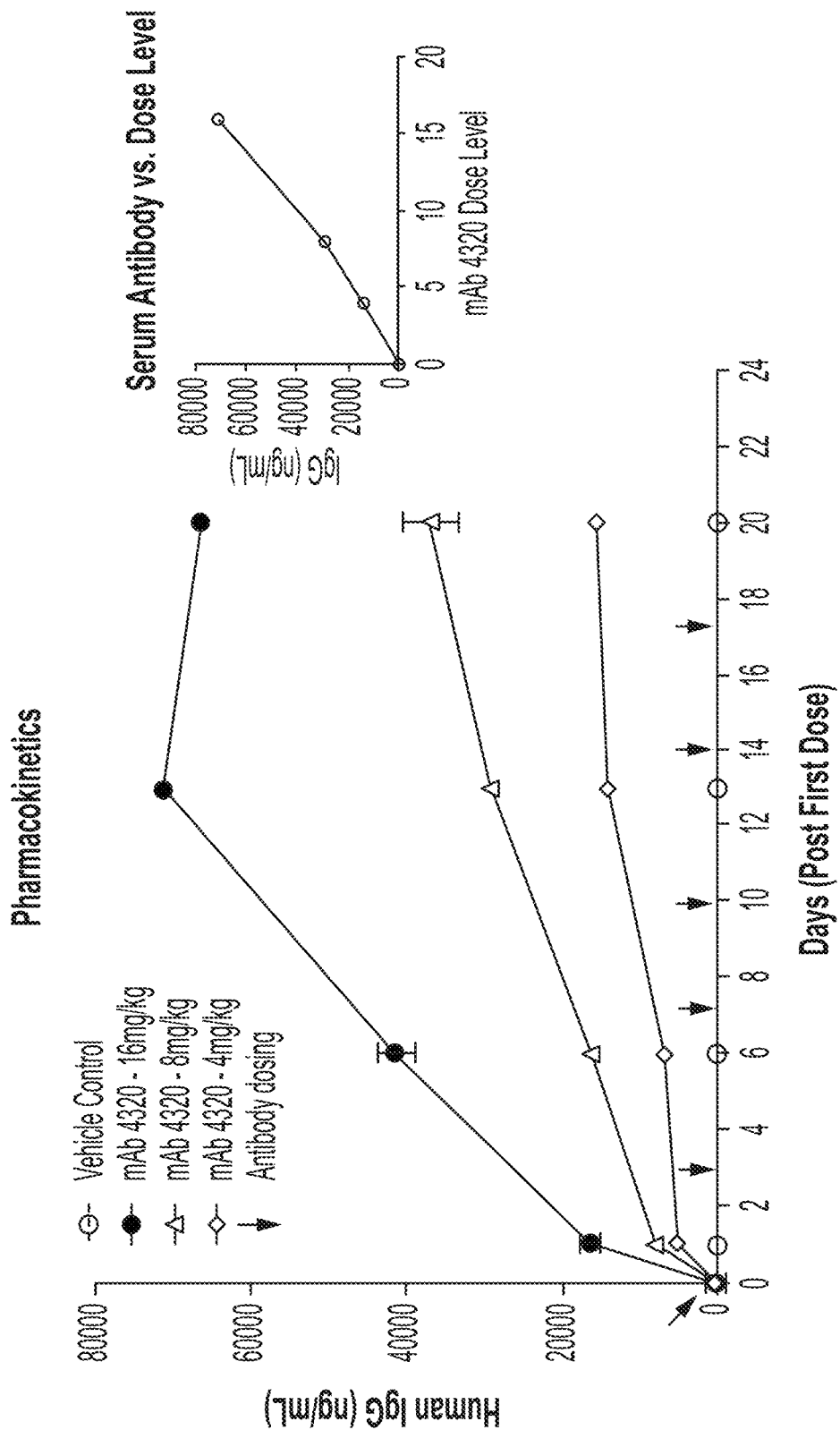
FIG. 17 is a graph showing pharmacokinetic (PK) results from the multiple myeloma xenograft study in the form of antibody molecule serum titers. Serum samples were taken once weekly (N=4 mice group). Antibody serum titers were quantified by ELISA optimized to detect human IgG1 Fc. Sera from VC group was used as a negative control. Inset: plot of antibody molecule serum titers for mAb 4320 on day 13 plotted vs. dose level (antibody concentration).

Antibody Pharmacokinetics (PK)

mAb 4320 antibody levels resulting from repeat dosing at three varying concentrations were evaluated in tandem to its biological efficacy described above. These data indicated a clear and reasonably linear dose response, especially after the first week of dosing (FIG. 17). These data, in conjunction with the efficacy data (PD) indicated sufficient exposure of antibody at the lowest dose to effect a maximal biological response. No anti-mAb 4320 antibody response (ADA) was evident from these data despite the fact of mAb 4320 being a humanized IgG1 antibody.

mAb 4320 possessed a modestly better PK profile compared to parental mAb 2810, the mouse-human chimeric antibody on which basis it was humanized Summary This report summarizes the in vivo efficacy of mAb 4320, an exemplary humanized monoclonal antibody targeting human CD138 (syndecan-1), in a mouse xenograft model of multiple myeloma. In this study, mAb 4320 treatment effectively reduced disease burden as evidenced by a prolonged time to evaluation (tumor growth delay), prolonged median survival, and clear reduction of disseminated tumor in relevant skeletal tissues. No clear dose response was observed with respect to mAb 4320 efficacy at the three dose levels (4-16 mg/kg) evaluated. These findings, in conjunction with a linear dose response observed with respect to serum antibody levels (PK) indicated sufficient exposure of mAb 4320 at the lowest dose level (4 mg/kg) evaluated to achieve a biological response. Lower dose levels may also be sufficient such a response.

Administration of mAb 4320 appeared to be well tolerated with no overt treatment related morbidities or toxicities based on a similar observation of disease related morbidities in the vehicle control group. Limitations of this particular model with respect to the full replication of the human immune response (e.g., human vs. mouse Fcγ receptors) are likely to influence the maximum potency of an immune-based mechanism of action for mAb 4320 leading to cell-mediated cytotoxicity (ADCC) making such a comparison impractical.

Taken collectively, the positive efficacy data of this study both validate the strategy of an antibody targeting CD138 approach in tandem with an effective immune-based mechanism of malignant plasma cell killing. These results further support mAb 4320 as a therapeutic for the treatment of multiple myeloma and other indications in which CD138 is implicated.

Example 8: Evaluation of Anti-CD138 Efficacy as a Single Agent or in Combination with Bortezomib in a Mouse Xenograft Model of Multiple Myeloma This Example summarizes in vivo evaluation of the efficacy of an exemplary humanized anti-CD138 antibody molecule, mAb 4320, in an MM1.S xenograft model of multiple myeloma, both as a single agent therapy or in combination with a proteasome inhibitor (bortezomib). Here, effective reduction of disease (disseminated tumor burden) was shown in animals receiving mAb 4320 monotherapy, leading to complete regression in select animals (22%), demonstrative tumor growth delay relative to untreated animals, and a clear survival benefit (>50%). Combination of mAb 4320 with bortezomib resulted in additional and demonstrative efficacy as evidenced by a complete regression in nearly all treated animals leading to tumor free survival (TFS) and an apparent demonstration of minimally residual disease (MRD) based on tumor imaging. Moreover, the combination of mAb 4320 with bortezomib resulted in 100% survival out to 74 days, consistent with observation of MRD based on the primary efficacy data. This persistence of efficacy was observed even after discontinuation of treatment for three weeks of either mAb 4320 alone or in combination with bortezomib in this aggressive model. mAb 4320 was well tolerated with no treatment-related deaths observed either as a monotherapy or combination with the use of bortezomib. In contrast, the use of bortezomib alone led to treatment-related toxicity meriting a reduction in the initial dose. Inclusion of mAb 4320 effectively rescued the lower dosing of bortezomib for improved efficacy and lesser toxicity, thereby expanding the therapeutic window of use of this combination treatment.

Methods
Production of mAb 4320

In brief, humanization was based on parental mouse-derived mAb 2810. The resultant humanized antibody (mAb 4320) was designed to have the fewest number of changes from a functional human germline to most closely resemble a human-derived antibody for purposes of reduced immunogenicity while retaining or improving upon the antibody properties of parental mAb 2810. mAb 4320 was produced by transient vector transfection in Chinese hamster ovary cells (ExpiCHO, Thermo Fisher Scientific). Cell culture was carried out in shake flasks at 600 mL cell culture scale for a period of seven days without feed supplementation. mAb 4320 was produced under cell culture conditions designed to minimize core fucose in the respective N-glycans at asparagine 297 and ultimately for the purpose of further enhancing Fc-mediated ADCC activity as also previously described. The secreted monoclonal antibody was subsequently purified from cell culture media using protein A affinity capture on Fast Protein Liquid chromatography (FPLC). Purified mAb 4320 was functionally evaluated for ADCC activity against CD138+ human lymphoblastic myeloma U266 cells in a luciferase-based ADCC reporter assay using engineered Jurkat cells stably transfected with the human Fcγ RIIIa receptor (Promega Corporation). mAb 4320 was also tested for endotoxin and adventitious agents prior to being deemed acceptable for in vivo use in mice.

MM.1S Luciferase Xenograft Multiple Myeloma Model

The in vivo efficacy of humanized anti-CD138 mAb 4320 and bortezomib (either used as single agents or in combination) were assessed using a mouse xenograft multiple myeloma model involving the dissemination of myeloma cell line MM.1S implanted by intravenous (i.v.) injection in C.B-17 SCID mice generally as described but with some modification. Five-to-seven-week-old female C.B-17 SCID mice (C.B-17/IcrHsd-Prkdc$^{scid}$) were injected intravenously with $5.0 \times 10^6$ live (trypan-excluding) MM1.S (Luc) cells on day 0 and staged for therapeutic dosing on day 14 after normalizing the baseline tumor burden between the groups set by BLI as $2.90 \times 10^6$ photons/second (p/s, range of group means, $2.81-3.07 \times 10^6$ p/s). The mice (N=9 per group) were distributed to ensure that the mean whole-body tumor burden for all groups was within 10% of the overall mean whole-body tumor burden for the study population. Treatment was initiated on day 14 post tumor implant. Vehicle (PBS) was dosed once daily by oral gavage (0.2 mL/20 g); mAb 4320 (4 mg/kg) and bortezomib (1 mg/kg) were dosed twice weekly by intraperitoneal (i.p.) injection for 52 days. Animals in the bortezomib single agent treatment group and in combination with mAb 4320 were initially treated at a bortezomib dose level of 2 mg/kg but this dosage was lowered to 1 mg/kg at day 18 due to observed toxicity (body weight changes) including the death of one study animal in the bortezomib-only treatment cohort after the administration of a single dose. Treatment in all groups was discontinued at Day 53; surviving animals were monitored for an additional 3 weeks out to Day 73 (discontinuation phase of the study).

Whole body tumor burden was monitored by bioluminescence. Bioluminescence imaging (BLI) of luciferase-expressing MM1.S (luc) human MM tumor cell lines also enables a noninvasive determination of site-localized tumor burden. BLI was performed using an IVIS Lumina S5 (PerkinElmer, MA). Animals were imaged five at a time under 1-2% isoflurane gas anesthesia. Each mouse was injected IP with 150 mg/kg (15 mg/mL) D-luciferin (Promega, lot #0000307215) formulated in saline for injection and imaged in the prone then supine positions 10 minutes after the injection. Large binning of the CCD chip was used, and the exposure time was adjusted (5 seconds to 2 minutes) to obtain at least several hundred counts per image and to avoid saturation of the CCD chip Animals were imaged once weekly at staging and on days 14, 21, 29, 36, 43, 53, and 73 (end of study) for all animals remaining on study. Images were analyzed using Living Image 4.7.1 (PerkinElmer, MA) software. Whole body fixed-volume regions of interest (ROIs) were placed on prone and supine images for each individual animal and labeled based on animal identification. Total flux (photons/sec) was calculated and exported for all ROIs to facilitate analyses between groups. The prone and supine ROIs were summed together to estimate whole body tumor burden. Subject ROIs were also placed over each mouse, and region-specific ROIs were placed over spine and hindlimbs for each animal. These ROIs were then quantified independent of the whole-body ROIs in order to calculate signal from only hind limbs or spine.

Primary and secondary efficacy endpoints were generated using in vivo whole body BLI and included tumor burden assessment as described herein. Endpoints included whole body BLI ratio T/C (where T=treatment group and C=vehicle control) measured on each imaging day and reported on day 36 and tumor growth delay as measured as time to tumor burden as pre-defined as a BLI signal of $1.0 \times 10^9$ p/s. Additional efficacy endpoints included tumor regression, tumor free survival (TFS), and median life span normalized to vehicle control (% increased life span); this latter endpoint was calculated based on the first day of treatment and not the day of implant. Overall survival was calculated based on animals remaining on study.

Additional measurements included body weights (3× weekly), daily clinical observations and necropsy following euthanasia. Pre-defined euthanasia criteria were related to disease progression and included >20% loss in body weight or disease-related morbidity such as hind limb paralysis, paresthesia, or other signs of severe CNS or musculoskeletal impairment.

Results
mAb 4320/CD138 Binding Assay and MM1.S Cell Culture Analysis

As a confirmatory analysis, the human MM1.S (luc) cell line used in this xenograft model was evaluated for CD138 target expression levels and mAb 4320 binding by flow cytometry prior to implantation into CB.17 SCID mice. The xenograft study involved a two-week staging phase prior to initiation of treatment and a six-week dosing phase followed by a three-week discontinuation phase for animals still in the study, as described herein. mAb 4320 demonstrated robust and saturable binding at 2.5 µg/mL, with greater than 96% of live cells staining positive for mAb 4320 and with corresponding MFI values indicative of high expression levels of CD138 (e.g., relative to CD38 or the negative controls as described herein).

Efficacy

Figure 18A:
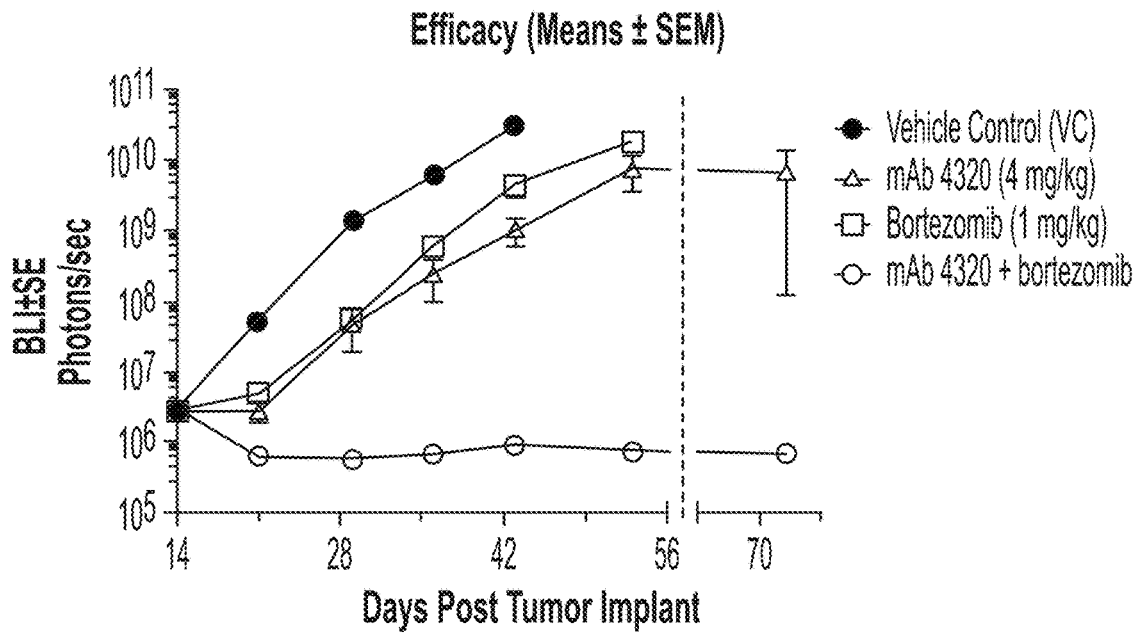
FIGS. 18A-18B are a series of graphs showing efficacy of treatment with mAb 4320 and bortezomib. CB17 SCID mice were injected with MM1.S (Luc) cells by i.v. route of administration at day 0 and staged on day 14, which also corresponds to the first day of dosing with vehicle control, mAb 4320 (4 mg/kg), bortezomib (1 mg/kg, or combination of mAb 4320 and bortezomib. N=9 mice/treatment group. Tumor burden was assessed by whole body bioluminescence (BLI) and quantified by IVIS imaging as described in Methods (Section 3.2). Treatment was discontinued at day 53 (dosing phase) followed by a three-week washout period with end of study at day 73. (A) Group efficacy data. Disseminated tumor burden was reported as bioluminescence (BLI)±standard error of the means at each time point. (B) Individual mice.
Figure 18B:
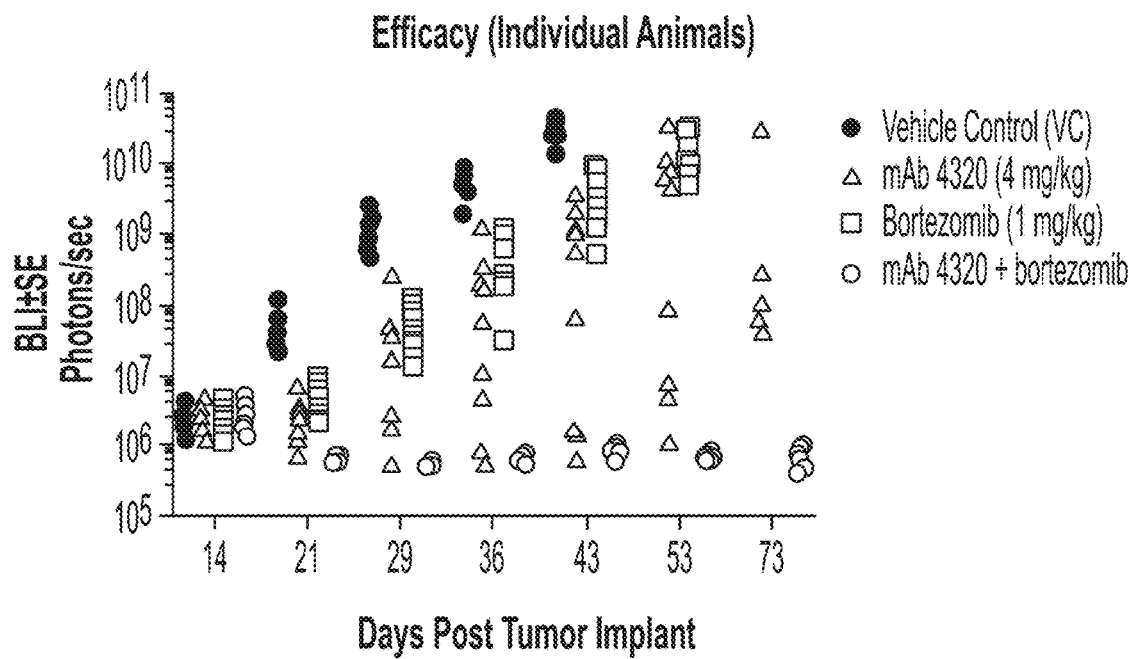
Figure 19A:
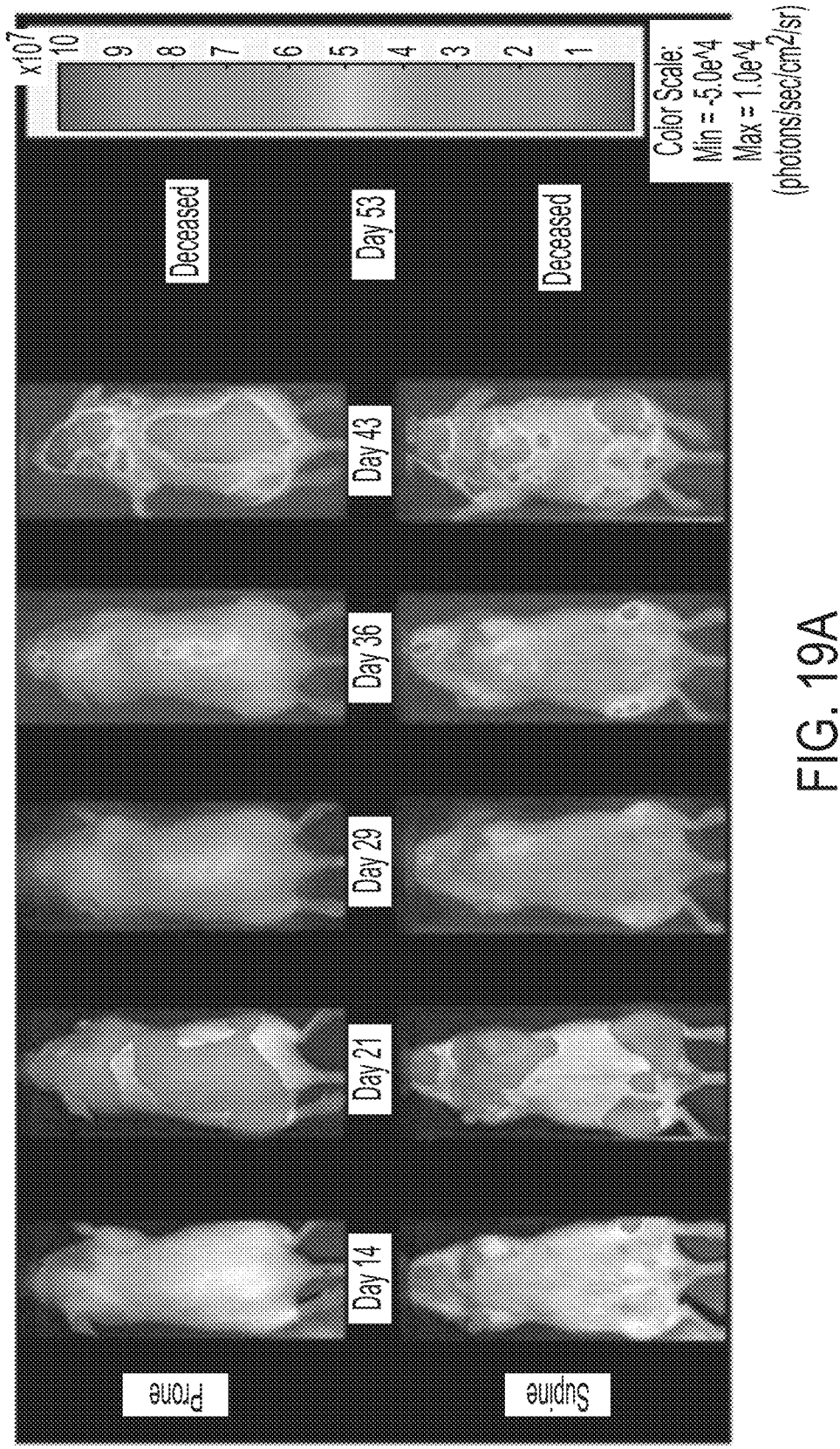
FIGS. 19A-19D are a series of representative bioluminescence (BLI) images of individual mice administered the indicated treatments, chosen on the basis of their proximity to median BLI at day 36. Image intensity was adjusted for purposes of normalization (min of $1.0 \times 10^6$; max of $3.0 \times 10^8$)
Figure 19B:
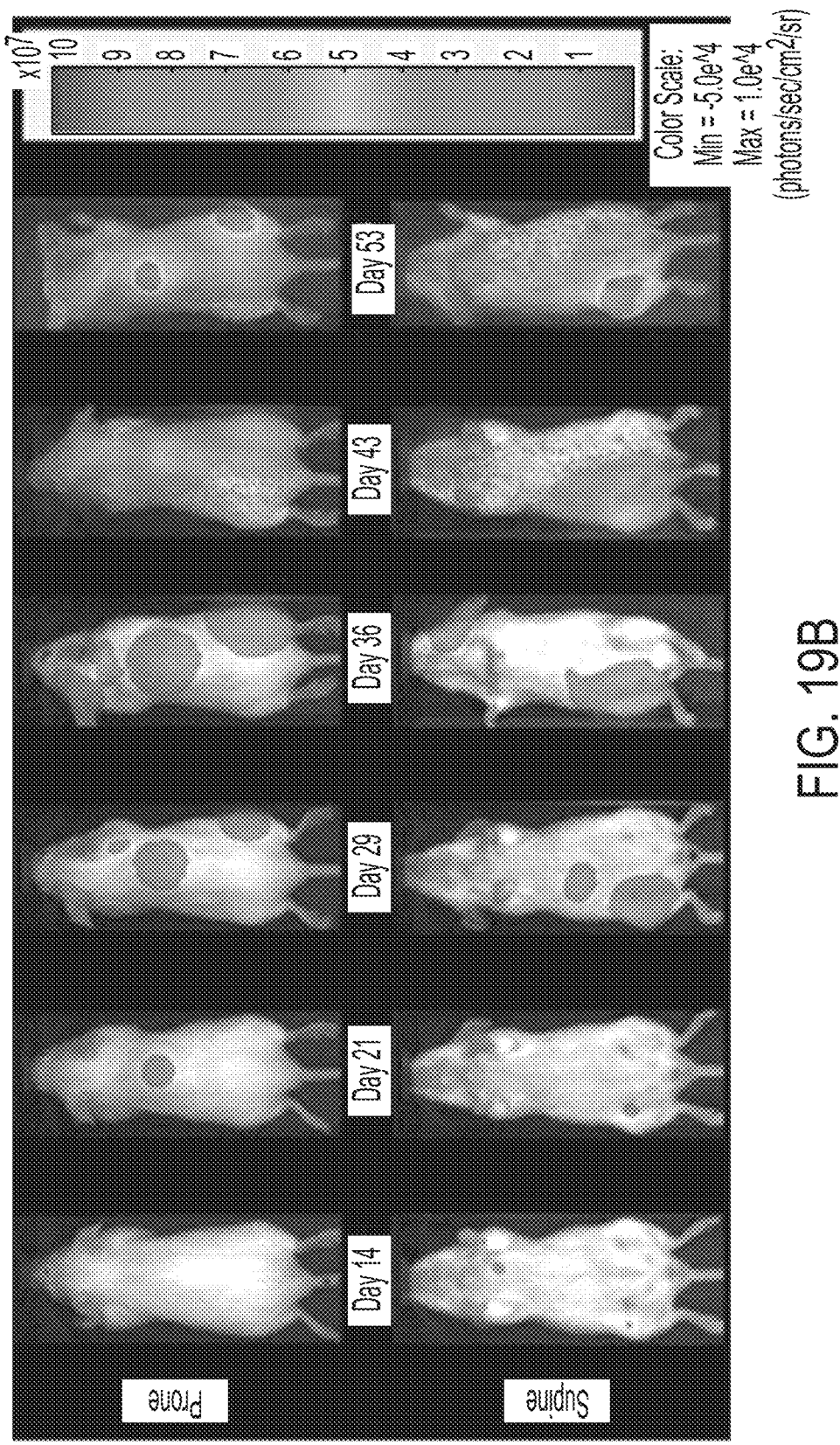
Figure 19C:
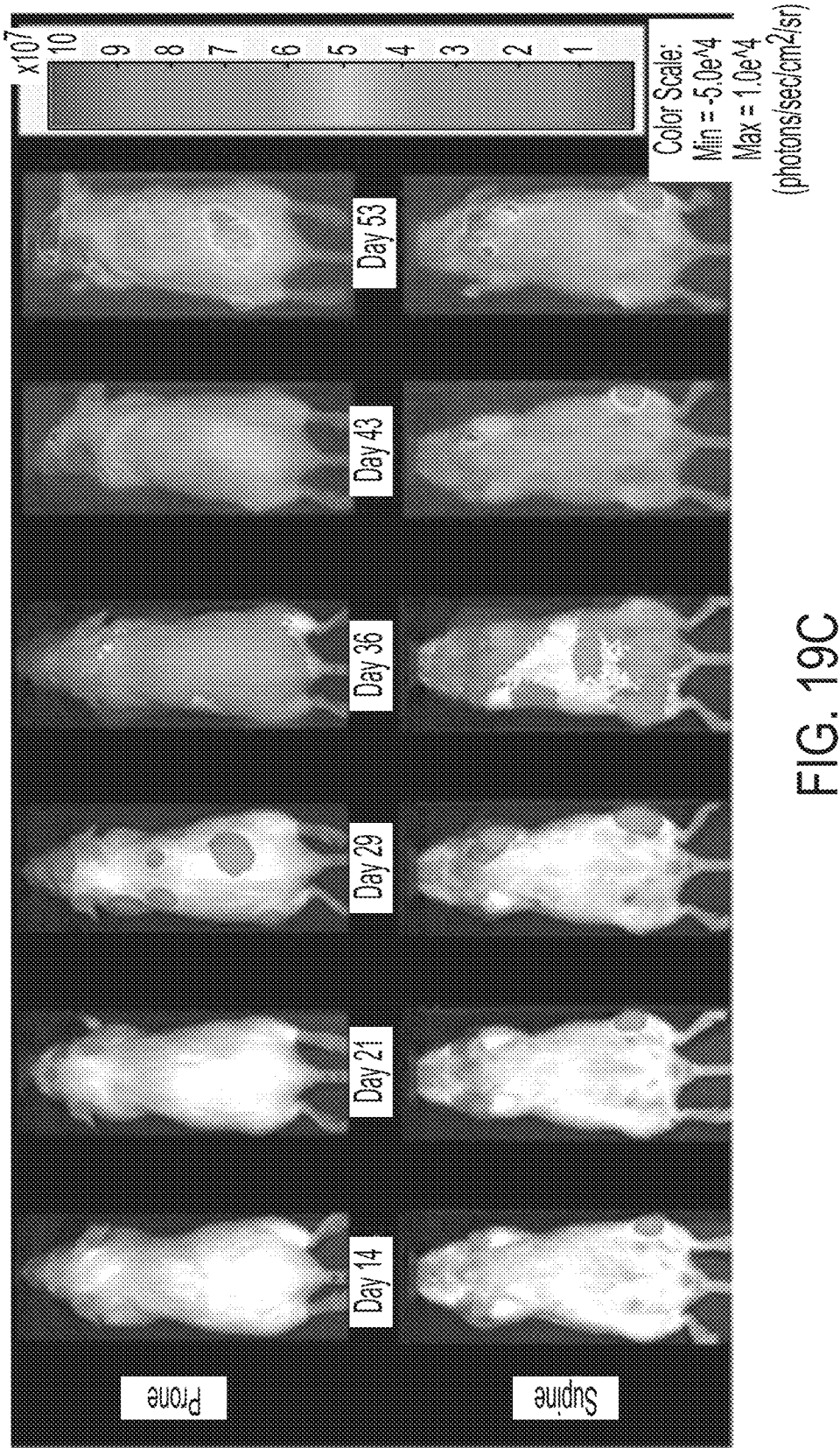
Figure 19D:
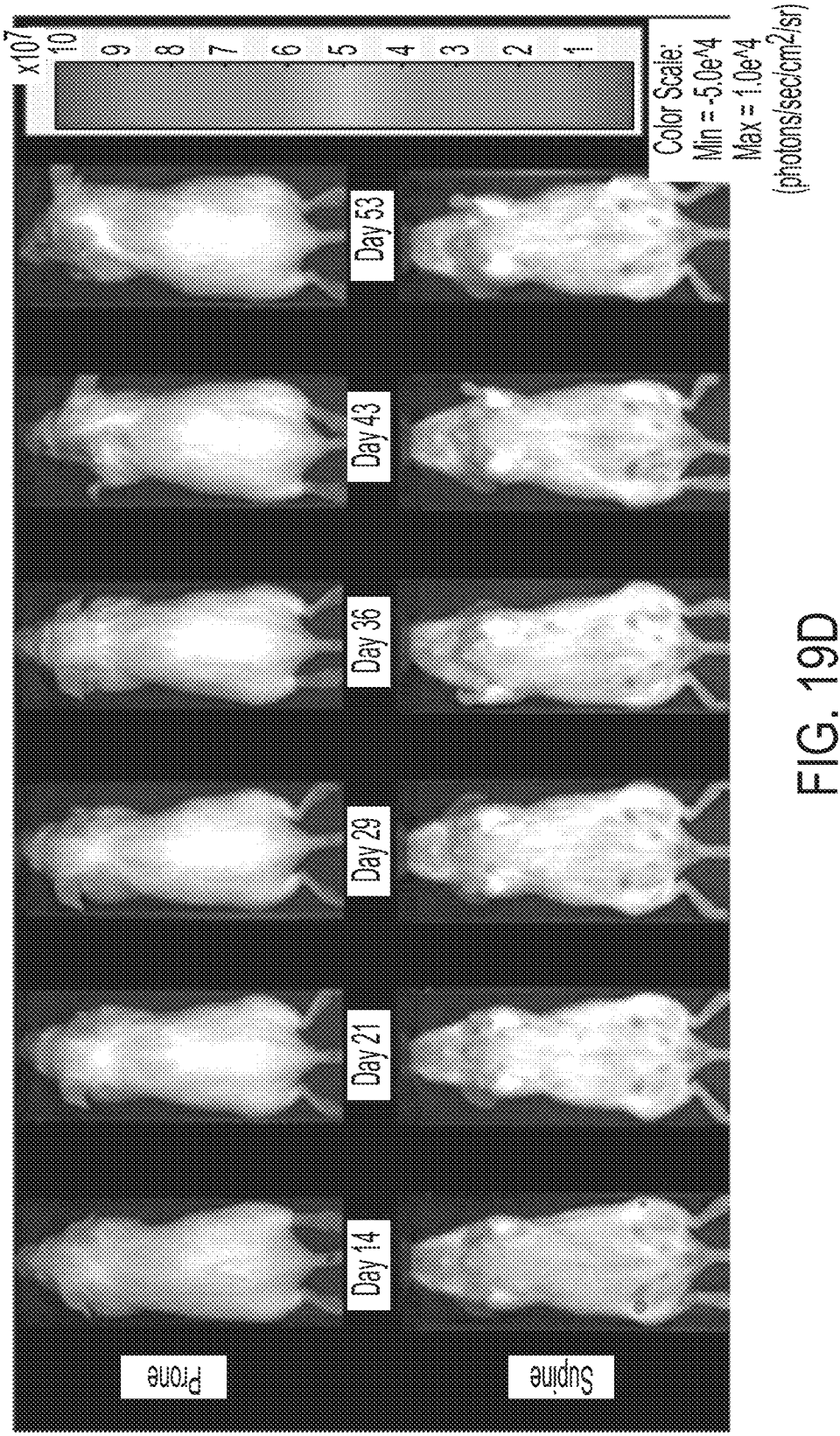

The mean estimated tumor burden for all groups in the experiment on the first day of treatment was $2.90 \times 10^6$ p/s and all of the groups in the experiment were well-matched (range of group means, $2.81-2.98 \times 10^6$ p/s). All animals weighed at least 14.3 g at the initiation of therapy. Mean group body weights at first treatment were also well-matched (range of group means, 18.3-19.2 g). BLI background signal for this study was measured at $7.20 \times 10^5$ p/s. A tumor burden of $1.00 \times 10^9$ p/s was chosen for evaluation of efficacy by tumor growth delay. Efficacy data based on BLI imaging are summarized in FIG. 18 and FIG. 19. Survival data (Kaplan-Meier curves) are presented in FIG. 20.

Control Group

The control group had a median life span of 30 days. There were no spontaneous regressions in the vehicle control (VC) Group. Tumor growth in the VC group was consistent with historical norms (Tumor doubling time range: 1.5-2.2 days). The experiment was judged to be technically satisfactory and the data appropriate for evaluation. In the VC Group, the median time to evaluation size was 28.2 days, and the median tumor volume doubling time was 2.1 days. All animals in the VC Group were off study by day 51.

mAb 4320 Single Agent Therapy

The mAb 4320 single agent treatment at the administered dose level produced a greater than 100.0% increase in animal life span with a tumor growth delay of 13.9 days and a 22% incidence of complete or partial regression at the end of the dosing phase. Significant reduction in tumor burden was visibly apparent in select mice based on acquired BLI images, however. 5/9 animals (56%) remained on study for the duration of the study (day 73). This clear survival benefit was observed despite treatment discontinuation three weeks prior at day 53. No treatment-related death was observed for mAb 4320 monotherapy. These data confirmed effective reduction of disease in animals receiving mAb 4320 monotherapy, with partial regression observed in several animals Bortezomib Single Agent Therapy Administration of bortezomib at the dose level chosen resulted in efficacy with respect to the reduction in tumor burden and kinetics of disease progression relative to the vehicle control group. Bortezomib-treated mice exhibited a tumor growth delay of 10.6 days and a 40% increase in life span. None of the animals exhibited either partial or complete regression and none of the animals survived to the end of study at Day 73. One animal was euthanized early in the initial dosing phase as described above.

mAb 4320 and Bortezomib Combination Therapy

Treatment of tumor-implanted mice with mAb 4320 and bortezomib in combination resulted in the most demonstrative efficacy with improvement over the use of either mAb 4320 or bortezomib as single agents. Combination of mAb 4320 with bortezomib lead to complete regression with demonstration of minimally residual disease (MRD). This demonstrative efficacy was apparent based on all endpoints, including tumor growth delay (greater than 44.8 days, the maximum calculated at the time of study termination), greater than 100% increased lifespan and a 100% survival benefit (with all animals remaining on study through study duration). This survival benefit would likely project beyond the study termination at day 73 based on this efficacy profile. This combination also produced a 100% incidence of complete disease regression and a conservative calculation of greater than 55% incidence of tumor-free survivors at the time of study termination. TFS is likely substantially higher than this conservative calculation, being technically calculated based on a very low BLI signal in wildtype (untreated) CB.17 mice measured prior to tumor implant and used to set the very low disease-free baseline. This number is more likely to be closer to 100% (see FIG. 18 and FIG. 19D), in agreement with a calculated 100% CR. Treatment efficacy that was achieved through the combined use of mAb 4320 and bortezomib was very effectively maintained even following discontinuation of treatment at day 53 post tumor implant. No treatment-related death was observed for mAb 4320 in combination with bortezomib.

Tolerability

Treatment with mAb 4320 appears to have been very well tolerated. There were no deaths reported related to any infection, sampling or trauma or other morbidities clearly unrelated to disease. Loss of body weight during the first week of treatment was minimal and mean body weight change was likewise minimal (generally less than 5%) (FIG. 21). The greatest treatment-related weight loss was seen in the vehicle control (VC) group indicating disease progression as the primary cause of weight loss. Animals treated with 4 mg/kg mAb 4320 actually experienced an upward trend in mean body weight in spite of anticipated body weight loss due to disease progression. No animal deaths were reported in any of the mAb 4320 treatment groups. As most clinical signs and necropsy findings described for the antibody treatment groups matched the control group, a causality of disease progression rather than treatment most logically should be ascribed as the primary cause of morbidity. Nothing observed in this study suggested that mice were adversely affected by administration of mAb 4320.

In contrast, treatment related toxicity was observed in the two groups (3 and 7) initially receiving bortezomib at the 2 mg/kg dose level. Several bortezomib treated animals in these groups experienced greater loss of weight in the first week of dosing (relative to the vehicle control); related to this toxicity, there was 11% related death in the bortezomib single treatment group (Group 3) due to early euthanasia on day 23 following a rapid loss of weight (−24%). Reduction in dose level of bortezomib from 2 mg/kg to 1 mg/kg in all animals receiving this treatment was merited starting at day 18. Of note is the fact that these animals recovered in part with respect to changes in body weight following reduction of this dosage but primarily so in group 7 where mice receiving 1 mg/kg of bortezomib were also administered mAb 4320 at a 4 mg/kg dose level.

Summary

This Example demonstrated the in vivo efficacy of mAb 4320, a humanized monoclonal antibody targeting human CD138 (syndecan-1), in a mouse xenograft model of multiple myeloma. Here, mAb 4320 efficacy was evaluated both as a single agent or in combination with bortezomib, a proteasome inhibitor currently approved for the treatment of myeloma and constituting a standard of care in clinical practice (typically in combination with dexamethasone and an immunomodulating drug such as lenalidomide (REVLIMID®) or pomalidomide (POMALYST®). mAb 4320 monotherapy at 4 mg/kg dose effectively reduced disease burden as evidenced by a prolonged time to evaluation (tumor growth delay), prolonged median survival of greater than 100%, and clear reduction of disseminated tumor in relevant skeletal tissues. mAb 4320 treatment also led to disease regression in a subset of mice as evaluated up to day 53 (the last day of dosing) and at the dose level chosen. An evaluation of mAb 4320 PK/PD correlation in a prior study indicated a sufficient exposure of mAb 4320 at this dose level (4 mg/kg) to achieve a biological response. Without wishing to be bound by theory, it is believed that in an embodiment, even lower dose levels can also be sufficient to achieve such a response.

Administration of mAb 4320 was well tolerated with no overt treatment related morbidities or toxicities based on a similar observation of disease related morbidities in the vehicle control group.

mAb 4320 therapy was also evaluated in combination with bortezomib. A suboptimal dose level (1 mg/kg) was chosen due to observed toxicities as manifested by pronounced loss in body weight and mortality in one animal resultant from initial treatment at the higher 2 mg/kg dose chosen. Here, combined treatment of tumor-bearing mice with both mAb 4320 and bortezomib resulted in demonstrative efficacy as evident in complete disease regression and 100% survival of all animals out to the end of study at day 73. This demonstrative efficacy was sustained even after discontinuation of treatment on Day 53 three weeks prior to study termination. The apparent lack of any discernible tumor burden indicated an achievement of minimal residual disease in animals receiving the two therapies in combination. Moreover, the improved efficacy of combined use of mAb 4320 and bortezomib in comparison to either monotherapies indicated a synergistic effect of treatment (efficacy) rather than an exclusively additive effect. The augmentation of bortezomib activity at a lower, non-limiting dose also indicated a therapeutic benefit for rescuing bortezomib due to such limiting toxicities for improved use in the cytotoxic killing of myeloma cells.

Taken collectively, the positive efficacy data of this study both validated the strategy of an antibody targeting CD138 in tandem with an effective immune-based mechanism of malignant plasma cell killing. These results further support mAb 4320 as a therapeutic for the treatment of multiple myeloma and other indications in which CD138 is implicated. Additional utility for the use of mAb 4320 either as a single therapeutic agent or in combination with an (immune) proteasome inhibitor in the treatment of other plasma cell dyscrasias and/or autoimmune disorders is indicated.

INCORPORATION BY REFERENCE

All publications, patents, and Accession numbers mentioned herein are hereby incorporated by reference in their entirety as if each individual publication or patent was specifically and individually indicated to be incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A monoclonal anti-CD138 antibody molecule comprising:
  (a) a heavy chain variable region (VH), wherein the VH comprises three heavy chain complementarity determining regions (HCDR1, HCDR2, and HCDR3), wherein the VH comprises an HCDR1 comprising the amino acid sequence of SEQ ID NO: 380, an HCDR2 comprising the amino acid sequence of SEQ ID NO: 514, and an HCDR3 comprising the amino acid sequence of SEQ ID NO: 508; and
  (b) a light chain variable region (VL), wherein the VL comprises three light chain complementarity determining regions (LCDR1, LCDR2, and LCDR3), wherein the VL comprises an LCDR1 comprising the amino acid sequence of SEQ ID NO: 510, an LCDR2 comprising the amino acid sequence of SEQ ID NO: 353, and an LCDR3 comprising the amino acid sequence of SEQ ID NO: 354.

2. The antibody molecule of claim 1, wherein:
  (a) the VH comprises the amino acid sequence of SEQ ID NO: 471;
  (b) the VL comprises the amino acid sequence of SEQ ID NO: 475; or
  (c) both (a) and (b).

3. The antibody molecule of claim 1, comprising an Fc region.

4. The antibody molecule of claim 1, comprising:
  (a) a heavy chain (HC) comprising the amino acid sequence of SEQ ID NO: 527;

(b) a light chain (LC) comprising the amino acid sequence of SEQ ID NO: 528; or (c) both (a) and (b).

5. The antibody molecule of claim 1, which comprises two VHs and two VLs.

6. An antibody-molecule drug conjugate (ADC) comprising the antibody molecule of claim 1 coupled to a therapeutic agent.

7. A pharmaceutical composition comprising the antibody molecule of claim 1 and a pharmaceutically acceptable carrier.

8. A kit comprising the antibody molecule of claim 1 and instructions for use of the antibody molecule.

9. A container comprising the antibody molecule of claim 1.

10. The antibody molecule of claim 1, which is a monovalent antibody molecule or a monospecific antibody molecule.

11. The antibody molecule of claim 1, which is a humanized antibody molecule.

12. The antibody molecule of claim 1, which is an IgG antibody.

13. The antibody molecule of claim 1, which comprises a heavy chain constant region of an IgG chosen from IgG1, IgG2, IgG3, or IgG4.

14. The antibody molecule of claim 1, which comprises a light chain constant region of a kappa light chain or a lambda light chain.

15. The antibody molecule of claim 1, which comprises an Fc region comprising one or more mutations to increase the binding affinity to FcRn.

16. The antibody molecule of claim 1, which comprises an Fc region comprising one or more mutations to increase one or more of half-life, antibody-dependent cellular cytotoxicity (ADCC), complement-dependent cytotoxicity (CDC), or antibody-dependent cellular phagocytosis (ADCP).

17. A monoclonal anti-CD138 antibody molecule comprising a VH comprising the amino acid sequence of SEQ ID NO: 471 and a VL comprising the amino acid sequence of SEQ ID NO: 475.

18. A pharmaceutical composition comprising the antibody molecule of claim 17 and a pharmaceutically acceptable carrier.

19. A monoclonal anti-CD138 antibody molecule comprising a heavy chain (HC) comprising the amino acid sequence of SEQ ID NO: 527 and a light chain (LC) comprising the amino acid sequence of SEQ ID NO: 528.

20. A pharmaceutical composition comprising the antibody molecule of claim 19 and a pharmaceutically acceptable carrier.

21. The antibody molecule of claim 1, which is a multivalent antibody molecule or a multispecific antibody molecule.

* * * * *